United States Patent
Chun et al.

(10) Patent No.: US 6,953,682 B2
(45) Date of Patent: Oct. 11, 2005

(54) NUCLEIC ACID SEQUENCES ENCODING ADENYLATE KINASE, PHOSPHOLIPID SCRAMBLASE-LIKE, DNA FRAGMENTATION FACTOR-LIKE, PHOSPHATIDYLSERINE SYNTHASE-LIKE, AND ATPASE-LIKE MOLECULES AND USES THEREFOR

(75) Inventors: Miyoung Chun, Belmont, MA (US); Maria Alexandra Glucksmann, Lexington, MA (US); Rosana Kapeller-Libermann, Chestnut Hill, MA (US); Rachel E. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 267 days.

(21) Appl. No.: 10/165,800

(22) Filed: Jun. 7, 2002

(65) Prior Publication Data

US 2003/0092116 A1 May 15, 2003

Related U.S. Application Data

(63) Continuation-in-part of application No. 09/795,038, filed on Feb. 26, 2001, now abandoned, and a continuation-in-part of application No. 09/790,838, filed on Feb. 22, 2001, now Pat. No. 6,489,152, and a continuation-in-part of application No. 09/790,180, filed on Feb. 21, 2001, now abandoned, and a continuation-in-part of application No. 09/790,179, filed on Feb. 21, 2001, now Pat. No. 6,479,268, and a continuation-in-part of application No. 09/781,677, filed on Feb. 12, 2001, now abandoned.

(60) Provisional application No. 60/186,234, filed on Feb. 29, 2000, provisional application No. 60/185,947, filed on Feb. 29, 2000, provisional application No. 60/185,946, filed on Feb. 29, 2000, provisional application No. 60/185,609, filed on Feb. 29, 2000, and provisional application No. 60/181,705, filed on Feb. 10, 2000.

(51) Int. Cl.[7] .............................. C12N 9/26; C12Q 1/00; C12Q 1/34; A01N 25/00

(52) U.S. Cl. .............................. 435/201; 435/4; 435/18; 514/789

(58) Field of Search .............................. 435/201, 4, 18, 435/440; 514/789; 536/23.2, 23.1; 530/350

(56) References Cited

U.S. PATENT DOCUMENTS

| 5,932,444 A | 8/1999 | Hillman et al. | |
|---|---|---|---|
| 2002/0151681 A1 * | 10/2002 | Rosen et al. | 530/350 |

FOREIGN PATENT DOCUMENTS

| EP | 1130094 A2 | 9/2001 |
|---|---|---|
| WO | WO 98/45437 A2 | 10/1998 |
| WO | WO 00/55174 A1 | 9/2000 |
| WO | WO 01/54733 A1 | 8/2001 |
| WO | WO 01/66689 A2 | 9/2001 |
| WO | WO 01/90304 A2 | 11/2001 |

OTHER PUBLICATIONS

Sequence alignment for U.S. Appl. No. 2002/0151681.*

(Continued)

*Primary Examiner*—Ponnathapu Achutamurthy
*Assistant Examiner*—Yong D. Pak
(74) *Attorney, Agent, or Firm*—Millennium Pharmaceutical Inc.

(57) ABSTRACT

The invention provides isolated nucleic acids molecules that encode novel polypeptides. The invention also provides antisense nucleic acid molecules, recombinant expression vectors containing the nucleic acid molecules of the invention, host cells into which the expression vectors have been introduced, and nonhuman transgenic animals in which a sequence of the invention has been introduced or disrupted. The invention still further provides isolated proteins, fusion proteins, antigenic peptides and antibodies. Diagnostic methods utilizing compositions of the invention are also provided.

5 Claims, 43 Drawing Sheets

OTHER PUBLICATIONS

Kawai, et al., "Functional Annotation of a Full–Length Mouse cDNA Collection," Nature, 2001, pp. 685–690, vol. 409, The Riken Genome Exploration Research Group Phase II Team and the Fantom Consortium, Macmillan Magazines, USA.

Federspiel, N.A., et al., "Unknown Protein [*Arabidopsis Thaliana*]," Oct. 18, 1999, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AAF02877.

Celniker, S.E., et al., "Hypothetical Protein [*Drosophila Melanogaster*]," Mar. 21, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AAF44893.

Theologis, A., et al., "Contains Similarity to p60 Katanin from Chlamydomonas Reinhardtii gb / AF205377 and contains an AAA Domain PF/00004. [*Arabidopsis Thaliana*]," Jun. 16, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AAF76434.

Ohara, O., et al., "Homo Sapiesn mRNA for KIAA1083 Protein, Complete Cds," Aug. 4, 1999, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AB029006.

Celniker, S.E., et al., "*Drosophila Melanogaster*, Chromosome 2R, Region 31C1–31D6, P1 Clone DS08879, Complete Sequence," Dec. 15, 1998, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AC005454.

Birren, B., et al., "Homo Sapiens Chromosome 17, Clone hCIT.187_K_10, Complete Sequence," Jan. 1, 1999, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AC006263.

Strausberg, R., et al., "wh42c04.x1 NCI_CGAP_Kid11 Homo Sapiens cDNA Clone Image: 2383398 3' Similar to WP:K04D7.2 CEO6091 MSP1 Protein Homolog ;, mRNA Sequence," Jul. 6, 1999 (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AI796091.

Fonknechten, N., et al., "Homo Sapiens mRNA for Spastin Protein (Spast Gene)" Mar. 10, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AJ246001.

Hazan, J., et al., "Mus Musculus mRNA for Spastin Protein Othologue (Spast Gene)" Nov. 5, 1999, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AJ246002.

Lorenzo, O., et al., "Fagus Sylvatica mRNA for 26S Proteasome Subunit 8 (Tat Binding Protein) (a1 gene)" Dec. 16, 1999, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AJ251819.

Tanaka, T., et al., "Pyrococcus Horikoshii OT3 Genomic DNA, 994001–1166000 nt. Position (5/7)" Apr. 6, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AP000005.

Hashimoto, K., et al., "AU080226 Sugano Mouse Brain mncb Mus Musculus cDNA Clone MNCb–5378 5', mRNA Sequence" Jul. 12, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. AU080226.

Nakamura, Y., et al., "26S Proteasome Regulatory Particle Chain RPT6–Like Protein [*Arabidopsis Thaliana*]" Dec. 27, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. BAB09730.

Strausberg, R., et al., "601474043F1 NIH_MGC_68 Homo Sapiens cDNA Clone Image: 3876875 5', mRNA Sequence" Oct. 20, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. BE784612.

Strausberg, R., et al., "601457812F NIH_MGC_66 Homo Sapiens cDNA Clone Image: 3861530 5', mRNA Sequence" Oct. 20, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. BF035901.

Strausberg, R., et al., "601882963F1 nih_mgc_57 Homo Sapiens cDNA Clone Image: 4095543 5', mRNA Sequence" Nov. 6, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. BF216662.

Strausberg, R., et al., "602155010F1 NIH_NGC_83 Homo Sapiens cDNA Clone Image: 4295762 5', mRNA Sequence" Dec. 21, 2000, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. BF680249.

Nakai, M., et al., "MSP1 Protein (TAT–Binding Homolog 4)," Nov. 1, 1997, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. P28737.

Wild, A., "MSP1 Protein Homolog," Oct. 1, 1996, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. P54815.

Volckaert, G., et al., "S.pombe Chromosome II Cosmid C16E9," Mar. 23, 2001, (sequence) GenBank [online] Bethesda, MD, USA: National Center for Biotechnology Information [retrieved on Nov. 15, 2001]. Retrieved from the Internet: URL: http://www.ncbi.nlm.nih.gov/>. GenBank Accession No. Z99759.

Adams, M.D., et al., "EST176069 Colon Carcinoma (Caco–2) Cell Line II Homo Spaiens cDNA 5' End," Apr. 18, 1997, (sequence) EMBL Database [online] Hinxton, Cambridge, U.K., European Bioinformatics Institute, [retrieved on Aug. 31, 2001]. Retrieved from the Internet: URL: http://www.ebi.ac.uk/embl/>. EMBL Accession No. AA304993.

Plumg, B., "Human DNA Sequence—Sequencing in Progress—From Clone RP11–77F13," Dec. 3, 1999, (sequence) EMBL Database [online] Hinxton, Cambridge, U.K., European Bioinformatics Institute, [retrieved on Aug. 31, 2001]. Retrieved from the Internet: URL: http://www.ebi.ac.uk/embl/>. EMBL Accession No. AL133327.

Adachi, J. et al., "Mus Musculus Adult Male Testis cDNA, Riken full–Length Enriched Library, Clone: 4921525H23, Full Insert Sequence," Feb. 8, 2001, (sequence) EMBL Database [online] Hinxton, Cambridge, U.K., European Bioinformatics Institute, [retrieved on Aug. 31, 2001]. Retrieved from the Internet: URL: http://www.ebi.ac.uk/embl/>. EMBL Accession No. AK014967.

Notification of Transmittal of the International Search Report mailed Sep. 11, 2001 (for International Application No. PCT/US01/05597 filed Feb. 22, 2001).

Smith, D.R., et al., "Putative AAA–Family Atpase ML1316," created Nov. 1, 1995 (sequence) Swiss Prot [online]Bethesda, MD, USA: National Center for Biotechnology Information [retrieved on Jan. 15, 2002]. Retrieved from the Internet: URL: http://www.ncbi.nlm.nih.gov/>. Swiss Prot Accession No. YL15_MYCLE.

Smith, D.R., et al., "Mycobacterium Leprae Cosmid B2126," Mar. 19, 1997 (sequence), EMBL Database [online], Hinxton, Cambridge, U.K., European Bioinformatics Institute, [retrieved on Jan. 15, 2002]. Retrieved from the Internet: URL: http://www.ebi.ac.uk/embl/>. EMBL Accession No. AK014967.

Kawai, J. et al., "4921525H23RIK Protein," Jun. 1, 2001, (sequence), EMBL Database [online], Hinxton, Cambridge, U.K., European Bioinformatics Institute, [retrieved on Aug. 31, 2001]. Retrieved from the Internet: URL: http://www.ebi.ac.uk/embl/>. EMBL Accession No. Q9D5TO.

Blast 1.4 Nucleotide Alignment of Sequence ID No. 4017 disclosed in EP 1130094 (cited as BF) with Seq. ID No. 2 of present application.

* cited by examiner

Parsed for domains:
```
Model      Domain   seq-f  seq-t    hmm-f  hmm-t    score   E-value
-------    ------   -----  -----    -----  -----    -----   -------
AAA         1/1      128    312 ..    1    220 []   244.2   1.8e-69
```

AAA: domain 1 of 1, from 128 to 312: score 244.2, E = 1.8e-69

```
            *->GvLLyGPPGTGKTlLAkAvAnelgslrkapFlslsGyselvskyvGe
               GvLLyGPPG+GKTl+AkA A+e+g     +Fi ++   s+l +k++Ge
   7970 128    GVLLYGPPGCGKTLIAKATAKEAG----CRFINLQP-STLTDKWYGE 169 sekrvRalFelArelrkraaPcplIFiDEIDalapkRg...gevsrrvvn
               s k+  a+F+lA +l   +P+ IIFiDEID+  ++R++++te ++ +++
   7970 170    SQKLAAAVFSLAIKL----QPS-IIFIDEIDSFLRNRSssdHEATAMMKA 214 qLLtemDleraGfsknssrgedtidlsnVlvlaATNrpdtlDpALlRpGR
               q+++++D    G++ +            + +V+v++ATNrp++lD+A++R  R
   7970 215    QFMSLWD----GLDTDH--------SCQVIVMGATNRPQDLDSAIMR--R 250 fDreieiplppdeegRldllkihlkkmplssslkqselaedvdldelaee
               +++i +p    ++R +llk   lk+ +++              vdl e
   7970 251    MPTRFHINQP-ALKQREAILKLILKNENVD---------RHVDLLE---- 286 latrtegfsGADLkalcreAalrair<-*
               +a+ t+gfsG+DLk+ cr+Aal+++r
   7970 287    VAQETDGFSGSDLKEMCRDAALLCVR    312
```

| | Lung/ normal | Lung/ tumor | Lung/ COPD | Spleen/ normal | Tonsil/ normal | Lymph node/ normal | Thymus/ normal | Epithe lial Cells (prost) | Epithe lial Cells (aortic) | Skeletal Muscle | Fibrob lasts (Dermal) | Skin/ normal | Adipo se/ Normal | Osteo blasts (prima ry) | Osteo blasts (Undiff) | Osteo blasts (Diff) | Osteo clasts | Aortic SMC Early | Aortic SMC Late | shear HUVEC | static HUVEC | Osteo clasts (Undiff) |
|---|---|---|---|---|---|---|---|---|---|---|---|---|---|---|---|---|---|---|---|---|---|---|
| | 29.37 | 29.07 | 29.58 | 33.92 | 30.19 | 30.04 | 29.21 | 27.83 | 32.09 | 30.67 | 30.20 | 32.13 | 31.77 | 30.72 | 29.71 | 28.80 | 30.41 | 29.18 | 31.24 | 29.49 | 29.64 | 30.57 |
| | 18.94 | 19.33 | 19.05 | 21.49 | 18.72 | 19.60 | 20.33 | 21.52 | 21.94 | 21.37 | 20.10 | 21.76 | 19.79 | 21.13 | 20.02 | 19.03 | 18.41 | 21.25 | 23.61 | 21.40 | 21.83 | 17.42 |
| | 10.43 | 9.74 | 10.53 | 12.43 | 11.47 | 10.44 | 8.88 | 6.31 | 10.16 | 9.30 | 10.10 | 10.38 | 11.98 | 9.59 | 9.59 | 9.78 | 12.00 | 7.94 | 7.64 | 8.10 | 7.81 | 13.16 |
| | 0.72 | 1.17 | 0.68 | 0.18 | 0.35 | 0.72 | 2.12 | 12.60 | 0.88 | 1.59 | 0.91 | 0.75 | 0.25 | 1.30 | 1.21 | 1.14 | 0.24 | 4.09 | 5.03 | 3.66 | 4.45 | 0.11 |

FROM FIG. 4A.

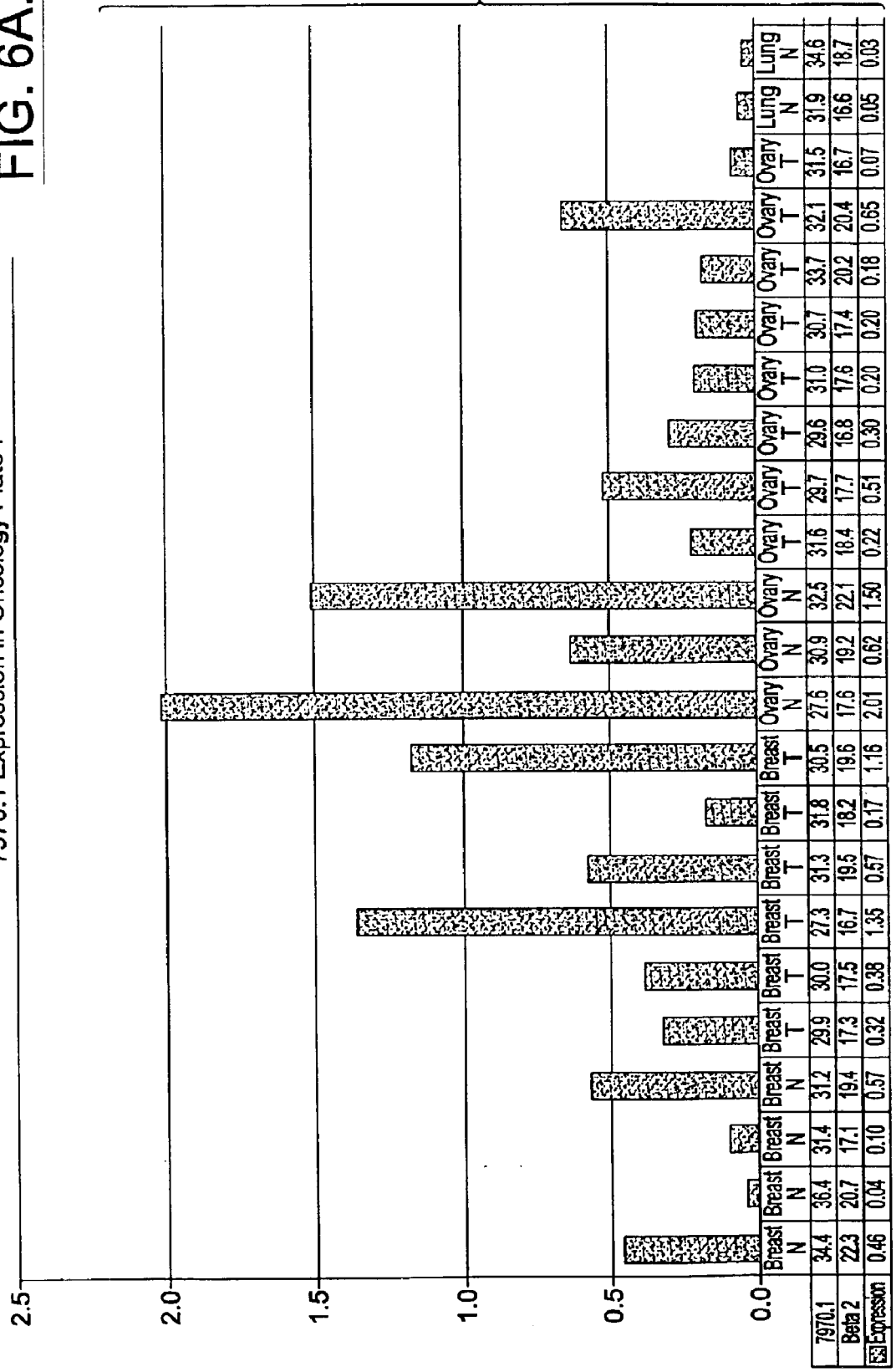

FROM FIG. 6A.

CLUSTAL W (1.74) multiple sequence alignment

```
2190007    MRRAERRVAGGSGSGSPLLE--------------------GRRSTESEVYDDGTNTFF
4063700    MRRAERRVAGGSGSESPLLK--------------------GRRSTESEVYDDGTNTFF
32670      MRRGERRDAGGPRPESPVPAGRASLEEPPDGPSAGQATGPGEGRRSTESEVYDDGTNTFF
           ***.***.***. .**:                       ******************

2190007    WRAHTLTVLFILTCSLGYVTLLEETPQDTAYNTKRGIVASILVFLCFGVTQAKDGPFSRP
4063700    WRAHTLTVLFILTCALGYVTLLEETPQDTAYNTKRGIVASILVFLCFGVTQAKDGPFSRP
32670      WRAHTLTVLFILTCTLGYVTLLEETPQDTAYNTKRGIVASILVFLCFGVTQAKDGPFSRP
           **************:*********************************************

2190007    HPAYWRFWLCVSVVYELFLIFILFQTVQDGRQFLKYVDPRLGVPLPERDYGGNCLIYDAD
4063700    HPAYWRFWLCVSVVYELFLIFILFQTVQDGRQFLKYVDPRLGVPLPERDYGGNCLIYDAD
32670      HPAYWRFWLCVSVVYELFLIFILFQTVQDGRQFLKYVDPKLGVPLPERDYGGNCLIYDPD
           ***************************************:****************. *

2190007    NKTDPFHNIWDKLDGFVPAHFIGWYLKTLMIRDWWMCMIISVMFEFLEYSLEHQLPNFSE
4063700    NKTDPFHNIWDKLDGFVPAHFIGWYLKTLMIRDWWMCMIISVMFEFLEYSLEHQLPNFSE
32670      NETDPFHNIWDKLDGFVPAHFLGWYLKTLMIRDWWMCMIISVMFEFLEYSLEHQLPNFSE
           *:*******************:**************************************

2190007    CWWDHWIMDVLICNGLGIYCGMKTLEWLSLKTYKWQGLWNIPTYKGKMKRIAFQFTPYSW
4063700    CWWDHWIMDVLVCNGLGIYCGMKTLEWLSLKTYKWQGLWNIPTYKGKMKRIAFQFTPYSW
32670      CWWDHWIMDVLVCNGLGIYCGMKTLEWLSLKTYKWQGLWNIPTYKGKMKRIAFQFTPYSW
           **********:*************************************************

2190007    VRFEWKPASSLHRWLAVCGIILVFLLAELNTFYLKFVLWMPPEHYLVLLRLVFFVNVGGV
4063700    VRFEWKPASSLHRWLAVCGIILVFLLAELNTFYLKFVLWMPPEHYLVLLRLVFFVNVGGV
32670      VRFEWKPASSLRRWLAVCGIILVFLLAELNTFYLKFVLWMPPEHYLVLLRLVFFVNVGGV
           ***********:*************************************************

2190007    AMREIYDFMDELKPHRKLGQQAWLVAAITVTELLIVVKYDPHTLTLSLPFYISQCWTLGS
4063700    AMREIYDFMDELKPHRKLGQQAWLVAAITVTELLIVVKYDPHTLTLSLPFYISQCWTLGS
32670      AMREIYDFMDDPKPHKKLGPQAWLVAAITATELLIVVKYDPHTLTLSLPFYISQCWTLGS
           **********: ***.***.********.*******************************

2190007    ILVLTWTVWRFFLRDITMRYKETRRQKQQS--HQGRAINNGDGHP-GPDDDLLGTGTAEE
4063700    ILVLTWTVWRFFLRDITMRYKETRRQKQQS--HQARAVNNRDGHP-GPDDDLLGTGTAEE
32670      VLALTWTVWRFFLRDITLRYKETRWQKWQNKDDQGSTVGNGDQHPLGLDEDLLGPGVAEG
           :*.**************:***** ** **.   . *. :: * * ** *: ****.*.**

2190007    EGSTNDSVPAEKEGASAAS
4063700    EGTTNDGVTAE-EGASAAS
32670      EGAPTPN------------
           **:..
```

FIG. 13.

```
Input file Fbh32670.seq; Output File 32670.trans
Sequence length 1852
                     M   R   R   G   E   R   R   D   A   G   G   P   R   P   E   S      16
CACGCGTCCGGCC ATG CGG AGG GGC GAG CGC AGG GAC GCC GGA GGT CCG CGG CCC GAG TCC            48
  P   V   P   A   G   R   A   S   L   E   E   P   P   D   G   P   S   A   G   Q         36
CCG GTG CCC GCG GGC AGG GCC TCG CTG GAG GAG CCG CCT GAC GGG CCG TCT GCC GGC CAA          108
  A   T   G   P   G   E   G   R   R   S   T   E   S   E   V   Y   D   D   G   T         56
GCC ACC GGG CCG GGC GAG GGC CGC CGC AGC ACC GAG TCC GAG GTC TAC GAC GAC GGC ACC          168
  N   T   F   F   W   R   A   H   T   L   T   V   L   F   I   L   T   C   T   L         76
AAC ACC TTC TTC TGG CGA GCC CAC ACC TTA ACC GTG CTC TTC ATC CTC ACC TGT ACG CTT          228
  G   Y   V   T   L   L   E   E   T   P   Q   D   T   A   Y   N   T   K   R   G         96
GGC TAT GTG ACG CTG CTG GAG GAA ACA CCT CAG GAC ACG GCC TAC AAC ACC AAG AGA GGT          288
  I   V   A   S   I   L   V   F   L   C   F   G   V   T   Q   A   K   D   G   P         116
ATT GTG GCC AGT ATT TTG GTT TTC TTA TGT TTT GGA GTC ACA CAA GCT AAA GAC GGG CCA          348
  F   S   R   P   H   P   A   Y   W   R   F   W   L   C   V   S   V   V   Y   E         136
TTT TCC AGA CCT CAT CCA GCT TAC TGG AGG TTT TGG CTC TGC GTG AGT GTG GTC TAC GAG          408
  L   F   L   I   F   I   L   F   Q   T   V   Q   D   G   R   Q   F   L   K   Y         156
CTG TTT CTC ATC TTT ATA CTC TTC CAG ACT GTC CAG GAC GGC CGG CAG TTT CTA AAG TAT          468
  V   D   P   K   L   G   V   P   L   P   E   R   D   Y   G   G   N   C   L   I         176
GTT GAC CCC AAG CTG GGA GTC CCA CTG CCA GAG AGA GAC TAC GGG GGA AAC TGC CTC ATC          528
  Y   D   P   D   N   E   T   D   P   F   H   N   I   W   D   K   L   D   G   F         196
TAC GAC CCA GAC AAT GAG ACT GAC CCC TTT CAC AAC ATC TGG GAC AAG TTG GAT GGC TTT          588
  V   P   A   H   F   L   G   W   Y   L   K   T   L   M   I   R   D   W   W   M         216
GTT CCC GCG CAC TTT CTT GGC TGG TAC CTG AAG ACC CTG ATG ATC CGA GAC TGG TGG ATG          648
  C   M   I   I   S   V   M   F   E   F   L   E   Y   S   L   E   H   Q   L   P         236
TGC ATG ATC ATC AGC GTG ATG TTC GAG TTC CTG GAG TAC AGC CTG GAG CAC CAG CTG CCC          708
  N   F   S   E   C   W   W   D   H   W   I   M   D   V   L   V   C   N   G   L         256
AAC TTC AGC GAG TGC TGG TGG GAT CAC TGG ATC ATG GAC GTG CTC GTC TGC AAC GGG CTG          768
  G   I   Y   C   G   M   K   T   L   E   W   L   S   L   K   T   Y   K   W   Q         276
GGC ATC TAC TGC GGC ATG AAG ACC CTT GAG TGG CTG TCC CTG AAG ACG TAC AAG TGG CAG          828
  G   L   W   N   I   P   T   Y   K   G   K   M   K   R   I   A   F   Q   F   T         296
GGC CTC TGG AAC ATT CCG ACC TAC AAG GGC AAG ATG AAG AGG ATC GCC TTC CAG TTC ACG          888
  P   Y   S   W   V   R   F   E   W   K   P   A   S   S   L   R   R   W   L   A         316
CCG TAC AGC TGG GTT CGC TTC GAG TGG AAG CCG GCC TCC AGC CTG CGT CGC TGG CTG GCC          948
  V   C   G   I   I   L   V   F   L   L   A   E   L   N   T   F   Y   L   K   F         336
GTG TGC GGC ATC ATC CTG GTG TTC CTG TTG GCA GAA CTG AAC ACG TTC TAC CTG AAG TTT          1008
  V   L   W   M   P   P   E   H   Y   L   V   L   L   R   L   V   F   F   V   N         356
GTG CTG TGG ATG CCC CCG GAG CAC TAC CTG GTC CTC CTG CGG CTC GTC TTC TTC GTG AAC          1068
  V   G   G   V   A   M   R   E   I   Y   D   F   M   D   D   P   K   P   H   K         376
GTG GGT GGC GTG GCC ATG CGT GAG ATC TAC GAC TTC ATG GAT GAC CCG AAG CCC CAC AAG          1128
  K   L   G   P   Q   A   V   L   V   A   A   I   T   A   E   L   L   I   V             396
```

FIG. 14A.

```
AAG CTG GGC CCG CAG GCC TGG CTG GTG GCG GCC ATC ACG GCC ACG GAG CTG CTC ATC GTG   1188
 V   K   Y   D   P   H   T   L   T   L   S   L   P   F   Y   I   S   Q   C   V    416
GTG AAG TAC GAC CCC CAC ACG CTC ACC CTG TCC CTG CCC TTC TAC ATC TCC CAG TGC TGG   1248
 T   L   G   S   V   L   A   L   T   V   T   V   W   R   F   F   L   R   D   I    436
ACC CTC GGC TCC GTC CTG GCG CTC ACC TGG ACC GTC TGG CGC TTC TTC CTG CGG GAC ATC   1308
 T   L   R   Y   K   E   T   R   W   Q   K   W   Q   N   K   D   D   Q   G   S    456
ACA TTG AGG TAC AAG GAG ACC CGG TGG CAG AAG TGG CAG AAC AAG GAT GAC CAG GGC AGC   1368
 T   V   G   N   G   D   Q   H   P   L   G   L   D   E   D   L   L   G   P   G    476
ACC GTC GGC AAC GGG GAC CAG CAC CCA CTG GGG CTG GAC GAA GAC CTG CTG GGG CCT GGG   1428
 V   A   E   G   E   G   A   P   T   P   N   *                                    488
GTG GCC GAG GGC GAG GGA GCA CCA ACT CCA AAC TGA                                   1464
```

CCTGGGCCGTGGCTGCCTCGTGAGCCTCCCAGAGCCCAGGCCTCCGTGGCCTCCTCCTGTGTGAGTCCCACCAGGAGCC

ACGTGCCCGGCCTTGCCCTCAAGGTTTTTTGCTTTTCTCCTGTGCACCTGGCGAGGCTGAAGGCGAGGGGTGGAGGAGG

CCCCAGCACAGCCTCATCTCCATGTGTACACGTGTGTACGTGTGTATGCGTGTGTGTACGCCGTGTGTACGCGCGTGTG

TACACATGCGTGGCCCGCTGTGGTGTGCACSTGTGCTCTGGGCTCCGAGGCTTSTTCHAGARCTGGGARCTGGCTGGCGT

GGCAAGGGCATGCTCTGGGGCAGTGTGTTCCTYAAGAACCARGGGTCCTTCCTYCCTTT

FIG. 14B.

```
Query: 5698

Scores for sequence family classification (score includes all domains):
Model     Description                                    Score    E-value   N
CAD_1                                                    138.3    1.4e-37   1

Parsed for domains:
Model     Domain   seq-f  seq-t    hmm-f  hmm-t      score  E-value
CAD_1     1/1      36     108  ..  1      76   []    138.3  1.4e-37

Alignments of top-scoring domains:
CAD_1:  domain 1 of 1, from 36 to 108: score 138.3, E = 1.4e-37
                  *->rPfkvrdhdRnvrkGVaAsSLEELLsKvldkLklpdsLepvtLVLeE
                     rPf+v+dh+R++rkG++A++ +ELL K+l++L l + ++tLVLeE
          5698  36  RPFRVCDHKRTIRKGLTAATRQELLAKALETLLLNG---VLTLVLEE 79

DGTeVedeeYFrtLpnNTeLvaLeqGEkW<-*
                  DGT+V++e++F+ L+++T+L++L +G++W
          5698  80 DGTAVDSEDFFQLLEDDTCLMVLQSGQSW  108
```

FIG. 17.

CLUSTAL W (1.74) multiple sequence alignment

```
3114594    MEYLSAFNPNGLLRSVSTVSSELSRRVWNSAPPPQRPFRVCDHKRTVRKGLIAASLQELL
5698       MEYLSALNPSDLLRSVSNISSEFGRRVWTSAPPPQRPFRVCDHKRTIRKGLTAATRQELL
3114596    MEAARDYAG-ALIRPLTFMGSQTKRVLFTPLMHPARPFRVSNHDRSSRRGVMASSLQELI
           **        *.*.:: :.*    *  !!..  * *****.!*.*: *!*! *:! ***!

3114594    DKVLETLLLR-GVLTLVLEEDGTAVDSEDFFQLLEDDTCLMVLEQGQSWSP-KSGMLSYG
5698       AKALETLLLN-GVLTLVLEEDGTAVDSEDFFQLLEDDTCLMVLQSGQSWSPTRSGVLSYG
3114596    SKTLDALVIATGLVTLVLEEDGTVVDTEEFFQTLGDNTHFMILEKGQKWMP---GSQHVP
           *.*!:*::   *!:**********.**!*!*** *.*!* !*!*!,**.* *   *

3114594    LGREKPKHSKDIARITFDVYKQNPRDLFGSLNVKATFYGLYSMSCDFQGVGPKRVLRELL
5698       LGRERPKHSKDIARFTFDVYKQNPRDLFGSLNVKATFYGLYSMSCDFQGLGPKKVLRELL
3114596    TCSP-PKRS-GIARVTFDLYRLNPKDFIGCLNVKATMYEMYSVSYDIRCTGLKGLLRSLL
           **!*  .***.***!*!  **!*!!*.******** !**!* *!!  * *  !**.**

3114594    RGTSSQLQGLGHMLLGISSTLRHVVEGAD-----RWQWHGQRHLHS
5698       RWTSTLLQGLGHMLLGISSTLRHAVEGAE-----QWQQKGRLHSY-
3114596    RFLSYSAQVTGQFLIYLGTYMLRVLDDKEERPSLRSQAKGRFTCG-
           *   *    *   *!!*!  !.!  !  !,!!.  !   ! * !*!
```

FIG. 19.

```
CLUSTAL V (1.74) multiple sequence alignment
2935163   -------MEAPRS-GTYLPAGYAP--QYPPAAVQ-GPPEHTG--RPTFQTNYQVPQSGYP
3510297   MDKQNSQMNASHP-ETNLPVGYPP--QYPPTAFQ-GPPGYSG--YPGPQVSYPPPPAGHS
32621     -------MSGVVPTAPEQPAGEMENQTKPPDPRPDAPPEYNSHFLPGPPGTAVPPPTGYP
              *. . **.*   **, .**:.,  *    .  * :*:.

2935163   GPQASYTVSTSGHEGYAATR-----LPIQN------NQTIVLANTQWMPAPPPILNCPPGL
3510297   GP---------GPAGFPVPN-----QPVYNQP-VYNQPVGAAGVPWMPAPQPPLNCPPGL
32621     GGLPMGYYSPQQPSTFPLYQPVGGIHPVRYQPGKYPMPNQSVPITWMPGPTPMANCPPGL
          *           :. ,       *:        . ,      ***.* * ******

2935163   EYLNQIDQLLIHQQVELLEVLTGFETNNKFEIKNSLGQMVYVAVEDTDCCTRNCCEASRP
3510297   EYLSQIDQILIHQQIELLEVLTGFETNNKYEIKNSFGQRVYFAAEDTDCCTRNCCGPSRP
32621     EYLVQLDNIHVLQHFEPLEMMTCFETNNRYDIKNNSDQMVYIVTEDTDDFTRNAYRTLRP
          *** *: *:::  : *:.* **::* ******::***  ,* **,..**** ***,  **

2935163   FTLRILDHLGQEVMTLERPLRCSSCCFPCC---LQEIEIQAPPGVPIGYVTQTWHPCLPK
3510297   FTLRIIDNMGQEVITLERPLRCSSCCCPCC---LQEIEIQAPPGVPIGYVIQTWHPCLPK
32621     FVLRVTDCMGREIMTMQRPFRCT-CCCFCCPSARQELEVQCPPGVTIGFVAEHWNLCRAV
          *.**: * :*.*: *::* **: ** ** **:*:* ****,**:* : *:   *

2935163   LTLQNDKRENVLKVVGPCVACTCCSDIDFEIKSLDEVTRIGKITKQWSGCVKEAFTDSDN
3510297   FTIQNEKREDVLKISGPCVVCSCCGDVDFEIKSLDEQCVVGKISKHWTGILREAFTDADN
32621     YSIQNEKKENVMRVRGPCSTYGCGSDSVFEVKSLDGISNIGSIIRKWNGLL-SAMADADH
          : **:*:*:*:::  ***  ,  * .* ** ****   :*.* *,* :  ,*::*:*:

2935163   FGIQFPLDLEVKMKAVTLGACFLIDYMFFEGCE---------
3510297   FGIQFPLDLDVKMKAVMIGACFLIDFMFFESTGSQEQKSGVW
32621     FDIHFPLDLDVKMKAMIFGACFLIDFMYFERSPPQRSR----
          *,*:*****:*****: :*******:*:** :*: **
```

FIG. 21.

Input file Fbh32621.seq; Output File 32621.trans
Sequence length 1542

CACGCGTCCGGGCGTCTGGCGTCCCCGGTGCCCAGCATTCTGCGGGGCAGGCGGTCTCGCTTGATTGGGTTTCTCATGG

GTCTCTGGCGTTTCTACGGCGCGGCTCTCACGGACTCAGGCCAGGCCACTCGCAGGATTAATTGGAATTCTTCAAA

| | | | | | | | | | | | | | | | | | | | | |
|---|---|---|---|---|---|---|---|---|---|---|---|---|---|---|---|---|---|---|---|---|
| M | S | G | V | V | P | T | A | P | E | Q | P | A | G | E | M | E | N | Q | T | 20 |
| ATG | TCA | GGT | GTG | GTA | CCC | ACA | GCC | CCT | GAA | CAG | CCT | GCA | GGT | GAA | ATG | GAA | AAT | CAA | ACA | 60 |
| K | P | P | D | P | R | P | D | A | P | P | E | Y | N | S | H | F | L | P | G | 40 |
| AAA | CCA | CCA | GAT | CCA | AGG | CCT | GAT | GCT | CCT | CCT | GAA | TAC | AAT | TCT | CAT | TTT | TTA | CCA | GGA | 120 |
| P | P | G | T | A | V | P | P | P | T | G | Y | P | G | G | L | P | M | G | Y | 60 |
| CCC | CCT | GGA | ACA | GCT | GTC | CCT | CCA | CCT | ACT | GGC | TAC | CCA | GGA | GGC | TTG | CCT | ATG | GGA | TAC | 180 |
| Y | S | P | Q | Q | P | S | T | F | P | L | Y | Q | P | V | G | G | I | H | P | 80 |
| TAC | AGT | CCA | CAG | CAA | CCC | AGT | ACC | TTC | CCT | TTG | TAC | CAG | CCA | GTT | GGT | GGT | ATC | CAT | CCT | 240 |
| V | R | Y | Q | P | G | K | Y | P | M | P | N | Q | S | V | P | I | T | W | M | 100 |
| GTC | CGG | TAT | CAG | CCT | GGC | AAA | TAT | CCT | ATG | CCA | AAT | CAG | TCT | GTT | CCA | ATA | ACA | TGG | ATG | 300 |
| P | G | P | T | P | M | A | N | C | P | P | G | L | E | Y | L | V | Q | L | D | 120 |
| CCA | GGG | CCA | ACT | CCT | ATG | GCA | AAC | TGC | CCT | CCT | GGT | CTG | GAA | TAC | TTA | GTT | CAG | TTG | GAC | 360 |
| N | I | H | V | L | Q | H | F | E | P | L | E | M | M | T | C | F | E | T | N | 140 |
| AAC | ATA | CAT | GTT | CTT | CAG | CAT | TTT | GAG | CCT | CTG | GAA | ATG | ATG | ACA | TGT | TTT | GAA | ACT | AAT | 420 |
| N | R | Y | D | I | K | N | N | S | D | Q | M | V | Y | I | V | T | E | D | T | 160 |
| AAT | AGA | TAT | GAT | ATT | AAA | AAC | AAC | TCA | GAC | CAG | ATG | GTT | TAC | ATT | GTA | ACC | GAA | GAC | ACA | 480 |
| D | D | F | T | R | N | A | Y | R | T | L | R | P | F | V | L | R | V | T | D | 180 |
| GAT | GAC | TTT | ACC | AGG | AAT | GCC | TAT | CGG | ACA | CTA | AGG | CCC | TTC | GTC | CTC | CGG | GTC | ACT | GAT | 540 |
| C | M | G | R | E | I | M | T | M | Q | R | P | F | R | C | T | C | C | C | F | 200 |
| TGT | ATG | GGC | CGA | GAA | ATC | ATG | ACA | ATG | CAG | AGA | CCC | TTC | AGA | TGC | ACC | TGC | TGT | TGC | TTC | 600 |
| C | C | P | S | A | R | Q | E | L | E | V | Q | C | P | P | G | V | T | I | G | 220 |
| TGT | TGC | CCC | TCT | GCC | AGA | CAA | GAG | CTG | GAG | GTG | CAG | TGT | CCT | CCT | GGT | GTC | ACC | ATT | GGC | 660 |
| F | V | A | E | H | W | N | L | C | R | A | V | Y | S | I | Q | N | E | K | K | 240 |
| TTT | GTT | GCG | GAA | CAT | TGG | AAC | CTG | TGC | AGG | GCG | GTG | TAC | AGC | ATC | CAA | AAT | GAG | AAG | AAA | 720 |
| E | N | V | M | R | V | R | G | P | C | S | T | Y | G | C | G | S | D | S | V | 260 |
| GAA | AAT | GTG | ATG | AGA | GTT | CGT | GGG | CCA | TGC | TCA | ACC | TAT | GGC | TGT | GGT | TCA | GAT | TCT | GTT | 780 |
| F | E | V | K | S | L | D | G | I | S | N | I | G | S | I | I | R | K | W | N | 280 |
| TTT | GAG | GTC | AAA | TCC | CTT | GAT | GGC | ATA | TCC | AAC | ATC | GGC | AGT | ATT | ATC | CGG | AAG | TGG | AAT | 840 |
| G | L | L | S | A | M | A | D | A | D | H | F | D | I | H | F | P | L | D | L | 300 |
| GGT | TTG | TTA | TCA | GCA | ATG | GCA | GAT | GCT | GAC | CAT | TTT | GAC | ATT | CAC | TTC | CCA | CTA | GAC | CTG | 900 |
| D | V | K | M | K | A | M | I | F | G | A | C | F | L | I | D | F | M | Y | F | 320 |
| GAT | GTG | AAG | ATG | AAA | GCC | ATG | ATT | TTT | GGA | GCT | TGC | TTC | CTC | ATT | GAC | TTC | ATG | TAT | TTT | 960 |
| E | R | S | P | P | Q | R | S | R | * | | | | | | | | | | | 330 |
| GAA | AGA | TCT | CCA | CCA | CAA | CGT | TCA | AGA | TAG | | | | | | | | | | | 990 |

AGAGACACAGCAAGCCATCAACTATGGTTAATTTTGAAAAATGGAAAAGTTGGATTGGGCTTACAGTCAGCACTCAGTT

FIG. 22A.

ATTTGCAAGTGTATTTCTTTGCTTTGTAGAGTATTTTTATTGGGTGTTAACTTTGACAGCTGAAAGTGGGCTTGCAAGA

ACACAATCTAAAAGTGTGTTTCAATTGAGTATCTCTCTAGTAGAATAGGAGTTCATCCTGAAAAGCTGTGACTCATTAA

CCCAGTAAACATATACAAAGTAAGCTTAAAACACTATAAACATGAGATAAGGGAAAATGAATCCAGAGTTCTCATATTA

ATAGGTAGTGAAACAATAAGGCTTTTTAGAGCAGACTTTGNTGGCATAAAATAACCTGGCTTCTATCCCTAACCCTTTC

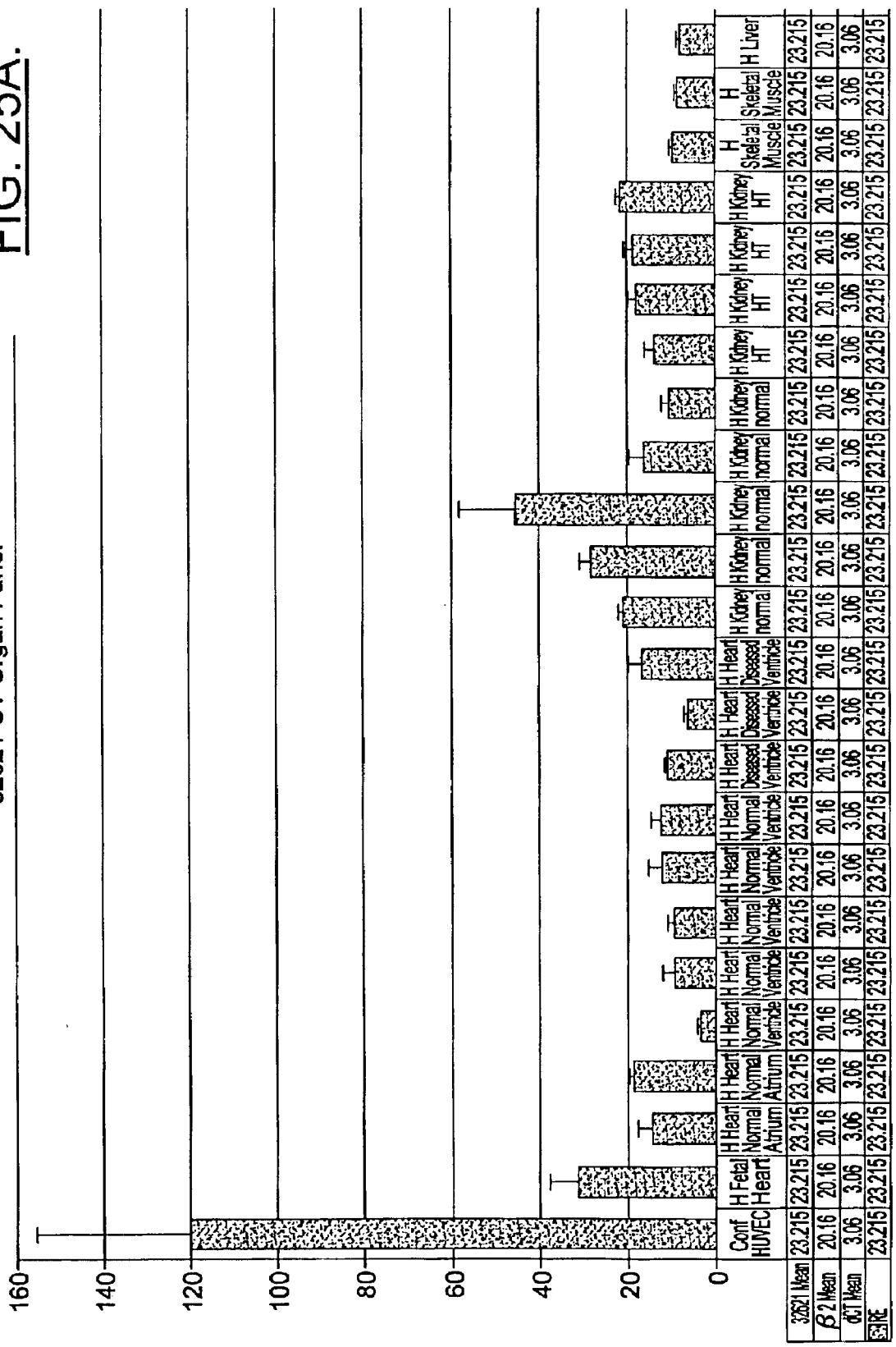

```
CGGAATTCCCGGGTCGACCCACGCGTCCGGAGCGGCGAGCCGAGACGGCTACATGGACGCCACTATCGCCCCGCACCGT
ATCCCCCCGAGATGCCCCAGTACGGGGAGGAGAACCACGTCTTCGAGTTGATGCAGAACATGCTGGAGCAACTCCTGA
                                                          M   A   M   W         4
TCCACCAGCCCGAAGATCCCATCCCCTTCATGATCCAGCACTTGCATAGAGACAACGACA ATG GCA ATG TGG     12
 L   C   K   H   L   N   S   S   L   L   L   T   L   E   N   L   I   L   N   E   F   24
CTC TGC AAA CAT CTG AAC AGC AGT CTC CTC ACC CTG GAG AAC CTG ATC TTA AAT GAG TTT     72
 S   Y   T   A   T   E   A   R   R   L   Y   L   Q   R   K   T   V   P   S   A      44
TCC TAT ACG GCC ACC GAA GCC AGA AGG CTT TAT CTG CAA AGG AAG ACA GTT CCC AGT GCG    132
 L   L   V   Q   L   I   Q   E   R   L   A   E   E   D   C   I   K   Q   G   W      64
CTG CTC GTC CAG CTG ATT CAG GAA CGC CTG GCT GAA GAG GAT TGC ATC AAG CAG GGC TGG    192
 I   L   D   G   I   P   E   T   R   E   Q   A   L   R   I   Q   T   L   G   I      84
ATT CTG GAT GGC ATC CCT GAG ACG CGT GAG CAG GCT CTG AGG ATC CAG ACC CTG GGG ATC    252
 T   P   R   H   V   I   V   L   S   A   P   D   T   V   L   I   E   R   N   L     104
ACA CCC AGA CAC GTC ATT GTG CTG AGT GCT CCA GAC ACG GTC CTG ATC GAG AGA AAC TTG    312
 G   K   R   I   D   P   Q   T   G   E   I   Y   H   T   T   F   D   W   P   P     124
GGG AAG AGA ATC GAC CCT CAA ACT GGA GAG ATT TAT CAC ACC ACC TTT GAC TGG CCA CCC    372
 E   S   E   I   Q   N   R   L   M   V   P   E   D   I   S   E   L   E   T   A     144
GAA TCT GAA ATC CAG AAC CGT CTC ATG GTG CCA GAG GAC ATC TCA GAG CTG GAG ACG GCT    432
 Q   K   L   L   E   Y   H   R   N   I   V   R   V   I   P   S   Y   P   K   I     164
CAG AAA CTG CTG GAG TAT CAT AGG AAC ATC GTC AGG GTC ATT CCC TCC TAC CCC AAA ATC    492
 L   K   V   I   S   A   D   Q   P   C   V   D   V   F   Y   Q   A   L   T   Y     184
CTC AAA GTC ATC AGT GCT GAC CAG CCA TGT GTG GAC GTC TTC TAC CAG GCT CTG ACC TAT    552
 V   Q   S   N   H   R   T   N   A   P   F   T   P   R   V   L   L   L   G   P     204
GTC CAA AGC AAC CAT CGT ACT AAT GCC CCG TTC ACC CCG AGG GTG CTG CTC CTC GGG CCT    612
 V   G   S   G   K   S   L   Q   A   A   L   L   A   Q   K   Y   R   L   V   N     224
GTG GGC AGT GGG AAA AGT CTG CAG GCC GCC CTC CTG GCC CAG AAA TAC AGG CTT GTC AAT    672
 V   C   C   G   Q   L   L   K   E   A   V   A   D   R   T   T   F   G   E   L     244
GTC TGC TGT GGG CAA CTG CTG AAA GAG GCT GTG GCA GAT AGG ACC ACG TTT GGC GAG CTC    732
 I   Q   P   F   F   E   K   E   M   A   G   C   F   S   *                         259
ATC CAG CCC TTC TTT GAA AAG GAG ATG GCA GGG TGT TTT TCC TGA                        777
ATGTGCCATTTGATTCCATCATGGAGCGGCTGACTCTGAGAAGAATTGATCCAGTCACTGGGGAAAGGTACCACCTCAT
GTACAAGCCACCTCCCACCATGGAGATCCAGGCTCGCCTCCTGCAGAACCCAAAGGATGCTGAAGAGCAGGTCAAGCTG
AAAATGGACCTGTTCTACAGGAACTCAGCTGACTTGGAGCAGTTGTATGGGTCGGCCATCACCCTCAATGGGGACCAGG
ACCCATACACAGTCTTCGAATACATCGAGTGGGATCATTAATCCCCTGCCCAAGAAAATCCCCTGATGGGTTCAGAG
CCAGGAGCGCTGCCCCAGGGAAAGAGTTAATCCCCTGCCCCCAGCCCCCCAGCCTCGGCACAGCTCCCCTAAAAAGCCA
ATAAAGCCTGCTGGATACAGAAAAAAAAAAAAAAAAAAAAAAAAAAAAAAAAAAAAAAAAAA
```

FIG. 28.

Prosite Pattern Matches for 27802

Prosite version: Release 12.2 of February 1995

>PS00001/PDOC00001/ASN_GLYCOSYLATION N-glycosylation site.

NSSL    13
Query: 10

>PS00005/PDOC00005/PKC_PHOSPHO_SITE Protein kinase C phosphorylation site.

TPR    87
Query: 85
          TPR    198
Query: 196
          SGK    209
Query: 207

>PS00006/PDOC00006/CK2_PHOSPHO_SITE Casein kinase II phosphorylation site.

TATE   30
Query: 27
          SAPD   96
Query: 93
          TTFD   121
Query: 118
          SELE   142
Query: 139
          TFGE   243
Query: 240

>PS00008/PDOC00008/MYRISTYL N-myristoylation site.

GIPETR 73
Query: 68
          GSGKSL 211
Query: 206

>PS00009/PDOC00009/AMIDATION Amidation site.

LGKR   107
Query: 104

>PS00017/PDOC00017/ATP_GTP_A ATP/GTP-binding site motif A (P-loop).

GPVGSGKS     210
Query: 203

FIG. 31.

PSORT Prediction of Protein Localization

MITDISC: discrimination of mitochondrial targeting seq
R content:        0         Hyd Moment (75):   5.85
Hyd Moment (95):  6.25      G content:         0
D/E content:      1         S/T content:       3
Score: -4.11

Gavel: prediction of cleavage sites for mitochondrial preseq
cleavage site motif not found NUCDISC: discrimination of nuclear localization signals
pat4: none
pat7: none
bipartite: none
content of basic residues: 10.5%
NLS Score: -0.47

Final Results (k = 9/23):
    52.2 %: cytoplasmic
    21.7 %: mitochondrial
    17.4 %: nuclear
     4.3 %: extracellular, including cell wall
     4.3 %: vacuolar prediction for 27802 is cyt (k=23)

| Start | End | Feature | Seq |

FIG. 32.

| ProdomId | Start | End | Description | Score |
|---|---|---|---|---|
| View Prodom 582 Boxer | 35 | 251 | p99.2 (74) KAD1(7) KAD2(4) KAD1(24)//DINASE ADDENYLATE TRANSFERASE ATP-BINDING ATP-ATP TRANSPHOSPHORYLASE ISOENZYME PROTEIN 3D-STRUCTURE MITOCHONDRION | 193 |
| Showing match Go | | | | |
| ProdomId | Start | End | Description | Score |

FIG. 33.

Protein Family / Domain Matches, HMMER version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL)
---
HMM file:                /prod/ddm/seqanal/PFAM/pfam4.4/Pfam
Sequence file:           /prod/ddm/wspace/orfanal/oa-script.25818.seq
---

Query: 27802
Scores for sequence family classification (score includes all domains):
Model            Description                         Score    E-value   N
---              ---                                 ---      ---       ---
adenylatekinase  Adenylate kinase                    50.6     4.8e-13   2

Parsed for domains:
Model            Domain  seq-f seq-t    hmm-f hmm-t    score   E-value
---              ---     ---   ---      ---   ---      ---     ---
adenylatekinase  1/2     41    120 ..   55    138 ..   37.4    2.4e-09
adenylatekinase  2/2     201   251 ..   1     51  [.   13.2    0.015

Alignments of top-scoring domains:
adenylatekinase: domain 1 of 2, from 41 to 120: score 37.4, E = 2.4e-09

```
              *->VPDEvviglvkerLeqnddcknGFLLDGFPRTvpQAeaLeemLeeag
                 VP  +  ++1+ erL+ +d  k+G++LDG P T +QA   ++     +g
    27802   41   VPSALLVQLTQERLAEEDCIKQGWILDGIPETREQALRIQT----LG  83 ikldaVieldVpdevLveRlltgRrihptSGRsYHleF<-*
                 i +  Vi 1 +pd vL+eR +g ri+p++G +YH++F
    27802   84   ITPRHVIVLSAPDTVLIERNLGKRIDPQTGEIYHTTF      120 yMDk<-*
                 + +k
    27802  248   FFEK      251
```

FIG. 34.

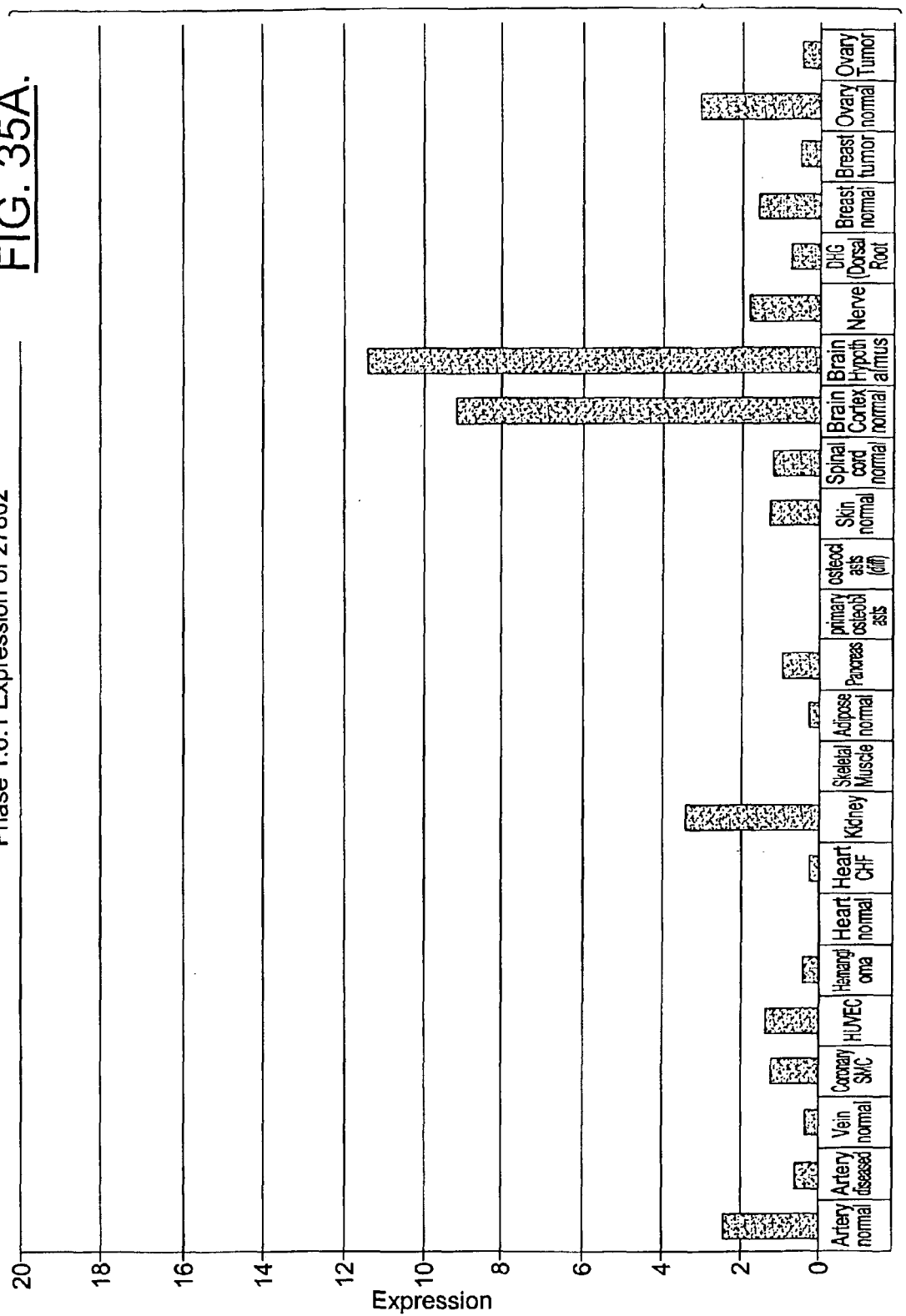

FROM FIG. 35A.

SEQUENCE LISTING

<160> NUMBER OF SEQ ID NOS: 25

<210> SEQ ID NO 1
<211> LENGTH: 1748
<212> TYPE: DNA
<213> ORGANISM: Homo sapiens
<220> FEATURE:
<221> NAME/KEY: CDS
<222> LOCATION: (79)...(1164)

<400> SEQUENCE: 1

```
ctatagggag tcgccccgcg tccgggccgg ctgagggcac ttgctcttgc tgtttctgcc         60
cctgggttaa cattcaag atg gta cat gct gaa gcc ttt tct cgt cct ttg        111
                    Met Val His Ala Glu Ala Phe Ser Arg Pro Leu
                     1               5                  10 agt cgg aat gaa gtt gtt ggt tta att ttc cgt ttg aca ata ttt ggt        159
Ser Arg Asn Glu Val Val Gly Leu Ile Phe Arg Leu Thr Ile Phe Gly
         15                  20                  25 gca gtg aca tac ttt act atc aaa tgg atg gta gat gca att gat cca        207
Ala Val Thr Tyr Phe Thr Ile Lys Trp Met Val Asp Ala Ile Asp Pro
     30                  35                  40 acc aga aag caa aaa gta gaa gct cag aaa cag gca gaa aaa cta atg        255
Thr Arg Lys Gln Lys Val Glu Ala Gln Lys Gln Ala Glu Lys Leu Met
 45                  50                  55 aag caa att gga gtg aaa aat gtg aag ctc tca gaa tat gaa atg agt        303
Lys Gln Ile Gly Val Lys Asn Val Lys Leu Ser Glu Tyr Glu Met Ser
 60                  65                  70                  75 att gct gct cat ctt gta gac cct ctt aat atg cat gtt act tgg agt        351
Ile Ala Ala His Leu Val Asp Pro Leu Asn Met His Val Thr Trp Ser
                 80                  85                  90 gat ata gca ggt tta gat gat gtc att acg gat ctg aaa gac aca gtc        399
Asp Ile Ala Gly Leu Asp Asp Val Ile Thr Asp Leu Lys Asp Thr Val
             95                 100                 105 atc tta cct atc aaa aag aaa cat ttg ttt gag aat tcc agg ctt ctg        447
Ile Leu Pro Ile Lys Lys Lys His Leu Phe Glu Asn Ser Arg Leu Leu
        110                 115                 120 cag cct cca aaa ggt gtt ctt ctc tat ggg cct cca ggc tgt ggt aaa        495
Gln Pro Pro Lys Gly Val Leu Leu Tyr Gly Pro Pro Gly Cys Gly Lys
    125                 130                 135 acg ttg att gcc aag gcc aca gcc aaa gaa gca ggc tgt cga ttt att        543
Thr Leu Ile Ala Lys Ala Thr Ala Lys Glu Ala Gly Cys Arg Phe Ile
140                 145                 150                 155 aac ctt cag cct tcg aca ctg acc gat aag tgg tat gga gaa tct cag        591
Asn Leu Gln Pro Ser Thr Leu Thr Asp Lys Trp Tyr Gly Glu Ser Gln
                160                 165                 170 aaa ttg gct gct gct gtc ttc tcc ctt gcc ata aag cta caa cca tcc        639
Lys Leu Ala Ala Ala Val Phe Ser Leu Ala Ile Lys Leu Gln Pro Ser
            175                 180                 185 atc atc ttt ata gat gaa ata gac tcc ttt cta cga aac cgt tca agt        687
Ile Ile Phe Ile Asp Glu Ile Asp Ser Phe Leu Arg Asn Arg Ser Ser
        190                 195                 200 tct gac cat gaa gct aca gcc atg atg aaa gct cag ttt atg agt ctc        735
Ser Asp His Glu Ala Thr Ala Met Met Lys Ala Gln Phe Met Ser Leu
    205                 210                 215 tgg gat gga ttg gat act gat cac agc tgc cag gtc ata gta atg gga        783
Trp Asp Gly Leu Asp Thr Asp His Ser Cys Gln Val Ile Val Met Gly
220                 225                 230                 235
```

```
gct acc aat cgt cct cag gac ctt gac tcg gct ata atg aga aga atg      831
Ala Thr Asn Arg Pro Gln Asp Leu Asp Ser Ala Ile Met Arg Arg Met
            240                 245                 250 cct aca aga ttt cat atc aac cag cct gct tta aaa cag aga gaa gca      879
Pro Thr Arg Phe His Ile Asn Gln Pro Ala Leu Lys Gln Arg Glu Ala
            255                 260                 265 atc ctg aaa ctc atc ttg aaa aat gaa aat gtg gat agg cat gta gac      927
Ile Leu Lys Leu Ile Leu Lys Asn Glu Asn Val Asp Arg His Val Asp
            270                 275                 280 ctg cta gaa gtt gcc cag gaa act gat ggg ttt tca gga agt gac cta      975
Leu Leu Glu Val Ala Gln Glu Thr Asp Gly Phe Ser Gly Ser Asp Leu
285                 290                 295 aaa gag atg tgt cga gat gct gcc ctc ctc tgt gtt aga gaa tat gtt     1023
Lys Glu Met Cys Arg Asp Ala Ala Leu Leu Cys Val Arg Glu Tyr Val
300                 305                 310                 315 aat tct aca tca gaa gaa agc cat gac gaa gat gaa att cgg cct gtt     1071
Asn Ser Thr Ser Glu Glu Ser His Asp Glu Asp Glu Ile Arg Pro Val
                320                 325                 330 caa cag cag gac ctg cat cgg gca att gaa aag atg aag aaa tca aag     1119
Gln Gln Gln Asp Leu His Arg Ala Ile Glu Lys Met Lys Lys Ser Lys
                335                 340                 345 gat gca gca ttt cag aat gtt tta aca cat gtt tgt tta gat taa         1164
Asp Ala Ala Phe Gln Asn Val Leu Thr His Val Cys Leu Asp *
            350                 355                 360 gagtaaagat catttgtaca gttcagtgat ctagtttggt gtgtcctctt atcagttagt   1224
ggaaatagaa cggaaagagt gctctttaaa caatgaggga gctcagtgtt tatggtttta   1284
tactctgaat tctaagttat tgagatatag ttgttacata ggtggtatta ctgttggtca   1344
aaaatcatga ggaggaacag ttgaatccag cctgaacgtg ggtgcttgtg tttgacctt    1404 tcagccatat attgtacagc cttatagaat ctaagctggt cttaaagtca taaatgattc   1464
attgggtcat tagtgagaaa cggggatgtg gttaggtgct ggttcctaga catgtgagta   1524
tgcgtttgtg tgtgtgcgtg tatgtatgtg tatattaaat gtatatatcc acacatttta   1584
tattgacatt ctgtagatat gttttgaatat agaaactttt tttacccccaa ctactgaatc  1644 caggagtacc aaataatata tagtaaaact aagatttaag gttgtgtcaa aaaggtacag   1704
tggattcagc catttccatt tgtcatttgt ttcaaccttt ttta                   1748

<210> SEQ ID NO 2
<211> LENGTH: 361
<212> TYPE: PRT
<213> ORGANISM: Homo sapiens

<400> SEQUENCE: 2

Met Val His Ala Glu Ala Phe Ser Arg Pro Leu Ser Arg Asn Glu Val
 1               5                  10                  15

Val Gly Leu Ile Phe Arg Leu Thr Ile Phe Gly Ala Val Thr Tyr Phe
                20                  25                  30

Thr Ile Lys Trp Met Val Asp Ala Ile Asp Pro Thr Arg Lys Gln Lys
            35                  40                  45

Val Glu Ala Gln Lys Gln Ala Glu Lys Leu Met Lys Gln Ile Gly Val
        50                  55                  60

Lys Asn Val Lys Leu Ser Glu Tyr Glu Met Ser Ile Ala Ala His Leu
65                  70                  75                  80

Val Asp Pro Leu Asn Met His Val Thr Trp Ser Asp Ile Ala Gly Leu
                85                  90                  95
```

-continued

| Asp | Asp | Val | Ile | Thr | Asp | Leu | Lys | Asp | Thr | Val | Ile | Leu | Pro | Ile | Lys |
| | | | | 100 | | | | | 105 | | | | | 110 | |

| Lys | Lys | His | Leu | Phe | Glu | Asn | Ser | Arg | Leu | Leu | Gln | Pro | Pro | Lys | Gly |
| | | | 115 | | | | | 120 | | | | | 125 | | |

| Val | Leu | Leu | Tyr | Gly | Pro | Pro | Gly | Cys | Gly | Lys | Thr | Leu | Ile | Ala | Lys |
| | | 130 | | | | | 135 | | | | | 140 | | | |

| Ala | Thr | Ala | Lys | Glu | Ala | Gly | Cys | Arg | Phe | Ile | Asn | Leu | Gln | Pro | Ser |
| 145 | | | | | 150 | | | | | 155 | | | | | 160 |

| Thr | Leu | Thr | Asp | Lys | Trp | Tyr | Gly | Glu | Ser | Gln | Lys | Leu | Ala | Ala | Ala |
| | | | | 165 | | | | | 170 | | | | | 175 | |

| Val | Phe | Ser | Leu | Ala | Ile | Lys | Leu | Gln | Pro | Ser | Ile | Ile | Phe | Ile | Asp |
| | | | 180 | | | | | 185 | | | | | 190 | | |

| Glu | Ile | Asp | Ser | Phe | Leu | Arg | Asn | Arg | Ser | Ser | Asp | His | Glu | Ala |
| | | | 195 | | | | | 200 | | | | | 205 | |

| Thr | Ala | Met | Met | Lys | Ala | Gln | Phe | Met | Ser | Leu | Trp | Asp | Gly | Leu | Asp |
| | | | 210 | | | | | 215 | | | | | 220 | | |

| Thr | Asp | His | Ser | Cys | Gln | Val | Ile | Val | Met | Gly | Ala | Thr | Asn | Arg | Pro |
| 225 | | | | | 230 | | | | | 235 | | | | | 240 |

| Gln | Asp | Leu | Asp | Ser | Ala | Ile | Met | Arg | Arg | Met | Pro | Thr | Arg | Phe | His |
| | | | | 245 | | | | | 250 | | | | | 255 | |

| Ile | Asn | Gln | Pro | Ala | Leu | Lys | Gln | Arg | Glu | Ala | Ile | Leu | Lys | Leu | Ile |
| | | | 260 | | | | | 265 | | | | | 270 | | |

| Leu | Lys | Asn | Glu | Asn | Val | Asp | Arg | His | Val | Asp | Leu | Leu | Glu | Val | Ala |
| | | | 275 | | | | | 280 | | | | | 285 | | |

| Gln | Glu | Thr | Asp | Gly | Phe | Ser | Gly | Ser | Asp | Leu | Lys | Glu | Met | Cys | Arg |
| | | 290 | | | | | 295 | | | | | 300 | | | |

| Asp | Ala | Ala | Leu | Leu | Cys | Val | Arg | Glu | Tyr | Val | Asn | Ser | Thr | Ser | Glu |
| 305 | | | | | 310 | | | | | 315 | | | | | 320 |

| Glu | Ser | His | Asp | Glu | Asp | Glu | Ile | Arg | Pro | Val | Gln | Gln | Gln | Asp | Leu |
| | | | | 325 | | | | | 330 | | | | | 335 | |

| His | Arg | Ala | Ile | Glu | Lys | Met | Lys | Lys | Ser | Lys | Asp | Ala | Ala | Phe | Gln |
| | | | 340 | | | | | 345 | | | | | 350 | | |

| Asn | Val | Leu | Thr | His | Val | Cys | Leu | Asp |
| | | | 355 | | | | | 360 |

```
<210> SEQ ID NO 3
<211> LENGTH: 1086
<212> TYPE: DNA
<213> ORGANISM: Homo sapiens

<400> SEQUENCE: 3
atggtacatg ctgaagcctt ttctcgtcct ttgagtcgga atgaagttgt tggtttaatt      60
ttccgtttga caatatttgg tgcagtgaca tactttacta tcaaatggat ggtagatgca     120
attgatccaa ccagaaagca aaaagtagaa gctcagaaac aggcagaaaa actaatgaag     180
caaattggag tgaaaaatgt gaagctctca gaatatgaaa tgagtattgc tgctcatctt     240
gtagaccctc ttaatatgca tgttacttgg agtgatatag caggtttaga tgatgtcatt     300
acggatctga agacacagt catcttacct atcaaaaaga acatttgtt tgagaattcc      360 aggcttctgc agcctccaaa aggtgttctt ctctatgggc ctccaggctg tggtaaaacg     420
ttgattgcca aggccacagc caaagaagca ggctgtcgat ttattaacct tcagccttcg     480
acactgaccg ataagtggta tggagaatct cagaaattgg ctgctgctgt cttctcccctt    540 gccataaagc tacaaccatc catcatcttt atagatgaaa tagactcctt tctacgaaac     600
```

-continued

```
cgttcaagtt ctgaccatga agctacagcc atgatgaaag ctcagtttat gagtctctgg    660
gatggattgg atactgatca cagctgccag gtcatagtaa tgggagctac caatcgtcct    720
caggaccttg actcggctat aatgagaaga atgcctacaa gatttcatat caaccagcct    780
gctttaaaac agagagaagc aatcctgaaa ctcatcttga aaaatgaaaa tgtggatagg    840
catgtagacc tgctagaagt tgcccaggaa actgatgggt tttcaggaag tgacctaaaa    900
gagatgtgtc gagatgctgc cctcctctgt gttagagaat atgttaattc tacatcagaa    960
gaaagccatg acgaagatga aattcggcct gttcaacagc aggacctgca tcgggcaatt   1020
gaaaagatga agaaatcaaa ggatgcagca tttcagaatg ttttaacaca tgtttgttta   1080
gattaa                                                              1086
```

<210> SEQ ID NO 4
<211> LENGTH: 220
<212> TYPE: PRT
<213> ORGANISM: Artificial Sequence
<220> FEATURE:
<223> OTHER INFORMATION: Consensus sequence for the AAA domain

<400> SEQUENCE: 4

```
Gly Val Leu Leu Tyr Gly Pro Pro Gly Thr Gly Lys Thr Leu Leu Ala
 1               5                  10                  15

Lys Ala Val Ala Asn Glu Leu Gly Ser Leu Arg Lys Ala Pro Phe Ile
            20                  25                  30

Ser Ile Ser Gly Tyr Ser Glu Leu Val Ser Lys Tyr Val Gly Glu Ser
        35                  40                  45

Glu Lys Arg Val Arg Ala Leu Phe Glu Leu Ala Arg Glu Leu Arg Lys
    50                  55                  60

Arg Ala Ala Pro Cys Pro Ile Ile Phe Ile Asp Glu Ile Asp Ala Ile
65                  70                  75                  80

Ala Pro Lys Arg Gly Gly Glu Val Ser Arg Arg Val Val Asn Gln Leu
                85                  90                  95

Leu Thr Glu Met Asp Leu Glu Arg Ala Gly Phe Ser Lys Asn Ser Ser
            100                 105                 110

Arg Gly Glu Asp Thr Ile Asp Leu Ser Asn Val Leu Ile Ala Ala
        115                 120                 125

Thr Asn Arg Pro Asp Thr Leu Asp Pro Ala Leu Leu Arg Pro Gly Arg
    130                 135                 140

Phe Asp Arg Glu Ile Glu Ile Pro Leu Pro Pro Asp Glu Gly Arg
145                 150                 155                 160

Leu Asp Ile Leu Lys Ile His Leu Lys Lys Met Pro Leu Ser Ser Ser
                165                 170                 175

Leu Lys Gln Ser Glu Leu Ala Glu Asp Val Asp Leu Asp Glu Leu Ala
            180                 185                 190

Glu Glu Ile Ala Thr Arg Thr Glu Gly Phe Ser Gly Ala Asp Leu Lys
        195                 200                 205

Ala Leu Cys Arg Glu Ala Ala Leu Arg Ala Ile Arg
    210                 215                 220
```

<210> SEQ ID NO 5
<211> LENGTH: 1852
<212> TYPE: DNA
<213> ORGANISM: Homo sapiens
<220> FEATURE:
<221> NAME/KEY: CDS
<222> LOCATION: (14)...(1477)

<400> SEQUENCE: 5

| | |
|---|---|
| cacgcgtccg gcc atg cgg agg ggc gag cgc agg gac gcc gga ggt ccg<br>           Met Arg Arg Gly Glu Arg Arg Asp Ala Gly Gly Pro<br>            1                  5                       10 | 49 |
| cgg ccc gag tcc ccg gtg ccc gcg ggc agg gcc tcg ctg gag gag ccg<br>Arg Pro Glu Ser Pro Val Pro Ala Gly Arg Ala Ser Leu Glu Glu Pro<br>        15                    20                   25 | 97 |
| cct gac ggg ccg tct gcc ggc caa gcc acc ggg ccg ggc gag ggc cgc<br>Pro Asp Gly Pro Ser Ala Gly Gln Ala Thr Gly Pro Gly Glu Gly Arg<br>      30                    35                  40 | 145 |
| cgc agc acc gag tcc gag gtc tac gac gac ggc acc aac acc ttc ttc<br>Arg Ser Thr Glu Ser Glu Val Tyr Asp Asp Gly Thr Asn Thr Phe Phe<br>45                   50                   55                   60 | 193 |
| tgg cga gcc cac acc tta acc gtg ctc ttc atc ctc acc tgt acg ctt<br>Trp Arg Ala His Thr Leu Thr Val Leu Phe Ile Leu Thr Cys Thr Leu<br>                  65                    70                   75 | 241 |
| ggc tat gtg acg ctg ctg gag gaa aca cct cag gac acg gcc tac aac<br>Gly Tyr Val Thr Leu Leu Glu Glu Thr Pro Gln Asp Thr Ala Tyr Asn<br>              80                    85                   90 | 289 |
| acc aag aga ggt att gtg gcc agt att ttg gtt ttc tta tgt ttt gga<br>Thr Lys Arg Gly Ile Val Ala Ser Ile Leu Val Phe Leu Cys Phe Gly<br>            95                   100                 105 | 337 |
| gtc aca caa gct aaa gac ggg cca ttt tcc aga cct cat cca gct tac<br>Val Thr Gln Ala Lys Asp Gly Pro Phe Ser Arg Pro His Pro Ala Tyr<br>110                    115                 120 | 385 |
| tgg agg ttt tgg ctc tgc gtg agt gtg gtc tac gag ctg ttt ctc atc<br>Trp Arg Phe Trp Leu Cys Val Ser Val Val Tyr Glu Leu Phe Leu Ile<br>125                  130                 135                140 | 433 |
| ttt ata ctc ttc cag act gtc cag gac ggc cgg cag ttt cta aag tat<br>Phe Ile Leu Phe Gln Thr Val Gln Asp Gly Arg Gln Phe Leu Lys Tyr<br>                  145                 150                155 | 481 |
| gtt gac ccc aag ctg gga gtc cca ctg cca gag aga gac tac ggg gga<br>Val Asp Pro Lys Leu Gly Val Pro Leu Pro Glu Arg Asp Tyr Gly Gly<br>              160                 165                170 | 529 |
| aac tgc ctc atc tac gac cca gac aat gag act gac ccc ttt cac aac<br>Asn Cys Leu Ile Tyr Asp Pro Asp Asn Glu Thr Asp Pro Phe His Asn<br>            175                 180                185 | 577 |
| atc tgg gac aag ttg gat ggc ttt gtt ccc gcg cac ttt ctt ggc tgg<br>Ile Trp Asp Lys Leu Asp Gly Phe Val Pro Ala His Phe Leu Gly Trp<br>190                    195                 200 | 625 |
| tac ctg aag acc ctg atg atc cga gac tgg tgg atg tgc atg atc atc<br>Tyr Leu Lys Thr Leu Met Ile Arg Asp Trp Trp Met Cys Met Ile Ile<br>205                    210                 215                220 | 673 |
| agc gtg atg ttc gag ttc ctg gag tac agc ctg gag cac cag ctg ccc<br>Ser Val Met Phe Glu Phe Leu Glu Tyr Ser Leu Glu His Gln Leu Pro<br>                  225                 230                235 | 721 |
| aac ttc agc gag tgc tgg tgg gat cac tgg atc atg gac gtg ctc gtc<br>Asn Phe Ser Glu Cys Trp Trp Asp His Trp Ile Met Asp Val Leu Val<br>            240                 245                250 | 769 |
| tgc aac ggg ctg ggc atc tac tgc ggc atg aag acc ctt gag tgg ctg<br>Cys Asn Gly Leu Gly Ile Tyr Cys Gly Met Lys Thr Leu Glu Trp Leu<br>                255                 260                265 | 817 |
| tcc ctg aag acg tac aag tgg cag ggc ctc tgg aac att ccg acc tac<br>Ser Leu Lys Thr Tyr Lys Trp Gln Gly Leu Trp Asn Ile Pro Thr Tyr<br>270                    275                 280 | 865 |
| aag ggc aag atg aag agg atc gcc ttc cag ttc acg ccg tac agc tgg<br>Lys Gly Lys Met Lys Arg Ile Ala Phe Gln Phe Thr Pro Tyr Ser Trp<br>285                    290                 295                300 | 913 |

```
gtt cgc ttc gag tgg aag ccg gcc tcc agc ctg cgt cgc tgg ctg gcc         961
Val Arg Phe Glu Trp Lys Pro Ala Ser Ser Leu Arg Arg Trp Leu Ala
            305                 310                 315 gtg tgc ggc atc atc ctg gtg ttc ctg ttg gca gaa ctg aac acg ttc        1009
Val Cys Gly Ile Ile Leu Val Phe Leu Leu Ala Glu Leu Asn Thr Phe
320                 325                 330 tac ctg aag ttt gtg ctg tgg atg ccc ccg gag cac tac ctg gtc ctc        1057
Tyr Leu Lys Phe Val Leu Trp Met Pro Pro Glu His Tyr Leu Val Leu
            335                 340                 345 ctg cgg ctc gtc ttc ttc gtg aac gtg ggt ggc gtg gcc atg cgt gag        1105
Leu Arg Leu Val Phe Phe Val Asn Val Gly Gly Val Ala Met Arg Glu
        350                 355                 360 atc tac gac ttc atg gat gac ccg aag ccc cac aag aag ctg ggc ccg        1153
Ile Tyr Asp Phe Met Asp Asp Pro Lys Pro His Lys Lys Leu Gly Pro
365                 370                 375                 380 cag gcc tgg ctg gtg gcg gcc atc acg gcc acg gag ctg ctc atc gtg        1201
Gln Ala Trp Leu Val Ala Ala Ile Thr Ala Thr Glu Leu Leu Ile Val
            385                 390                 395 gtg aag tac gac ccc cac acg ctc acc ctg tcc ctg ccc ttc tac atc        1249
Val Lys Tyr Asp Pro His Thr Leu Thr Leu Ser Leu Pro Phe Tyr Ile
        400                 405                 410 tcc cag tgc tgg acc ctc ggc tcc gtc ctg gcg ctc acc tgg acc gtc        1297
Ser Gln Cys Trp Thr Leu Gly Ser Val Leu Ala Leu Thr Trp Thr Val
    415                 420                 425 tgg cgc ttc ttc ctg cgg gac atc aca ttg agg tac aag gag acc cgg        1345
Trp Arg Phe Phe Leu Arg Asp Ile Thr Leu Arg Tyr Lys Glu Thr Arg
    430                 435                 440 tgg cag aag tgg cag aac aag gat gac cag ggc agc acc gtc ggc aac        1393
Trp Gln Lys Trp Gln Asn Lys Asp Asp Gln Gly Ser Thr Val Gly Asn
445                 450                 455                 460 ggg gac cag cac cca ctg ggg ctg gac gaa gac ctg ctg ggg cct ggg        1441
Gly Asp Gln His Pro Leu Gly Leu Asp Glu Asp Leu Leu Gly Pro Gly
                465                 470                 475 gtg gcc gag ggc gag gga gca cca act cca aac tga cctgggccgt            1487
Val Ala Glu Gly Glu Gly Ala Pro Thr Pro Asn *
            480                 485 ggctgcctcg tgagcctccc agagcccagg cctccgtggc ctcctcctgt gtgagtccca      1547
ccaggagcca cgtgcccggc cttgccctca aggttttttg cttttctcct gtgcacctgg      1607
cgaggctgaa ggcgaggggt ggaggaggcc ccagcacagc ctcatctcca tgtgtacacg      1667
tgtgtacgtg tgtatgcgtg tgtgtacgcc gtgtgtacgc gcgtgtgtac acatgcgtgg      1727
ccgctgtggt gtgcacstgt gctctgggct ccgaggctts ttcmagarct gggarctggc      1787
tggcgtggca aggcatgct  ctggggcagt gtgttcctya agaaccaggg gtccttccty      1847
cctttt                                                                  1852

<210> SEQ ID NO 6
<211> LENGTH: 487
<212> TYPE: PRT
<213> ORGANISM: Homo sapiens

<400> SEQUENCE: 6

Met Arg Arg Gly Glu Arg Arg Asp Ala Gly Gly Pro Arg Pro Glu Ser
  1               5                  10                  15

Pro Val Pro Ala Gly Arg Ala Ser Leu Glu Glu Pro Asp Gly Pro
             20                  25                  30

Ser Ala Gly Gln Ala Thr Gly Pro Gly Glu Gly Arg Arg Ser Thr Glu
         35                  40                  45
```

```
Ser Glu Val Tyr Asp Asp Gly Thr Asn Thr Phe Phe Trp Arg Ala His
     50                  55                  60

Thr Leu Thr Val Leu Phe Ile Leu Thr Cys Thr Leu Gly Tyr Val Thr
 65              70                  75                      80

Leu Leu Glu Glu Thr Pro Gln Asp Thr Ala Tyr Asn Thr Lys Arg Gly
                 85                  90                  95

Ile Val Ala Ser Ile Leu Val Phe Leu Cys Phe Gly Val Thr Gln Ala
            100                 105                 110

Lys Asp Gly Pro Phe Ser Arg Pro His Pro Ala Tyr Trp Arg Phe Trp
        115                 120                 125

Leu Cys Val Ser Val Val Tyr Glu Leu Phe Leu Ile Phe Ile Leu Phe
    130                 135                 140

Gln Thr Val Gln Asp Gly Arg Gln Phe Leu Lys Tyr Val Asp Pro Lys
145                 150                 155                 160

Leu Gly Val Pro Leu Pro Glu Arg Asp Tyr Gly Gly Asn Cys Leu Ile
                165                 170                 175

Tyr Asp Pro Asp Asn Glu Thr Asp Pro Phe His Asn Ile Trp Asp Lys
            180                 185                 190

Leu Asp Gly Phe Val Pro Ala His Phe Leu Gly Trp Tyr Leu Lys Thr
        195                 200                 205

Leu Met Ile Arg Asp Trp Trp Met Cys Met Ile Ile Ser Val Met Phe
    210                 215                 220

Glu Phe Leu Glu Tyr Ser Leu Glu His Gln Leu Pro Asn Phe Ser Glu
225                 230                 235                 240

Cys Trp Trp Asp His Trp Ile Met Asp Val Leu Val Cys Asn Gly Leu
                245                 250                 255

Gly Ile Tyr Cys Gly Met Lys Thr Leu Glu Trp Leu Ser Leu Lys Thr
            260                 265                 270

Tyr Lys Trp Gln Gly Leu Trp Asn Ile Pro Thr Tyr Lys Gly Lys Met
        275                 280                 285

Lys Arg Ile Ala Phe Gln Phe Thr Pro Tyr Ser Trp Val Arg Phe Glu
    290                 295                 300

Trp Lys Pro Ala Ser Ser Leu Arg Arg Trp Leu Ala Val Cys Gly Ile
305                 310                 315                 320

Ile Leu Val Phe Leu Leu Ala Glu Leu Asn Thr Phe Tyr Leu Lys Phe
                325                 330                 335

Val Leu Trp Met Pro Pro Glu His Tyr Leu Val Leu Arg Leu Val
            340                 345                 350

Phe Phe Val Asn Val Gly Gly Val Ala Met Arg Glu Ile Tyr Asp Phe
        355                 360                 365

Met Asp Asp Pro Lys Pro His Lys Lys Leu Gly Pro Gln Ala Trp Leu
    370                 375                 380

Val Ala Ala Ile Thr Ala Thr Glu Leu Leu Ile Val Val Lys Tyr Asp
385                 390                 395                 400

Pro His Thr Leu Thr Leu Ser Leu Pro Phe Tyr Ile Ser Gln Cys Trp
                405                 410                 415

Thr Leu Gly Ser Val Leu Ala Leu Thr Trp Thr Val Trp Arg Phe Phe
            420                 425                 430

Leu Arg Asp Ile Thr Leu Arg Tyr Lys Glu Thr Arg Trp Gln Lys Trp
        435                 440                 445

Gln Asn Lys Asp Asp Gln Gly Ser Thr Val Gly Asn Gly Asp Gln His
    450                 455                 460
```

```
Pro Leu Gly Leu Asp Glu Asp Leu Leu Gly Pro Gly Val Ala Glu Gly
465                 470                 475                 480

Glu Gly Ala Pro Thr Pro Asn
                485

<210> SEQ ID NO 7
<211> LENGTH: 1464
<212> TYPE: DNA
<213> ORGANISM: Homo sapiens

<400> SEQUENCE: 7
atgcggaggg gcgagcgcag ggacgccgga ggtccgcggc ccgagtcccc ggtgcccgcg      60
ggcagggcct cgctggagga gccgcctgac gggccgtctg ccggccaagc caccgggccg     120
ggcgagggcc gccgcagcac cgagtccgag gtctacgacg acggcaccaa caccttcttc     180
tggcgagccc acaccttaac cgtgctcttc atcctcacct gtacgcttgg ctatgtgacg     240
ctgctggagg aaacacctca ggacacggcc tacaacacca gagaggtat tgtggccagt     300 attttggttt tcttatgttt tggagtcaca caagctaaag acgggccatt ttccagacct     360
catccagctt actggaggtt ttggctctgc gtgagtgtgg tctacgagct gtttctcatc     420
tttatactct tccagactgt ccaggacggc cggcagtttc taaagtatgt tgaccccaag     480
ctgggagtcc cactgccaga gagagactac ggggaaact gcctcatcta cgacccagac     540
aatgagactg acccctttca acatctggg acaagttgg atggctttgt tcccgcgcac     600
tttcttggct ggtacctgaa gaccctgatg atccgagact ggtggatgtg catgatcatc     660
agcgtgatgt tcgagttcct ggagtacagc ctggagcacc agctgcccaa cttcagcgag     720
tgctggtggg atcactggat catggacgtg ctcgtctgca acgggctggg catctactgc     780
ggcatgaaga cccttgagtg ctgtccctg aagacgtaca agtggcaggg cctctggaac     840
attccgacct acaagggcaa gatgaagagg atcgccttcc agttcacgcc gtacagctgg     900
gttcgcttcg agtggaagcc ggcctccagc ctgcgtcgct ggctggccgt gtgcggcatc     960
atcctggtgt cctgttggc agaactgaac acgttctacc tgaagtttgt gctgtggatg    1020
cccccggagc actacctggt cctcctgcgg ctcgtcttct tcgtgaacgt gggtggcgtg    1080
gccatgcgtg agatctacga cttcatggat gacccgaagc cccacaagaa gctgggcccg    1140
caggcctggc tggtggcggc catcacggcc acggagctgc tcatcgtggt gaagtacgac    1200
ccccacacgc tcaccctgtc cctgcccttc tacatctccc agtgctggac cctcggctcc    1260
gtcctggcgc tcacctggac cgtctggcgc ttcttcctgc gggacatcac attgaggtac    1320
aaggagaccc ggtggcagaa gtggcagaac aaggatgacc aggcagcac cgtcggcaac    1380 ggggaccagc acccactggg gctggacgaa gacctgctgg ggcctggggt ggccgagggc    1440
gagggagcac caactccaaa ctga                                          1464

<210> SEQ ID NO 8
<211> LENGTH: 474
<212> TYPE: PRT
<213> ORGANISM: Cricetulus griseus

<400> SEQUENCE: 8

Met Arg Arg Ala Glu Arg Arg Val Ala Gly Gly Ser Gly Ser Gly Ser
1               5                   10                  15

Pro Leu Leu Glu Gly Arg Arg Ser Thr Glu Ser Glu Val Tyr Asp Asp
                20                  25                  30
```

-continued

```
Gly Thr Asn Thr Phe Phe Trp Arg Ala His Thr Leu Thr Val Leu Phe
         35                  40                  45

Ile Leu Thr Cys Ser Leu Gly Tyr Val Thr Leu Leu Glu Glu Thr Pro
 50                  55                  60

Gln Asp Thr Ala Tyr Asn Thr Lys Arg Gly Ile Val Ala Ser Ile Leu
 65                  70                  75                  80

Val Phe Leu Cys Phe Gly Val Thr Gln Ala Lys Asp Gly Pro Phe Ser
                 85                  90                  95

Arg Pro His Pro Ala Tyr Trp Arg Phe Trp Leu Cys Val Ser Val Val
                100                 105                 110

Tyr Glu Leu Phe Leu Ile Phe Ile Leu Phe Gln Thr Val Gln Asp Gly
                115                 120                 125

Arg Gln Phe Leu Lys Tyr Val Asp Pro Arg Leu Gly Val Pro Leu Pro
        130                 135                 140

Glu Arg Asp Tyr Gly Gly Asn Cys Leu Ile Tyr Asp Ala Asp Asn Lys
145                 150                 155                 160

Thr Asp Pro Phe His Asn Ile Trp Asp Lys Leu Asp Gly Phe Val Pro
                165                 170                 175

Ala His Phe Ile Gly Trp Tyr Leu Lys Thr Leu Met Ile Arg Asp Trp
                180                 185                 190

Trp Met Cys Met Ile Ile Ser Val Met Phe Glu Phe Leu Glu Tyr Ser
        195                 200                 205

Leu Glu His Gln Leu Pro Asn Phe Ser Glu Cys Trp Trp Asp His Trp
        210                 215                 220

Ile Met Asp Val Leu Ile Cys Asn Gly Leu Gly Ile Tyr Cys Gly Met
225                 230                 235                 240

Lys Thr Leu Glu Trp Leu Ser Leu Lys Thr Tyr Lys Trp Gln Gly Leu
                245                 250                 255

Trp Asn Ile Pro Thr Tyr Lys Gly Lys Met Lys Arg Ile Ala Phe Gln
                260                 265                 270

Phe Thr Pro Tyr Ser Trp Val Arg Phe Glu Trp Lys Pro Ala Ser Ser
        275                 280                 285

Leu His Arg Trp Leu Ala Val Cys Gly Ile Ile Leu Val Phe Leu Leu
        290                 295                 300

Ala Glu Leu Asn Thr Phe Tyr Leu Lys Phe Val Leu Trp Met Pro Pro
305                 310                 315                 320

Glu His Tyr Leu Val Leu Leu Arg Leu Val Phe Phe Val Asn Val Gly
                325                 330                 335

Gly Val Ala Met Arg Glu Ile Tyr Asp Phe Met Asp Glu Leu Lys Pro
                340                 345                 350

His Arg Lys Leu Gly Gln Gln Ala Trp Leu Val Ala Ala Ile Thr Val
        355                 360                 365

Thr Glu Leu Leu Ile Val Val Lys Tyr Asp Pro His Thr Leu Thr Leu
        370                 375                 380

Ser Leu Pro Phe Tyr Ile Ser Gln Cys Trp Thr Leu Gly Ser Ile Leu
385                 390                 395                 400

Val Leu Thr Trp Thr Val Trp Arg Phe Phe Leu Arg Asp Ile Thr Met
                405                 410                 415

Arg Tyr Lys Glu Thr Arg Arg Gln Lys Gln Ser His Gln Gly Arg
                420                 425                 430

Ala Ile Asn Asn Gly Asp Gly His Pro Gly Pro Asp Asp Leu Leu
        435                 440                 445
```

-continued

Gly Thr Gly Thr Ala Glu Glu Gly Ser Thr Asn Asp Ser Val Pro
        450                 455                 460

Ala Glu Lys Glu Gly Ala Ser Ala Ala Ser
465                 470

<210> SEQ ID NO 9
<211> LENGTH: 473
<212> TYPE: PRT
<213> ORGANISM: Mus musculus

<400> SEQUENCE: 9

Met Arg Arg Ala Glu Arg Val Ala Gly Ser Gly Ser Glu Ser
1               5                   10                  15

Pro Leu Lys Gly Arg Arg Ser Thr Glu Ser Glu Val Tyr Asp Asp
            20                  25                  30

Gly Thr Asn Thr Phe Phe Trp Arg Ala His Thr Leu Thr Val Leu Phe
        35                  40                  45

Ile Leu Thr Cys Ala Leu Gly Tyr Val Thr Leu Leu Glu Glu Thr Pro
50                  55                  60

Gln Asp Thr Ala Tyr Asn Thr Lys Arg Gly Ile Val Ala Ser Ile Leu
65                  70                  75                  80

Val Phe Leu Cys Phe Gly Val Thr Gln Ala Lys Asp Gly Pro Phe Ser
                85                  90                  95

Arg Pro His Pro Ala Tyr Trp Arg Phe Trp Leu Cys Val Ser Val Val
            100                 105                 110

Tyr Glu Leu Phe Leu Ile Phe Ile Leu Phe Gln Thr Val Gln Asp Gly
        115                 120                 125

Arg Gln Phe Leu Lys Tyr Val Asp Pro Arg Leu Gly Val Pro Leu Pro
    130                 135                 140

Glu Arg Asp Tyr Gly Gly Asn Cys Leu Ile Tyr Asp Ala Asp Asn Lys
145                 150                 155                 160

Thr Asp Pro Phe His Asn Ile Trp Asp Lys Leu Asp Gly Phe Val Pro
                165                 170                 175

Ala His Phe Ile Gly Trp Tyr Leu Lys Thr Leu Met Ile Arg Asp Trp
            180                 185                 190

Trp Met Cys Met Ile Ile Ser Val Met Phe Glu Phe Leu Glu Tyr Ser
        195                 200                 205

Leu Glu His Gln Leu Pro Asn Phe Ser Glu Cys Trp Trp Asp His Trp
    210                 215                 220

Ile Met Asp Val Leu Val Cys Asn Gly Leu Gly Ile Tyr Cys Gly Met
225                 230                 235                 240

Lys Thr Leu Glu Trp Leu Ser Leu Lys Thr Tyr Lys Trp Gln Gly Leu
                245                 250                 255

Trp Asn Ile Pro Thr Tyr Lys Gly Lys Met Lys Arg Ile Ala Phe Gln
            260                 265                 270

Phe Thr Pro Tyr Ser Trp Val Arg Phe Glu Trp Lys Pro Ala Ser Ser
        275                 280                 285

Leu His Arg Trp Leu Ala Val Cys Gly Ile Ile Leu Val Phe Leu Leu
    290                 295                 300

Ala Glu Leu Asn Thr Phe Tyr Leu Lys Phe Val Leu Trp Met Pro Pro
305                 310                 315                 320

Glu His Tyr Leu Val Leu Leu Arg Leu Val Phe Phe Val Asn Val Gly
                325                 330                 335

Gly Val Ala Met Arg Glu Ile Tyr Asp Phe Met Asp Glu Leu Lys Pro
            340                 345                 350

```
His Arg Lys Leu Gly Gln Gln Ala Trp Leu Val Ala Ala Ile Thr Val
            355                 360                 365

Thr Glu Leu Leu Ile Val Val Lys Tyr Asp Pro His Thr Leu Thr Leu
        370                 375                 380

Ser Leu Pro Phe Tyr Ile Ser Gln Cys Trp Thr Leu Gly Ser Ile Leu
385                 390                 395                 400

Val Leu Thr Trp Thr Val Trp Arg Phe Leu Arg Asp Ile Thr Met
                405                 410                 415

Arg Tyr Lys Glu Thr Arg Arg Gln Lys Gln Gln Ser His Gln Ala Arg
            420                 425                 430

Ala Val Asn Asn Arg Asp Gly His Pro Gly Pro Asp Asp Leu Leu
            435                 440                 445

Gly Thr Gly Thr Ala Glu Glu Gly Thr Thr Asn Asp Gly Val Thr
    450                 455                 460

Ala Glu Glu Gly Ala Ser Ala Ala Ser
465                 470

<210> SEQ ID NO 10
<211> LENGTH: 1284
<212> TYPE: DNA
<213> ORGANISM: Homo sapiens
<220> FEATURE:
<221> NAME/KEY: CDS
<222> LOCATION: (169)...(828)

<400> SEQUENCE: 10
cacgcgtccg agatgaccta agtgtgactg cagcaggcag ctctggaaaa tgaagccaga     60
gcagtgagcc agcccctcct ccgaccaagg aggaaggaaa gagcagcccc agcacaggag    120
agaaccaccc agcccagaag ttccagggaa ggaactctcc ggtccacc atg gag tac     177
                                                    Met Glu Tyr
                                                      1 ctc tca gct ctg aac ccc agt gac tta ctc agg tca gta tct aat ata     225
Leu Ser Ala Leu Asn Pro Ser Asp Leu Leu Arg Ser Val Ser Asn Ile
    5                  10                   15 agc tcg gag ttt gga cgg agg gtc tgg acc tca gct cca cca ccc cag     273
Ser Ser Glu Phe Gly Arg Arg Val Trp Thr Ser Ala Pro Pro Pro Gln
 20                  25                   30                  35 cga cct ttc cgt gtc tgt gat cac aag cgg acc atc cgg aaa ggc ctg     321
Arg Pro Phe Arg Val Cys Asp His Lys Arg Thr Ile Arg Lys Gly Leu
                 40                  45                  50 aca gct gcc acc cgc cag gag ctg cta gcc aaa gca ttg gag acc cta     369
Thr Ala Ala Thr Arg Gln Glu Leu Leu Ala Lys Ala Leu Glu Thr Leu
             55                  60                  65 ctg ctg aat gga gtg cta acc ctg gtg cta gag gag gat gga act gca     417
Leu Leu Asn Gly Val Leu Thr Leu Val Leu Glu Glu Asp Gly Thr Ala
         70                  75                  80 gtg gac agt gag gac ttc ttc cag ctg ctg gag gat gac acg tgc ctg     465
Val Asp Ser Glu Asp Phe Phe Gln Leu Leu Glu Asp Asp Thr Cys Leu
     85                  90                  95 atg gtg ttg cag tct ggt cag agc tgg agc cct aca agg agt gga gtg     513
Met Val Leu Gln Ser Gly Gln Ser Trp Ser Pro Thr Arg Ser Gly Val
100                 105                 110                 115 ctg tca tat ggc ctg gga cgg gag agg ccc aag cac agc aag gac atc     561
Leu Ser Tyr Gly Leu Gly Arg Glu Arg Pro Lys His Ser Lys Asp Ile
                120                 125                 130 gcc cga ttc acc ttt gac gtg tac aag caa aac cct cga gac ctc ttt     609
Ala Arg Phe Thr Phe Asp Val Tyr Lys Gln Asn Pro Arg Asp Leu Phe
            135                 140                 145
```

-continued

| | | | | | | | | | | | | | | | | |
|---|---|---|---|---|---|---|---|---|---|---|---|---|---|---|---|---|
| ggc | agc | ctg | aat | gtc | aaa | gcc | aca | ttc | tac | ggg | ctc | tac | tct | atg | agt | 657 |
| Gly | Ser | Leu | Asn | Val | Lys | Ala | Thr | Phe | Tyr | Gly | Leu | Tyr | Ser | Met | Ser | |
| | | 150 | | | | | 155 | | | | | 160 | | | | |
| tgt | gac | ttt | caa | gga | ctt | ggc | cca | aag | aaa | gta | ctc | agg | gag | ctc | ctt | 705 |
| Cys | Asp | Phe | Gln | Gly | Leu | Gly | Pro | Lys | Lys | Val | Leu | Arg | Glu | Leu | Leu | |
| 165 | | | | | 170 | | | | | 175 | | | | | | |
| cgt | tgg | acc | tcc | aca | ctg | ctg | caa | ggc | ctg | ggc | cat | atg | ttg | ctg | gga | 753 |
| Arg | Trp | Thr | Ser | Thr | Leu | Leu | Gln | Gly | Leu | Gly | His | Met | Leu | Leu | Gly | |
| 180 | | | | | 185 | | | | | 190 | | | | | 195 | |
| att | tcc | tcc | acc | ctt | cgt | cat | gca | gtg | gag | ggg | gct | gag | cag | tgg | cag | 801 |
| Ile | Ser | Ser | Thr | Leu | Arg | His | Ala | Val | Glu | Gly | Ala | Glu | Gln | Trp | Gln | |
| | | | | 200 | | | | | 205 | | | | | 210 | | |
| cag | aag | ggc | cgc | ctc | cat | tcc | tac | taa | ggggctctga | | gcttctgccc | | | | | 848 |
| Gln | Lys | Gly | Arg | Leu | His | Ser | Tyr | * | | | | | | | | |
| | | | 215 | | | | | | | | | | | | | | ccagaatcat tccaaccgac ccactgcaaa gactatgaca gcatcaaatt tcaggacctg   908 cagacagtac aggctagata acccacccaa tttccccact gtcctctgat cccctcgtga   968 cagaaccttt cagcataacg cctcacatcc caagtctata cccttacctg aagaatgctg  1028 ttctttccta gccacctttc tagcctccca cttgccctga aaggccaaga tcaagatgtc  1088 ccccaggcat cttgatccca gcctgactgc tgctacatct aatcccctac caatgcctcc  1148 tgtccctaaa ctccccagca tactgatgac agccctctct gactttacct tgagatctgt  1208 cttcatacccc ttcccctcaa actaacaaaa acatttccaa taaaaatatc aaatatttaa  1268 aaaaaaaaaa aaaagg  1284

<210> SEQ ID NO 11
<211> LENGTH: 219
<212> TYPE: PRT
<213> ORGANISM: Homo sapiens

<400> SEQUENCE: 11

Met Glu Tyr Leu Ser Ala Leu Asn Pro Ser Asp Leu Leu Arg Ser Val
 1               5                  10                  15

Ser Asn Ile Ser Ser Glu Phe Gly Arg Arg Val Trp Thr Ser Ala Pro
             20                  25                  30

Pro Pro Gln Arg Pro Phe Arg Val Cys Asp His Lys Arg Thr Ile Arg
         35                  40                  45

Lys Gly Leu Thr Ala Ala Thr Arg Gln Glu Leu Leu Ala Lys Ala Leu
     50                  55                  60

Glu Thr Leu Leu Leu Asn Gly Val Leu Thr Leu Val Leu Glu Glu Asp
 65                  70                  75                  80

Gly Thr Ala Val Asp Ser Glu Asp Phe Phe Gln Leu Leu Glu Asp Asp
                 85                  90                  95

Thr Cys Leu Met Val Leu Gln Ser Gly Gln Ser Trp Ser Pro Thr Arg
            100                 105                 110

Ser Gly Val Leu Ser Tyr Gly Leu Gly Arg Glu Arg Pro Lys His Ser
        115                 120                 125

Lys Asp Ile Ala Arg Phe Thr Phe Asp Val Tyr Lys Gln Asn Pro Arg
    130                 135                 140

Asp Leu Phe Gly Ser Leu Asn Val Lys Ala Thr Phe Tyr Gly Leu Tyr
145                 150                 155                 160

Ser Met Ser Cys Asp Phe Gln Gly Leu Gly Pro Lys Lys Val Leu Arg
                165                 170                 175

```
Glu Leu Leu Arg Trp Thr Ser Thr Leu Leu Gln Gly Leu Gly His Met
                180                 185                 190

Leu Leu Gly Ile Ser Ser Thr Leu Arg His Ala Val Glu Gly Ala Glu
        195                 200                 205

Gln Trp Gln Gln Lys Gly Arg Leu His Ser Tyr
    210                 215

<210> SEQ ID NO 12
<211> LENGTH: 657
<212> TYPE: DNA
<213> ORGANISM: Homo sapiens

<400> SEQUENCE: 12
atggagtacc tctcagctct gaacccagt gacttactca ggtcagtatc taatataagc        60
tcggagtttg dacggagggt ctggacctca gctccaccac cccagcgacc tttccgtgtc     120
tgtgatcaca gcggaccat ccggaaaggc ctgacagctg ccacccgcca ggagctgcta      180
gccaaagcat ggagaccct actgctgaat ggagtgctaa ccctggtgct agaggaggat      240
ggaactgcag tggacagtga ggacttcttc cagctgctgg aggatgacac gtgcctgatg     300
gtgttgcagt ctggtcagag ctggagccct acaaggagtg gagtgctgtc atatggcctg     360
ggacgggaga ggcccaagca cagcaaggac atcgcccgat tcacctttga cgtgtacaag     420
caaaaccctc gagacctctt tggcagcctg aatgtcaaag ccacattcta cgggctctac     480
tctatgagtt gtgactttca aggcttggc ccaaagaaag tactcaggga gctccttcgt     540
tggacctcca cactgctgca aggcctgggc catatgttgc tgggaatttc ctccacccct     600
cgtcatgcag tggagggggc tgagcagtgg cagcagaagg gccgcctcca ttcctac        657

<210> SEQ ID NO 13
<211> LENGTH: 76
<212> TYPE: PRT
<213> ORGANISM: Artificial Sequence
<220> FEATURE:
<223> OTHER INFORMATION: Consensus sequence for the CAD domain

<400> SEQUENCE: 13

Arg Pro Phe Lys Val Arg Asp His Asp Arg Asn Val Arg Lys Gly Val
  1               5                  10                  15

Ala Ala Ser Ser Leu Glu Glu Leu Leu Ser Lys Val Leu Asp Lys Leu
                 20                  25                  30

Lys Leu Pro Asp Ser Leu Glu Pro Val Thr Leu Val Leu Glu Glu Asp
         35                  40                  45

Gly Thr Glu Val Glu Asp Glu Glu Tyr Phe Arg Thr Leu Pro Asn Asn
     50                  55                  60

Thr Glu Leu Val Ala Leu Glu Gln Gly Glu Lys Trp
 65                 70                  75

<210> SEQ ID NO 14
<211> LENGTH: 219
<212> TYPE: PRT
<213> ORGANISM: Mus musculus

<400> SEQUENCE: 14

Met Glu Tyr Leu Ser Ala Phe Asn Pro Asn Gly Leu Leu Arg Ser Val
  1               5                  10                  15

Ser Thr Val Ser Ser Glu Leu Ser Arg Arg Val Trp Asn Ser Ala Pro
                 20                  25                  30
```

```
Pro Pro Gln Arg Pro Phe Arg Val Cys Asp His Lys Arg Thr Val Arg
        35                  40                  45

Lys Gly Leu Thr Ala Ala Ser Leu Gln Glu Leu Leu Asp Lys Val Leu
 50                  55                  60

Glu Thr Leu Leu Leu Arg Gly Val Leu Thr Leu Val Leu Glu Glu Asp
 65                  70                  75                  80

Gly Thr Ala Val Asp Ser Glu Asp Phe Phe Gln Leu Leu Glu Asp Asp
                 85                  90                  95

Thr Cys Leu Met Val Leu Glu Gln Gly Gln Ser Trp Ser Pro Lys Ser
                100                 105                 110

Gly Met Leu Ser Tyr Gly Leu Gly Arg Glu Lys Pro Lys His Ser Lys
            115                 120                 125

Asp Ile Ala Arg Ile Thr Phe Asp Val Tyr Lys Gln Asn Pro Arg Asp
130                 135                 140

Leu Phe Gly Ser Leu Asn Val Lys Ala Thr Phe Tyr Gly Leu Tyr Ser
145                 150                 155                 160

Met Ser Cys Asp Phe Gln Gly Val Gly Pro Lys Arg Val Leu Arg Glu
                165                 170                 175

Leu Leu Arg Gly Thr Ser Ser Gln Leu Gln Gly Leu His Met Leu
            180                 185                 190

Leu Gly Ile Ser Ser Thr Leu Arg His Val Val Glu Gly Ala Asp Arg
            195                 200                 205

Trp Gln Trp His Gly Gln Arg His Leu His Ser
        210                 215

<210> SEQ ID NO 15
<211> LENGTH: 219
<212> TYPE: PRT
<213> ORGANISM: Homo sapiens

<400> SEQUENCE: 15

Met Glu Ala Ala Arg Asp Tyr Ala Gly Ala Leu Ile Arg Pro Leu Thr
  1               5                  10                  15

Phe Met Gly Ser Gln Thr Lys Arg Val Leu Phe Thr Pro Leu Met His
             20                  25                  30

Pro Ala Arg Pro Phe Arg Val Ser Asn His Asp Arg Ser Ser Arg Arg
        35                  40                  45

Gly Val Met Ala Ser Ser Leu Gln Glu Leu Ile Ser Lys Thr Leu Asp
 50                  55                  60

Ala Leu Val Ile Ala Thr Gly Leu Val Thr Leu Val Leu Glu Glu Asp
 65                  70                  75                  80

Gly Thr Val Val Asp Thr Glu Glu Phe Phe Gln Thr Leu Gly Asp Asn
                 85                  90                  95

Thr His Phe Met Ile Leu Glu Lys Gly Gln Lys Trp Met Pro Gly Ser
                100                 105                 110

Gln His Val Pro Thr Cys Ser Pro Lys Arg Ser Gly Ile Ala Arg
            115                 120                 125

Val Thr Phe Asp Leu Tyr Arg Leu Asn Pro Lys Asp Phe Ile Gly Cys
130                 135                 140

Leu Asn Val Lys Ala Thr Met Tyr Glu Met Tyr Ser Val Ser Tyr Asp
145                 150                 155                 160

Ile Arg Cys Thr Gly Leu Lys Gly Leu Leu Arg Ser Leu Arg Phe
            165                 170                 175

Leu Ser Tyr Ser Ala Gln Val Thr Gly Gln Phe Leu Ile Tyr Leu Gly
            180                 185                 190
```

```
Thr Tyr Met Leu Arg Val Leu Asp Asp Lys Glu Glu Arg Pro Ser Leu
        195                 200                 205

Arg Ser Gln Ala Lys Gly Arg Phe Thr Cys Gly
    210                 215

<210> SEQ ID NO 16
<211> LENGTH: 1542
<212> TYPE: DNA
<213> ORGANISM: Homo sapiens
<220> FEATURE:
<221> NAME/KEY: CDS
<222> LOCATION: (156)...(1145)
<220> FEATURE:
<221> NAME/KEY: misc_feature
<222> LOCATION: 1502
<223> OTHER INFORMATION: n = A,T,C or G

<400> SEQUENCE: 16
cacgcgtccg ggcgtctggc gtccccggtg cccagcattc tgcggggcag gcggtctcgc      60
ttgattgggt ttctcatggg tctctggcgt ttctacggcg cggctctcac ggactcaggc     120
caggccactc gcaggattaa ttggaattct tcaaa atg tca ggt gtg gta ccc        173
                                       Met Ser Gly Val Val Pro
                                         1               5 aca gcc cct gaa cag cct gca ggt gaa atg gaa aat caa aca aaa cca       221
Thr Ala Pro Glu Gln Pro Ala Gly Glu Met Glu Asn Gln Thr Lys Pro
            10                  15                  20 cca gat cca agg cct gat gct cct cct gaa tac aat tct cat ttt tta       269
Pro Asp Pro Arg Pro Asp Ala Pro Pro Glu Tyr Asn Ser His Phe Leu
        25                  30                  35 cca gga ccc cct gga aca gct gtc cct cca cct act ggc tac cca gga       317
Pro Gly Pro Pro Gly Thr Ala Val Pro Pro Pro Thr Gly Tyr Pro Gly
    40                  45                  50 ggc ttg cct atg gga tac tac agt cca cag caa ccc agt acc ttc cct       365
Gly Leu Pro Met Gly Tyr Tyr Ser Pro Gln Gln Pro Ser Thr Phe Pro
 55                  60                  65                  70 ttg tac cag cca gtt ggt ggt atc cat cct gtc cgg tat cag cct ggc       413
Leu Tyr Gln Pro Val Gly Gly Ile His Pro Val Arg Tyr Gln Pro Gly
                75                  80                  85 aaa tat cct atg cca aat cag tct gtt cca ata aca tgg atg cca ggg       461
Lys Tyr Pro Met Pro Asn Gln Ser Val Pro Ile Thr Trp Met Pro Gly
            90                  95                 100 cca act cct atg gca aac tgc cct cct ggt ctg gaa tac tta gtt cag       509
Pro Thr Pro Met Ala Asn Cys Pro Pro Gly Leu Glu Tyr Leu Val Gln
        105                 110                 115 ttg gac aac ata cat gtt ctt cag cat ttt gag cct ctg gaa atg atg       557
Leu Asp Asn Ile His Val Leu Gln His Phe Glu Pro Leu Glu Met Met
    120                 125                 130 aca tgt ttt gaa act aat aat aga tat gat att aaa aac aac tca gac       605
Thr Cys Phe Glu Thr Asn Asn Arg Tyr Asp Ile Lys Asn Asn Ser Asp
135                 140                 145                 150 cag atg gtt tac att gta acc gaa gac aca gat gac ttt acc agg aat       653
Gln Met Val Tyr Ile Val Thr Glu Asp Thr Asp Asp Phe Thr Arg Asn
                155                 160                 165 gcc tat cgg aca cta agg ccc ttc gtc ctc cgg gtc act gat tgt atg       701
Ala Tyr Arg Thr Leu Arg Pro Phe Val Leu Arg Val Thr Asp Cys Met
            170                 175                 180 ggc cga gaa atc atg aca atg cag aga ccc ttc aga tgc acc tgc tgt       749
Gly Arg Glu Ile Met Thr Met Gln Arg Pro Phe Arg Cys Thr Cys Cys
        185                 190                 195 tgc ttc tgt tgc ccc tct gcc aga caa gag ctg gag gtg cag tgt cct       797
```

-continued

```
Cys Phe Cys Cys Pro Ser Ala Arg Gln Glu Leu Glu Val Gln Cys Pro
        200                 205                 210 cct ggt gtc acc att ggc ttt gtt gcg gaa cat tgg aac ctg tgc agg    845
Pro Gly Val Thr Ile Gly Phe Val Ala Glu His Trp Asn Leu Cys Arg
215                 220                 225                 230 gcg gtg tac agc atc caa aat gag aag aaa gaa aat gtg atg aga gtt    893
Ala Val Tyr Ser Ile Gln Asn Glu Lys Lys Glu Asn Val Met Arg Val
                235                 240                 245 cgt ggg cca tgc tca acc tat ggc tgt ggt tca gat tct gtt ttt gag    941
Arg Gly Pro Cys Ser Thr Tyr Gly Cys Gly Ser Asp Ser Val Phe Glu
            250                 255                 260 gtc aaa tcc ctt gat ggc ata tcc aac atc ggc agt att atc cgg aag    989
Val Lys Ser Leu Asp Gly Ile Ser Asn Ile Gly Ser Ile Ile Arg Lys
        265                 270                 275 gg aat ggt ttg tta tca gca atg gca gat gct gac cat ttt gac att    1037
Trp Asn Gly Leu Leu Ser Ala Met Ala Asp Ala Asp His Phe Asp Ile
    280                 285                 290 ac ttc cca cta gac ctg gat gtg aag atg aaa gcc atg att ttt gga    1085
His Phe Pro Leu Asp Leu Asp Val Lys Met Lys Ala Met Ile Phe Gly
295                 300                 305                 310 ct tgc ttc ctc att gac ttc atg tat ttt gaa aga tct cca cca caa    1133
Ala Cys Phe Leu Ile Asp Phe Met Tyr Phe Glu Arg Ser Pro Pro Gln
            315                 320                 325 gt tca aga tag agagacacag caagccatca actatggtta attttgaaaa        1185
Arg Ser Arg * atggaaaagt tggattgggc ttacagtcag cactcagtta tttgcaagtg tatttctttg    1245
ctttgtagag tattttttatt gggtgttaac tttgacagct gaaagtgggc ttgcaagaac    1305
acaatctaaa agtgtgtttc aattgagtat ctctctagta gaataggagt tcatcctgaa    1365
aagctgtgac tcattaaccc agtaaacata tacaaagtaa gcttaaaaca ctataaacat    1425
gagataaggg aaaatgaatc cagagttctc atattaatag gtagtgaaac aataaggctt    1485
tttagagcag actttgntgg cataaaataa cctggcttct atccctaacc ctttcct    1542
```

<210> SEQ ID NO 17
<211> LENGTH: 329
<212> TYPE: PRT
<213> ORGANISM: Homo sapiens
<220> FEATURE:
<221> NAME/KEY: VARIANT
<222> LOCATION: 434
<223> OTHER INFORMATION: Xaa = Any Amino Acid

<400> SEQUENCE: 17

```
Met Ser Gly Val Val Pro Thr Ala Pro Glu Gln Pro Ala Gly Glu Met
  1               5                  10                  15

Glu Asn Gln Thr Lys Pro Pro Asp Pro Arg Pro Asp Ala Pro Pro Glu
                 20                  25                  30

Tyr Asn Ser His Phe Leu Pro Gly Pro Gly Thr Ala Val Pro Pro
             35                  40                  45

Pro Thr Gly Tyr Pro Gly Gly Leu Pro Met Gly Tyr Tyr Ser Pro Gln
     50                  55                  60

Gln Pro Ser Thr Phe Pro Leu Tyr Gln Pro Val Gly Gly Ile His Pro
 65                  70                  75                  80

Val Arg Tyr Gln Pro Gly Lys Tyr Pro Met Pro Asn Gln Ser Val Pro
                 85                  90                  95

Ile Thr Trp Met Pro Gly Pro Thr Pro Met Ala Asn Cys Pro Pro Gly
                100                 105                 110
```

-continued

```
Leu Glu Tyr Leu Val Gln Leu Asp Asn Ile His Val Leu Gln His Phe
            115                 120                 125
Glu Pro Leu Glu Met Met Thr Cys Phe Glu Thr Asn Asn Arg Tyr Asp
        130                 135                 140
Ile Lys Asn Asn Ser Asp Gln Met Val Tyr Ile Val Thr Glu Asp Thr
145                 150                 155                 160
Asp Asp Phe Thr Arg Asn Ala Tyr Arg Thr Leu Arg Pro Phe Val Leu
                165                 170                 175
Arg Val Thr Asp Cys Met Gly Arg Glu Ile Met Thr Met Gln Arg Pro
            180                 185                 190
Phe Arg Cys Thr Cys Cys Phe Cys Cys Pro Ser Ala Arg Gln Glu
        195                 200                 205
Leu Glu Val Gln Cys Pro Pro Gly Val Thr Ile Gly Phe Val Ala Glu
        210                 215                 220
His Trp Asn Leu Cys Arg Ala Val Tyr Ser Ile Gln Asn Glu Lys Lys
225                 230                 235                 240
Glu Asn Val Met Arg Val Arg Gly Pro Cys Ser Thr Tyr Gly Cys Gly
                245                 250                 255
Ser Asp Ser Val Phe Glu Val Lys Ser Leu Asp Gly Ile Ser Asn Ile
            260                 265                 270
Gly Ser Ile Ile Arg Lys Trp Asn Gly Leu Leu Ser Ala Met Ala Asp
        275                 280                 285
Ala Asp His Phe Asp Ile His Phe Pro Leu Asp Leu Asp Val Lys Met
        290                 295                 300
Lys Ala Met Ile Phe Gly Ala Cys Phe Leu Ile Asp Phe Met Tyr Phe
305                 310                 315                 320
Glu Arg Ser Pro Pro Gln Arg Ser Arg
                325
```

<210> SEQ ID NO 18
<211> LENGTH: 990
<212> TYPE: DNA
<213> ORGANISM: Homo sapiens
<220> FEATURE:
<221> NAME/KEY: CDS
<222> LOCATION: (1)...(990)

<400> SEQUENCE: 18

```
atg tca ggt gtg gta ccc aca gcc cct gaa cag cct gca ggt gaa atg    48
Met Ser Gly Val Val Pro Thr Ala Pro Glu Gln Pro Ala Gly Glu Met
 1               5                  10                  15 gaa aat caa aca aaa cca cca gat cca agg cct gat gct cct cct gaa    96
Glu Asn Gln Thr Lys Pro Pro Asp Pro Arg Pro Asp Ala Pro Pro Glu
            20                  25                  30 tac aat tct cat ttt tta cca gga ccc cct gga aca gct gtc cct cca   144
Tyr Asn Ser His Phe Leu Pro Gly Pro Pro Gly Thr Ala Val Pro Pro
        35                  40                  45 cct act ggc tac cca gga ggc ttg cct atg gga tac tac agt cca cag   192
Pro Thr Gly Tyr Pro Gly Gly Leu Pro Met Gly Tyr Tyr Ser Pro Gln
    50                  55                  60 caa ccc agt acc ttc cct ttg tac cag cca gtt ggt ggt atc cat cct   240
Gln Pro Ser Thr Phe Pro Leu Tyr Gln Pro Val Gly Gly Ile His Pro
65                  70                  75                  80 gtc cgg tat cag cct ggc aaa tat cct atg cca aat cag tct gtt cca   288
Val Arg Tyr Gln Pro Gly Lys Tyr Pro Met Pro Asn Gln Ser Val Pro
                85                  90                  95
```

```
ata aca tgg atg cca ggg cca act cct atg gca aac tgc cct cct ggt         336
Ile Thr Trp Met Pro Gly Pro Thr Pro Met Ala Asn Cys Pro Pro Gly
            100                 105                 110 ctg gaa tac tta gtt cag ttg gac aac ata cat gtt ctt cag cat ttt         384
Leu Glu Tyr Leu Val Gln Leu Asp Asn Ile His Val Leu Gln His Phe
        115                 120                 125 gag cct ctg gaa atg atg aca tgt ttt gaa act aat aat aga tat gat         432
Glu Pro Leu Glu Met Met Thr Cys Phe Glu Thr Asn Asn Arg Tyr Asp
130                 135                 140 att aaa aac aac tca gac cag atg gtt tac att gta acc gaa gac aca         480
Ile Lys Asn Asn Ser Asp Gln Met Val Tyr Ile Val Thr Glu Asp Thr
145                 150                 155                 160 gat gac ttt acc agg aat gcc tat cgg aca cta agg ccc ttc gtc ctc         528
Asp Asp Phe Thr Arg Asn Ala Tyr Arg Thr Leu Arg Pro Phe Val Leu
                165                 170                 175 cgg gtc act gat tgt atg ggc cga gaa atc atg aca atg cag aga ccc         576
Arg Val Thr Asp Cys Met Gly Arg Glu Ile Met Thr Met Gln Arg Pro
            180                 185                 190 ttc aga tgc acc tgc tgt tgc ttc tgt tgc ccc tct gcc aga caa gag         624
Phe Arg Cys Thr Cys Cys Cys Phe Cys Cys Pro Ser Ala Arg Gln Glu
        195                 200                 205 ctg gag gtg cag tgt cct cct ggt gtc acc att ggc ttt gtt gcg gaa         672
Leu Glu Val Gln Cys Pro Pro Gly Val Thr Ile Gly Phe Val Ala Glu
210                 215                 220 cat tgg aac ctg tgc agg gcg gtg tac agc atc caa aat gag aag aaa         720
His Trp Asn Leu Cys Arg Ala Val Tyr Ser Ile Gln Asn Glu Lys Lys
225                 230                 235                 240 gaa aat gtg atg aga gtt cgt ggg cca tgc tca acc tat ggc tgt ggt         768
Glu Asn Val Met Arg Val Arg Gly Pro Cys Ser Thr Tyr Gly Cys Gly
                245                 250                 255 tca gat tct gtt ttt gag gtc aaa tcc ctt gat ggc ata tcc aac atc         816
Ser Asp Ser Val Phe Glu Val Lys Ser Leu Asp Gly Ile Ser Asn Ile
            260                 265                 270 ggc agt att atc cgg aag tgg aat ggt ttg tta tca gca atg gca gat         864
Gly Ser Ile Ile Arg Lys Trp Asn Gly Leu Leu Ser Ala Met Ala Asp
        275                 280                 285 gct gac cat ttt gac att cac ttc cca cta gac ctg gat gtg aag atg         912
Ala Asp His Phe Asp Ile His Phe Pro Leu Asp Leu Asp Val Lys Met
290                 295                 300 aaa gcc atg att ttt gga gct tgc ttc ctc att gac ttc atg tat ttt         960
Lys Ala Met Ile Phe Gly Ala Cys Phe Leu Ile Asp Phe Met Tyr Phe
305                 310                 315                 320 gaa aga tct cca cca caa cgt tca aga tag                                 990
Glu Arg Ser Pro Pro Gln Arg Ser Arg *
                325
```

<210> SEQ ID NO 19
<211> LENGTH: 307
<212> TYPE: PRT
<213> ORGANISM: Mus musculus

<400> SEQUENCE: 19

```
Met Glu Ala Pro Arg Ser Gly Thr Tyr Leu Pro Ala Gly Tyr Ala Pro
1               5                   10                  15

Gln Tyr Pro Pro Ala Ala Val Gln Gly Pro Pro Glu His Thr Gly Arg
            20                  25                  30

Pro Thr Phe Gln Thr Asn Tyr Gln Val Pro Gln Ser Gly Tyr Pro Gly
        35                  40                  45
```

```
Pro Gln Ala Ser Tyr Thr Val Ser Thr Ser Gly His Glu Gly Tyr Ala
 50                  55                  60

Ala Thr Arg Leu Pro Ile Gln Asn Asn Gln Thr Ile Val Leu Ala Asn
 65                  70                  75                  80

Thr Gln Trp Met Pro Ala Pro Pro Ile Leu Asn Cys Pro Pro Gly
                 85                  90                  95

Leu Glu Tyr Leu Asn Gln Ile Asp Gln Leu Leu Ile His Gln Gln Val
                100                 105                 110

Glu Leu Leu Glu Val Leu Thr Gly Phe Glu Thr Asn Asn Lys Phe Glu
            115                 120                 125

Ile Lys Asn Ser Leu Gly Gln Met Val Tyr Val Ala Val Glu Asp Thr
130                 135                 140

Asp Cys Cys Thr Arg Asn Cys Cys Glu Ala Ser Arg Pro Phe Thr Leu
145                 150                 155                 160

Arg Ile Leu Asp His Leu Gly Gln Glu Val Met Thr Leu Glu Arg Pro
                165                 170                 175

Leu Arg Cys Ser Ser Cys Cys Phe Pro Cys Cys Leu Gln Glu Ile Glu
                180                 185                 190

Ile Gln Ala Pro Pro Gly Val Pro Ile Gly Tyr Val Thr Gln Thr Trp
            195                 200                 205

His Pro Cys Leu Pro Lys Leu Thr Leu Gln Asn Asp Lys Arg Glu Asn
210                 215                 220

Val Leu Lys Val Val Gly Pro Cys Val Ala Cys Thr Cys Ser Asp
225                 230                 235                 240

Ile Asp Phe Glu Ile Lys Ser Leu Asp Glu Val Thr Arg Ile Gly Lys
                245                 250                 255

Ile Thr Lys Gln Trp Ser Gly Cys Val Lys Glu Ala Phe Thr Asp Ser
            260                 265                 270

Asp Asn Phe Gly Ile Gln Phe Pro Leu Asp Leu Glu Val Lys Met Lys
            275                 280                 285

Ala Val Thr Leu Gly Ala Cys Phe Leu Ile Asp Tyr Met Phe Phe Glu
290                 295                 300

Gly Cys Glu
305

<210> SEQ ID NO 20
<211> LENGTH: 318
<212> TYPE: PRT
<213> ORGANISM: Homo sapiens

<400> SEQUENCE: 20

Met Asp Lys Gln Asn Ser Gln Met Asn Ala Ser His Pro Glu Thr Asn
 1               5                  10                  15

Leu Pro Val Gly Tyr Pro Pro Gln Tyr Pro Pro Thr Ala Phe Gln Gly
                 20                  25                  30

Pro Pro Gly Tyr Ser Gly Tyr Pro Gly Pro Gln Val Ser Tyr Pro Pro
             35                  40                  45

Pro Pro Ala Gly His Ser Gly Pro Gly Ala Gly Phe Pro Val Pro
         50                  55                  60

Asn Gln Pro Val Tyr Asn Gln Pro Val Tyr Asn Gln Pro Val Gly Ala
 65                  70                  75                  80

Ala Gly Val Pro Trp Met Pro Ala Pro Gln Pro Pro Leu Asn Cys Pro
                 85                  90                  95
```

-continued

```
Pro Gly Leu Glu Tyr Leu Ser Gln Ile Asp Gln Ile Leu Ile His Gln
            100                 105                 110

Gln Ile Glu Leu Leu Glu Val Leu Thr Gly Phe Glu Thr Asn Asn Lys
        115                 120                 125

Tyr Glu Ile Lys Asn Ser Phe Gly Gln Arg Val Tyr Phe Ala Ala Glu
    130                 135                 140

Asp Thr Asp Cys Cys Thr Arg Asn Cys Cys Gly Pro Ser Arg Pro Phe
145                 150                 155                 160

Thr Leu Arg Ile Ile Asp Asn Met Gly Gln Glu Val Ile Thr Leu Glu
                165                 170                 175

Arg Pro Leu Arg Cys Ser Ser Cys Cys Pro Cys Leu Gln Glu
            180                 185                 190

Ile Glu Ile Gln Ala Pro Pro Gly Val Pro Ile Gly Tyr Val Ile Gln
        195                 200                 205

Thr Trp His Pro Cys Leu Pro Lys Phe Thr Ile Gln Asn Glu Lys Arg
    210                 215                 220

Glu Asp Val Leu Lys Ile Ser Gly Pro Cys Val Val Cys Ser Cys Cys
225                 230                 235                 240

Gly Asp Val Asp Phe Glu Ile Lys Ser Leu Asp Glu Gln Cys Val Val
                245                 250                 255

Gly Lys Ile Ser Lys His Trp Thr Gly Ile Leu Arg Glu Ala Phe Thr
            260                 265                 270

Asp Ala Asp Asn Phe Gly Ile Gln Phe Pro Leu Asp Leu Asp Val Lys
        275                 280                 285

Met Lys Ala Val Met Ile Gly Ala Cys Phe Leu Ile Asp Phe Met Phe
    290                 295                 300

Phe Glu Ser Thr Gly Ser Gln Glu Gln Lys Ser Gly Val Trp
305                 310                 315

<210> SEQ ID NO 21
<211> LENGTH: 1452
<212> TYPE: DNA
<213> ORGANISM: Homo sapiens
<220> FEATURE:
<221> NAME/KEY: CDS
<222> LOCATION: (219)...(995)

<400> SEQUENCE: 21
cggaattccc gggtcgaccc acgcgtccgg agcggcgagc cgagacggct acatggacgc      60
cactatcgcc ccgcaccgta tcccccccga gatgccccag tacggggagg agaaccacgt     120
cttcgagttg atgcagaaca tgctggagca actcctgatc caccagcccg aagatcccat     180
ccccttcatg atccagcact tgcatagaga caacgaca atg gca atg tgg ctc tgc    236
                                              Met Ala Met Trp Leu Cys
                                                1               5 aaa cat ctg aac agc agt ctc ctc acc ctg gag aac ctg atc tta aat      284
Lys His Leu Asn Ser Ser Leu Leu Thr Leu Glu Asn Leu Ile Leu Asn
        10                  15                  20 gag ttt tcc tat acg gcc acc gaa gcc aga agg ctt tat ctg caa agg      332
Glu Phe Ser Tyr Thr Ala Thr Glu Ala Arg Arg Leu Tyr Leu Gln Arg
    25                  30                  35 aag aca gtt ccc agt gcg ctg ctc gtc cag ctg att cag gaa cgc ctg      380
Lys Thr Val Pro Ser Ala Leu Leu Val Gln Leu Ile Gln Glu Arg Leu
40                  45                  50 gct gaa gag gat tgc atc aag cag ggc tgg att ctg gat ggc atc cct      428
Ala Glu Glu Asp Cys Ile Lys Gln Gly Trp Ile Leu Asp Gly Ile Pro
55                  60                  65                  70
```

```
gag acg cgt gag cag gct ctg agg atc cag acc ctg ggg atc aca ccc        476
Glu Thr Arg Glu Gln Ala Leu Arg Ile Gln Thr Leu Gly Ile Thr Pro
                75                  80                  85 aga cac gtc att gtg ctg agt gct cca gac acg gtc ctg atc gag aga        524
Arg His Val Ile Val Leu Ser Ala Pro Asp Thr Val Leu Ile Glu Arg
        90                  95                 100 aac ttg ggg aag aga atc gac cct caa act gga gag att tat cac acc        572
Asn Leu Gly Lys Arg Ile Asp Pro Gln Thr Gly Glu Ile Tyr His Thr
            105                 110                 115 acc ttt gac tgg cca ccc gaa tct gaa atc cag aac cgt ctc atg gtg        620
Thr Phe Asp Trp Pro Pro Glu Ser Glu Ile Gln Asn Arg Leu Met Val
    120                 125                 130 cca gag gac atc tca gag ctg gag acg gct cag aaa ctg ctg gag tat        668
Pro Glu Asp Ile Ser Glu Leu Glu Thr Ala Gln Lys Leu Leu Glu Tyr
135                 140                 145                 150 cat agg aac atc gtc agg gtc att ccc tcc tac ccc aaa atc ctc aaa        716
His Arg Asn Ile Val Arg Val Ile Pro Ser Tyr Pro Lys Ile Leu Lys
                155                 160                 165 gtc atc agt gct gac cag cca tgt gtg gac gtc ttc tac cag gct ctg        764
Val Ile Ser Ala Asp Gln Pro Cys Val Asp Val Phe Tyr Gln Ala Leu
            170                 175                 180 acc tat gtc caa agc aac cat cgt act aat gcc ccg ttc acc ccg agg        812
Thr Tyr Val Gln Ser Asn His Arg Thr Asn Ala Pro Phe Thr Pro Arg
    185                 190                 195 gtg ctg ctg ctc ggg cct gtg ggc agt ggg aaa agt ctg cag gcc gcc        860
Val Leu Leu Leu Gly Pro Val Gly Ser Gly Lys Ser Leu Gln Ala Ala
200                 205                 210 ctc ctg gcc cag aaa tac agg ctt gtc aat gtc tgc tgt ggg caa ctg        908
Leu Leu Ala Gln Lys Tyr Arg Leu Val Asn Val Cys Cys Gly Gln Leu
215                 220                 225                 230 ctg aaa gag gct gtg gca gat agg acc acg ttt ggc gag ctc atc cag        956
Leu Lys Glu Ala Val Ala Asp Arg Thr Thr Phe Gly Glu Leu Ile Gln
                235                 240                 245 ccc ttc ttt gaa aag gag atg gca ggg tgt ttt tcc tga atgtgccatt       1005
Pro Phe Phe Glu Lys Glu Met Ala Gly Cys Phe Ser *
            250                 255 tgattccatc atggagcggc tgactctgag aagaattgat ccagtcactg gggaaaggta    1065
ccacctcatg tacaagccac ctcccaccat ggagatccag gctcgcctcc tgcagaaccc    1125
aaaggatgct gaagagcagg tcaagctgaa aatggacctg ttctacagga actcagctga    1185
cttggagcag ttgtatgggt cggccatcac cctcaatggg gaccaggacc catacacagt    1245
cttcgaatac atcgagagtg ggatcattaa tcccctgccc aagaaaatcc cctgatgggt    1305
tcagagccag gagcgctgcc ccagggaaag agtaatccc ctgccccag ccccccagcc      1365 tcggcacagc tcccctaaaa agccaataaa gcctgctgga tacagaaaaa aaaaaaaaa    1425 aaaaaaaaa aaaaaaaaaa aaaaaaa                                        1452

<210> SEQ ID NO 22
<211> LENGTH: 258
<212> TYPE: PRT
<213> ORGANISM: Homo sapiens

<400> SEQUENCE: 22

Met Ala Met Trp Leu Cys Lys His Leu Asn Ser Ser Leu Leu Thr Leu
1               5                   10                  15

Glu Asn Leu Ile Leu Asn Glu Phe Ser Tyr Thr Ala Thr Glu Ala Arg
            20                  25                  30
```

```
Arg Leu Tyr Leu Gln Arg Lys Thr Val Pro Ser Ala Leu Leu Val Gln
             35                  40                  45

Leu Ile Gln Glu Arg Leu Ala Glu Glu Asp Cys Ile Lys Gln Gly Trp
 50                  55                  60

Ile Leu Asp Gly Ile Pro Glu Thr Arg Glu Gln Ala Leu Arg Ile Gln
 65                  70                  75                  80

Thr Leu Gly Ile Thr Pro Arg His Val Ile Val Leu Ser Ala Pro Asp
                 85                  90                  95

Thr Val Leu Ile Glu Arg Asn Leu Gly Lys Arg Ile Asp Pro Gln Thr
                100                 105                 110

Gly Glu Ile Tyr His Thr Thr Phe Asp Trp Pro Glu Ser Glu Ile
                115                 120                 125

Gln Asn Arg Leu Met Val Pro Glu Asp Ile Ser Glu Leu Glu Thr Ala
            130                 135                 140

Gln Lys Leu Leu Glu Tyr His Arg Asn Ile Val Arg Val Ile Pro Ser
145                 150                 155                 160

Tyr Pro Lys Ile Leu Lys Val Ile Ser Ala Asp Gln Pro Cys Val Asp
                165                 170                 175

Val Phe Tyr Gln Ala Leu Thr Tyr Val Gln Ser Asn His Arg Thr Asn
            180                 185                 190

Ala Pro Phe Thr Pro Arg Val Leu Leu Gly Pro Val Gly Ser Gly
            195                 200                 205

Lys Ser Leu Gln Ala Ala Leu Leu Ala Gln Lys Tyr Arg Leu Val Asn
    210                 215                 220

Val Cys Cys Gly Gln Leu Leu Lys Glu Ala Val Ala Asp Arg Thr Thr
225                 230                 235                 240

Phe Gly Glu Leu Ile Gln Pro Phe Phe Glu Lys Glu Met Ala Gly Cys
                245                 250                 255

Phe Ser
```

<210> SEQ ID NO 23
<211> LENGTH: 774
<212> TYPE: DNA
<213> ORGANISM: Homo sapiens

<400> SEQUENCE: 23

```
atggcaatgt ggctctgcaa acatctgaac agcagtctcc tcaccctgga gaacctgatc      60
ttaaatgagt tttcctatac ggccaccgaa gccagaaggc tttatctgca aaggaagaca     120
gttcccagtg cgctgctcgt ccagctgatt caggaacgcc tggctgaaga ggattgcatc     180
aagcagggct ggattctgga tggcatccct gagacgcgtg agcaggctct gaggatccag     240
accctgggga tcacacccag acacgtcatt gtgctgagtg ctccagacac ggtcctgatc     300
gagagaaact tggggaagag aatcgaccct caaactggag agatttatca caccaccttt     360
gactggccac ccgaatctga aatccagaac cgtctcatgg tgccagagga catctcagag     420
ctggagacgg ctcagaaact gctggagtat cataggaaca tcgtcagggt cattccctcc     480
taccccaaaa tcctcaaagt catcagtgct gaccagccat gtgtggacgt cttctaccag     540
gctctgacct atgtccaaag caaccatcgt actaatgccc cgttcacccc gagggtgctg     600
ctgctcgggc ctgtgggcag tgggaaaagt ctgcaggccg ccctcctggc ccagaaatac     660
aggcttgtca atgtctgctg tgggcaactg ctgaaagagg ctgtggcaga taggaccacg     720
tttggcgagc tcatccagcc cttctttgaa aaggagatgg cagggtgttt ttcc           774
```

-continued

```
<210> SEQ ID NO 24
<211> LENGTH: 84
<212> TYPE: PRT
<213> ORGANISM: Artificial Sequence
<220> FEATURE:
<223> OTHER INFORMATION: Adenylate kinase consensus domain 1

<400> SEQUENCE: 24

Val Pro Asp Glu Val Val Ile Gly Leu Val Lys Glu Arg Leu Glu Gln
 1               5                  10                  15

Asn Asp Asp Cys Lys Asn Gly Phe Leu Leu Asp Gly Phe Pro Arg Thr
            20                  25                  30

Val Pro Gln Ala Glu Ala Leu Glu Glu Met Leu Glu Glu Ala Gly Ile
        35                  40                  45

Lys Leu Asp Ala Val Ile Glu Leu Asp Val Pro Asp Glu Val Leu Val
    50                  55                  60

Glu Arg Leu Thr Gly Arg Arg Ile His Pro Thr Ser Gly Arg Ser Tyr
65                  70                  75                  80

His Leu Glu Phe

<210> SEQ ID NO 25
<211> LENGTH: 51
<212> TYPE: PRT
<213> ORGANISM: Artificial Sequence
<220> FEATURE:
<223> OTHER INFORMATION: Adenylate kinase consensus domain 2

<400> SEQUENCE: 25

Leu Leu Gly Pro Pro Gly Ala Gly Lys Gly Thr Gln Ala Glu Arg Ile
 1               5                  10                  15

Val Lys Lys Tyr Gly Ile Pro His Leu Ser Thr Gly Asp Leu Leu Arg
            20                  25                  30

Ala Glu Val Lys Ser Gly Thr Glu Leu Gly Lys Glu Ala Lys Glu Tyr
        35                  40                  45

Met Asp Lys
    50
```

NUCLEIC ACID SEQUENCES ENCODING ADENYLATE KINASE, PHOSPHOLIPID SCRAMBLASE-LIKE, DNA FRAGMENTATION FACTOR-LIKE, PHOSPHATIDYLSERINE SYNTHASE-LIKE, AND ATPASE-LIKE MOLECULES AND USES THEREFOR

CROSS-REFERENCE TO RELATED APPLICATIONS

This application is a continuation-in-part Ser. No. 09/781,677, filed Feb. 12, 2001 now abandoned, which claims the benefit of U.S. Provisional Application No. 60/181,705, filed Feb. 10, 2000; and a continuation-in-part of Ser. No. 09/795,038, filed Feb. 26, 2001 now abandoned, which claims the benefit of U.S. Provisional Application No. 60/186,234, filed Feb. 29, 2000; and a continuation-in-part of Ser. No. 09/790,180, filed Feb. 21, 2001 now abandoned, which claims the benefit of U.S. Provisional Application No. 60/185,947, filed Feb. 29, 2000; and a continuation-in-part of Ser. No. 09/790,838, filed Feb. 22, 2001 now U.S. Pat. No. 6,489,152, which claims the benefit of U.S. Provisional Application No. 60/185,946, filed Feb. 29, 2000; and a continuation-in-part of Ser. No. 09/790,179, filed Feb. 21, 2001 now U.S. Pat. No. 6,479,268, which claims the benefit of U.S. Provisional 60/185,609, filed Feb. 29, 2000; all of which are hereby incorporated herein in their entirety by reference.

FIELD OF THE INVENTION

The invention relates to novel nucleic acid sequences and polypeptides. Also provided are vectors, host cells, and recombinant methods for making and using the novel molecules.

TABLE OF CONTENTS

Chapter 1  7970, Novel ATPase-Like Molecule and Uses Thereof
   i) SEQ ID NOS: 1–4
   ii) FIGS. 1–12
   iii) Continuation-In-Part of 09/790,179, filed Feb. 21, 2001, which claims the benefit of U.S. Provisional 60/185,609, filed Feb. 29, 2000

Chapter 2  32670, Novel Human Phosphatidylserine Synthase-Like Molecules and Uses Thereof
   i) SEQ ID NOS: 5–9
   ii) FIGS. 13–15
   iii) Continuation-In-Part of 09/790,838, filed Feb. 22, 2001, which claims the benefit of U.S. Provisional 60/185,946, filed Feb. 29, 2000

Chapter 3  5698, A DNA Fragmentation Factor-Like Molecule and Uses Thereof
   i) SEQ ID NOS: 10–15
   ii) FIGS. 16–20B
   iii) Continuation-In-Part of 09/790,180, filed Feb. 21, 2001, which claims the benefit of U.S. Provisional Application No. 60/185,947, filed Feb. 29, 2000

Chapter 4  32621, Novel Human Phospholipid Scramblase-Like Molecules and Uses Thereof
   i) SEQ ID NOS: 16–20
   ii) FIGS. 21–27
   iii) Continuation-In-Part of 09/795.038, filed Feb. 26, 2001, which claims the benefit of U.S. Provisional Application No. 60/186,234, filed Feb. 29, 2000

Chapter 5  27802, A Novel Adenylate Kinase
   i) SEQ ID NOS: 21–25
   ii) FIGS. 28–35B
   iii) Continuation-In-Part of 09/781, 677 filed Feb. 12, 2001, which claims the benefit of U.S. Provisional Application No. 60/181,705, filed Feb. 10, 2000

BRIEF DESCRIPTION OF THE DRAWINGS

FIG. 2 depicts an alignment of the AAA (ATPases Associated to a variety of cellular Activities) domain of the human ATPase-like sequence of the invention with a consensus amino acid sequence derived from a hidden Markov model. The upper sequence is the consensus amino acid sequence (SEQ ID NO:4), while the lower amino acid sequence corresponds to amino acids 128 to 312 of SEQ ID NO:2.

FIGS. 6A–B show the expression level of the 7970 mRNA transcript in various normal and tumorous tissues.

FIG. 13 shows the amino acid sequence alignment for the protein (32670; SEQ ID NO:6) encoded by human 32670 (SEQ ID NO:5) with the phosphatidylserine synthase II from *Cricetulus griseus* (GI 2190007; NCBI Accession Number BAA20355; SEQ ID NO:8) and the phosphatidylserine synthase-2 from *Mus musculus* (GI 4063700; NCBI Accession Number AAC98383; SEQ ID NO:9). The sequence alignment was generated using the Clustal method. The 32670 protein shares approximately 85% identity with the phosphatidylserine synthase II from *Cricetulus griseus* and approximately 86% identity with the murine phosphatidylserine synthase-2 as determined by pairwise alignment.

FIGS. 14A–B provide the nucleotide and amino acid sequence (SEQ ID NO:5 and 6, respectively) for clone 32670. The coding sequence for 32670 is shown in SEQ ID NO:7.

FIG. 17 depicts an alignment of the CAD domain of the human DFF-like molecule with a consensus amino acid sequence derived from a hidden Markov model. The upper sequence is the consensus amino acid sequence (SEQ ID NO:13), while the lower amino acid sequence corresponds to amino acids 36 to 108 of SEQ ID NO:11.

FIG. 19 shows the amino acid sequence alignment for the protein (5698; SEQ ID NO:11) encoded by human 5698 (SEQ ID NO:10 or 12) with the *Mus musculus* cell death activator CIDE-B (SP Accession Number 3114594; Genbank Accession Number AAC34986; SEQ ID NO:14) and with the *Homo sapiens* cell death activator CIDE-A (SP Accession Number 3114596; Genbank Accession Number AAC34987; SEQ ID NO:15). The sequence alignment was generated using the Clustal method. The 5698 protein shares approximately 83% identity with the murine CIDE-B and approximately 40% identity with the human CIDE-A amino acid sequence as determined by pairwise alignment.

FIG. 21 shows the amino acid sequence alignment for the protein (32621; SEQ ID NO:17) encoded by human 32621 (SEQ ID NO:16) with the murine phospholipid scramblase-like (SP Accession Number 2935163; Genbank Accession Number AAC40053; SEQ ID NO:19), and human Mm-1 cell derived transplantability-associated gene 1b (hMmTRA1b; SP Accession Number 3510297; Genbank Accession Number BAA32568; SEQ ID NO:20). The sequence alignment was generated using the Clustal method. The 32621 protein shares approximately 45% identity to the *Mus musculus* phospholipid scramblase-like and approximately 41% identity to the *Homo sapiens* hMmTRA1b protein as determined by pairwise alignment.

FIGS. 22A–B provide the nucleotide and amino acid sequence (SEQ ID NO:16 and 17, respectively) for clone 32621.

FIGS. 25A–B depict relative expression levels of 32621 in various organs: conf HMVEC, human microvascular endothelial cells (column 1); human fetal heart (column 2); human normal atrium (column 3); human normal atrium (column 4); human normal ventricle (column 5); human normal ventricle (column 6); human normal ventricle (column 7); human normal ventricle (column 8); human normal ventricle (column 9); human heart diseased ventricle (column 10); human heart diseased ventricle (column 11); human heart diseased ventricle (column 12); normal human kidney (column 13); normal human kidney (column 14); normal human kidney (column 15); normal human kidney (column 16); human kidney HT (column 17); human kidney HT (column 18); human kidney HT (column 19); human kidney HT (column 20); human skeletal muscle (column 21); human skeletal muscle (column 22); human liver (column 23); human liver with inflammation (column 24); fetal adrenal (column 25); Wilms Tumor (column 26); Wilms Tumor (column 27); normal human spinal cord (column 28); diseased human cartilage (column 29); normal mouse atrium (column 30); normal mouse atrium (column 31); normal mouse ventricle (column 32); and normal mouse ventricle (column 33). Relative expression levels were determined as described in FIGS. 24A–B.

FIG. 28 shows the 27802 nucleotide sequence (SEQ ID NO:21) and the deduced amino acid sequence (SEQ ID NO:22).

FIG. 31 shows an analysis of the 27802 open reading frame for amino acids corresponding to specific functional sites. These sites are relevant with regard to providing fragments of the 27802 nucleic acid or peptide as disclosed herein.

FIG. 32 shows PSORT prediction of protein localization showing a high score in the cytoplasm and significant scores in other cellular locations.

FIG. 33 shows a description of ProDom matches for the 27802 protein.

FIG. 34 depicts an alignment of the adenylate kinase domains of human 27802 with two consensus amino acid sequences derived from hidden Markov models. The upper sequence for domain 1 is the consensus amino acid sequence (SEQ ID NO:24) and the lower amino acid sequence corresponds to amino acids 41–120 of SEQ ID NO:22. The upper sequence for domain 2 is the consensus amino acid sequence (SEQ ID NO:25) and the lower amino acid sequence corresponds to amino acids 201–251 of SEQ ID NO:22.

FIGS. 35A–B display the expression levels of 27802 in various tissues determined by quantitative PCR. The highest levels of expression of 27802 were observed in artery, kidney, brain cortex and brain hypothalamus, ovary, lung (tumor), and tonsil. The tissue types are as follows from left to right: Artery Normal, Aorta Diseased, Vein Normal, Coronary SMC, HUVEC, Hemangioma, Heart Normal, Heart CHF, Kidney, Skeletal Muscle, Adipose Normal, Pancreas, Primary Osteoblasts, Osteoclasts (diff), Skin Normal, Spinal Cord Normal, Brain Cortex Normal, Brain Hypothalamus Normal, Nerve, DRG (Dorsal Root Ganglion), Breast Normal, Breast Tumor, Ovary Normal, Ovary Tumor, Prostate Normal, Prostate Tumor, Salivary Glands, Colon Normal, Colon Tumor, Lung Normal, Lung Tumor, Lung COPD, Colon IBD, Liver Normal, Liver Fibrosis, Spleen Normal, Tonsil Normal, Lymph Node Normal, Small Intestine Normal, Macrophages, Synovium, BM-MNC, Activated PBMC, Neutrophils, Megakaryocytes, Erythroid, Positive Control.

CHAPTER 1

Figure 1:
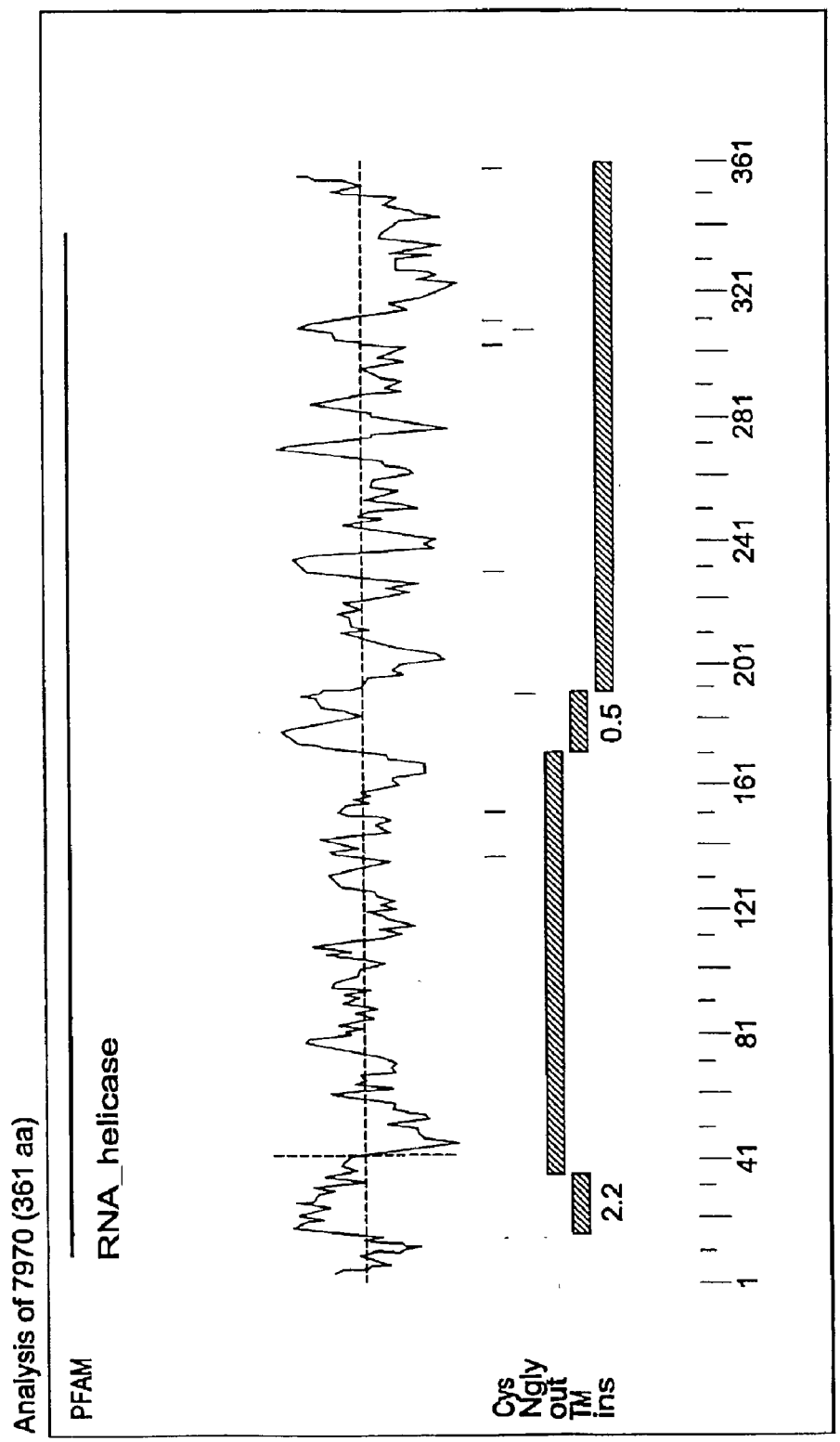
FIG. 1 depicts a hydropathy plot of a human ATPase-like molecule. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human ATPase-like sequence are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

7970, A Novel ATPASE-Like Molecule and Uses Thereof

BACKGROUND OF THE INVENTION

Enzymes that bind to and hydrolyze ATP play a pivotal role in translating chemically stored energy into biological activity. ATPases can function in a variety of cellular processes including, selective ion transport events, actin-based motility, membrane traffic and numerous biosynthetic pathways. Multiple ATPase families exist, including ion pumps, DEAD box-helicases, ABC transporters, and AAA (ATPases Associated to a variety of cellular Activities).

AAA proteins play essential roles in cellular housekeeping, cell division and differentiation and have been identified in prokaryotes and eukaryotes. All members of the AAA family are $Mg^{2+}$ dependent ATPases and comprise a conserved region that binds ATP. Cytosolic, transmembrane, as well as, membrane-associated AAA family members have been identified in various cellular locations and multimeric states.

The biological role of the AAA family members in the cell is diverse. Currently, members of this ATPase family are known to be involved in organelle biogenesis, cell-cycle regulation, vesicle-mediated transport, assembly of proteins through membranes, peroxisome biogenesis, gene expression in yeast and in human, and 26S proteasome function. For a review, see, Confalonieri et al. (1995) *BioEssays* 17:639–650.

The SEC 18 gene product from *S. cerevisiae* is an AAA family member that influences the transport of proteins between the endoplasmic reticulum and the golgi complex. It has been shown that SEC18 is an essential component of a multisubunit 20S "fusion machine" that promotes membrane bilayer fusion coupled to ATP hydrolysis. The 20S fusion machine has been proposed to be involved in the assembly, fusion or division of a variety of other membrane-bound subcellular compartments such as vacuoles, nuclei, mitochondria, or peroxisomes (Wilson et al (1992) *J. Cell.*

*Bio.* 117:531–538). Other AAA family members are involved in mitochondrial function. YME1 is a putative ATP and zinc-dependent protease. Its inactivation leads to several morphological and functional defects, such as the escape of DNA from mitochondria (Thorsness et al (1993) *Mol Cell Biol* 13: 5418–5426).

MSP1 is another AAA ATPase protein family member from yeast that influences mitochondrial function. MSP1 is an intrinsic mitochondrial outer membrane protein with an apparent molecular mass of 40 KDa. MSP1 is known to influence intramitochondrial protein sorting. Nakai et al. have demonstrated that the 61 mC1 fusion protein, normally localized to the outer mitochondrial membrane, is mislocalized to the inner membrane of the mitochondria upon overexpression of MSP1 in yeast cell (Nakai et al. (1993) *J. Biol. Chem.* 268:24262–9).

Several members of the AAA family are involved in the biogenesis of peroxisomes. These organelles contain enzymes responsible for fatty acid oxidation and the elimination of peroxides. AAA family members, such as the PAS genes of *S. cerevisiae*, appear to be required for peroxisome growth, and proliferation (Subramani et al. (1993) *Annu. Rev. Cell Biol.* 9:445–478). Furthermore, mutations in the AAA proteins Pex1p or Pex6p accumulate abnormal peroxisomal vesicles, suggesting a defect in vesicle fusion during peroxisome assembly (Song et al. (1993) *J. Cell Biol.* 123:535–548 and Heyman et al. (1994) *J. Cell Biol.* 127:1269–1273).

AAA family members are also known to regulate transcription. Nelbock et al. described the TBP1 protein that binds human HIV TAT transactivator, thus impairing its activity in cotransfection experiments (Nelbock et al. (1990) *Science* 248: 1650–1653). TBP1 has since been identified as an AAA family member which acts as a transcriptional activator for various promoters (Ohana et al. (1993) *Proc. Natl. Acad. Sci.* 90:138–142).

Various ATP-dependent protease, such as the regulatory components Lon and Clp, are also members of the AAA ATPase family. Evidence suggests the Lon and Clp proteases are involved in DNA replication, recombination and restriction. For instance, human Lon binds specifically to single-stranded DNA in a region of the mitochondrial genome involved in regulation of DNA replication and transcription. It has been suggested that Lon may target and remodel specific DNA binding proteins either for selective degradation or for assembly (Fu et al. (1998) *Biochemistry* 37:1905–1909).

Dubiel et al. discovered that subunit 4 of the human proteasome was in fact a member of the AAA family (Dubiel et al. (1992) *J. Biol. Chem.* 267:22699–22702). Subsequently, at least 5 of the 26S-proteasome subunits already described as transcription factors or cell cycle proteins have now been identified as representatives of the AAA family. Therefore, members of the family are likely to play an essential role in ATP-dependent and ubiquitin-dependent degradation of abnormal proteins and short-lived regulatory proteins and in antigen processing.

Macromolecular machines (protein complexes) carry out nearly every major process in a cell with highly coordinated moving parts driven by energy dependent conformational changes. Examples of such structures include the proteasomes, spliceosomes, ribosomes, peroxisomes and chromosomal replicases. The intricacy of these machines require additional devices to assist in their assembly. The AAA family of ATPase is thought of as a class of molecular chaperones that assist in the noncovalent assembly of other proteins or protein complexes. Thus, the AAA family members play critical regulatory roles in the assembly or regulation of various molecular machines associated with diverse cellular activities. Accordingly, it is valuable to the field of pharmaceutical development to identify and characterize novel ATPases. The present invention advances the state of the art by providing a novel human ATPase-like nucleic acid and polypeptide.

SUMMARY OF THE INVENTION

Isolated nucleic acid molecules corresponding to ATPase-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:2. Further provided are ATPase-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The ATPase molecules of the present invention are useful for modulating agents in a variety of cellular processes including organelle biogenesis, cell-cycle regulation, vesicle-mediated transport, assembly of proteins through membranes, peroxisome biogenesis, protein sorting, gene expression, and 26S proteasome function. The molecules are also useful for the diagnosis and treatment of a variety of clinical conditions.

Accordingly, in one aspect, this invention provides isolated nucleic acid molecules encoding ATPase-like proteins or biologically active portions thereof, as well as nucleic acid fragments suitable as primers or hybridization probes for the detection of ATPase-like-encoding nucleic acids.

Another aspect of this invention features isolated or recombinant ATPase-like proteins and polypeptides. Preferred ATPase-like proteins and polypeptides possess at least one biological activity possessed by naturally occurring ATPase proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the ATPase-like polypeptides and fragments are provided. Such antibodies are useful in detecting the ATPase-like polypeptides as well as in regulating the cellular activities influenced by the ATPase-like polypeptide.

In another aspect, the present invention provides a method for detecting the presence of ATPase-like activity or expression in a biological sample by contacting the biological sample with an agent capable of detecting an indicator of ATPase-like activity such that the presence of ATPase-like activity is detected in the biological sample.

In yet another aspect, the invention provides a method for modulating ATPase-like activity comprising contacting a cell with an agent that modulates (inhibits or stimulates) ATPase-like activity or expression such that ATPase-like activity or expression in the cell is modulated. In one embodiment, the agent is an antibody that specifically binds to ATPase-like proteins. In another embodiment, the agent modulates expression of ATPase-like protein by modulating transcription of an ATPase-like gene, splicing of an ATPase-like mRNA, or translation of an ATPase-like mRNA. In yet another embodiment, the agent is a nucleic acid molecule having a nucleotide sequence that is antisense to the coding strand of the ATPase-like mRNA or the ATPase-like gene.

In one embodiment, the methods of the present invention are used to treat a subject having a disorder characterized by aberrant ATPase-like protein activity or nucleic acid expression by administering an agent that is an ATPase-like modulator to the subject. In one embodiment, the ATPase-like modulator is an ATPase-like protein. In another embodiment, the ATPase-like modulator is an ATPase-like nucleic acid molecule. In other embodiments, the ATPase-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding an ATPase-like protein; (2) misregulation of a gene encoding an ATPase-like protein; and (3) aberrant post-translational modification of an ATPase-like protein, wherein a wild-type form of the gene encodes a protein with an ATPase-like activity.

In another aspect, the invention provides a method for identifying a compound that binds to or modulates the activity of an ATPase-like protein. In general, such methods entail measuring a biological activity of an ATPase-like protein in the presence and absence of a test compound and identifying those compounds that alter the activity of the ATPase-like protein.

The invention also features methods for identifying a compound that modulates the expression of ATPase-like genes by measuring the expression of the ATPase-like sequences in the presence and absence of the compound.

Other features and advantages of the invention will be apparent from the following detailed description and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides ATPase-like molecules. By "ATPase-like molecules" is intended a novel human sequence referred to as 7970, and variants and fragments thereof. These full-length gene sequences or fragments thereof are referred to as "ATPase-like" sequences, indicating they share sequence similarity with ATPase genes. Isolated nucleic acid molecules comprising nucleotide sequences encoding the 7970 polypeptide whose amino acid sequence is given in SEQ ID NO:2, or a variant or fragment thereof, are provided. A nucleotide sequence encoding the 7970 polypeptide is set forth in SEQ ID NO:1 and 3. The sequences are members of the secretin family of ATPases.

A novel human ATPase-like gene sequence, referred to as 7970, is provided. This gene sequence and variants and fragments thereof are encompassed by the term "ATPase-like" molecules or sequences as used herein. The ATPase-like sequences find use in modulating a ATPase function. By "modulating" is intended the upregulating or downregulating of a response. The sequences of the invention find use in modulating organelle biogenesis, cell-cycle regulation, protein degradation, vesicle-mediated transport, assembly of proteins through membranes, peroxisome biogenesis, gene expression, and 26S proteasome function response. That is, the compositions of the invention, affect the targeted activity in either a positive or negative fashion.

Proteins and/or antibodies of the invention are also useful in modulating the above mentioned cellular process.

The present invention provides isolated nucleic acid molecules comprising nucleotide sequences encoding the ATPase-like polypeptides whose amino acid sequences are given in SEQ ID NO:2, or a variant or fragment of the polypeptides. Nucleotide sequences encoding the ATPase-like polypeptides of the invention are set forth in SEQ ID NO:1 and 3.

The disclosed invention relates to methods and compositions for the modulation, diagnosis, and treatment of a variety of disorders. Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sezary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myclocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIG. 2-8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lymphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse-cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, Leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sezary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors. Bone-forming cells include the osteoprogenitor cells, osteoblasts, and osteocytes.

The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

The ATPase-like gene, clone 7970, was identified in a cDNA library. Clone 7970 encodes a mRNA transcript having the corresponding cDNA set forth in SEQ ID NO:1. This transcript has a 1086 nucleotide open reading frame (nucleotides 79–1165 of SEQ ID NO:1), which encodes a 361 amino acid protein (SEQ ID NO:2). An analysis of the full-length 7970 polypeptide predicts that the N-terminal 41 amino acids represent a signal peptide. Transmembrane segments from amino acids (aa) 16–34 and 173–191 were predicted by MEMSAT. Transmembrane segments were also predicted from aa 133–151 of the presumed mature peptide sequence. Prosite program analysis was used to predict various sites within the 7970 protein. N-glycosylation sites were predicted at aa 200–203 and 316–319. Protein kinase C phosphorylation sites were predicted at aa 33–35, 44–46, 146–148, 163–165, 170–172 and 273–239. Casein kinase II phosphorylation sites were predicted at aa 12–15, 70–73, 89–92, 146–149, 161–164, 202–205, 218–212, 295–298, 317–320, and 322–325. An N-myristoylation site is predicted at aa 136–141. An ATP/GTP-binding site motif A (P-loop) was predicted at aa 133–140. A Leucine zipper pattern was predicted at aa 109–130.

The ATPase-like protein possesses a NB-ARC domain, from aa 131–145, an AAA domain from aa 128–312, an adenylate kinase domain from aa 131–139, a RNA helicase domain from aa 7–337, as predicted by HMMer, Version 2. For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html. The NB-ARC domain is a novel signaling motif shared by plant resistant gene products and regulators of cell death in animals. See for example, Van der Biezen et al. (1998) *Curr Biol* 8:229–227. Adenylate kinase is a small monomeric enzyme that catalyzes the reversible transfer of MgATP to AMP. In mammals there are three different isozymes: AK1 (or myokinase), which is cytosolic; AK2, which is located in the outer compartment of mitochondria; and, AK3 (or GTP:AMP phosphotransferase), which is located in the mitochondrial matrix and which uses MgGTP instead of MgATP. The RNA helices domain is found in a family of RNA helices thought to be involved in duplex unwinding during viral RNA replication. Members of this family are found in a variety of single stranded RNA viruses. See for example, Gorbalenya et al. (1989) *NAR* 17:4713–4730. The AAA domain (ATPase Associated with various cellular Activities) is found in a family of proteins that often perform chaperone-like functions that assist in the assembly, operation, or disassembly of protein complexes. See for example, Confalonieri et al. (1995) *Bioessays* 17:639–650 and Neuwald et al. (1999) *Genome Research* 9:27–43.

The 7970 protein displays 37% identity from aa 202–312, 34% identity from aa 154–292, and 57% identity to aa 128–165 to a Prodom consensus sequence found in members of the Lon family of ATP-dependent proteases; 25% identity from aa 13–127 to a Prodom consensus sequence found in the MSP1 protein homolog; 25% identity from aa 126–336 to a Prodom consensus sequence found in a putative cell division protein from *Treponema pallidum;* 22% identity from aa 130–347 to a Prodom consensus sequence found in a probable Peroxin-6 protein which may play a role in biogenesis of peroxisomes; 35% identity from aa 77–351 and 31% identity from aa 324–351 to a Prodom consensus sequence found in members of the peptidase family 16S; 20% identity from aa 129–355 to a Prodom consensus sequence found in a chromosomal replication initiator protein; and, 32% identity from aa 117–198 to a Prodom consensus sequence found in a TAT-binding homolog. Furthermore, the amino acid sequence of the 7970 sequence shares approximately 47% sequence identity with the *C. elegans* MSPI protein homolog (Genbank Accession No. P54815). This sequence alignment was generated using the clustal method.

The ATPase-like sequences of the invention are members of a family of molecules (the "ATPase family") having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Figure 3:
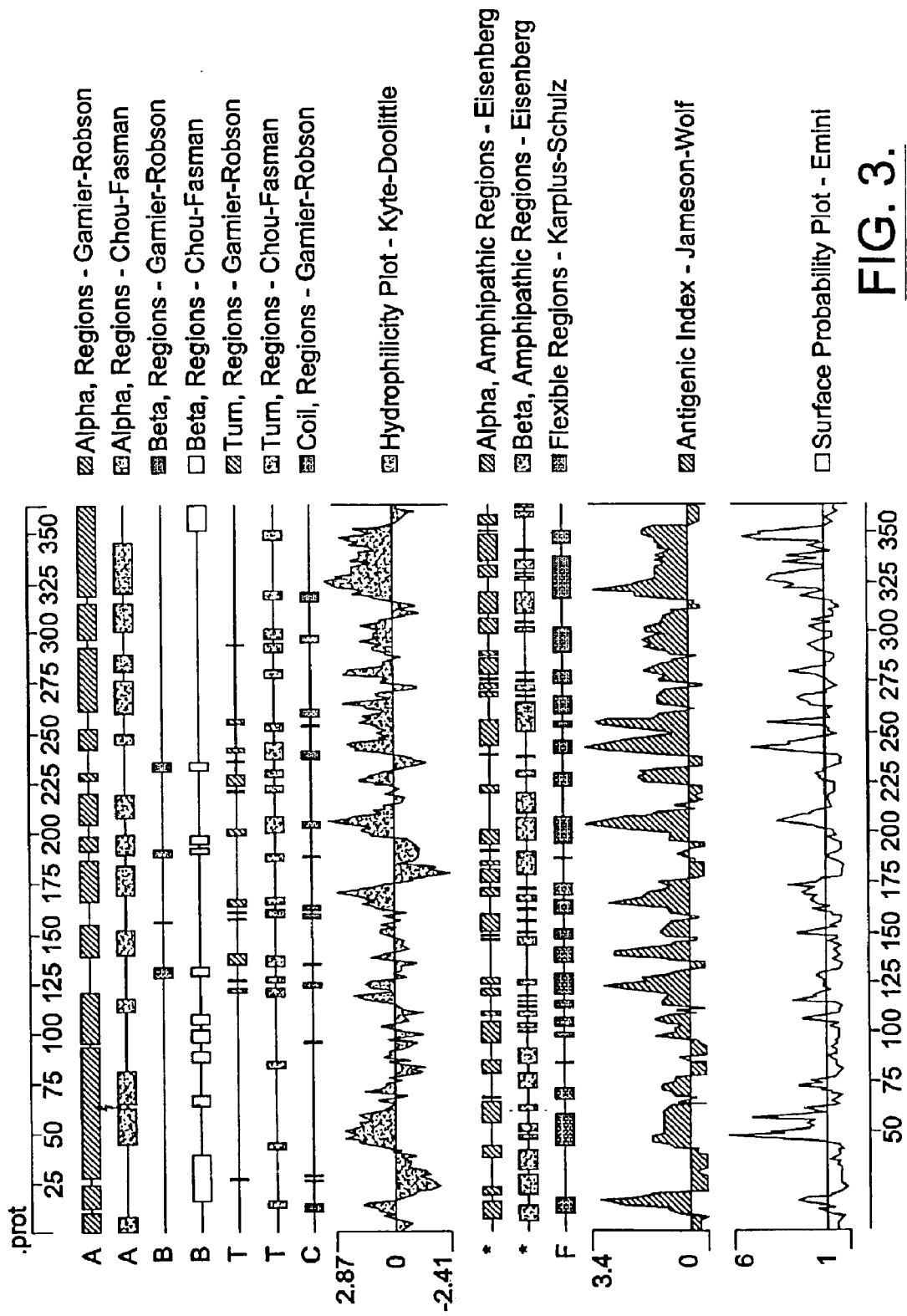
FIG. 3 shows an analysis of the 7970 amino acid sequence: $\alpha\beta$ turn and coil regions; hydrophilicity; amphipathic regions; flexible regions; antigenic index; and surface probability plot.

As used herein, the term "AAA domain" includes an amino acid sequence of about 80–184 amino acid residues in length and having a bit score for the alignment of the sequence to the AAA domain (HMM) of at least 8. Preferably, an AAA domain includes at least about 50–200 amino acids, more preferably about 100–185 amino acid residues, or about 81–185 amino acids and has a bit score for the alignment of the sequence to the AAA domain (HMM) of at least 16 or greater. The AAA domain (HMM) has been assigned the PFAM Accession No. PF00004 (http://pfam.wustl.edu/). An alignment of the AAA domain (amino acids 128 to 312 of SEQ ID NO:2) of the human ATPase-like sequence with a consensus amino acid sequence derived from a hidden Markov model is depicted in FIG. 3.

In a preferred embodiment ATPase-like polypeptide or protein has a "AAA domain" or a region which includes at least about 100–250 more preferably about 130–200 or 160–200 amino acid residues and has at least about 60%, 70%, 80%, 90%, 95%, 99%, or 100% sequence identity with an "AAA domain," e.g., the AAA domain of human ATPase-like molecule (e.g., amino acid residues 128–312 of SEQ ID NO:2).

To identify the presence of an "AAA" domain in an ATPase-like protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, an ATPase-like protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, http://pfam.wustl.edu/cgi-bin/getdesc?name=7tm-1, and Zagotta W. N. et al. (1996) *Annual Rev. Neuronsci.* 19:235–63, the contents of which are incorporated herein by reference.

In a preferred embodiment, an ATPase-like] polypeptide or protein has at least one transmembrane domain or a region which includes at least 18, 20, 22, 24, 25, 30, 35 or 40 amino acid residues and has at least about 60%, 70% 80% 90% 95%, 99%, or 100% sequence identity with a "transmembrane domain," e.g., at least one transmembrane domain of human ATPase-like (e.g., amino acid residues 18 of SEQ ID NO:2).

In another embodiment, an ATPase-like protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring ATPase-like, or ATPase-like protein.

In a preferred embodiment, an ATPase-like polypeptide or protein has a "non-transmembrane domain" or a region which includes at least about 1–170, preferably about 100–170, about 50–160, and about 20–125 amino acid residues, and has at least about 60%, 70% 80% 90% 95%, 99% or 100% sequence identity with a "non-transmembrane domain", e.g., a non-transmembrane domain of human ATPase-like (e.g., residues 191 and 361 of SEQ ID NO:2). Preferably, a non-transmembrane domain is capable of catalytic activity (e.g., ATPase-like activity).

A non-transmembrane domain located at the N-terminus of an ATPase-like protein or polypeptide is referred to herein as an "N-terminal non-transmembrane domain." As used herein, an "N-terminal non-transmembrane domain" includes an amino acid sequence having about 1–350, preferably about 30–325, more preferably about 50–320, or even more preferably about 80–310 amino acid residues in length and is located outside the boundaries of a membrane. For example, an N-terminal non-transmembrane domain is located at about amino acid residues 1–15 of SEQ ID NO:2.

Similarly, a non-transmembrane domain located at the C-terminus of an ATPase-like protein or polypeptide is referred to herein as a "C-terminal non-transmembrane domain." As used herein, an "C-terminal non-transmembrane domain" includes an amino acid sequence having about 1–300, preferably about 15–290, preferably about 20–270, more preferably about 25–255 amino acid residues in length and is located outside the boundaries of a membrane. For example, an C-terminal non-transmembrane domain is located at about amino acid residues 191–361 of SEQ ID NO:2.

An ATPase-like molecule can further include a signal sequence. As used herein, a "signal sequence" refers to a peptide of about 20–80 amino acid residues in length which occurs at the N-terminus of secretory and integral membrane proteins and which contains a majority of hydrophobic amino acid residues. For example, a signal sequence contains at least about 12–25 amino acid residues, preferably about 30–70 amino acid residues, more preferably about 61 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, an ATPase-like protein contains a signal sequence of about amino acids 1–41 of SEQ ID NO:2. The "signal sequence" is cleaved during processing of the mature protein. The mature ATPase-like protein corresponds to amino acids 42–361 of SEQ ID NO:2.

Preferred ATPase-like polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to ATPase-like nucleic acid molecules of the invention. BLAST protein searches can be performed with the XBLAST program, score=50, wordlength=3, to obtain amino acid sequences homologous to ATPase-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated ATPase-like proteins and polypeptides having an ATPase-like protein activity. As used interchangeably herein, a "ATPase-like protein activity", "biological activity of an ATPase-like protein", or "functional activity of an ATPase-like protein" refers to an activity exerted by an ATPase-like protein, polypeptide, or nucleic acid molecule on an ATPase-like responsive cell as determined in vivo, or in vitro, according to standard assay techniques. An ATPase-like activity can be a direct activity, such as an association with or an enzymatic activity on a second protein, or an indirect activity, such as a cellular signaling activity mediated by interaction of the ATPase-like protein with a second protein. In a preferred embodiment, an ATPase-like activity includes at least one or more of the following activities: (1) modulating (stimulating and/or enhancing or inhibiting) cellular division; (2) modulating organelle biogenesis; (3) modulating protein sorting; (4) modulating gene expression; (5) modulating protein degradation; and (6) modulating the function of the 26S proteosome.

An "isolated" or "purified" ATPase-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated ATPase-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An ATPase-like protein that is substantially free of cellular material includes preparations of ATPase-like protein having less than about 30%, 20%, 10%, or 5% (by dry weight) of non-ATPase protein (also referred to herein as a "contaminating protein"). When the ATPase-like protein or biologically active portion thereof is recombinantly produced, preferably, culture medium represents less than about 30%, 20%, 10%, or 5% of the volume of the protein preparation. When ATPase-like protein is produced by chemical synthesis, preferably the protein preparations have less than about 30%, 20%, 10%, or 5% (by dry weight) of chemical precursors or non-ATPase chemicals.

Various aspects of the invention are described in further detail in the following subsections.

I. Isolated Nucleic Acid Molecules

One aspect of the invention pertains to isolated nucleic acid molecules comprising nucleotide sequences encoding ATPase-like proteins and polypeptides or biologically active portions thereof, as well as nucleic acid molecules sufficient for use as hybridization probes to identify ATPase-like-encoding nucleic acids (e.g., ATPase-like mRNA) and fragments for use as PCR primers for the amplification or mutation of ATPase-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the ATPase-like proteins of the present invention include sequences set forth in SEQ ID NO:1, 3, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the ATPase-like protein encoded by these nucleotide sequences is set forth in SEQ ID NO:2. The invention also encompasses nucleic acid molecules comprising nucleotide sequences encoding partial-length ATPase-like proteins, including the sequence set forth in SEQ ID NO:1, 3, and complements thereof.

Nucleic acid molecules that are fragments of these ATPase-like nucleotide sequences are also encompassed by the present invention. By "fragment" is intended a portion of the nucleotide sequence encoding an ATPase-like protein. A fragment of an ATPase-like nucleotide sequence may encode a biologically active portion of an ATPase-like protein, or it may be a fragment that can be used as a hybridization probe or PCR primer using methods disclosed below. A biologically active portion of an ATPase-like protein can be prepared by isolating a portion of one of the ATPase-like nucleotide sequences of the invention, expressing the encoded portion of the ATPase-like protein (e.g., by recombinant expression in vitro), and assessing the activity of the encoded portion of the ATPase-like protein. Nucleic acid molecules that are fragments of an ATPase-like nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 nucleotides, or up to the number of nucleotides present in a full-length ATPase-like nucleotide sequence disclosed herein (for example, 1748 nucleotides for SEQ ID NO:1 and 1086 nucleotides for SEQ ID NO:3) depending upon the intended use. Alternatively, a nucleic acid molecules that is a fragment of an ATPase-like nucleotide sequence of the present invention comprises a nucleotide sequence consisting of nucleotides 1–100, 100–200, 200–300, 300–400, 400–500, 500–600, 600–700, 700–800, 800–900, 900–1086, 1086–1100, 1100–1200, 1200–1300, 1300–1400, 1400–1500, 1500–1600, 1600–1700, or 1700–1748 of SEQ ID NO:1 or 3.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of an ATPase-like nucleotide sequence that encodes a biologically active portion of an ATPase-like protein of the invention will encode at least 15, 25, 30, 50, 75, 100, 125, 150, 175, 200, 250, or 300 contiguous amino acids, or up to the total number of amino acids present in a full-length ATPase-like protein of the invention (for example, 362 amino acids). Fragments of an ATPase-like nucleotide sequence that are useful as hybridization probes for PCR primers generally need not encode a biologically, active portion of an ATPase-like protein.

Nucleic acid molecules that are variants of the ATPase-like nucleotide sequences disclosed herein are also encompassed by the present invention. "Variants" of the ATPase-like nucleotide sequences include those sequences that encode the ATPase-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the ATPase-like proteins disclosed in the present invention as discussed below. Generally, nucleotide sequence variants of the invention will have at least 45%, 55%, 65%, 75%, 85%, 95%, or 98% identity to a particular nucleotide sequence disclosed herein. A variant ATPase-like nucleotide sequence will encode an ATPase-like protein that has an amino acid sequence having at least 45%, 55%, 65%, 75%, 85%, 95%, or 98% identity to the amino acid sequence of an ATPase-like protein disclosed herein.

In addition to the ATPase-like nucleotide sequences shown in SEQ ID NOS: 1 and 3, it will be appreciated by those skilled in the art that DNA sequence polymorphisms that lead to changes in the amino acid sequences of ATPase-like proteins may exist within a population (e.g., the human population). Such genetic polymorphism in an ATPase-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an ATPase-like protein, preferably a mammalian ATPase-like protein. As used herein, the phrase "allelic variant" refers to a nucleotide sequence that occurs at an ATPase-like locus or to a polypeptide encoded by the nucleotide sequence. Such natural allelic variations can typically result in 1–5% variance in the nucleotide sequence of the ATPase-like gene. Any and all such nucleotide variations and resulting amino acid polymorphisms or variations in an ATPase-like sequence that are the result of natural allelic variation and that do not alter the functional activity of ATPase-like proteins are intended to be within the scope of the invention.

Moreover, nucleic acid molecules encoding ATPase-like proteins from other species (ATPase-like homologues), which have a nucleotide sequence differing from that of the ATPase-like sequences disclosed herein, are intended to be within the scope of the invention. For example, nucleic acid molecules corresponding to natural allelic variants and homologues of the human ATPase-like cDNA of the invention can be isolated based on their identity to the human ATPase-like nucleic acid disclosed herein using the human cDNA, or a portion thereof, as a hybridization probe according to standard hybridization techniques under stringent hybridization conditions as disclosed below.

In addition to naturally-occurring allelic variants of the ATPase-like sequences that may exist in the population, the skilled artisan will further appreciate that changes can be introduced by mutation into the nucleotide sequences of the invention thereby leading to changes in the amino acid sequence of the encoded ATPase-like proteins, without altering the biological activity of the ATPase-like proteins. Thus, an isolated nucleic acid molecule encoding an ATPase-like protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an ATPase-like protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the growth factor and cytokine receptor signature 2 sequence and the U-PAR/Ly-6 domain sequence of SEQ ID NO:2, where such residues are essential for protein activity.

Alternatively, variant ATPase-like nucleotide sequences can be made by introducing mutations randomly along all or part of an ATPase-like coding sequence, such as by saturation mutagenesis, and the resultant mutants can be screened for ATPase-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The ATPase-like nucleotide sequences of the invention, and fragments and variants thereof, can be used as probes and/or primers to identify and/or clone ATPase-like homologues in other cell types, e.g., from other tissues, as well as ATPase-like homologues from other mammals. Such probes can be used to detect transcripts or genomic sequences encoding the same or identical proteins. These probes can be used as part of a diagnostic test kit for identifying cells or tissues that misexpress an ATPase-like protein, such as by measuring levels of an ATPase-like-encoding nucleic acid in a sample of cells from a subject, e.g., detecting ATPase-like mRNA levels or determining whether a genomic ATPase-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). ATPase-like nucleotide sequences isolated based on their sequence identity to the ATPase-like nucleotide sequences set forth herein or to fragments and variants thereof are encompassed by the present invention.

In a hybridization method, all or part of a known ATPase-like nucleotide sequence can be used to screen cDNA or genomic libraries. Methods for construction of such cDNA and genomic libraries are generally known in the art and are disclosed in Sambrook et al (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known ATPase-like nucleotide sequence disclosed herein. Degenerate primers designed on the basis of conserved nucleotides or amino acid residues in a known ATPase-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an ATPase-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified ATPase-like nucleic acid molecule hybridizes under stringent conditions to a probe that is a nucleic acid molecule comprising one of the ATPase-like nucleotide sequences of the invention or a fragment thereof. In another embodiment, the previously unknown ATPase-like nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the ATPase-like nucleotide sequences disclosed herein or a fragment thereof.

Accordingly, in another embodiment, an isolated previously unknown ATPase-like nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, 3, or a complement, fragment, or variant thereof.

As used herein, the term "hybridizes under stringent conditions" is intended to describe conditions for hybridization and washing under which nucleotide sequences typically remain hybridized to each other. Such stringent conditions are known to those skilled in the art and can be found in *Current Protocols in Molecular Biology* (John Wiley & Sons, New York (1989)), 6.3.1–6.3.6. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule that hybridizes under stringent conditions to an ATPase-like sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the ATPase-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the ATPase-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire ATPase-like coding strand, or to only a portion thereof, e.g., all or part of the protein coding region (or open reading frame). An antisense nucleic acid molecule can be antisense to a noncoding region of the coding strand of a nucleotide sequence encoding an ATPase-like protein. The noncoding regions are the 5' and 3' sequences that flank the coding region and are not translated into amino acids.

Given the coding-strand sequence encoding an ATPase-like protein disclosed herein (e.g., SEQ ID NO:1), antisense nucleic acids of the invention can be designed according to the rules of Watson and Crick base pairing. The antisense nucleic acid molecule can be complementary to the entire coding region of ATPase-like mRNA, but more preferably is an oligonucleotide that is antisense to only a portion of the coding or noncoding region of ATPase-like mRNA. For example, the antisense oligonucleotide can be complementary to the region surrounding the translation start site of ATPase-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an ATPase-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave ATPase-like mRNA transcripts to thereby inhibit translation of ATPase-like mRNA. A ribozyme having specificity for an ATPase-like—encoding nucleic acid can be designed based upon the nucleotide sequence of an ATPase-like cDNA disclosed herein (e.g., SEQ ID NO:1). See, e.g., Cech et al., U.S. Pat. No. 4,987,071; and Cech et al., U.S. Pat. No. 5,116,742. Alternatively, ATPase-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, ATPase-like gene expression can be inhibited by targeting nucleotide sequences complementary to the regulatory region of the ATPase-like protein (e.g., the ATPase-like promoter and/or enhancers) to form triple helical structures that prevent transcription of the ATPase-like gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of an ATPase-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of an ATPase-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated ATPase-Like Proteins and Anti-ATPase-Like Antibodies

ATPase-like proteins are also encompassed within the present invention. By "ATPase-like protein" is intended a protein having the amino acid sequence set forth in SEQ ID NO: 2, as well as fragments, biologically active portions, and variants thereof.

"Fragments" or "biologically active portions" include polypeptide fragments suitable for use as immunogens to raise anti-ATPase-like antibodies. Fragments include peptides comprising amino acid sequences sufficiently identical to or derived from the amino acid sequence of an ATPase-like protein, or partial-length protein, of the invention and exhibiting at least one activity of an ATPase-like protein, but which include fewer amino acids than the full-length (SEQ ID NO:2) ATPase-like protein disclosed herein. Typically, biologically active portions comprise a domain or motif with at least one activity of the ATPase-like protein. A biologically active portion of an ATPase-like protein can be a polypeptide which is, for example, 10, 25, 50, 100 or more amino acids in length. Such biologically active portions can be prepared by recombinant techniques and evaluated for one or more of the functional activities of a native ATPase-like protein. As used here, a fragment comprises at least 5 contiguous amino acids of SEQ ID NO:2. The invention encompasses other fragments, however, such as any fragment in the protein greater than 6, 7, 8, or 9 amino acids.

By "variants" is intended proteins or polypeptides having an amino acid sequence that is at least about 45%, 55%, 65%, preferably about 75%, 85%, 95%, or 98% identical to the amino acid sequence of SEQ ID NO:2. Variants also include polypeptides encoded by a nucleic acid molecule that hybridizes to the nucleic acid molecule of SEQ ID NO:2, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:2. If alignment is needed for this comparison the sequences should be aligned for maximum identity. "Looped" out sequences from deletions or insertions, or mismatches, are considered differences. Such variants generally retain the functional activity of the ATPase-like proteins of the invention. Variants include polypeptides that differ in amino acid sequence due to natural allelic variation or mutagenesis.

The invention also provides ATPase-like chimeric or fusion proteins. As used herein, an ATPase-like "chimeric protein" or "fusion protein" comprises an ATPase-like polypeptide operably linked to a non-ATPase polypeptide. An "ATPase-like polypeptide" refers to a polypeptide having an amino acid sequence corresponding to an ATPase-like protein, whereas a "non-ATPase-like polypeptide" refers to a polypeptide having an amino acid sequence corresponding to a protein that is not substantially identical to the ATPase-like protein, e.g., a protein that is different from the ATPase-like protein and which is derived from the same or a different organism. Within an ATPase-like fusion protein, the ATPase-like polypeptide can correspond to all or a portion of an ATPase-like protein, preferably at least one biologically active portion of an ATPase-like protein. Within the fusion protein, the term "operably linked" is intended to indicate that the ATPase-like polypeptide and the non-ATPase-like polypeptide are fused in-frame to each other. The non-ATPase-like polypeptide can be fused to the N-terminus or C-terminus of the ATPase-like polypeptide.

One useful fusion protein is a GST-ATPase-like fusion protein in which the ATPase-like sequences are fused to the C-terminus of the GST sequences. Such fusion proteins can facilitate the purification of recombinant ATPase-like proteins.

In yet another embodiment, the fusion protein is an ATPase-like-immunoglobulin fusion protein in which all or part of an ATPase-like protein is fused to sequences derived from a member of the immunoglobulin protein family. The ATPase-like-immunoglobulin fusion proteins of the invention can be incorporated into pharmaceutical compositions and administered to a subject to inhibit an interaction between an ATPase-like ligand and an ATPase-like protein on the surface of a cell, thereby suppressing ATPase-like-mediated signal transduction in vivo. The ATPase-like-immunoglobulin fusion proteins can be used to affect the bioavailability of an ATPase-like cognate ligand. Inhibition of the ATPase-like ligand/ATPase-like interaction may be useful therapeutically, both for treating proliferative and differentiative disorders and for modulating (e.g., promoting or inhibiting) cell survival. Moreover, the ATPase-like-immunoglobulin fusion proteins of the invention can be used as immunogens to produce anti-ATPase-like antibodies in a subject, to purify ATPase-like ligands, and in screening assays to identify molecules that inhibit the interaction of an ATPase-like protein with an ATPase-like ligand.

Preferably, an ATPase-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, an ATPase-like-encoding nucleic acid can be cloned into a commercially available expression vector such that it is linked in-frame to an existing fusion moiety. Variants of the ATPase-like proteins can function as either ATPase-like agonists (mimetics) or as ATPase-like antagonists. Variants of the ATPase-like protein can be generated by mutagenesis, e.g., discrete point mutation or truncation of the ATPase-like protein. An agonist of the ATPase-like protein can retain substantially the same, or a subset, of the biological activities of the naturally occurring form of the ATPase-like protein. An antagonist of the ATPase-like protein can inhibit one or more of the activities of the naturally occurring form of the ATPase-like protein by, for example, competitively binding to a downstream or upstream member of a cellular signaling cascade that includes the ATPase-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the ATPase-like proteins.

Variants of an ATPase-like protein that function as either ATPase-like agonists or as ATPase-like antagonists can be identified by screening combinatorial libraries of mutants, e.g., truncation mutants, of an ATPase-like protein for ATPase-like protein agonist or antagonist activity. In one embodiment, a variegated library of ATPase-like variants is generated by combinatorial mutagenesis at the nucleic acid level and is encoded by a variegated gene library. A variegated library of ATPase-like variants can be produced by, for example, enzymatically ligating a mixture of synthetic oligonucleotides into gene sequences such that a degenerate set of potential ATPase-like sequences is expressible as individual polypeptides, or alternatively, as a set of larger fusion proteins (e.g., for phage display) containing the set of ATPase-like sequences therein. There are a variety of methods that can be used to produce libraries of potential ATPase-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ATPase-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of an ATPase-like protein coding sequence can be used to generate a variegated population of ATPase-like fragments for screening and subsequent selection of variants of an ATPase-like protein. In one embodiment, a library of coding sequence fragments can be generated by treating a double-stranded PCR fragment of an ATPase-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the ATPase-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of ATPase-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify ATPase-like variants (Arkin and Yourvan (1992) *Proc. Natl. Acad. Sci. USA* 89:7811–7815; Delgrave et al. (1993) *Protein Engineering* 6(3):327–331).

An isolated ATPase-like polypeptide of the invention can be used as an immunogen to generate antibodies that bind ATPase-like proteins using standard techniques for polyclonal and monoclonal antibody preparation. The full-length ATPase-like protein can be used or, alternatively, the invention provides antigenic peptide fragments of ATPase-like proteins for use as immunogens. The antigenic peptide of an ATPase-like protein comprises at least 8, preferably 10, 15, 20, or 30 amino acid residues of the amino acid sequence shown in SEQ ID NO:2 and encompasses an epitope of an ATPase-like protein such that an antibody raised against the peptide forms a specific immune complex with the ATPase-like protein. Preferred epitopes encompassed by the antigenic peptide are regions of a ATPase-like protein that are located on the surface of the protein, e.g., hydrophilic regions.

Accordingly, another aspect of the invention pertains to anti-ATPase-like polyclonal and monoclonal antibodies that bind an ATPase-like protein. Polyclonal anti-ATPase-like antibodies can be prepared by immunizing a suitable subject (e.g., rabbit, goat, mouse, or other mammal) with an ATPase-like immunogen. The anti-ATPase-like antibody titer in the immunized subject can be monitored over time by standard techniques, such as with an enzyme linked immunosorbent assay (ELISA) using immobilized ATPase-like protein. At an appropriate time after immunization, e.g., when the anti-ATPase-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-ATPase-like antibody can be identified and isolated by screening a recombinant combinatorial immunoglobulin library (e.g., an antibody phage display library) with an ATPase-like protein to thereby isolate immunoglobulin library members that bind the ATPase-like protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-ATPase-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-ATPase-like antibody (e.g., monoclonal antibody) can be used to isolate ATPase-like proteins by standard techniques, such as affinity chromatography or immunoprecipitation. An anti-ATPase-like antibody can facilitate the purification of natural ATPase-like protein from cells and of recombinantly produced ATPase-like protein expressed in host cells. Moreover, an anti-ATPase-like antibody can be used to detect ATPase-like protein (e.g., in a cellular lysate or cell supernatant) in order to evaluate the abundance and pattern of expression of the ATPase-like protein. Anti-ATPase-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding an ATPase-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ATPase-like proteins, mutant forms of ATPase-like proteins, fusion proteins, etc.). It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of ATPase-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Bane ji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to ATPase-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an ATPase-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) ATPase-like protein. Accordingly, the invention further provides methods for producing ATPase-like protein using the host cells of the invention. In one embodiment, the method comprises culturing the host cell of the invention, into which a recombinant expression vector encoding an ATPase-like protein has been introduced, in a suitable medium such that ATPase-like protein is produced. In another embodiment, the method further comprises isolating ATPase-like protein from the medium or the host cell.

The host cells of the invention can also be used to produce nonhuman transgenic animals. For example, in one embodiment, a host cell of the invention is a fertilized oocyte or an embryonic stem cell into which ATPase-like-coding sequences have been introduced. Such host cells can then be used to create nonhuman transgenic animals in which exogenous ATPase-like sequences have been introduced into their genome or homologous recombinant animals in which endogenous ATPase-like sequences have been altered. Such animals are useful for studying the function and/or activity of ATPase-like genes and proteins and for identifying and/or evaluating modulators of ATPase-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous ATPase-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing ATPase-like-encoding nucleic acid into the male pronuclei of a fertilized oocyte, e.g., by microinjection, retroviral infection, and allowing the oocyte to develop in a pseudopregnant female foster animal. The ATPase-like cDNA sequence can be introduced as a transgene into the genome of a nonhuman animal. Alternatively, a homologue of the mouse ATPase-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the ATPase-like transgene to direct expression of ATPase-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the ATPase-like transgene in its genome and/or expression of ATPase-like mRNA in tissues or cells of the animals. A transgenic founder animal can then be used to breed additional animals carrying the transgene. Moreover, transgenic animals carrying a transgene encoding ATPase-like gene can further be bred to other transgenic animals carrying other transgenes.

To create a homologous recombinant animal, one prepares a vector containing at least a portion of an ATPase-like gene or a homolog of the gene into which a deletion, addition, or substitution has been introduced to thereby alter, e.g., functionally disrupt, the ATPase-like gene. In a preferred embodiment, the vector is designed such that, upon homologous recombination, the endogenous ATPase-like gene is functionally disrupted (i.e., no longer encodes a functional protein; also referred to as a "knock out" vector). Alternatively, the vector can be designed such that, upon homologous recombination, the endogenous ATPase-like gene is mutated or otherwise altered but still encodes functional protein (e.g., the upstream regulatory region can be altered to thereby alter the expression of the endogenous ATPase-like protein). In the homologous recombination vector, the altered portion of the ATPase-like gene is flanked at its 5' and 3' ends by additional nucleic acid of the ATPase-like gene to allow for homologous recombination to occur between the exogenous ATPase-like gene carried by the vector and an endogenous ATPase-like gene in an embryonic stem cell. The additional flanking ATPase-like nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced ATPase-like gene has homologously recombined with the endogenous ATPase-like gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The ATPase-like nucleic acid molecules, ATPase-like proteins, and anti-ATPase-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an ATPase-like protein or anti-ATPase-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express ATPase-like protein (e.g., via a recombinant expression vector in a host cell in gene therapy applications), to detect ATPase-like mRNA (e.g., in a biological sample) or a genetic lesion in an ATPase-like gene, and to modulate ATPase-like activity. In addition, the ATPase-like proteins can be used to screen drugs or compounds that modulate the cellular activities described above as well as to treat disorders characterized by insufficient or excessive production of ATPase-like protein or production of ATPase-like protein forms that have decreased or aberrant activity compared to ATPase-like wild type protein. In addition, the anti-ATPase-like antibodies of the invention can be used to detect and isolate ATPase-like proteins and modulate ATPase-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to ATPase-like proteins or have a stimulatory or inhibitory effect on, for example, ATPase-like expression or ATPase-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the ATPase-like protein can be accomplished, for example, by coupling the test compound with a radioisotope or enzymatic label such that binding of the test compound to the ATPase-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the ATPase-like protein to bind to or interact with an ATPase-like target molecule. By "target molecule" is intended a molecule with which an ATPase-like protein binds or interacts in nature. In a preferred embodiment, the ability of the ATPase-like protein to bind to or interact with an ATPase-like target molecule can be determined by monitoring the activity of the target molecule. For example, the activity of the target molecule can be monitored by detecting alterations in protein sorting, cell division, protein degradation, organelle biogenesis, etc., detecting catalytic/enzymatic activity of the target on an appropriate substrate, detecting the induction of a reporter gene (e.g., an ATPase-like-responsive regulatory element operably linked to a nucleic acid encoding a detectable marker, e.g., luciferase), or detecting a cellular response, for example, cellular differentiation or cell proliferation.

In yet another embodiment, an assay of the present invention is a cell-free assay comprising contacting an ATPase-like protein or biologically active portion thereof with a test compound and determining the ability of the test compound to bind to the ATPase-like protein or biologically active portion thereof. Binding of the test compound to the ATPase-like protein can be determined either directly or indirectly as described above. In a preferred embodiment, the assay includes contacting the ATPase-like protein or biologically active portion thereof with a known compound that binds ATPase-like protein to form an assay mixture, contacting the assay mixture with a test compound, and determining the ability of the test compound to preferentially bind to ATPase-like protein or biologically active portion thereof as compared to the known compound.

In another embodiment, an assay is a cell-free assay comprising contacting ATPase-like protein or biologically active portion thereof with a test compound and determining the ability of the test compound to modulate (e.g., stimulate or inhibit) the activity of the ATPase-like protein or biologically active portion thereof Determining the ability of the test compound to modulate the activity of an ATPase-like protein can be accomplished, for example, by determining the ability of the ATPase-like protein to bind to an ATPase-like target molecule as described above for determining direct binding. In an alternative embodiment, determining the ability of the test compound to modulate the activity of an ATPase-like protein can be accomplished by determining the ability of the ATPase-like protein to further modulate an ATPase-like target molecule. For example, the catalytic/enzymatic activity of the target molecule on an appropriate substrate can be determined as previously described.

In yet another embodiment, the cell-free assay comprises contacting the ATPase-like protein or biologically active portion thereof with a known compound that binds an ATPase-like protein to form an assay mixture, contacting the assay mixture with a test compound, and determining the ability of the test compound to preferentially bind to or modulate the activity of an ATPase-like target molecule.

In the above-mentioned assays, it may be desirable to immobilize either an ATPase-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/ATPase-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or ATPase-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of ATPase-like binding or activity determined using standard techniques.

Other techniques for immobilizing proteins on matrices can also be used in the screening assays of the invention. For example, either ATPase-like protein or its target molecule can be immobilized utilizing conjugation of biotin and streptavidin. Biotinylated ATPase-like molecules or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with an ATPase-like protein or target molecules but which do not interfere with binding of the ATPase-like protein to its target molecule can be derivatized to the wells of the plate, and unbound target or ATPase-like protein trapped in the wells by antibody conjugation. Methods for detecting such complexes, in addition to those described above for the GST-immobilized complexes, include immunodetection of complexes using antibodies reactive with the ATPase-like protein or target molecule, as well as enzyme-linked assays that rely on detecting an enzymatic activity associated with the ATPase-like protein or target molecule.

In another embodiment, modulators of ATPase-like expression are identified in a method in which a cell is contacted with a candidate compound and the expression of ATPase-like mRNA or protein in the cell is determined relative to expression of ATPase-like mRNA or protein in a cell in the absence of the candidate compound. When expression is greater (statistically significantly greater) in the presence of the candidate compound than in its absence, the candidate compound is identified as a stimulator of ATPase-like mRNA or protein expression. Alternatively, when expression is less (statistically significantly less) in the presence of the candidate compound than in its absence, the candidate compound is identified as an inhibitor of ATPase-like mRNA or protein expression. The level of ATPase-like mRNA or protein expression in the cells can be determined by methods described herein for detecting ATPase-like mRNA or protein.

In yet another aspect of the invention, the ATPase-like proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with ATPase-like protein ("ATPase-like-binding proteins" or "ATPase-like-bp") and modulate ATPase-like activity. Such ATPase-like-binding proteins are also likely to be involved in the propagation of signals by the ATPase-like proteins as, for example, upstream or downstream elements of the ATPase-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial ATPase-like gene sequences of the invention can be used to map their respective ATPase-like genes on a chromosome, thereby facilitating the location of gene regions associated with genetic disease. Computer analysis of ATPase-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the ATPase-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map an ATPase-like sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma eta a. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of ATPase-like genes uses ATPase-like polypeptides and fragments and sequences of the present invention and antibodies specific thereto. This mapping can be carried out by specifically detecting the presence of a ATPase-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a ATPase-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the ATPase-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The ATPase-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the ATPase-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The ATPase-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:2, is used, a more appropriate number of primers for positive individual identification would be 500 to 2,000.

3. Use of Partial ATPase-Like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the ATPase-like sequences or portions thereof, e.g., fragments derived from the noncoding regions of SEQ ID NO:1 having a length of at least 20 or 30 bases.

The ATPase-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such ATPase-like probes, can be used to identify tissue by species and/or by organ type.

In a similar fashion, these reagents, e.g., ATPase-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting ATPase-like protein and/or nucleic acid expression as well as ATPase-like activity, in the context of a biological sample. An exemplary method for detecting the presence or absence of ATPase-like proteins in a biological sample involves obtaining a biological sample from a test subject and contacting the biological sample with a compound or an agent capable of detecting ATPase-like protein or nucleic acid (e.g., mRNA, genomic DNA) that encodes ATPase-like protein such that the presence of ATPase-like protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting ATPase-like mRNA or genomic DNA is a labeled nucleic acid probe capable of hybridizing to ATPase-like mRNA or genomic DNA. The nucleic acid probe can be, for example, a full-length ATPase-like nucleic acid, such as the nucleic acid of SEQ ID NOS:1, 3, or a portion thereof, such as a nucleic acid molecule of at least 15, 30, 50, 100, 250, or 500 nucleotides in length and sufficient to specifically hybridize under stringent conditions to ATPase-like mRNA or genomic DNA. Other suitable probes for use in the diagnostic assays of the invention are described herein.

A preferred agent for detecting ATPase-like protein is an antibody capable of binding to ATPase-like protein, preferably an antibody with a detectable label. Antibodies can be polyclonal, or more preferably, monoclonal. An intact antibody, or a fragment thereof (e.g., Fab or $F(abN)_2$)can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect ATPase-like mRNA, protein, or genomic DNA in a biological sample in vitro as well as in vivo. For example, in vitro techniques for detection of ATPase-like mRNA include Northern hybridizations and in situ hybridizations. In vitro techniques for detection of ATPase-like protein include enzyme linked immunosorbent assays (ELISAs), Western blots, immunoprecipitations, and immunofluorescence. In vitro techniques for detection of ATPase-like genomic DNA include Southern hybridizations. Furthermore, in vivo techniques for detection of ATPase-like protein include introducing into a subject a labeled anti-ATPase-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

The invention also encompasses kits for detecting the presence of ATPase-like proteins in a biological sample (a test sample). Such kits can be used to determine if a subject is suffering from or is at increased risk of developing a disorder associated with aberrant expression of ATPase-like protein. For example, the kit can comprise a labeled compound or agent capable of detecting ATPase-like protein or mRNA in a biological sample and means for determining the amount of an ATPase-like protein in the sample (e.g., an anti-ATPase-like antibody or an oligonucleotide probe that binds to DNA encoding an ATPase-like protein, e.g., SEQ ID NOS:1 and 3). Kits can also include instructions for observing that the tested subject is suffering from or is at risk of developing a disorder associated with aberrant expression of ATPase-like sequences if the amount of ATPase-like protein or mRNA is above or below a normal level.

For antibody-based kits, the kit can comprise, for example: (1) a first antibody (e.g., attached to a solid support) that binds to ATPase-like protein; and, optionally, (2) a second, different antibody that binds to ATPase-like protein or the first antibody and is conjugated to a detectable agent. For oligonucleotide-based kits, the kit can comprise, for example: (1) an oligonucleotide, e.g., a detectably labeled oligonucleotide, that hybridizes to an ATPase-like nucleic acid sequence or (2) a pair of primers useful for amplifying an ATPase-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of ATPase-like proteins.

2. Other Diagnostic Assays

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with an ATPase-like, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the ATPase-like nucleic acid, polypeptide, or antibody.

The capture probes can be a set of nucleic acids from a selected sample, e.g., a sample of nucleic acids derived from a control or non-stimulated tissue or cell.

The method can include contacting the ATPase-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of ATPase-like. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express ATPase-like or from a cell or subject in which an ATPase-like mediated response has been elicited, e.g., by contact of the cell with ATPase-like nucleic acid or protein, or administration to the cell or subject ATPase-like nucleic acid or protein; contacting the array with one or more inquiry probe, wherein an inquiry probe can be a nucleic acid, polypeptide, or antibody (which is preferably other than ATPase-like nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express ATPase-like (or does not express as highly as in the case of the ATPase-like positive plurality of capture probes) or from a cell or subject which in which an ATPase-like mediated response has not been elicited (or has been elicited to a lesser extent than in the first sample); contacting the array with one or more inquiry probes (which is preferably other than an ATPase-like nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing ATPase-like, e.g., analyzing structure, function, or relatedness to other nucleic acid or amino acid sequences. The method includes: providing an ATPase-like nucleic acid or amino acid sequence, e.g., a nucleotide sequence from 300–1916 or a portion thereof; comparing the ATPase-like sequence with one or more preferably a plurality of sequences from a collection of sequences, e.g., a nucleic acid or protein sequence database; to thereby analyze ATPase-like.

The method can include evaluating the sequence identity between an ATPase-like sequence and a database sequence. The method can be performed by accessing the database at a second site, e.g., over the internet.

In another aspect, the invention features, a set of oligonucleotides, useful, e.g., for identifying SNP's, or identifying specific alleles of an ATPase-like gene. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with ATPase-like protein, ATPase-like nucleic acid expression, or ATPase-like activity. Prognostic assays can be used for prognostic or predictive purposes to thereby prophylactically treat an individual prior to the onset of a disorder characterized by or associated with ATPase-like protein, ATPase-like nucleic acid expression, or ATPase-like activity.

Thus, the present invention provides a method in which a test sample is obtained from a subject, and ATPase-like protein or nucleic acid (e.g., mRNA, genomic DNA) is detected, wherein the presence of ATPase-like protein or nucleic acid is diagnostic for a subject having or at risk of developing a disease or disorder associated with aberrant ATPase-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease ATPase-like activity) to effectively treat a disease or disorder associated with aberrant ATPase-like expression or activity. In this manner, a test sample is obtained and ATPase-like protein or nucleic acid is detected. The presence of ATPase-like protein or nucleic acid is diagnostic for a subject that can be administered the agent to treat a disorder associated with aberrant ATPase-like expression or activity.

The methods of the invention can also be used to detect genetic lesions or mutations in an ATPase-like gene, thereby determining if a subject with the lesioned gene is at risk for a disorder characterized by aberrant cellular processes including, altered protein sorting, altered gene expression, altered cell division, altered protein stability, etc. In preferred embodiments, the methods include detecting, in a sample of cells from the subject, the presence or absence of a genetic lesion or mutation characterized by at least one of an alteration affecting the integrity of a gene encoding an ATPase-like-protein, or the misexpression of the ATPase-like gene. For example, such genetic lesions or mutations can be detected by ascertaining the existence of at least one of: (1) a deletion of one or more nucleotides from an ATPase-like gene; (2) an addition of one or more nucleotides to an ATPase-like gene; (3) a substitution of one or more nucleotides of an ATPase-like gene; (4) a chromosomal rearrangement of an ATPase-like gene; (5) an alteration in the level of a messenger RNA transcript of an ATPase-like gene; (6) an aberrant modification of an ATPase-like gene, such as of the methylation pattern of the genomic DNA; (7) the presence of a non-wild-type splicing pattern of a messenger RNA transcript of an ATPase gene; (8) a non-wild-type level of an ATPase-like-protein; (9) an allelic loss of an ATPase-like gene; and (10) an inappropriate post-translational modification of an ATPase-like-protein. As described herein, there are a large number of assay techniques known in the art that can be used for detecting lesions in an ATPase-like gene. Any cell type or tissue in which ATPase-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the ATPase-like-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ATPase-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in an ATPase-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the ATPase-like gene and detect mutations by comparing the sequence of the sample ATPase-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the ATPase-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in ATPase-like cDNAs obtained from samples of cells. See, e.g., Hsu et al. (1994) *Carcinogenesis* 15:1657–1662. According to an exemplary embodiment, a probe based on an ATPase-like sequence, e.g., a wild-type ATPase-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in ATPase-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3N end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3N end of the 5N sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving an ATPase-like gene.

4. Pharmacogenomics

Agents, or modulators that have a stimulatory or inhibitory effect on ATPase-like activity (e.g., ATPase-like gene expression) as identified by a screening assay described herein, can be administered to individuals to treat (prophylactically or therapeutically) disorders associated with aberrant ATPase-like activity as well as to modulate a cellular phenotype associated with aberrant ATPase-like activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of ATPase-like protein, expression of ATPase-like nucleic acid, or mutation content of ATPase-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a ATPase-like molecule or ATPase-like modulator as well as tailoring the dosage and/or therapeutic regimen of treatment with a ATPase-like molecule or ATPase-like modulator.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., an ATPase-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., an ATPase-like molecule or ATPase-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an ATPase-like molecule or ATPase-like modulator, such as a modulator identified by one of the exemplary screening assays described herein.

The present invention further provides methods for identifying new agents, or combinations, that are based on identifying agents that modulate the activity of one or more of the gene products encoded by one or more of the ATPase-like genes of the present invention, wherein these products may be associated with resistance of the cells to a therapeutic agent. Specifically, the activity of the proteins encoded by the ATPase-like genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a ATPase-like protein can be applied in clinical trials. For example, the effectiveness of an agent determined by a screening assay as described herein to increase ATPase-like gene expression, protein levels, or upregulate ATPase-like activity, can be monitored in clinical trials of subjects exhibiting decreased ATPase-like gene expression, protein levels, or downregulated ATPase-like activity. Alternatively, the effectiveness of an agent determined by a screening assay to decrease ATPase-like gene expression, protein levels, or downregulate ATPase-like activity, can be monitored in clinical trials of subjects exhibiting increased ATPase-like gene expression, protein levels, or upregulated ATPase-like activity. In such clinical trials, the expression or activity of a ATPase-like gene, and preferably, other genes that have been implicated in, for example, a ATPase-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of ATPase-like protein, expression of ATPase-like nucleic acid, or mutation content of ATPase-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an ATPase-like modulator, such as a modulator identified by one of the exemplary screening assays described herein.

5. Monitoring of Effects During Clinical Trials

Monitoring the influence of agents (e.g., drugs, compounds) on the expression or activity of ATPase-like genes can be applied not only in basic drug screening but also in clinical trials. For example, the effectiveness of an agent, as determined by a screening assay as described herein, to increase or decrease ATPase-like gene expression, protein levels, or protein activity, can be monitored in clinical trials of subjects exhibiting decreased or increased ATPase-like gene expression, protein levels, or protein activity. In such clinical trials, ATPase-like expression or activity and preferably that of other genes that have been implicated in influencing ATPase-like expression or activity, can be used as a marker of the immune responsiveness of a particular cell.

For example, and not by way of limitation, genes that are modulated in cells by treatment with an agent (e.g., compound, drug, or small molecule) that modulates ATPase-like activity (e.g., as identified in a screening assay described herein) can be identified. Thus, to study the effect of agents on cellular disorders resulting from aberrant ATPase-like activity, for example, in a clinical trial, cells can be isolated and RNA prepared and analyzed for the levels of expression of ATPase-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by. measuring the levels of activity of ATPase-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of an ATPase-like protein, mRNA, or genomic DNA in the preadministration sample; (3) obtaining one or more postadministration samples from the subject; (4) detecting the level of expression or activity of the ATPase-like protein, mRNA, or genomic DNA in the postadministration samples; (5) comparing the level of expression or activity of the ATPase-like protein, mRNA, or genomic DNA in the preadministration sample with the ATPase-like protein, mRNA, or genomic DNA in the postadministration sample or samples; and (vi) altering the administration of the agent to the subject accordingly to bring about the desired effect, i.e., for example, an increase or a decrease in the expression or activity of an ATPase-like protein.

C. Methods of Treatment

The present invention provides for both prophylactic and therapeutic methods of treating a subject at risk of (or susceptible to) a disorder or having a disorder associated with aberrant ATPase-like expression or activity. Additionally, the compositions of the invention find use in the treatment of disorders described herein. Thus, therapies for disorders associated with ATPase-like molecules are encompassed herein. "Subject", as used herein, can refer to a mammal, e.g., a human, or to an experimental or animal or disease model. The subject can also be a non-human animal, e.g., a horse, cow, goat, or other domestic animal.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

1. Prophylactic Methods

In one aspect, the invention provides a method for preventing in a subject a disease or condition associated with an aberrant ATPase-like expression or activity by administering to the subject an agent that modulates ATPase-like expression or at least one ATPase-like gene activity. Subjects at risk for a disease that is caused, or contributed to, by aberrant ATPase-like expression or activity can be identified by, for example, any or a combination of diagnostic or prognostic assays as described herein. Administration of a prophylactic agent can occur prior to the manifestation of symptoms characteristic of the ATPase-like aberrancy, such that a disease or disorder is prevented or, alternatively, delayed in its progression. Depending on the type of ATPase-like aberrancy, for example, an ATPase-like agonist or ATPase-like antagonist agent can be used for treating the subject. The appropriate agent can be determined based on screening assays described herein.

2. Therapeutic Methods

Another aspect of the invention pertains to methods of modulating ATPase-like expression or activity for therapeutic purposes. The modulatory method of the invention involves contacting a cell with an agent that modulates one or more of the activities of ATPase-like protein activity associated with the cell. An agent that modulates ATPase-like protein activity can be an agent as described herein, such as a nucleic acid or a protein, a naturally-occurring cognate ligand of an ATPase-like protein, a peptide, an ATPase-like peptidomimetic, or other small molecule. In one embodiment, the agent stimulates one or more of the biological activities of ATPase-like protein. Examples of such stimulatory agents include active ATPase-like protein and a nucleic acid molecule encoding an ATPase-like protein that has been introduced into the cell. In another embodiment, the agent inhibits one or more of the biological activities of ATPase-like protein. Examples of such inhibitory agents include antisense ATPase-like nucleic acid molecules and anti-ATPase-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of an ATPase-like protein or nucleic acid molecule. In one embodiment, the method involves administering an agent (e.g., an agent identified by a screening assay described herein), or a combination of agents, that modulates (e.g., upregulates or downregulates) ATPase-like expression or activity. In another embodiment, the method involves administering an ATPase-like protein or nucleic acid molecule as therapy to compensate for reduced or aberrant ATPase-like expression or activity.

Stimulation of ATPase-like activity is desirable in situations in which an ATPase-like protein is abnormally downregulated and/or in which increased ATPase-like activity is likely to have a beneficial effect. Conversely, inhibition of ATPase-like activity is desirable in situations in which ATPase-like activity is abnormally upregulated and/or in which decreased ATPase-like activity is likely to have a beneficial effect.

This invention is further illustrated by the following examples, which should not be construed as limiting.

EXPERIMENTAL

Example 1

Tissue Distribution of ATPase-Like mRNA

Northern blot hybridizations with various RNA samples can be performed under standard conditions and washed under stringent conditions, i.e., 0.2×SSC at 65° C. A DNA probe corresponding to all or a portion of the ATPase-like cDNA (SEQ ID NO:1 or 3) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Figure 4:
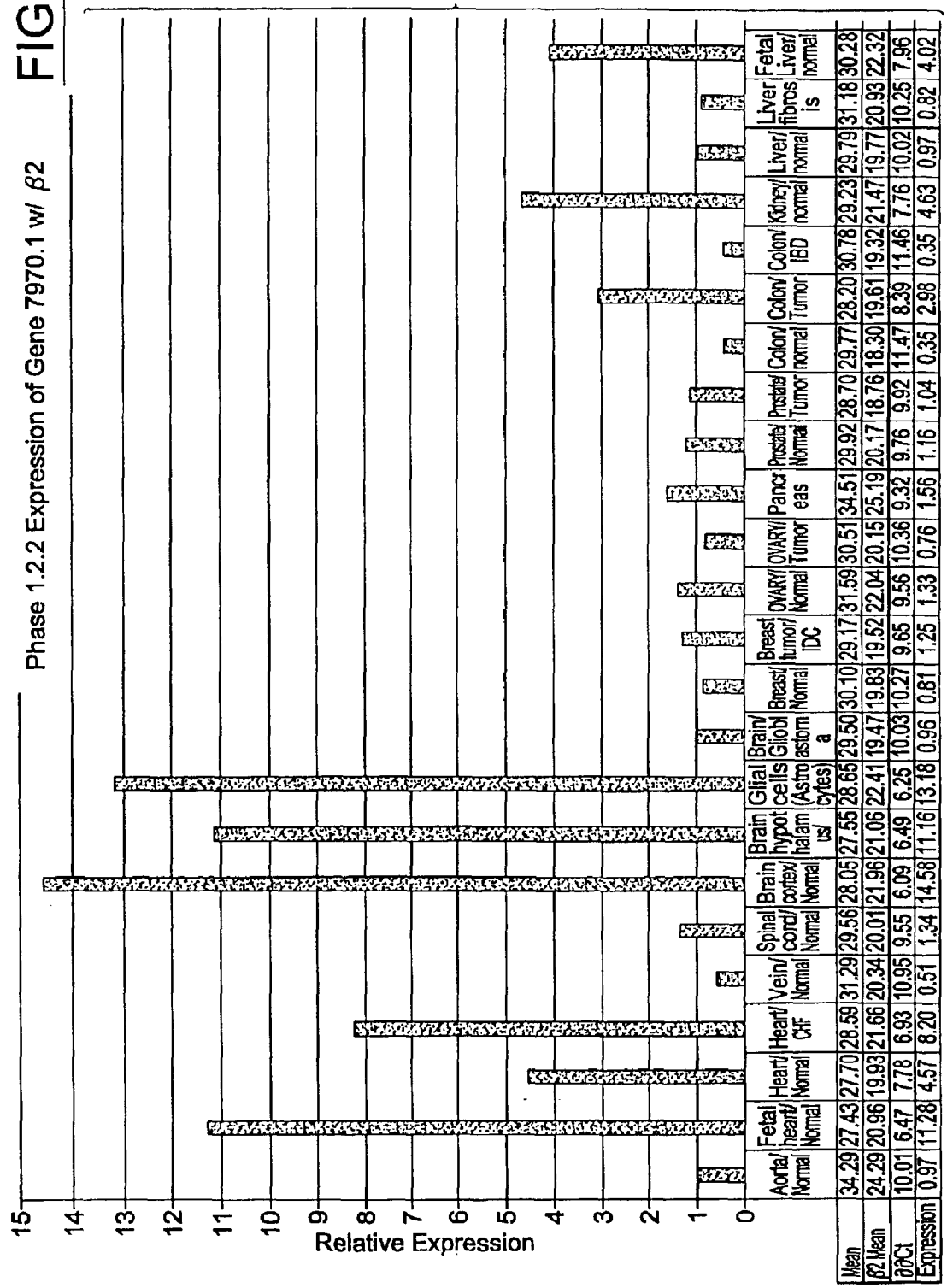
FIGS. 4A–B show the expression level of the 7970 mRNA transcript in various tissues and cell lines.
Figure 5:
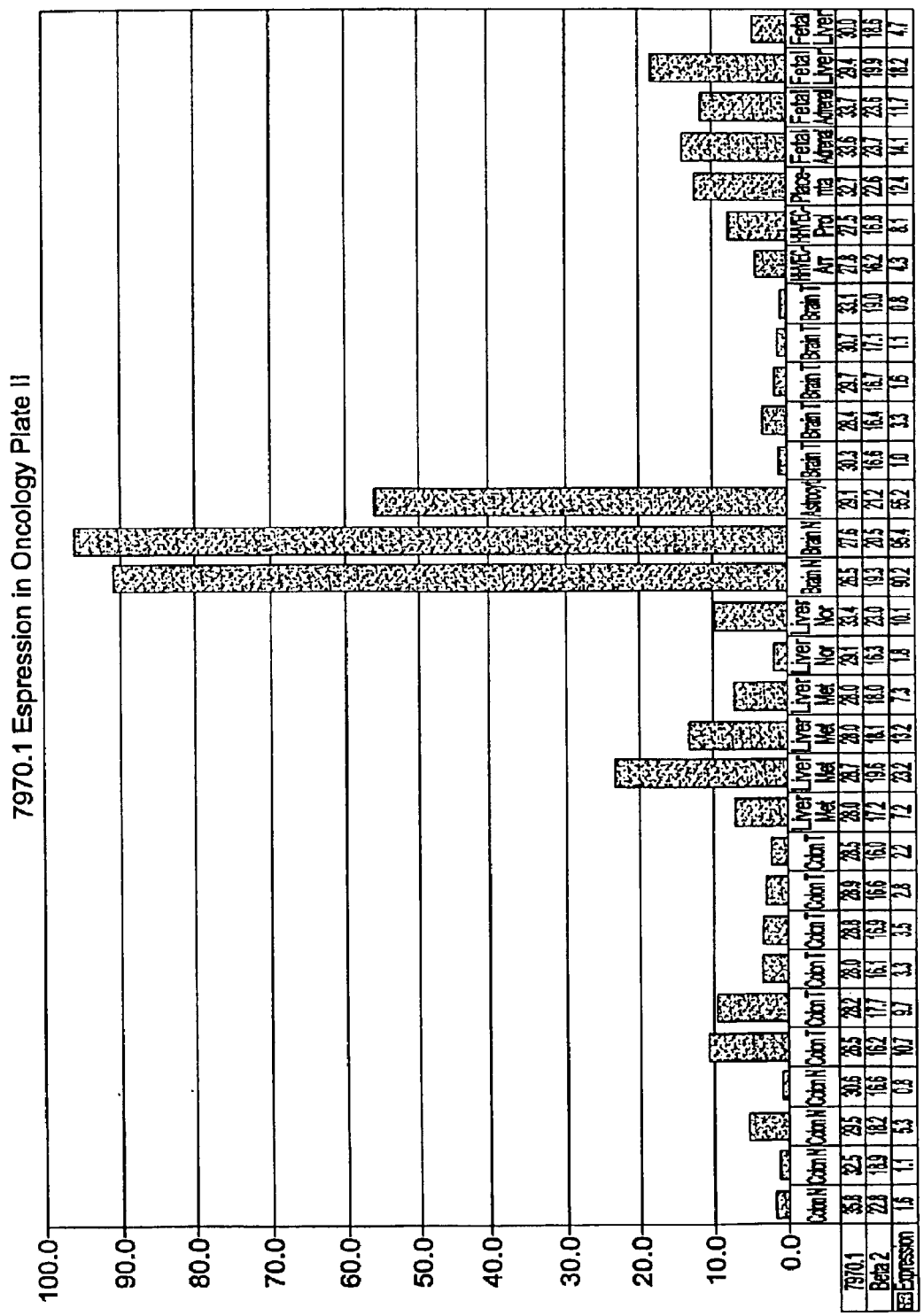
FIG. 5 shows the expression level of the 7970 mRNA transcript in various normal and tumorous tissues and cell lines.
Figure 6B:
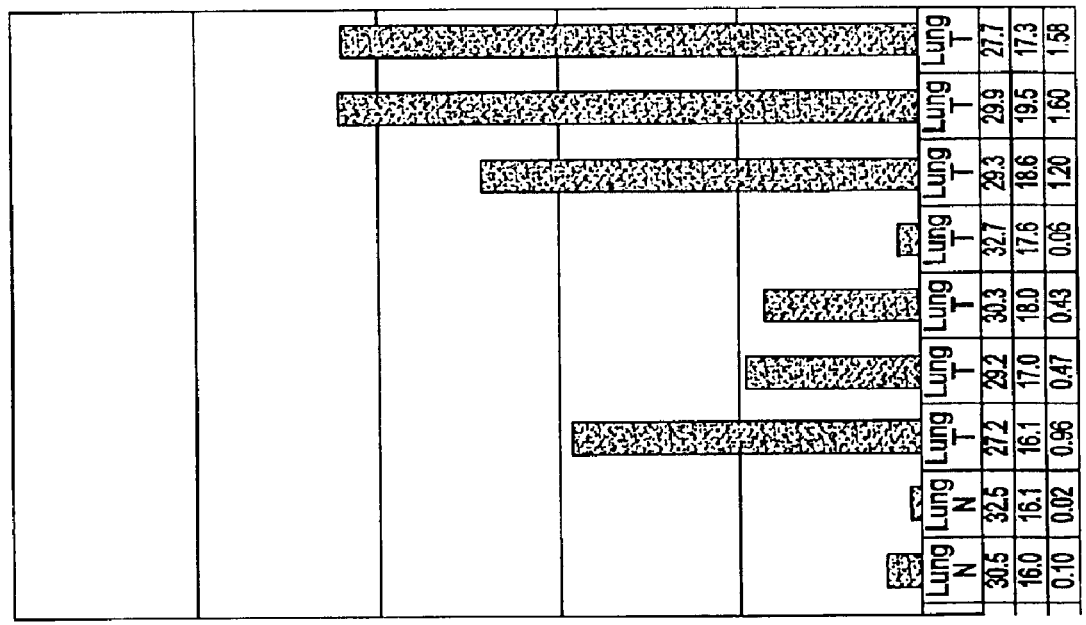
Figure 7:
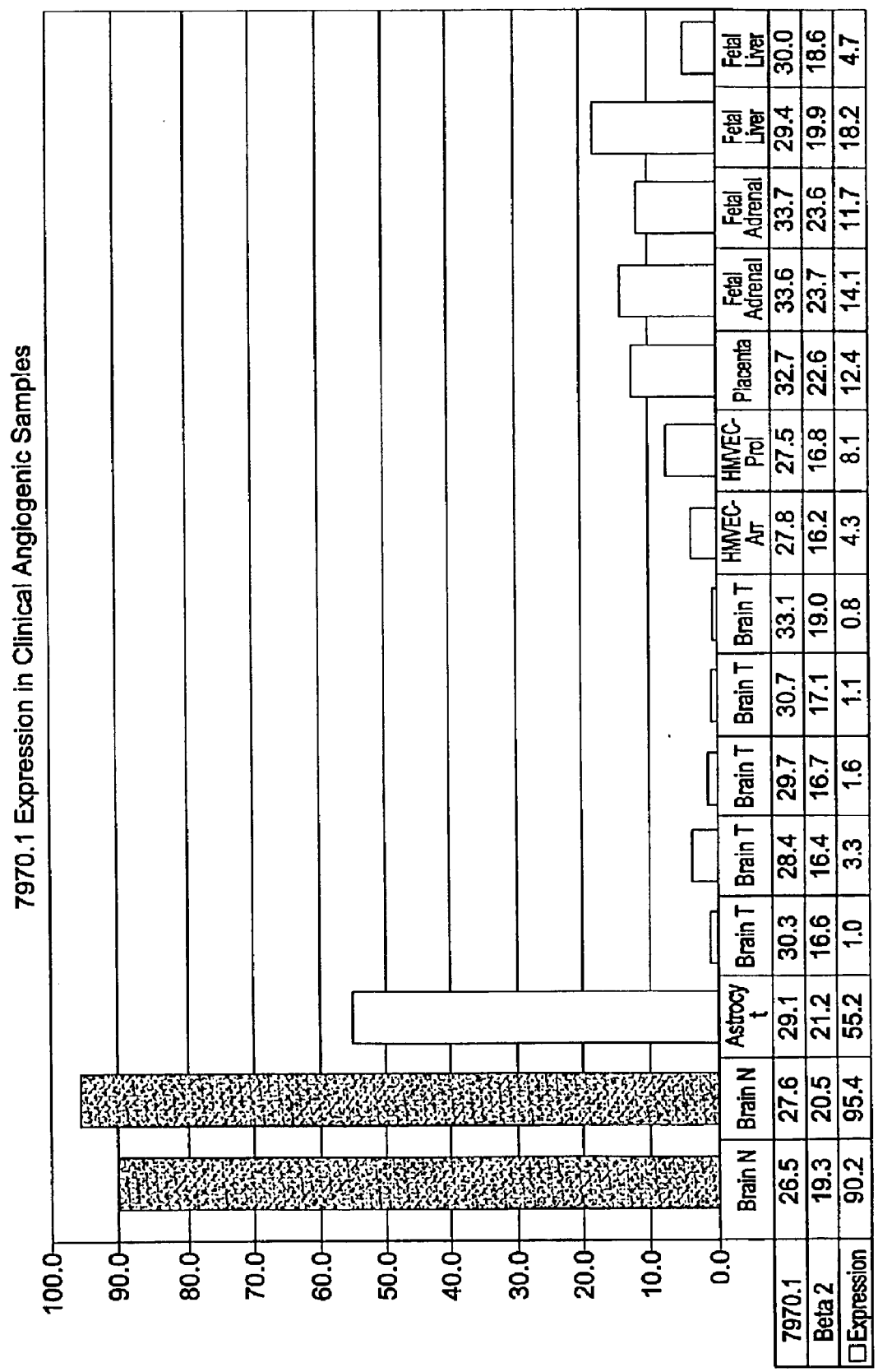
FIG. 7 shows the expression level of the 7970 mRNA transcript in clinical angiogenic samples.
Figure 8:
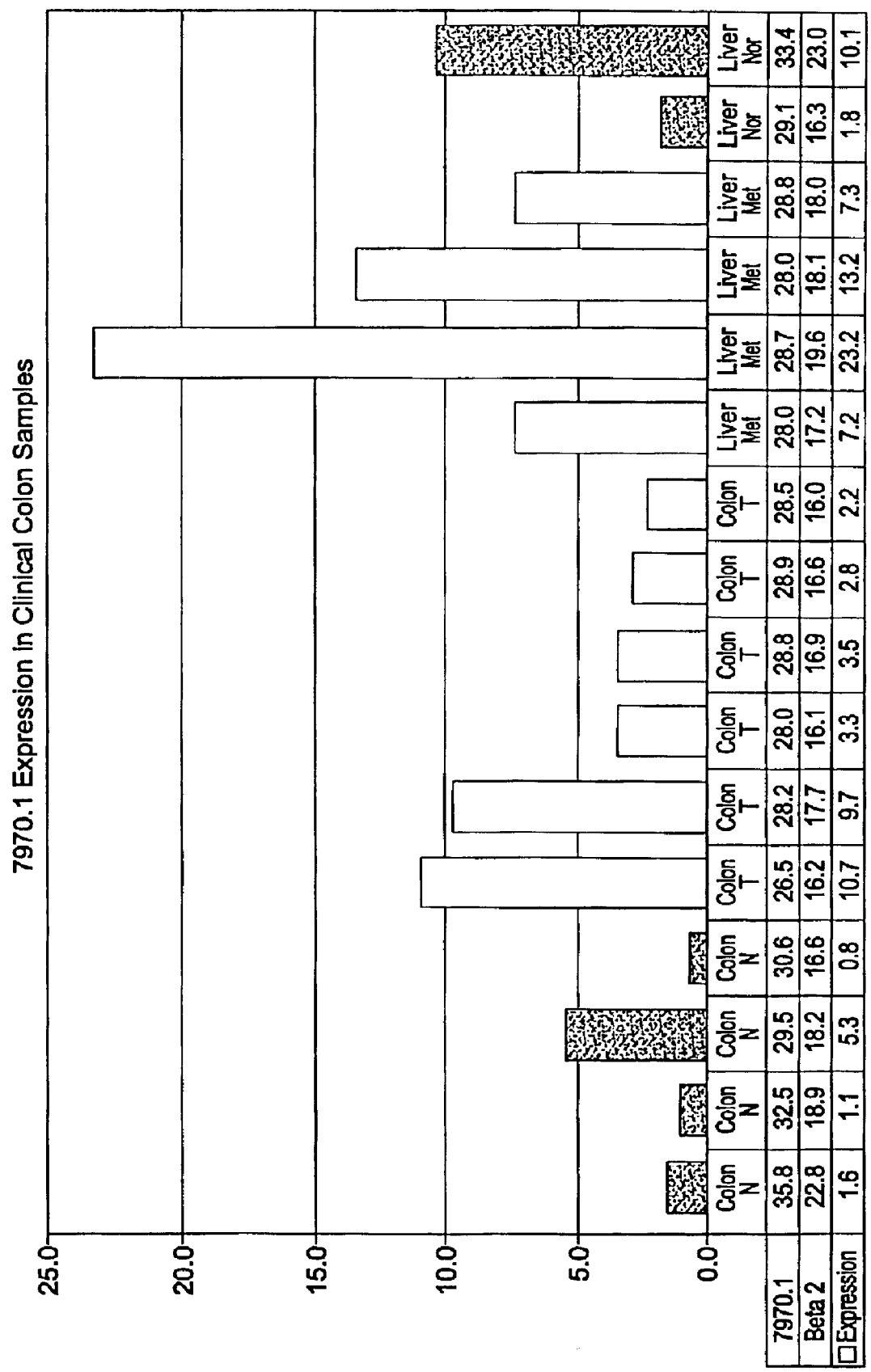
FIG. 8 shows the expression level of the 7970 transcript in clinical colon and liver samples.

TAQMAN analysis of the 7970 sequence revealed expression in a number of tissues as shown in FIG. 4. High levels of 7970 transcripts are seen in the fetal heart, normal heart, heart (CHF), brain cortex, brain hypothalamus, glial cells, and epithelial cells. Moderate levels of expression are found in kidney, fetal liver, aortic SMC early, aortic SMC late, shear HUVEC, and static HUVEC. Low levels of expression were found in the aorta, vein, spinal cord, brain, gioblastoma, breast, ovary, tumorous breast, tumorous ovary, pancreas, prostate, tumorous prostate, colon, tumorous colon, liver, liver fibrosis, lung, tumorous lung, lung (COPD), spleen, tonsil, lymph node, thymus, endothelial cells (aortic), skeletal muscle, fibroblasts, skin, adipose, osteoblasts (primary), osteoblasts (undifferentiated), osteoblasts (differentiated), and osteoclasts.

The expression of the 7970 sequence in various tumorous and normal tissues was also determined. FIGS. 5–8 and FIGS. 10–12 show the relative expression levels of the 7970 transcript in various tissues including, for example, normal and tumorous colon tissues, normal liver and metastatic liver tissues, normal brain and tumorous brain tissues, normal breast and tumorous breast tissues, normal ovary and tumorous ovary tissues, normal lung and tumorous lung tissues.

Figure 9:
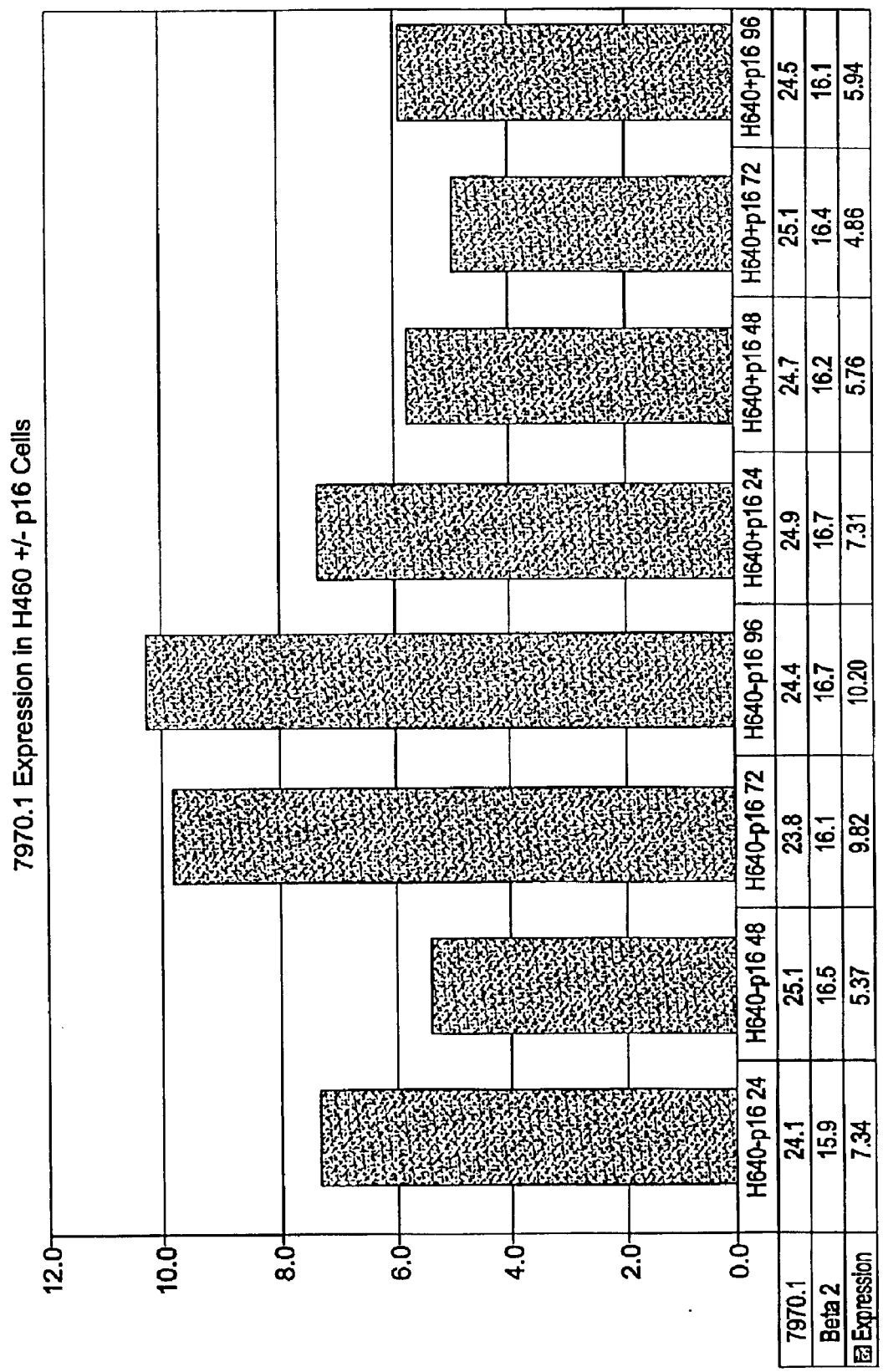
FIG. 9 shows the expression level of the 7970 transcript in a non-small cell lung cancer cell line (H640) in the presence and absence of the p16 gene.
Figure 10:
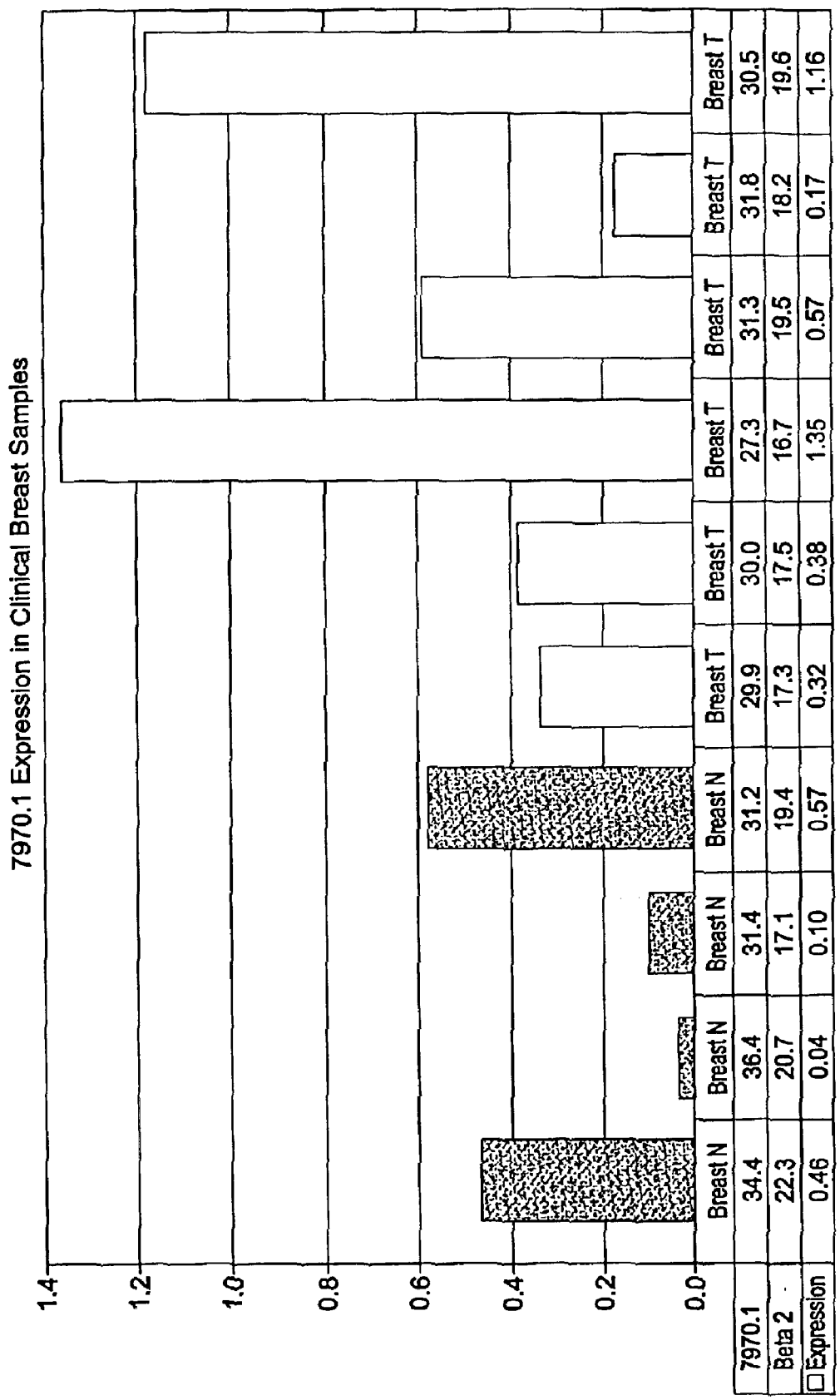
FIG. 10 shows the expression of the 7970 transcript in clinical breast samples.
Figure 11:
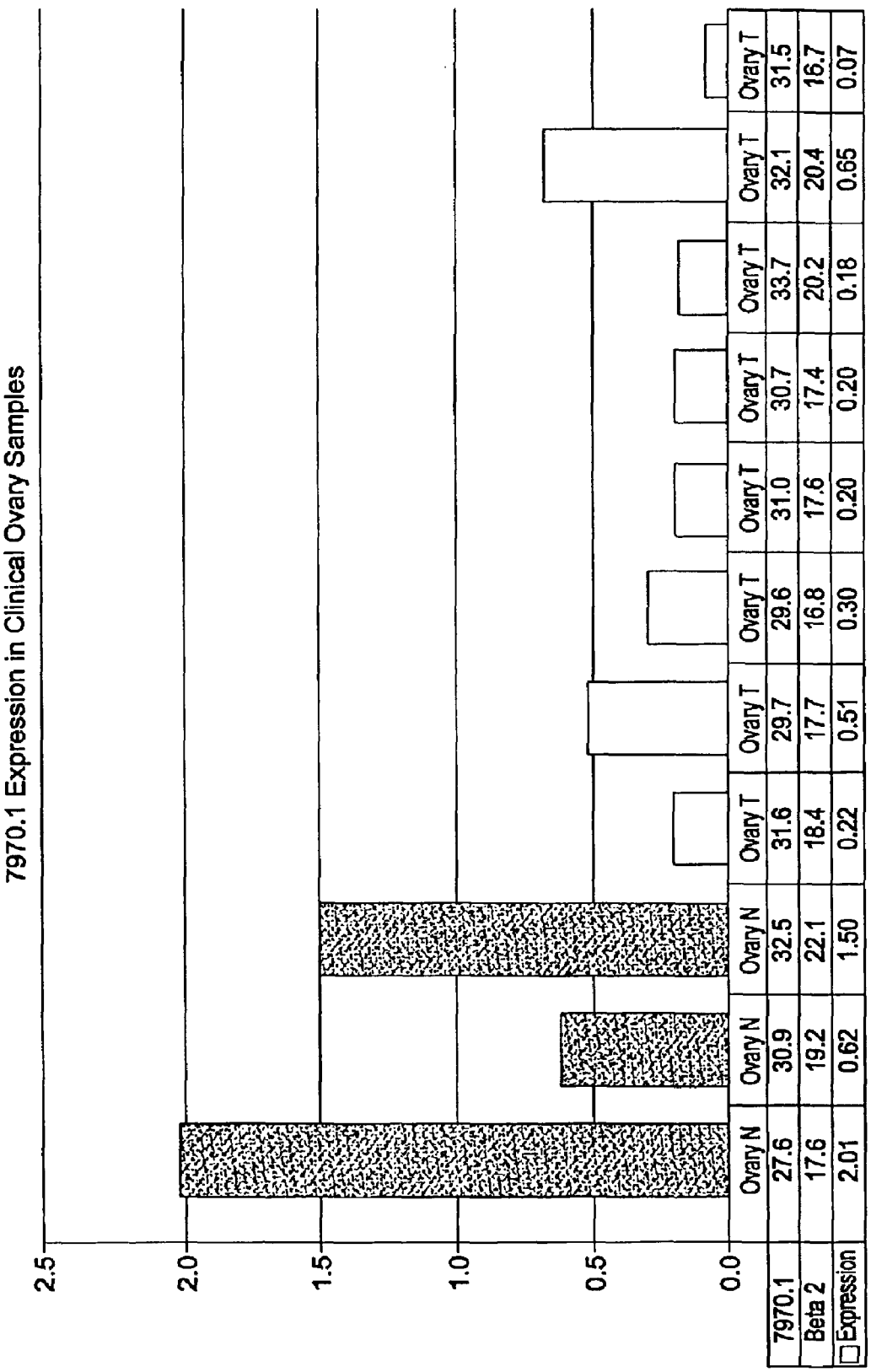
FIG. 11 shows the expression of the 7970 transcript in clinical ovary samples.
Figure 12:
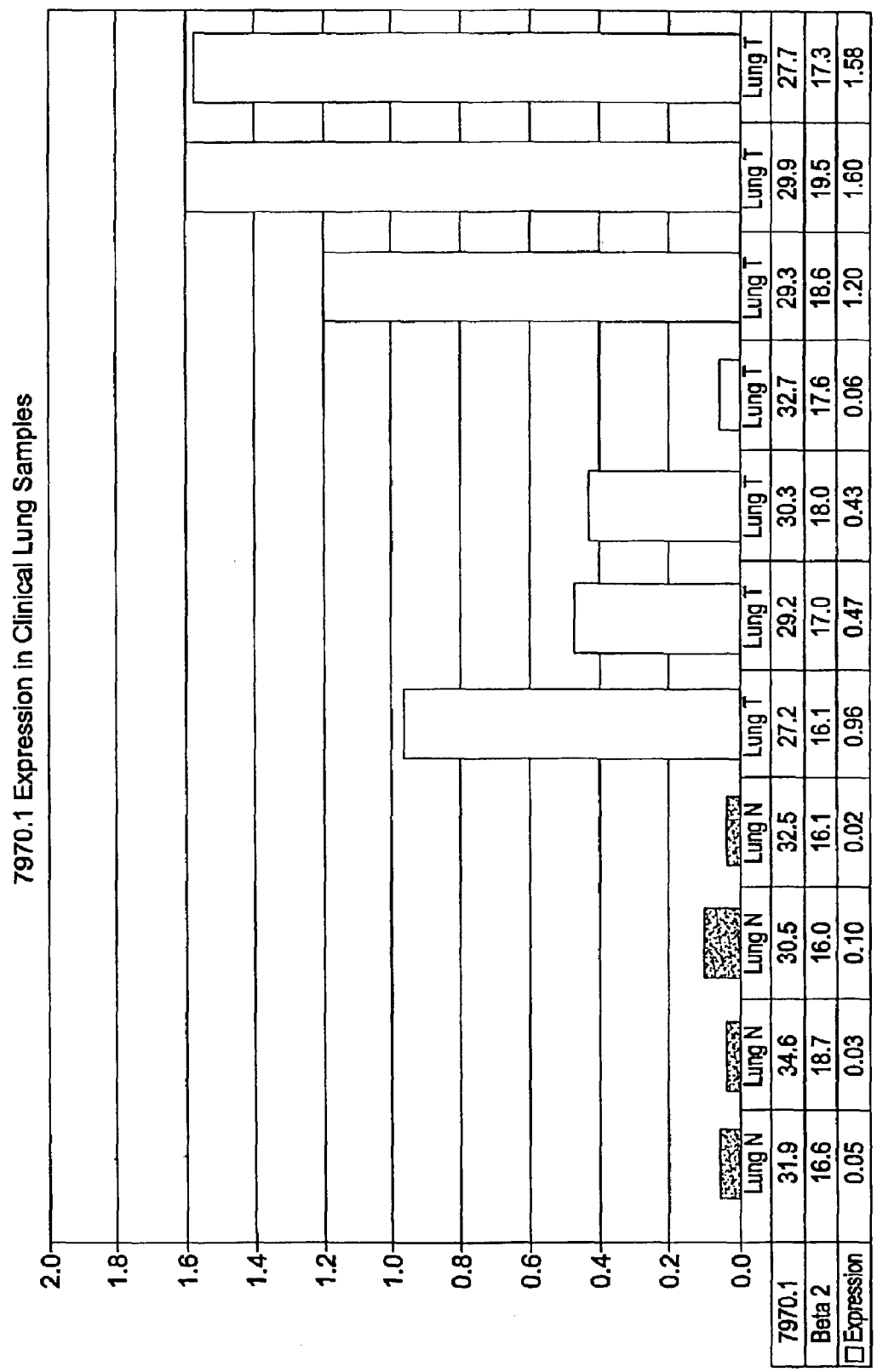
FIG. 12 shows the expression of the 7970 transcript in clinical lung samples.
Figure 15:
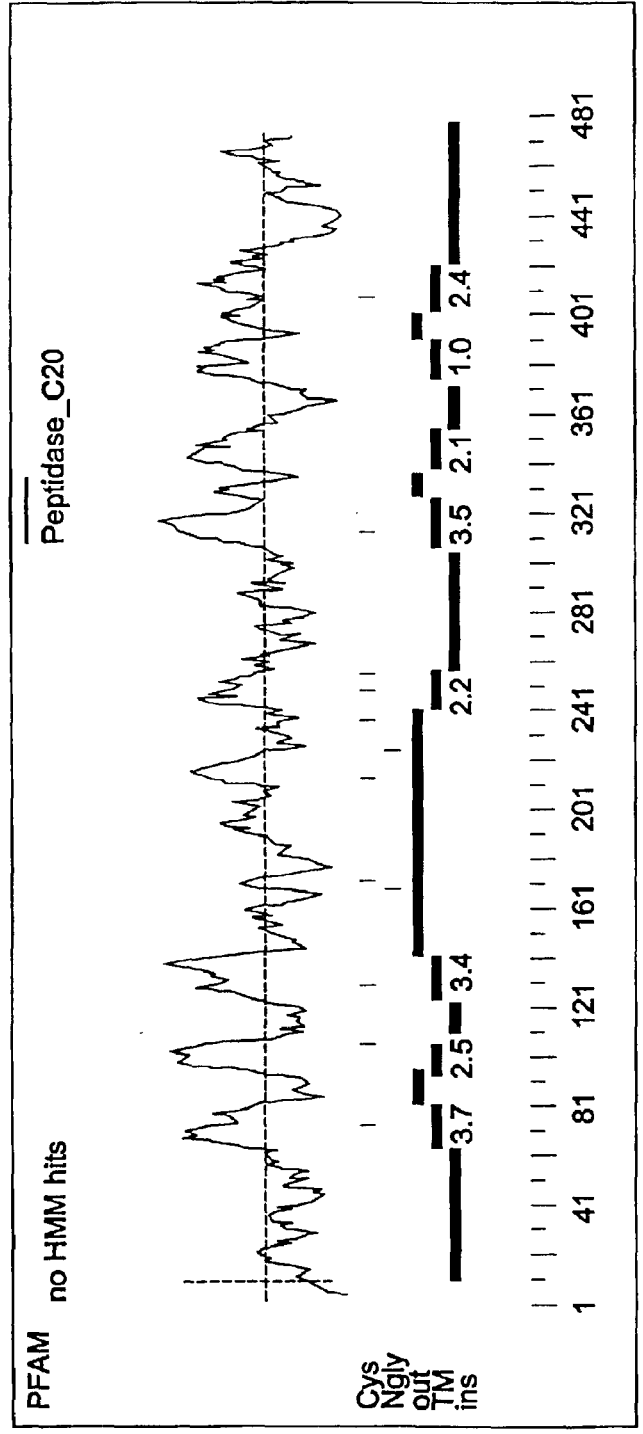
FIG. 15 shows a hydropathy plot of the 32670 polypeptide shown in SEQ ID NO:6. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:6) of human 32670 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 16:
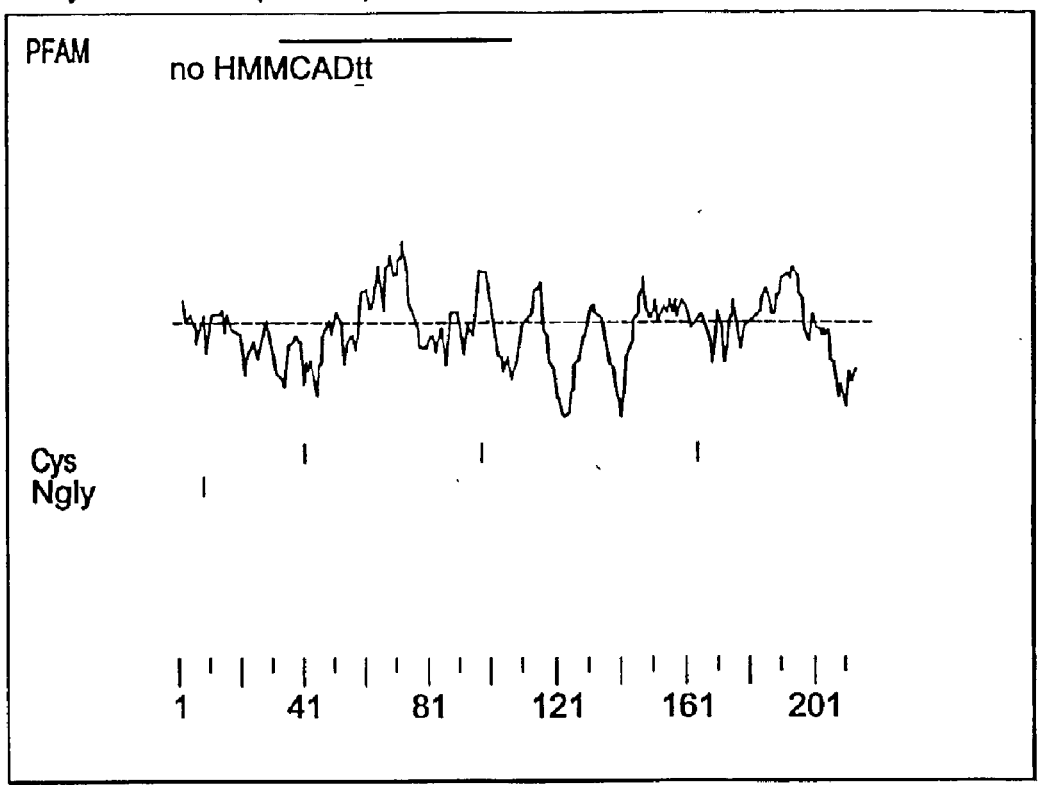
FIG. 16 depicts a hydropathy plot of human a DFF-like molecule. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:11) of human DFF-like molecule are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 18:
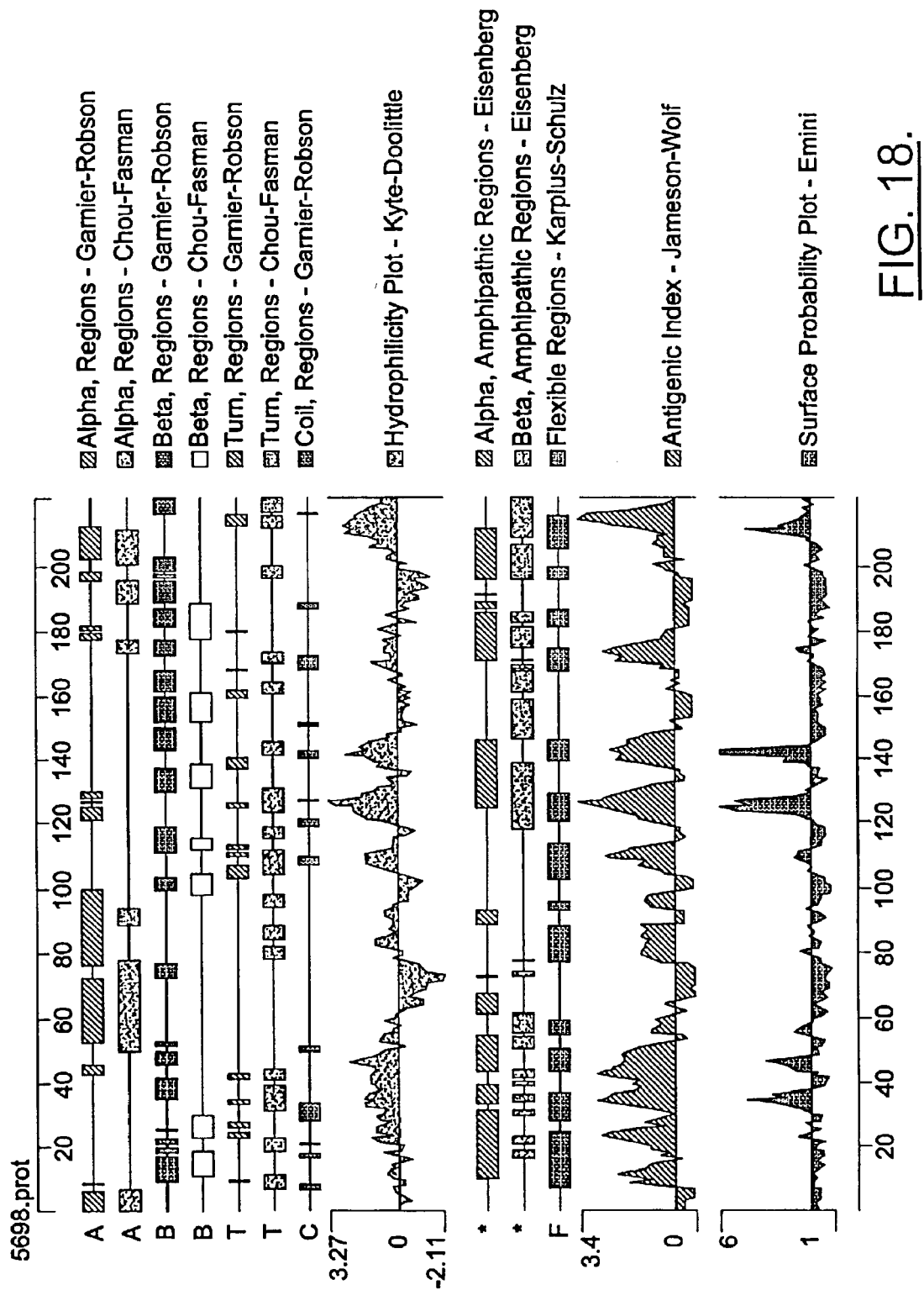
FIG. 18 shows an analysis of the 5698 amino acid sequence: αβturn and coil regions; hydrophilicity; amphipathic regions; flexible regions; antigenic index; and surface probability plot.

FIG. 9 further shows the expression level of the 7970 transcript in a non-small cell lung cancer cell line (H640) in the presence and the absence of the p16 gene.

Example 2

Recombinant Expression of ATPase-Like in Bacterial Cells

In this example, the ATPase-like sequence is expressed as a recombinant glutathione-S-transferase (GST) fusion polypeptide in *E. coli* and the fusion polypeptide is isolated and characterized. Specifically, the ATPase-like sequence is fused to GST and this fusion polypeptide is expressed in *E. coli*, e.g., strain PEB199. Expression of the GST-ATPase-like fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant ATPase-Like Protein in COS Cells

To express the ATPase-like gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire ATPase-like protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the ATPase-like DNA sequence is amplified by PCR using two primers. The 5' primer contains the restriction site of interest followed by approximately twenty nucleotides of the ATPase-like coding sequence starting from the initiation codon; the 3' end sequence contains complementary sequences to the other restriction site of interest, a translation stop codon, the HA tag or FLAG tag and the last 20 nucleotides of the ATPase-like coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the ATPase-like gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the ATPase-like-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the ATPase-like polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the ATPase-like coding sequence is cloned directly into the polylinker of the pcDNA/Amp vector using the appropriate restriction sites. The resulting plasmid is transfected into COS cells in the manner described above, and the expression of the ATPase-like polypeptide is detected by radiolabelling and immunoprecipitation using a ATPase-like specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

CHAPTER 2

32670, Novel Human Phosphatidylserine Synthase-Like Molecules and Uses Thereof

BACKGROUND OF THE INVENTION

The membranes of eukaryotic cells contain not only large amounts of cholesterol but a variety of phospholipids. For example, the major phospholipids in the human erythrocyte include phosphatidylethanolamine, phosphatidylcholine, phosphatidylserine, and sphingomyelin. The four major phospholipids in the yeast *Saccharomyces cerevisiae* are phosphatidylcholine (PC), phosphatidylethanolamine (PE), phosphatidylinositol (PI), and phosphatidylserine (PS) (Poole et al. (1986) *J. of Bacteriology* 168(2):668–672). PS accounts for 4 to 8% of the total membrane phospholipids in *S. cerevisiae* and is important to overall lipid metabolism (Atkinson et al. (1980) *J. Biol. Chem.* 255: 6653–6661). PS is the normal precursor to PE and PC. The synthesis of phospholipids in eukaryotic cells involves both cytoplasmic and membrane-associated enzymes, a number of which are coordinately regulated (Henry et al., (1984) *Annu. Rev. Genet.* 18:207–231).

Phosphatidylserine (PS) is an essential phospholipid for the growth of mammalian cells, comprising approximately 10% of the total membrane of various mammalian tissues and cultured cells (Kuge et al. (1986) *J. Biol. Chem.* 261:5790–5794).

The enzyme responsible for the biosynthesis of PS in *S. cerevisiae* is CDPdiacylglycerol:L-serine O-phoshphatidyl transferase (Phosphatidylserine synthase; EC 2.7.8.8). PS synthase catalyzes the formation of PS and CMP from CDP-diacylglycerol (CDP-DG) and serine by a sequential Bi Bi reaction mechanism (Bae-Lee et al. (1984) *J. Biol. Chem.* 259:10857–10862). PS synthase is an integral membrane protein. Detailed biochemical studies have shown that PS synthase activity is present in both the mitochondria and endoplasmic reticulum (Kuchler et al. (1986) *J. Bacteriol.* 165:901–910).

Phosphatidylserine (PS) synthase in Chinese Hamster Ovary cells (CHO) exists in two forms—(PSS) I and II. PSS I and PSS II are encoded by two genes pssA and pssB, respectively (Kuge et al. (1997) *J. Biol. Chem.* 272: 19133–19139). PSS I is responsible for the conversion of phosphatidylcholine to phosphatidylserine and PSS II is responsible for the conversion of phosphatidylethanolamine to phosphatidylserine (Saito et al. (1998) *J. Biol. Chem.* 273:17199–17205). PS biosynthesis in CHO-K1 cells is inhibited upon the addition of PS to the culture medium suggesting that feedback control is involved in the regulation of PS biosynthesis (Nishijima et al. (1986) *J. Biol. Chem.* 261:5784–5789).

Various CHO mutants have been identified which exhibit defective synthesis in PSS I and PSS II. PSS I and PSS II are similar in sequence to each other; there is a 38% amino acid identity between the two PS synthases (Kuge et al. (1997) *J. Biol. Chem.* 272:19133–19139). Results obtained by Kuge et al. indicate that PSS II in CHO-K1 cells is inhibited by exogenous PS and that the activity of over-produced PSS II in CHO-K1 cells is depressed for maintenance of the normal PS biosynthetic rate, probably through molecular mechanisms different from those for the exogenous PS-mediated inhibition. Also, the work of Kuge et al. demonstrated that the ARG-97 residue of PSS II is critical for both the exogenous PS-mediated inhibition of PS II and the depression of overproduced PSS II activity.

Because phospholipids such as PS are important components of eukaryotic membranes their proper biosynthesis is critical to cell homeostasis and function. Defects in PS synthase may yield membranes with altered functionality which could have implications in a wide range of disease states. Accordingly, PS synthases are a major target for drug action and development. Accordingly, it is valuable to the field of pharmaceutical development to identify and characterize novel PS synthases and tissues and disorders in which PS synthases are differentially expressed. The present invention advances the state of the art by providing novel human PS synthase molecules and the uses thereof.

SUMMARY OF THE INVENTION

Isolated nucleic acid molecules corresponding to human phosphatidylserine synthase-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:6. Further provided are human phosphatidylserine synthase-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The human phosphatidylserine synthase-like molecules of the present invention are useful for modulating the biosynthetic pathway involving the synthesis of the membrane phospholipid phosphatidylserine (PS). The molecules may be useful for a wide variety of human disorders as herein described.

Accordingly, in one aspect, this invention provides isolated nucleic acid molecules encoding human phosphatidylserine synthase-like proteins or biologically active portions thereof, as well as nucleic acid fragments suitable as primers or hybridization probes for the detection of human phosphatidylserine synthase-like encoding nucleic acids.

Another aspect of this invention features isolated or recombinant human phosphatidylserine synthase-like proteins and polypeptides. Preferred human phosphatidylserine synthase-like proteins and polypeptides possess at least one biological activity possessed by naturally occurring human phosphatidylserine synthase-like proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the human phosphatidylserine synthase-like polypeptides and fragments are provided. Such antibodies are useful in detecting the human phosphatidylserine synthase-like polypeptides.

In another aspect, the present invention provides a method for detecting the presence of human phosphatidylserine synthase-like activity or expression in a biological sample by contacting the biological sample with an agent capable of detecting an indicator of human phosphatidylserine synthase-like activity such that the presence of human phosphatidylserine synthase-like activity is detected in the biological sample.

In yet another aspect, the invention provides a method for modulating human phosphatidylserine synthase-like activity comprising contacting a cell with an agent that modulates (inhibits or stimulates) human phosphatidylserine synthase-like activity or expression such that human phosphatidylserine synthase-like activity or expression in the cell is modulated. In one embodiment, the agent is an antibody that specifically binds to human phosphatidylserine synthase-like protein. In another embodiment, the agent modulates expression of human phosphatidylserine synthase-like protein by modulating transcription of a human phosphatidylserine synthase-like gene, splicing of a human phosphatidylserine synthase-like mRNA, or translation of a human phosphatidylserine synthase-like mRNA. In yet another embodiment, the agent is a nucleic acid molecule having a nucleotide sequence that is antisense to the coding strand of the human phosphatidylserine synthase-like mRNA or the human phosphatidylserine synthase-like gene.

In one embodiment, the methods of the present invention are used to treat a subject having a disorder characterized by aberrant human phosphatidylserine synthase-like protein activity or nucleic acid expression by administering an agent that is a human phosphatidylserine synthase-like modulator to the subject. In one embodiment, the human phosphatidylserine synthase-like modulator is a human phosphatidylserine synthase-like protein. In another embodiment, the human phosphatidylserine synthase-like modulator is a human phosphatidylserine synthase-like nucleic acid molecule. In other embodiments, the human phosphatidylserine synthase-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a human phosphatidylserine synthase-like protein; (2) misregulation of a gene encoding a human phosphatidylserine synthase-like protein; and (3) aberrant post-translational modification of a human phosphatidylserine synthase-like protein, wherein a wild-type form of the gene encodes a protein with a human phosphatidylserine synthase-like activity.

In another aspect, the invention provides a method for identifying a compound that binds to or modulates the activity of a human phosphatidylserine synthase-like protein. In general, such methods entail measuring a biological activity of a human phosphatidylserine synthase-like protein in the presence and absence of a test compound and identifying those compounds that alter the activity of the human phosphatidylserine synthase-like protein.

The invention also features methods for identifying a compound that modulates the expression of human phosphatidylserine synthase-like genes by measuring the expression of the human phosphatidylserine synthase-like sequences in the presence and absence of the compound.

Other features and advantages of the invention will be apparent from the following detailed description and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides phosphatidylserine synthase-like molecules. By "phosphatidylserine synthase-like molecules" is intended a novel human sequence referred to as 32670, and variants and fragments thereof. These full-length gene sequences or fragments thereof are referred to as "phosphatidylserine synthase-like" sequences indicating they share sequence similarity with phosphatidylserine synthase genes. Isolated nucleic acid molecules comprising nucleotide sequences encoding the 32670 polypeptide whose amino acid sequence is given in SEQ ID NO:6, or a variant or fragment thereof, are provided. A nucleotide sequence encoding the 32670 polypeptide is set forth in SEQ ID NO:5, and a coding sequence encoding the 32670 polypeptide is set forth in SEQ ID NO:7.

The disclosed invention relates to methods and compositions for the modulation, diagnosis, and treatment of the disorders of the various cells and tissues herein described.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary cosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon- Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sezary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dernatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myclogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arterioyenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and interrnediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin $B_{12}$ deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, Leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sezary syndrome, peripheral T-cell lymphoma, unspecified, angio-immunoblastic T-cell lymphoma, angiocentric lymphoma (NK/T-cell lymphoma4a), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

A novel human phosphatidylserine synthase gene sequence, referred to as 32670, is provided. This gene sequence and variants and fragments thereof are encompassed by the term "phosphatidylserine synthase-like" molecules or sequences as used herein. The phosphatidylserine synthase-like sequences find use in modulating a phosphatidylserine synthase function. By "modulating" is intended the upregulating or downregulating of a response. That is, the compositions of the invention affect the targeted activity in either a positive or negative fashion.

The human phosphatidylserine synthase-like gene, clone 32670 was identified in a human osteoblast cDNA library. Clone 32670 encodes an mRNA transcript having the corresponding cDNA set forth in SEQ ID NO:5. This transcript has a 1461 nucleotide open reading frame (nucleotides 14–1474 of SEQ ID NO:5; SEQ ID NO:7), which encodes a 487 amino acid protein (SEQ ID NO:6).

In one embodiment, a 32670 protein includes at least one transmembrane domain. As used herein, the term "transmembrane domain" includes an amino acid sequence of about 17–22 amino acid residues in length that spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, http://pfam.wustl.edu/cgi-bin/getdesc?name=7tm-1, and Zagotta et al. (1996) Annual Rev. Neuronsci. 19:235–63, the contents of which are incorporated herein by reference.

In a preferred embodiment, a 32670 polypeptide or protein has at least one transmembrane domain or a region which includes at least 17, 18, 19, 20, 21, or 22 amino acid residues and has at least about 60%, 70% 80% 90% 95%, 99%, or 100% sequence identity with a "transmembrane domain," e.g., at least one transmembrane domain of human 32670 (e.g., amino acid residues 66–82, 96–112, 127–144, 246–262, 314–334, 345–362, 382–399, or 410–420 of SEQ ID NO:6).

In one embodiment, a 32670 protein includes at least one "non-transmembrane domain." As used herein, "non-transmembrane domains" are domains that reside outside of the membrane. When referring to plasma membranes, non-transmembrane domains include?extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring 32670, or 32670-like protein.

In a preferred embodiment, a 32670 polypeptide or protein has a "non-transmembrane domain" or a region which includes at least about 1–200, preferably about 5–150, more preferably about 10–105 amino acids, and has at least about 60%, 70% 80% 90% 95%, 99% or 100% sequence identity with a "non-transmembrane domain", e.g., a non-transmembrane domain of human 32670 (e.g., residues 1–65, 83–95, 113–126, 145–245, 263–313, 335–344, 363–381, 400–409, or 430–487 of SEQ ID NO:6). Preferably, a non-transmembrane domain is capable of catalytic activity (e.g., phosphatidylserine synthase activity).

A non-transmembrane domain located at the N-terminus of a 32670 protein or polypeptide is referred to herein as an "N-terminal non-transmembrane domain." As used herein, an "N-terminal non-transmembrane domain" includes an amino acid sequence having about 1–120, 25–105, or preferably 45–85 amino acid residues in length and is located outside the boundaries of a membrane. For example, an N-terminal non-transmembrane domain is located at about amino acid residues 1–65 of SEQ ID NO:6.

Similarly, a non-transmembrane domain located at the C-terminus of a 32670 protein or polypeptide is referred to herein as a "C-terminal non-transmembrane domain."As used herein, an "C-terminal non-transmembrane domain" includes an amino acid sequence having about 1–120, preferably about 20–100, more preferably about 40–80 amino acid residues in length and is located outside the boundaries of a membrane. For example, an C-terminal non-transmembrane domain is located at about amino acid residues 430–487 of SEQ ID NO:6.

A 32670 polypeptide can further include a signal sequence. As used herein, a "signal sequence" refers to a peptide of about 5–70 amino acid residues in length which occurs at the N-terminus of secretory and integral membrane proteins and which contains a majority of hydrophobic amino acid residues. For example, a signal sequence contains at least about 5–60 amino acid residues, preferably about 6–20 amino acid residues, more preferably about 7 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 32670 protein contains a signal sequence of about amino acids 1–7 of SEQ ID NO:6. The "signal sequence" is cleaved during processing of the mature protein. The mature 32670 protein corresponds to amino acids 8–487 of SEQ ID NO:6.

Prosite program analysis was used to predict various consensus sites within the 32670 protein. N-glycosylation sites were predicted at aa 181–184 and 237–240. A cAMP- and cGMP-dependent protein kinase phosphorylation site was predicted at aa 44–47. Protein kinase C phosphorylation sites were predicted at aa 93–95, 269–271, 272–274, 283–285, 310–312, and 437–439. Casein kinase II phosphorylation sites were predicted at aa 24–27, 47–50, 80–83, 85–88, 146–149, and 389–392. A tyrosine kinase phosphorylation site was predicted at aa 44–52. N-myristoylation sites were predicted at aa 96–101, 108–113, 257–262, 419–424, 455–460, and 476–481. An amidation site was predicted at aa 42–45. The human phosphatidylserine synthase-like protein possesses a type i leader peptidase domain from aa 314–338 as predicted by HMMer, Version 2.

The 32670 protein shares approximately 85% identity with the phosphatidylserine synthase II from *Cricetulus griseus* and approximately 86% identity with the murine phosphatidylserine synthase-2 as determined by pairwise alignment (FIG. 13).

The 32670 displays approximately 52% identity from aa 45–325 and approximately 33% identity from aa 305–464 to Prodom consensus sequences found in phosphatidylserine synthase I from *Cricetulus longicaudatus* (ProDom Accession No. PDO11831). H32670 also shares approximately 40% identity from aa 4–46 to a Prodom consensus sequence found in Hepatocyte Nuclear Factor 3 Forkhead Homolog 1 (HFH-1) from *Rattus norvegicus* and in the murine Fork Head Transcription Factor (Pro Dom Accession No. PD31440). Phosphatidylserine synthase I is a serine exchange enzyme (EC 2.7.8.8) involved in the synthesis of phosphatidylserine. Phosphatidylserine synthase I functions in a base-exchange between free L-serine and the polar head groups of pre-existing phospholipids. It can utilize phosphatidylcholine as a phosphatidyl donor. It also catalyzes the choline and ethanolamine base-exchange reactions. See, for example, Kuge et al. (1991) *J. Biol. Chem.* 266:24184–24189. The HFH-1 and the Fork Head Transcription Factor contain a conserved "fork head" domain involved in DNA-binding. See, for example, Haecker et al. (1995) *EMBO J.* 14:5306–5317, Clevidence et al. (1993) *Proc. Natl. Acad. Sci.* 90:3948–3952.

Preferred human phosphatidylserine synthase-like polypeptides of the present invention have an amino acid sequence sufficiently identical to the amino acid sequence of SEQ ID NO:6. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 60% identity, preferably 65% identity, more preferably 70%, 75%, or 80%, 85%, 90%, 91%, 92%, 93%, 94%, 95%, 96%, 97%, 98%, 99% or more identity are defined herein as sufficiently identical.

To determine the percent identity of two amino acid sequences,) or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) J. Mol. Biol. 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) CABIOS 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403–10. BLAST nucleotide searches can be performed with the NBLAST program, score=100, wordlength=12 to obtain nucleotide sequences homologous to 32670 nucleic acid molecules of the invention. BLAST protein searches can be performed with the XBLAST program, score=50, wordlength=3 to obtain amino acid sequences homologous to 32670 protein molecules of the invention. To obtain gapped alignments for comparison purposes, Gapped BLAST can be utilized as described in Altschul et al. (1997) Nucleic Acids Res. 25(17):3389–3402. When utilizing BLAST and Gapped BLAST programs, the default parameters of the respective programs (e.g., XBLAST and NBLAST) can be used. See http://www.ncbi.nlm.nih.gov.

Accordingly, another embodiment of the invention features isolated human phosphatidylserine synthase-like proteins and polypeptides having a human phosphatidylserine synthase-like protein activity. As used interchangeably herein, a "human phosphatidylserine synthase-like protein activity", "biological activity of a human phosphatidylserine synthase-like protein", or "functional activity of a human phosphatidylserine synthase-like protein" refers to an activity exerted by a human phosphatidylserine synthase-like protein, polypeptide, or nucleic acid molecule on a human phosphatidylserine synthase-like responsive cell as determined in vivo, or in vitro, according to standard assay techniques. A human phosphatidylserine synthase-like activity can be a direct activity, such as an association with or an enzymatic activity on a second protein, or an indirect activity, such as a cellular signaling activity mediated by interaction of the human phosphatidylserine synthase-like protein with a second protein. In a preferred embodiment, human phosphatidylserine synthase-like activity includes at least one or more modulating activities which may include stimulating and/or enhancing or inhibiting phosphatidylserine synthesis.

An "isolated" or "purified" human phosphatidylserine synthase-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated human phosphatidylserine synthase-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A human phosphatidylserine synthase-like protein that is substantially free of cellular material includes preparations of human phosphatidylserine synthase-like protein having less than about 30%, 20%, 10%, or 5% (by dry weight) of non-human phosphatidylserine synthase-like protein (also referred to herein as a "contaminating protein"). When the human phosphatidylserine synthase-like protein or biologically active portion thereof is recombinantly produced, preferably, culture medium represents less than about 30%, 20%, 10%, or 5% of the volume of the protein preparation. When human phosphatidylserine synthase-like protein is produced by chemical synthesis, preferably the protein preparations have less than about 30%, 20%, 10%, or 5% (by dry weight) of chemical precursors or non-human phosphatidylserine synthase-like chemicals.

Various aspects of the invention are described in further detail in the following subsections.

I. Isolated Nucleic Acid Molecules

One aspect of the invention pertains to isolated nucleic acid molecules comprising nucleotide sequences encoding human phosphatidylserine synthase-like proteins and polypeptides or biologically active portions thereof, as well as nucleic acid molecules sufficient for use as hybridization probes to identify human phosphatidylserine synthase-like encoding nucleic acids (e.g., human phosphatidylserine synthase-like mRNA) and fragments for use as PCR primers for the amplification or mutation of human phosphatidylserine synthase-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the human phosphatidylserine synthase-like proteins of the present invention include sequences set forth in SEQ ID NO:5, SEQ ID NO:7, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the human phosphatidylserine synthase-like protein encoded by these nucleotide sequences is set forth in SEQ ID NO:6. The invention also encompasses nucleic acid molecules comprising nucleotide sequences encoding partial-length human phosphatidylserine synthase-like proteins, including the sequence set forth in SEQ ID NO:6, and complements thereof.

Nucleic acid molecules that are fragments of these human phosphatidylserine synthase-like nucleotide sequences are also encompassed by the present invention. By "fragment" is intended a portion of the nucleotide sequence encoding a human phosphatidylserine synthase-like protein. A fragment of a human phosphatidylserine synthase-like nucleotide sequence may encode a biologically active portion of a human phosphatidylserine synthase-like protein, or it may be a fragment that can be used as a hybridization probe or PCR primer using methods disclosed below. A biologically active portion of a human phosphatidylserine synthase-like protein can be prepared by isolating a portion of one of the human phosphatidylserine synthase-like nucleotide sequences of the invention, expressing the encoded portion of the human phosphatidylserine synthase-like protein (e.g., by recombinant expression in vitro), and assessing the activity of the encoded portion of the human phosphatidylserine synthase-like protein. Nucleic acid molecules that are fragments of a human phosphatidylserine synthase-like nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800 nucleotides, or up to the number of nucleotides present in a full-length human phosphatidylserine synthase-like nucleotide sequence disclosed herein (for example, 1852 nucleotides for SEQ ID NO:5) depending upon the intended use.

Alternatively, a nucleic acid molecule that is a fragment of a human phosphatidylserine synthase-like nucleotide sequence of the present invention comprises a nucleotide sequence consisting of nucleotides 1–100, 101–200, 201–300, 301–400, 401–500, 501–600, 601–700, 701–800, 801–900, 901–1000, 1001–1100, 1101–1200, 1201–1300, 1301–1400, 1401–1500, 1501–1600, 1601–1700, 1701–1800, or 1801–1852 of SEQ ID NO:5.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a human phosphatidylserine synthase-like nucleotide sequence that encodes a biologically active portion of a human phosphatidylserine synthase-like protein of the invention will encode at least 15, 25, 30, 50, 75, 100, 125, 150, 175, 200, 250, or 300 contiguous amino acids, or up to the total number of amino acids present in a full-length human phosphatidylserine synthase-like protein of the invention (for example, 487 amino acids for SEQ ID NO:6). Fragments of a human phosphatidylserine synthase-like nucleotide sequence that are useful as hybridization probes for PCR primers generally need not encode a biologically active portion of a human phosphatidylscrine synthase-like protein.

Nucleic acid molecules that are variants of the human phosphatidylserine synthase-like nucleotide sequences disclosed herein are also encompassed by the present invention. "Variants" of the human phosphatidylserine synthase-like nucleotide sequences include those sequences that encode the human phosphatidylserine synthase-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the human phosphatidylserine synthase-like proteins disclosed in the present invention as discussed below. Generally, nucleotide sequence variants of the invention will have at least 60%, 65%, 70%, 75%, 80%, 85%, 90%, 91%, 92%, 93%, 94%, 95%, 96%, 97%, 98%, 99% or more identity to a particular nucleotide sequence disclosed herein. A variant human phosphatidylserine synthase-like nucleotide sequence will encode a human phosphatidylserine synthase-like protein that has an amino acid sequence having at least 45%, 55%, 65%, 75%, 85%, 90%, 91%, 92%, 93%, 94%, 95%, 96%, 97%, 98%, or 99% identity to the amino acid sequence of a human phosphatidylserine synthase-like protein disclosed herein.

In addition to the human phosphatidylserine synthase-like nucleotide sequences shown in SEQ ID NO:5 and SEQ ID NO:7, it will be appreciated by those skilled in the art that DNA sequence polymorphisms that lead to changes in the amino acid sequences of human phosphatidylserine synthase-like proteins may exist within a population (e.g., the human population). Such genetic polymorphism in a human phosphatidylserine synthase-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a human phosphatidylserine synthase-like protein, preferably a mammalia human phosphatidylserine synthase-like protein. As used herein, the phrase "allelic variant" refers to a nucleotide sequence that occurs at a human phosphatidylserine synthase-like locus or to a polypeptide encoded by the nucleotide sequence. Such natural allelic variations can typically result in 1–5% variance in the nucleotide sequence of the human phosphatidylserine synthase-like gene. Any and all such nucleotide variations and resulting amino acid polymorphisms or variations in a human phosphatidylserine synthase-like sequence that are the result of natural allelic variation and that do not alter the functional activity of human phosphatidylserine synthase-like proteins are intended to be within the scope of the invention.

Moreover, nucleic acid molecules encoding human phosphatidylserine synthase-like proteins from other species (human phosphatidylserine synthase-like homologues), which have a nucleotide sequence differing from that of the human phosphatidylserine synthase-like sequences disclosed herein, are intended to be within the scope of the invention. For example, nucleic acid molecules corresponding to natural allelic variants and homologues of the huma human phosphatidylserine synthase-like cDNA of the invention can be isolated based on their identity to the huma human phosphatidylserine synthase-like nucleic acid disclosed herein using the human cDNA, or a portion thereof, as a hybridization probe according to standard hybridization techniques under stringent hybridization conditions as disclosed below.

In addition to naturally-occurring allelic variants of the human phosphatidylserine synthase-like sequences that may exist in the population, the skilled artisan will further appreciate that changes can be introduced by mutation into the nucleotide sequences of the invention thereby leading to changes in the amino acid sequence of the encoded human phosphatidylserine synthase-like proteins, without altering the biological activity of the human phosphatidylserine synthase-like proteins. Thus, an isolated nucleic acid molecule encoding a human phosphatidylserine synthase-like protein having a sequence that differs from that of SEQ ID NO:5 or SEQ ID NO:7 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a human phosphatidylserine synthase-like protein (e.g., the sequence of SEQ ID NO:6) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Alternatively, variant human phosphatidylserine synthase-like nucleotide sequences can be made by introducing mutations randomly along all or part of a human phosphatidylserine synthase-like coding sequence, such as by saturation mutagenesis, and the resultant mutants can be screened for human phosphatidylserine synthase-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The human phosphatidylserine synthase-like nucleotide sequences of the invention, and fragments and variants thereof, can be used as probes and/or primers to identify and/or clone human phosphatidylserine synthase-like homologues in other cell types, e.g., from other tissues, as well as human phosphatidylserine synthase-like homologues from other mammals. Such probes can be used to detect transcripts or genomic sequences encoding the same or identical proteins. These probes can be used as part of a diagnostic test kit for identifying cells or tissues that misexpress a human phosphatidylserine synthase-like protein, such as by measuring levels of a human phosphatidylserine synthase-like—encoding nucleic acid in a sample of cells from a subject, e.g., detecting human phosphatidylserine synthase-like mRNA levels or determining whether a genomic human phosphatidylserine synthase-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis et al. (1990) *PCR Protocols: A Guide to Methods and Applications* (Academic Press, NY). Human phosphatidylserine synthase-like nucleotide sequences isolated based on their sequence identity to the human phosphatidylserine synthase-like nucleotide sequences set forth herein or to fragments and variants thereof are encompassed by the present invention.

In a hybridization method, all or part of a known human phosphatidylserine synthase-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known human phosphatidylserine synthase-like nucleotide sequence disclosed herein. Degenerate primers designed on the basis of conserved nucleotides or amino acid residues in a known human phosphatidylserine synthase-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a human phosphatidylserine synthase-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified human phosphatidylserine synthase-like nucleic acid molecule hybridizes under stringent conditions to a probe that is a nucleic acid molecule comprising one of the human phosphatidylserine synthase-like nucleotide sequences of the invention or a fragment thereof. In another embodiment, the previously unknown human phosphatidylserine synthase-like nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the human phosphatidylserine synthase-like nucleotide sequences disclosed herein or a fragment thereof.

Accordingly, in another embodiment, an isolated previously unknown human phosphatidylserine synthase-like nucleic acid molecule of the invention is at least 300, 325, 350, 375, 400, 425, 450, 500, 550, 600, 650, 700, 800, 900, 1000, 1,100, 1,200, 1,300, 1,400 nucleotides in length and hybridizes under stringent conditions to a probe that is a nucleic acid molecule comprising one of the nucleotide sequences of the invention, preferably the coding sequence set forth in SEQ ID NO:5 (shown in SEQ ID NO:7) or a complement, fragment, or variant thereof.

As used herein, the term "hybridizes under stringent conditions" describes conditions for hybridization and washing. Stringent conditions are known to those skilled in the art and can be found in Current Protocols in Molecular Biology John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:5 or SEQ ID NO:7 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

Thus, in addition to the human phosphatidylserine synthase-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the human phosphatidylserine synthase-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire human phosphatidylserine synthase-like coding strand, or to only a portion thereof, e.g., all or part of the protein coding region (or open reading frame). An antisense nucleic acid molecule can be antisense to a noncoding region of the coding strand of a nucleotide sequence encoding a human phosphatidylserine synthase-like protein. The noncoding regions are the 5' and 3' sequences that flank the coding region and are not translated into amino acids.

Given the coding-strand sequence encoding a human phosphatidylserine synthase-like protein disclosed herein (e.g., SEQ ID NO:6), antisense nucleic acids of the invention can be designed according to the rules of Watson and Crick base pairing. The antisense nucleic acid molecule can be complementary to the entire coding region of human phosphatidylserine synthase-like mRNA, but more preferably is an oligonucleotide that is antisense to only a portion of the coding or noncoding region of human phosphatidylserine synthase-like mRNA. For example, the antisense oligonucleotide can be complementary to the region surrounding the translation start site of human phosphatidylserine synthase-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a human phosphatidylserine synthase-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave human phosphatidylserine synthase-like mRNA transcripts to thereby inhibit translation of human phosphatidylserine synthase-like mRNA. A ribozyme having specificity for a human phosphatidylserine synthase-like—encoding nucleic acid can be designed based upon the nucleotide sequence of a human phosphatidylserine synthase-like cDNA disclosed herein (e.g., SEQ ID NO:5 or SEQ ID NO:7). See, e.g., Cech et al., U.S. Pat. No. 4,987,071; and Cech et al., U.S. Pat. No. 5,116,742. Alternatively, human phosphatidylserine synthase-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, human phosphatidylserine synthase-like gene expression can be inhibited by targeting nucleotide sequences complementary to the regulatory region of the human phosphatidylserine synthase-like protein (e.g., the human phosphatidylserine synthase-like promoter and/or enhancers) to form triple helical structures that prevent transcription of the human phosphatidylserine synthase-like gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a human phosphatidylserine synthase-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of a human phosphatidylserine synthase-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated Human Phosphatidylserine Synthase-Like Proteins and Anti-Human Phosphatidylserine Synthase-Like Antibodies Human phosphatidylserine synthase-like proteins are also encompassed within the present invention. By "human phosphatidylserine synthase-like protein" is intended a protein having the amino acid sequence set forth in SEQ ID NO: 2, as well as fragments, biologically active portions, and variants thereof.

"Fragments" or "biologically active portions" include polypeptide fragments suitable for use as immunogens to raise anti-human phosphatidylserine synthase-like antibodies. Fragments include peptides comprising amino acid sequences sufficiently identical to or derived from the amino acid sequence of a human phosphatidylserine synthase-like protein, or partial-length protein, of the invention and exhibiting at least one activity of a human phosphatidylserine synthase-like protein, but which include fewer amino acids than the full-length (SEQ ID NO:6) human phosphatidylserine synthase-like protein disclosed herein. Typically, biologically active portions comprise a domain or motif with at least one activity of the human phosphatidylserine synthase-like protein. A biologically active portion of a human phosphatidylserine synthase-like protein can be a polypeptide which is, for example, 10, 25, 50, 100 or more amino acids in length. Such biologically active portions can be prepared by recombinant techniques and evaluated for one or more of the functional activities of a native human phosphatidylserine synthase-like protein. As used here, a fragment comprises at least 5 contiguous amino acids of SEQ ID NO:6. The invention encompasses other fragments, however, such as any fragment in the protein greater than 6, 7, 8, 9, 10, 11, 12, 13, 14, 15 16, 17, 18, 19 or 20 amino acids.

By "variants" is intended proteins or polypeptides having an amino acid sequence that is at least about 60%, 65%, or 70%, preferably about 75%, 85%, 90%, 91%, 923, 93%, 94%, 95%, 96%, 97%, 98%, or 99% identical to the amino acid sequence of SEQ ID NO:6. Variants also include polypeptides encoded by a nucleic acid molecule that hybridizes to the nucleic acid molecule of SEQ ID NO:5, SEQ ID NO:7, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:6. If alignment is needed for this comparison the sequences should be aligned for maximum identity. "Looped" out sequences from deletions or insertions, or mismatches, are considered differences. Such variants generally retain the functional activity of the 32670 proteins of the invention. Variants include polypeptides that differ in amino acid sequence due to natural allelic variation or mutagenesis.

The invention also provides human phosphatidylserine synthase-like chimeric or fusion proteins. As used herein, a human phosphatidylserine synthase-like "chimeric protein" or "fusion protein" comprises a human phosphatidylserine synthase-like polypeptide operably linked to a non-human phosphatidylserine synthase-like polypeptide. A "human phosphatidylserine synthase-like polypeptide" refers to a polypeptide having an amino acid sequence corresponding to a human phosphatidylserine synthase-like protein, whereas a "non-human phosphatidylserine synthase-like polypeptide" refers to a polypeptide having an amino acid sequence corresponding to a protein that is not substantially identical to the human phosphatidylserine synthase-like protein, e.g., a protein that is different from the human phosphatidylserine synthase-like protein and which is derived from the same or a different organism. Within a human phosphatidylserine synthase-like fusion protein, the human phosphatidylserine synthase-like polypeptide can correspond to all or a portion of a human phosphatidylserine synthase-like protein, preferably at least one biologically active portion of a human phosphatidylserine synthase-like protein. Within the fusion protein, the term "operably linked" is intended to indicate that the human phosphatidylserine synthase-like polypeptide and the non-human phosphatidylserine synthase-like polypeptide are fused in-frame to each other. The non-human phosphatidylserine synthase-like polypeptide can be fused to the N-terminus or C-terminus of the human phosphatidylserine synthase-like polypeptide.

One useful fusion protein is a GST-human phosphatidylserine synthase-like fusion protein in which the human phosphatidylserine synthase-like sequences are fused to the C-terminus of the GST sequences. Such fusion proteins can facilitate the purification of recombinant human phosphatidylserine synthase-like proteins.

In yet another embodiment, the fusion protein is a human phosphatidylserine synthase-like—immunoglobulin fusion protein in which all or part of a human phosphatidylserine synthase-like protein is fused to sequences derived from a member of the immunoglobulin protein family. The human phosphatidylserine synthase-like—immunoglobulin fusion proteins of the invention can be incorporated into pharmaceutical compositions and administered to a subject to inhibit an interaction between a human phosphatidylserine synthase-like ligand and a human phosphatidylserine synthase-like protein on the surface of a cell, thereby suppressing human phosphatidylserine synthase-like— mediated signal transduction in vivo. The human phosphatidylserine synthase-like—immunoglobulin fusion proteins can be used to affect the bioavailability of a human phosphatidylserine synthase-like cognate ligand. Inhibition of the human phosphatidylserine synthase-like ligand/human phosphatidylserine synthase-like interaction may be useful therapeutically. Moreover, the human phosphatidylserine synthase-like—immunoglobulin fusion proteins of the invention can be used as immunogens to produce antihuman phosphatidylserine synthase-like antibodies in a subject, to purify human phosphatidylserine synthase-like ligands, and in screening assays to identify molecules that inhibit the interaction of a human phosphatidylserine synthase-like protein with a human phosphatidylserine synthase-like ligand.

Preferably, a human phosphatidylserine synthase-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a human phosphatidylserine synthase-like— encoding nucleic acid can be cloned into a commercially available expression vector such that it is linked in-frame to an existing fusion moiety. Variants of the human phosphatidylserine synthase-like proteins can function as either human phosphatidylserine synthase-like agonists (mimetics) or as human phosphatidylserine synthase-like antagonists. Variants of the human phosphatidylserine synthase-like protein can be generated by mutagenesis, e.g., discrete point mutation or truncation of the human phosphatidylserine synthase-like protein. An agonist of the human phosphatidylserine synthase-like protein can retain substantially the same, or a subset, of the biological activities of the naturally occurring form of the human phosphatidylserine synthase-like protein. An antagonist of the human phosphatidylserine synthase-like protein can inhibit one or more of the activities of the naturally occurring form of the human phosphatidylserine synthase-like protein by, for example, competitively binding to a downstream or upstream member of a cellular signaling cascade that includes the human phosphatidylserine synthase-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the human phosphatidylserine synthase-like proteins.

Variants of a human phosphatidylserine synthase-like protein that function as either human phosphatidylserine synthase-like agonists or as human phosphatidylserine synthase-like antagonists can be identified by screening combinatorial libraries of mutants, e.g., truncation mutants, of a human phosphatidylserine synthase-like protein for human phosphatidylserine synthase-like protein agonist or antagonist activity. In one embodiment, a variegated library of human phosphatidylserine synthase-like variants is generated by combinatorial mutagenesis at the nucleic acid level and is encoded by a variegated gene library. A variegated library of human phosphatidylserine synthase-like variants can be produced by, for example, enzymatically ligating a mixture of synthetic oligonucleotides into gene sequences such that a degenerate set of potential human phosphatidylserine synthase-like sequences is expressible as individual polypeptides, or alternatively, as a set of larger fusion proteins (e.g., for phage display) containing the set of human phosphatidylserine synthase-like sequences therein. There are a variety of methods that can be used to produce libraries of potential human phosphatidylserine synthase-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential human phosphatidylserine synthase-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a human phosphatidylserine synthase-like protein coding sequence can be used to generate a variegated population of human phosphatidylserine synthase-like fragments for screening and subsequent selection of variants of a human phosphatidylserine synthase-like protein. In one embodiment, a library of coding sequence fragments can be generated by treating a double-stranded PCR fragment of a human phosphatidylserine synthase-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the human phosphatidylserine synthase-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of human phosphatidylserine synthase-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify human phosphatidylserine synthase-like variants (Arkin and Yourvan (1992) *Proc. Natl. Acad. Sci. USA* 89:7811–7815; Delgrave et al. (1993) *Protein Engineering* 6(3):327–331).

An isolated human phosphatidylserine synthase-like polypeptide of the invention can be used as an immunogen to generate antibodies that bind human phosphatidylserine synthase-like proteins using standard techniques for polyclonal and monoclonal antibody preparation. The full-length human phosphatidylserine synthase-like protein can be used or, alternatively, the invention provides antigenic peptide fragments of human phosphatidylserine synthase-like proteins for use as immunogens. The antigenic peptide of a human phosphatidylserine synthase-like protein comprises at least 8, preferably 10, 15, 20, or 30 amino acid residues of the amino acid sequence shown in SEQ ID NO:6 and encompasses an epitope of a human phosphatidylserine synthase-like protein such that an antibody raised against the peptide forms a specific immune complex with the human phosphatidylserine synthase-like protein. Preferred epitopes encompassed by the antigenic peptide are regions of a human phosphatidylserine synthase-like protein that are located on the surface of the protein, e.g., hydrophilic regions.

Accordingly, another aspect of the invention pertains to anti-human phosphatidylserine synthase-like polyclonal and monoclonal antibodies that bind a human phosphatidylserine synthase-like protein. Polyclonal anti-human phosphatidylserine synthase-like antibodies can be prepared by immunizing a suitable subject (e.g., rabbit, goat, mouse, or other mammal) with a human phosphatidylserine synthase-like immunogen. The anti-human phosphatidylserine synthase-like antibody titer in the immunized subject can be monitored over time by standard techniques, such as with an enzyme linked immunosorbent assay (ELISA) using immobilized human phosphatidylserine synthase-like protein. At an appropriate time after immunization, e.g., when the anti-human phosphatidylserine synthase-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550–52; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-human phosphatidylserine synthase-like antibody can be identified and isolated by screening a recombinant combinatorial immunoglobulin library (e.g., an antibody phage display library) with a human phosphatidylserine synthase-like protein to thereby isolate immunoglobulin library members that bind the human phosphatidylserine synthase-like protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-human phosphatidylserine synthase-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-human phosphatidylserine synthase-like antibody (e.g., monoclonal antibody) can be used to isolate human phosphatidylserine synthase-like proteins by standard techniques, such as affinity chromatography or immunoprecipitation. An anti-human phosphatidylserine synthase-like antibody can facilitate the purification of natural human phosphatidylserine synthase-like protein from cells and of recombinantly produced human phosphatidylserine synthase-like protein expressed in host cells. Moreover, an anti-human phosphatidylserine synthase-like antibody can be used to detect human phosphatidylserine synthase-like protein (e.g., in a cellular lysate or cell supernatant) in order to evaluate the abundance and pattern of expression of the human phosphatidylserine synthase-like protein. Anti-human phosphatidylserine synthase-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a human phosphatidylserine synthase-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., human phosphatidylserine synthase-like proteins, mutant forms of human phosphatidylserine synthase-like proteins, fusion proteins, etc.).

It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of human phosphatidylserine synthase-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) Gene 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine homeobox (hox) promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to human phosphatidylserine synthase-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2nd ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromyciri, and methotrexate. Nucleic acid encoding a selectable marker can be introduced into a host cell on the same vector as that encoding a human phosphatidylserine synthase-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) human phosphatidylserine synthase-like protein. Accordingly, the invention further provides methods for producing human phosphatidylserine synthase-like protein using the host cells of the invention. In one embodiment, the method comprises culturing the host cell of the invention, into which a recombinant expression vector encoding a human phosphatidylserine synthase-like protein has been introduced, in a suitable medium such that human phosphatidylserine synthase-like protein is produced. In another embodiment, the method further comprises isolating human phosphatidylserine synthase-like protein from the medium or the host cell.

The host cells of the invention can also be used to produce nonhuman transgenic animals. For example, in one embodiment, a host cell of the invention is a fertilized oocyte or an embryonic stem cell into which human phosphatidylserine synthase-like—coding sequences have been introduced. Such host cells can then be used to create nonhuman transgenic animals in which exogenous human phosphatidylserine synthase-like sequences have been introduced into their genome or homologous recombinant animals in which endogenous human phosphatidylserine synthase-like sequences have been altered. Such animals are useful for studying the function and/or activity of human phosphatidylserine synthase-like genes and proteins and for identifying and/or evaluating modulators of human phosphatidylserine synthase-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous human phosphatidylserine synthase-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing human phosphatidylserine synthase-like—encoding nucleic acid into the male pronuclei of a fertilized oocyte, e.g., by microinjection, retroviral infection, and allowing the oocyte to develop in a pseudopregnant female foster animal. The human phosphatidylserine synthase-like cDNA sequence can be introduced as a transgene into the genome of a nonhuman animal. Alternatively, a homologue of the mouse human phosphatidylserine synthase-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the human phosphatidylserine synthase-like transgene to direct expression of human phosphatidylserine synthase-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the human phosphatidylserine synthase-like transgene in its genome and/or expression of human phosphatidylserine synthase-like mRNA in tissues or cells of the animals. A transgenic founder animal can then be used to breed additional animals carrying the transgene. Moreover, transgenic animals carrying a transgene encoding human phosphatidylserine synthase-like gene can further be bred to other transgenic animals carrying other transgenes.

To create a homologous recombinant animal, one prepares a vector containing at least a portion of a human phosphatidylserine synthase-like gene or a homolog of the gene into which a deletion, addition, or substitution has been introduced to thereby alter, e.g., functionally disrupt, the human phosphatidylserine synthase-like gene. In a preferred embodiment, the vector is designed such that, upon homologous recombination, the endogenous human phosphatidylserine synthase-like gene is functionally disrupted (i.e., no longer encodes a functional protein; also referred to as a "knock out" vector). Alternatively, the vector can be designed such that, upon homologous recombination, the endogenous human phosphatidylserine synthase-like gene is mutated or otherwise altered but still encodes functional protein (e.g., the upstream regulatory region can be altered to thereby alter the expression of the endogenous human phosphatidylserine synthase-like protein). In the homologous recombination vector, the altered portion of the human phosphatidylserine synthase-like gene is flanked at its 5' and 3' ends by additional nucleic acid of the human phosphatidylserine synthase-like gene to allow for homologous recombination to occur between the exogenous human phosphatidylserine synthase-like gene carried by the vector and an endogenous human phosphatidylserine synthase-like gene in an embryonic stem cell. The additional flanking human phosphatidylserine synthase-like nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced human phosphatidylserine synthase-like gene has homologously recombined with the endogenous human phosphatidylserine synthase-like gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The human phosphatidylserine synthase-like nucleic acid molecules, human phosphatidylserine synthase-like proteins, and anti-human phosphatidylserine synthase-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject", as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the skill of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a human phosphatidylserine synthase-like protein or anti-human phosphatidylserine synthase-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express human phosphatidylserine synthase-like protein (e.g., via a recombinant expression vector in a host cell in gene therapy applications), to detect human phosphatidylserine synthase-like mRNA (e.g., in a biological sample) or a genetic lesion in a human phosphatidylserine synthase-like gene, and to modulate human phosphatidylserine synthase-like activity. In addition, the human phosphatidylserine synthase-like proteins can be used to screen drugs or compounds in disorders characterized by insufficient or excessive production of human phosphatidylserine synthase-like protein or production of human phosphatidylserine synthase-like protein forms that have decreased or aberrant activity compared to human phosphatidylserine synthase-like wild type protein. In addition, the anti-human phosphatidylserine synthase-like antibodies of the invention can be used to detect and isolate human phosphatidylserine synthase-like proteins and modulate human phosphatidylserine synthase-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to human phosphatidylserine synthase-like proteins or have a stimulatory or inhibitory effect on, for example, human phosphatidylserine synthase-like expression or human phosphatidylserine synthase-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the human phosphatidylserine synthase-like protein can be accomplished, for example, by coupling the test compound with a radioisotope or enzymatic label such that binding of the test compound to the human phosphatidylserine synthase-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the human phosphatidylserine synthase-like protein to bind to or interact with a human phosphatidylserine synthase-like target molecule. By "target molecule" is intended a molecule with which a human phosphatidylserine synthase-like protein binds or interacts in nature. In a preferred embodiment, the ability of the human phosphatidylserine synthase-like protein to bind to or interact with a human phosphatidylserine synthase-like target molecule can be determined by monitoring the activity of the target molecule. For example, the activity of the target molecule can be monitored by detecting catalytic/enzymatic activity of the target on an appropriate substrate, detecting the induction of a reporter gene (e.g., a human phosphatidylserine synthase-like-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting a human phosphatidylserine synthase-like protein or biologically active portion thereof with a test compound and determining the ability of the test compound to bind to the human phosphatidylserine synthase-like protein or biologically active portion thereof. Binding of the test compound to the human phosphatidylserine synthase-like protein can be determined either directly or indirectly as described above. In a preferred embodiment, the assay includes contacting the human phosphatidylserine synthase-like protein or biologically active portion thereof with a known compound that binds human phosphatidylserine synthase-like protein to form an assay mixture, contacting the assay mixture with a test compound, and determining the ability of the test compound to preferentially bind to human phosphatidylserine synthase-like protein or biologically active portion thereof as compared to the known compound.

In another embodiment, an assay is a cell-free assay comprising contacting human phosphatidylserine synthase-like protein or biologically active portion thereof with a test compound and determining the ability of the test compound to modulate (e.g., stimulate or inhibit) the activity of the human phosphatidylserine synthase-like protein or biologically active portion thereof. Determining the ability of the test compound to modulate the activity of a human phosphatidylserine synthase-like protein can be accomplished, for example, by determining the ability of the human phosphatidylserine synthase-like protein to bind to a human phosphatidylserine synthase-like target molecule as described above for determining direct binding. In an alternative embodiment, determining the ability of the test compound to modulate the activity of a human phosphatidylserine synthase-like protein can be accomplished by determining the ability of the human phosphatidylserine synthase-like protein to further modulate a human phosphatidylserine synthase-like target molecule. For example, the catalytic/enzymatic activity of the target molecule on an appropriate substrate can be determined as previously described.

In yet another embodiment, the cell-free assay comprises contacting the human phosphatidylserine synthase-like protein or biologically active portion thereof with a known compound that binds a human phosphatidylserine synthase-like protein to form an assay mixture, contacting the assay mixture with a test compound, and determining the ability of the test compound to preferentially bind to or modulate the activity of a human phosphatidylserine synthase-like target molecule.

In the above-mentioned assays, it may be desirable to immobilize either a human phosphatidylserine synthase-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/human phosphatidylserine synthase-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or human phosphatidylserine synthase-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of human phosphatidylserine synthase-like binding or activity determined using standard techniques.

Other techniques for immobilizing proteins on matrices can also be used in the screening assays of the invention. For example, either human phosphatidylserine synthase-like protein or its target molecule can be immobilized utilizing conjugation of biotin and streptavidin. Biotinylated human phosphatidylserine synthase-like molecules or target molecules can be prepared from biotin-NHS(N-hydroxysuccinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a human phosphatidylserine synthase-like protein or target molecules but which do not interfere with binding of the human phosphatidylserine synthase-like protein to its target molecule can be derivatized to the wells of the plate, and unbound target or human phosphatidylserine synthase-like protein trapped in the wells by antibody conjugation. Methods for detecting such complexes, in addition to those described above for the GST-immobilized complexes, include immunodetection of complexes using antibodies reactive with the human phosphatidylserine synthase-like protein or target molecule, as well as enzyme-linked assays that rely on detecting an enzymatic activity associated with the human phosphatidylserine synthase-like protein or target molecule.

In another embodiment, modulators of human phosphatidylserine synthase-like expression are identified in a method in which a cell is contacted with a candidate compound and the expression of human phosphatidylserine synthase-like mRNA or protein in the cell is determined relative to expression of human phosphatidylserine synthase-like mRNA or protein in a cell in the absence of the candidate compound. When expression is greater (statistically significantly greater) in the presence of the candidate compound than in its absence, the candidate compound is identified as a stimulator of human phosphatidylserine synthase-like mRNA or protein expression. Alternatively, when expression is less (statistically significantly less) in the presence of the candidate compound than in its absence, the candidate compound is identified as an inhibitor of human phosphatidylserine synthase-like mRNA or protein expression. The level of human phosphatidylserine synthase-like mRNA or protein expression in the cells can be determined by methods described herein for detecting human phosphatidylserine synthase-like mRNA or protein.

In yet another aspect of the invention, the human phosphatidylserine synthase-like proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with human phosphatidylserine synthase-like protein ("human phosphatidylserine synthase-like—binding proteins" or "human phosphatidylserine synthase-like—bp") and modulate human phosphatidylserine synthase-like activity. Such human phosphatidylserine synthase-like—binding proteins are also likely to be involved in the propagation of signals by the human phosphatidylserine synthase-like proteins as, for example, upstream or downstream elements of the human phosphatidylserine synthase-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial human phosphatidylserine synthase-like gene sequences of the invention can be used to map their respective human phosphatidylserine synthase-like genes on a chromosome, thereby facilitating the location of gene regions associated with genetic disease. Computer analysis of human phosphatidylserine synthase-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the human phosphatidylserine synthase-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) Science 220:919–924). Somatic cell hybrids containing only fragments of human chromosomes can also be produced by using human chromosomes with translocations and deletions.

Other mapping strategies that can similarly be used to map a human phosphatidylserine synthase-like sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) Human Chromosomes: A Manual of Basic Techniques (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of human phosphatidylserine synthase-like genes uses human phosphatidylserine synthase-like polypeptides and fragments and sequences of the present invention and antibodies specific thereto. This mapping can be carried out by specifically detecting the presence of a human phosphatidylserine synthase-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a human phosphatidylserine synthase-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al.,(1987) *Nature* 325:783–787.

Moreover, differences in the DNA sequences between individuals affected and unaffected with a disease associated with the human phosphatidylserine synthase-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The human phosphatidylserine synthase-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the human phosphatidylserine synthase-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The human phosphatidylserine synthase-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:5 can comfortably provide positive individual identification with a panel of perhaps 10 to 1,000 primers that each yield a noncoding amplified sequence of 100 bases. If a predicted coding sequence, such as that in SEQ ID NO:5, is used, a more appropriate number of primers for positive individual identification would be 500 to 2,000.

3. Use of Partial Human Phosphatidylserine Synthase-Like Sequences in Forensic Biology DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:5 are particularly appropriate for this use as greater numbers of polymorphisms occur in the noncoding regions, making it easier to differentiate individuals using this technique. Examples of polynucleotide reagents include the human phosphatidylserine synthase-like sequences or portions thereof, e.g., fragments derived from the noncoding regions of SEQ ID NO:5 having a length of at least 20 or 30 bases.

The human phosphatidylserine synthase-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such human phosphatidylserine synthase-like probes, can be used to identify tissue by species and/or by organ type.

In a similar fashion, these reagents, e.g., human phosphatidylserine synthase-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting human phosphatidylserine synthase-like protein and/or nucleic acid expression as well as human phosphatidylserine synthase-like activity, in the context of a biological sample. An exemplary method for detecting the presence or absence of human phosphatidylserine synthase-like proteins in a biological sample involves obtaining a biological sample from a test subject and contacting the biological sample with a compound or an agent capable of detecting human phosphatidylserine synthase-like protein or nucleic acid (e.g., mRNA, genomic DNA) that encodes human phosphatidylserine synthase-like protein such that the presence of human phosphatidylserine synthase-like protein is detected in the biological sample. Results obtained with a biological sample from the test subject may be compared to results obtained with a biological sample from a control subject.

A preferred agent for detecting human phosphatidylserine synthase-like mRNA or genomic DNA is a labeled nucleic acid probe capable of hybridizing to human phosphatidylserine synthase-like mRNA or genomic DNA. The nucleic acid probe can be, for example, a full-length human phosphatidylserine synthase-like nucleic acid, such as the nucleic acid of SEQ ID NO:5, or a portion thereof, such as a nucleic acid molecule of at least 15, 30, 50, 100, 250, or 500 nucleotides in length and sufficient to specifically hybridize under stringent conditions to human phosphatidylserine synthase-like mRNA or genomic DNA. Other suitable probes for use in the diagnostic assays of the invention are described herein.

A preferred agent for detecting human phosphatidylserine synthase-like protein is an antibody capable of binding to human phosphatidylserine synthase-like protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect human phosphatidylserine synthase-like mRNA, protein, or genomic DNA in a biological sample in vitro as well as in vivo. For example, in vitro techniques for detection of human phosphatidylserine synthase-like mRNA include Northern hybridizations and in situ hybridizations. In vitro techniques for detection of human phosphatidylserine synthase-like protein include enzyme linked immunosorbent assays (ELISAs), Western blots, immunoprecipitations, and immunofluorescence. In vitro techniques for detection of human phosphatidylserine synthase-like genomic DNA include Southern hybridizations. Furthermore, in vivo techniques for detection of human phosphatidylserine synthase-like protein include introducing into a subject a labeled anti-human phosphatidylserine synthase-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood sample containing erythrocytes, lymphocytes and platelets which make for easily assayable cells.

The invention also encompasses kits for detecting the presence of human phosphatidylserine synthase-like proteins in a biological sample (a test sample). Such kits can be used to determine if a subject is suffering from or is at increased risk of developing a disorder associated with aberrant expression of human phosphatidylserine synthase-like protein (e.g., an immunological disorder). For example, the kit can comprise a labeled compound or agent capable of detecting human phosphatidylserine synthase-like protein or mRNA in a biological sample and means for determining the amount of a human phosphatidylserine synthase-like protein in the sample (e.g., an anti-human phosphatidylserine synthase-like antibody or an oligonucleotide probe that binds to DNA encoding a human phosphatidylserine synthase-like protein, e.g., SEQ ID NO:6). Kits can also include instructions for observing that the tested subject is suffering from or is at risk of developing a disorder associated with aberrant expression of human phosphatidylserine synthase-like sequences if the amount of human phosphatidylserine synthase-like protein or mRNA is above or below a normal level.

For antibody-based kits, the kit can comprise, for example: (1) a first antibody (e.g., attached to a solid support) that binds to human phosphatidylserine synthase-like protein; and, optionally, (2) a second, different antibody that binds to human phosphatidylserine synthase-like protein or the first antibody and is conjugated to a detectable agent. For oligonucleotide-based kits, the kit can comprise, for example: (1) an oligonucleotide, e.g., a detectably labeled oligonucleotide, that hybridizes to a human phosphatidylserine synthase-like nucleic acid sequence or (2) a pair of primers useful for amplifying a human phosphatidylserine synthase-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of human phosphatidylserine synthase-like proteins.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a phosphatidylserine synthase-like nucleic acid, preferably purified, polypeptide, preferably purified, or antibody, and thereby evaluating the plurality of capture probes. Binding, e.g., in the case of a nucleic acid, hybridization, with a capture probe at an address of the plurality, is detected, e.g., by signal generated from a label attached to the phosphatidylserine synthase-like nucleic acid, polypeptide, or antibody. The capture probes can be a set of nucleic acids from a selected sample, e.g., a sample of nucleic acids derived from a control or non-stimulated tissue or cell.

The method can include contacting the phosphatidylserine synthase-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a phosphatidylserine synthase-like sequence of the invention. Such methods can be used to diagnose a subject, e.g., to evaluate risk for a disease or disorder, to evaluate suitability of a selected treatment for a subject, to evaluate whether a subject has a disease or disorder. Thus, for example, the 32670 sequence set forth in SEQ ID NO:5 and SEQ ID NO:7 encodes a phosphatidylserine synthase-like polypeptide that is useful to evaluate a disease or disorder wherein there is defective cell membrane formation.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a phosphatidylserine synthase-like polypeptide of the invention or from a cell or subject in which a phosphatidylserine synthase-like-mediated response has been elicited, e.g., by contact of the cell with a phosphatidylserine synthase-like nucleic acid or protein of the invention, or administration to the cell or subject a phosphatidylserine synthase-like nucleic acid or protein of the invention; contacting the array with one or more inquiry probes, wherein an inquiry probe can be a nucleic acid, polypeptide, or antibody (which is preferably other than a phosphatidylserine synthase-like nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a phosphatidylserine synthase-like sequence of the invention (or does not express as highly as in the case of the phosphatidylserine synthase-like positive plurality of capture probes) or from a cell or subject in which a phosphatidylserine synthase-like-mediated response has not been elicited (or has been elicited to a lesser extent than in the first sample); contacting the array with one or more inquiry probes (which is preferably other than a phosphatidylserine synthase-like nucleic acid, polypeptide, or antibody of the invention), and thereby evaluating the plurality of capture probes. Binding, e.g., in the case of a nucleic acid, hybridization, with a capture probe at an address of the plurality, is detected, e.g., by signal generated from a label attached to the nucleic acid, polypeptide, or antibody.

In another aspect, the invention features a method of analyzing a phosphatidylserine synthase-like sequence of the invention, e.g., analyzing structure, function, or relatedness to other nucleic acid or amino acid sequences. The method includes: providing a phosphatidylserine synthase-like nucleic acid or amino acid sequence, e.g., the 32670 sequence set forth in SEQ ID NO:5, SEQ ID NO:7, or a portion thereof; comparing the phosphatidylserine synthase-like sequence with one or more preferably a plurality of sequences from a collection of sequences, e.g., a nucleic acid or protein sequence database; to thereby analyze the phosphatidylserine synthase-like sequence of the invention.

The method can include evaluating the sequence identity between a phosphatidylserine synthase-like sequence of the invention, e.g., the 32670 sequence, and a database sequence. The method can be performed by accessing the database at a second site, e.g., over the internet.

In another aspect, the invention features, a set of oligonucleotides, useful, e.g., for identifying SNP's, or identifying specific alleles of a Phosphatidylserine synthase-like sequence of the invention, e.g., the 15571 sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with human phosphatidylserine synthase-like protein, human phosphatidylserine synthase-like nucleic acid expression, or human phosphatidylserine synthase-like activity. Prognostic assays can be used for prognostic or predictive purposes to thereby prophylactically treat an individual prior to the onset of a disorder characterized by or associated with human phosphatidylserine synthase-like protein, human phosphatidylserine synthase-like nucleic acid expression, or human phosphatidylserine synthase-like activity.

Thus, the present invention provides a method in which a test sample is obtained from a subject, and human phosphatidylserine synthase-like protein or nucleic acid (e.g., mRNA, genomic DNA) is detected, wherein the presence of human phosphatidylserine synthase-like protein or nucleic acid is diagnostic for a subject having or at risk of developing a disease or disorder associated with aberrant human phosphatidylserine synthase-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease human phosphatidylserine synthase-like activity) to effectively treat a disease or disorder associated with aberrant human phosphatidylserine synthase-like expression or activity. In this manner, a test sample is obtained and human phosphatidylserine synthase-like protein or nucleic acid is detected. The presence of human phosphatidylserine synthase-like protein or nucleic acid is diagnostic for a subject that can be administered the agent to treat a disorder associated with aberrant human phosphatidylserine synthase-like expression or activity.

The methods of the invention can also be used to detect genetic lesions or mutations in a human phosphatidylserine synthase-like gene. In preferred embodiments, the methods include detecting, in a sample of cells from the subject, the presence or absence of a genetic lesion or mutation characterized by at least one of an alteration affecting the integrity of a gene encoding a human phosphatidylserine synthase-like—protein, or the misexpression of the human phosphatidylserine synthase-like gene. For example, such genetic lesions or mutations can be detected by ascertaining the existence of at least one of: (1) a deletion of one or more nucleotides from a human phosphatidylserine synthase-like gene; (2) an addition of one or more nucleotides to a human phosphatidylserine synthase-like gene; (3) a substitution of one or more nucleotides of a human phosphatidylserine synthase-like gene; (4) a chromosomal rearrangement of a human phosphatidylserine synthase-like gene; (5) an alteration in the level of a messenger RNA transcript of a human phosphatidylserine synthase-like gene; (6) an aberrant modification of a human phosphatidylserine synthase-like gene, such as of the methylation pattern of the genomic DNA; (7) the presence of a non-wild-type splicing pattern of a messenger RNA transcript of a human phosphatidylserine synthase-like gene; (8) a non-wild-type level of a human phosphatidylserine synthase-like—protein; (9) an allelic loss of a human phosphatidylserine synthase-like gene; and (10) an inappropriate post-translational modification of a human phosphatidylserine synthase-like—protein. As described herein, there are a large number of assay techniques known in the art that can be used for detecting lesions in a human phosphatidylserine synthase-like gene. Any cell type or tissue, preferably peripheral blood leukocytes, in which human phosphatidylserine synthase-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Nat. Acad. Sci. USA* 91:360–364), the latter of which can be particularly useful for detecting point mutations in the human phosphatidylserine synthase-like—gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a human phosphatidylserine synthase-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a human phosphatidylserine synthase-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the human phosphatidylserine synthase-like gene and detect mutations by comparing the sequence of the sample human phosphatidylserine synthase-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the human phosphatidylserine synthase-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in human phosphatidylserine synthase-like cDNAs obtained from samples of cells. See, e.g., Hsu et al. (1994) *Carcinogenesis* 15:1657–1662. According to an exemplary embodiment, a probe based on a human phosphatidylserine synthase-like sequence, e.g., a wild-type human phosphatidylserine synthase-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in human phosphatidylserine synthase-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) Mutat. Res. 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a human phosphatidylserine synthase-like gene.

4. Pharmacogenomics

Agents, or modulators that have a stimulatory or inhibitory effect on human phosphatidylserine synthase-like activity (e.g., human phosphatidylserine synthase-like gene expression) as identified by a screening assay described herein, can be administered to individuals to treat (prophylactically or therapeutically) disorders associated with aberrant human phosphatidylserine synthase-like activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of human phosphatidylserine synthase-like protein, expression of human phosphatidylserine synthase-like nucleic acid, or mutation content of human phosphatidylserine synthase-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a phosphatidylserine synthase-like molecule or phosphatidylserine synthase-like modulator of the invention as well as tailoring the dosage and/or therapeutic regimen of treatment with a phosphatidylserine synthase-like molecule or phosphatidylserine synthase-like modulator of the invention.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a phosphatidylserine synthase-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a phosphatidylserine synthase-like molecule or phosphatidylserine synthase-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a phosphatidylserine synthase-like molecule or phosphatidylserine synthase-like modulator of the invention, such as a modulator identified by one of the exemplary screening assays described herein.

The present invention further provides methods for identifying new agents, or combinations, that are based on identifying agents that modulate the activity of one or more of the gene products encoded by one or more of the Phosphatidylserine synthase-like genes of the present invention, wherein these products may be associated with resistance of the cells to a therapeutic agent. Specifically, the activity of the proteins encoded by the phosphatidylserine synthase-like genes of the present invention can be used as a basis for identifying agents for overcoming agent resistance. By blocking the activity of one or more of the resistance proteins, target cells, e.g., hepatic stellate cells, will become sensitive to treatment with an agent that the unmodified target cells were resistant to.

Monitoring the influence of agents (e.g., drugs) on the expression or activity of a phosphatidylserine synthase-like protein can be applied in clinical trials. For example, the effectiveness of an agent determined by a screening assay as described herein to increase phosphatidylserine synthase-like gene expression, protein levels, or upregulate phosphatidylserine synthase-like activity, can be monitored in clinical trials of subjects exhibiting decreased phosphatidylserine synthase-like gene expression, protein levels, or downregulated phosphatidylserine synthase-like activity. Alternatively, the effectiveness of an agent determined by a screening assay to decrease phosphatidylserine synthase-like gene expression, protein levels, or downregulate phosphatidylserine synthase-like activity, can be monitored in clinical trials of subjects exhibiting increased phosphatidylserine synthase-like gene expression, protein levels, or upregulated phosphatidylserine synthase-like activity. In such clinical trials, the expression or activity of a phosphatidylserine synthase-like gene, and preferably, other genes that have been implicated in, for example, a phosphatidylserine synthase-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of human phosphatidylserine synthase-like protein, expression of human phosphatidylserine synthase-like nucleic acid, or mutation content of human phosphatidylserine synthase-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a human phosphatidylserine synthase-like modulator, such as a modulator identified by one of the exemplary screening assays described herein.

5. Monitoring of Effects During Clinical Trials

Monitoring the influence of agents (e.g., drugs, compounds) on the expression or activity of human phosphatidylserine synthase-like genes can be applied not only in basic drug screening but also in clinical trials. For example, the effectiveness of an agent, as determined by a screening assay as described herein, to increase or decrease human phosphatidylserine synthase-like gene expression, protein levels, or protein activity, can be monitored in clinical trials of subjects exhibiting decreased or increased human phosphatidylserine synthase-like gene expression, protein levels, or protein activity.

For example, and not by way of limitation, genes that are modulated in cells by treatment with an agent (e.g., compound, drug, or small molecule) that modulates human phosphatidylserine synthase-like activity (e.g., as identified in a screening assay described herein) can be identified. Thus, to study the effect of agents on cellular proliferation disorders, for example, in a clinical trial, cells can be isolated and RNA prepared and analyzed for the levels of expression of human phosphatidylserine synthase-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of human phosphatidylserine synthase-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a human phosphatidylserine synthase-like protein, mRNA, or genomic DNA in the preadministration sample; (3) obtaining one or more postadministration samples from the subject; (4) detecting the level of expression or activity of the human phosphatidylserine synthase-like protein, mRNA, or genomic DNA in the postadministration samples; (5) comparing the level of expression or activity of the human phosphatidylserine synthase-like protein, mRNA, or genomic DNA in the preadministration sample with the human phosphatidylserine synthase-like protein, mRNA, or genomic DNA in the postadministration sample or samples; and (vi) altering the administration of the agent to the subject accordingly to bring about the desired effect, i.e., for example, an increase or a decrease in the expression or activity of a human phosphatidylserine synthase-like protein.

C. Methods of Treatment

The present invention provides for both prophylactic and therapeutic methods of treating a subject at risk of (or susceptible to) a disorder or having a disorder associated with aberrant human phosphatidylserine synthase-like expression or activity. Additionally, the compositions of the invention find use in the treatment of disorders described herein. Thus, therapies for disorders associated with CCC are encompassed herein.

1. Prophylactic Methods

In one aspect, the invention provides a method for preventing in a subject a disease or condition associated with an aberrant human phosphatidylserine synthase-like expression or activity by administering to the subject an agent that modulates human phosphatidylserine synthase-like expression or at least one human phosphatidylserine synthase-like gene activity. Subjects at risk for a disease that is caused, or contributed to, by aberrant human phosphatidylserine synthase-like expression or activity can be identified by, for example, any or a combination of diagnostic or prognostic assays as described herein. Administration of a prophylactic agent can occur prior to the manifestation of symptoms characteristic of the human phosphatidylserine synthase-like aberrancy, such that a disease or disorder is prevented or, alternatively, delayed in its progression. Depending on the type of human phosphatidylserine synthase-like aberrancy, for example, a human phosphatidylserine synthase-like agonist or human phosphatidylserine synthase-like antagonist agent can be used for treating the subject. The appropriate agent can be determined based on screening assays described herein.

2. Therapeutic Methods

Another aspect of the invention pertains to methods of modulating human phosphatidylserine synthase-like expression or activity for therapeutic purposes. The modulatory method of the invention involves contacting a cell with an agent that modulates one or more of the activities of human phosphatidylserine synthase-like protein activity associated with the cell. An agent that modulates human phosphatidylserine synthase-like protein activity can be an agent as described herein, such as a nucleic acid or a protein, a naturally-occurring cognate ligand of a human phosphatidylserine synthase-like protein, a peptide, a human phosphatidylserine synthase-like peptidomimetic, or other small molecule. In one embodiment, the agent stimulates one or more of the biological activities of human phosphatidylserine synthase-like protein. Examples of such stimulatory agents include active human phosphatidylserine synthase-like protein and a nucleic acid molecule encoding a human phosphatidylserine synthase-like protein that has been introduced into the cell. In another embodiment, the agent inhibits one or more of the biological activities of human phosphatidylserine synthase-like protein. Examples of such inhibitory agents include antisense human phosphatidylserine synthase-like nucleic acid molecules and anti-human phosphatidylserine synthase-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a human phosphatidylserine synthase-like protein or nucleic acid molecule. In one embodiment, the method involves administering an agent (e.g., an agent identified by a screening assay described herein), or a combination of agents, that modulates (e.g., upregulates or downregulates) human phosphatidylserine synthase-like expression or activity. In another embodiment, the method involves administering a human phosphatidylserine synthase-like protein or nucleic acid molecule as therapy to compensate for reduced or aberrant human phosphatidylserine synthase-like expression or activity.

Stimulation of human phosphatidylserine synthase-like activity is desirable in situations in which a human phosphatidylserine synthase-like protein is abnormally downregulated and/or in which increased human phosphatidylserine synthase-like activity is likely to have a beneficial effect. Conversely, inhibition of human phosphatidylserine synthase-like activity is desirable in situations in which human phosphatidylserine synthase-like activity is abnormally upregulated and/or in which decreased human phosphatidylserine synthase-like activity is likely to have a beneficial effect.

This invention is further illustrated by the following examples, which should not be construed as limiting.

EXAMPLES

Example 1

Identification and Characterization of Human 32670 cDNAs

The human 32670 sequence (FIGS. 14A–B; SEQ ID NO:5), which is approximately 1852 nucleotides long including untranslated regions, contains a predicted methionine-initiated coding sequence of about 1464 nucleotides (nucleotides 14–1477 of SEQ ID NO:5; SEQ ID NO:7). The coding sequence encodes a 487 amino acid protein (SEQ ID NO:6).

Example 2

Tissue Distribution of 32670 mRNA 32670 expression was determined by the PCR in cDNA libraries generated from various human tissues and cell types. 32670 expression was detectable in cDNA libraries generated from the following tissues: microvascular endothelial cells, umbilical vein endothelial cells, U937 cells, CaCo cells, HeLa cells, fetal brain, bronchial epithelium, astrocytes, prostate epithelium, primary osteoblasts, keratinocytes, melanocytes, coronary smooth muscle cells, cerebellum, pituitary, aortic endothelial cells, fetal kidney, fetal liver, mengial, bone marrow, fetal thymus, fetal heart, mammary gland, tissue from a subject with congestive heart failure, prostate smooth muscle cells, osteoblasts treated with LPS for 6 hours, fetal heart, tissue from a subject with Burkin's lymphoma, mammary epithelium, umbilical smooth muscle, bronchial smooth muscle, fetal spleen, esophagus, fetal liver, fetal skin, fetal adrenal gland, lung carcinoma tissue, A549 cells, fetal testes, pulmonary artery smooth muscle, erythroleukemia cells, embryonic keratinocytes, tongue squamous cell carcinoma, fetal hypothalamus, CD3 treated T cells, HPKII cells, testes, H160 cells, placenta, skeletal muscle, kidney, HPK cells, uterus, 9 week fetus, salivary gland, testes, K563 cells, lung, thymus, skeletal muscle, prostate, Hep-G2 insulinoma cells, normal breast epithelia, normal ovarian epithelia, normal megakaryocytes, Th-2 induced T cell, fetal dorsal spinal cord, colon to live metastasis, colon carcinoma, lung squamous cell carcinoma, d8 dendritic cells, skin, ovarian ascites, IBD colon, dorsal root ganglia, brain subcortical white matter, prostate tumor xenograft cell cline K10, prostate cancer to liver metastasis, umbilical vein endothelial cells grown under hypoxic conditions, melanoma G361 cell line, lumbosacaral spinal chord, and adult bone marrow CD34 positive cells.

Northern blot hybridizations with various RNA samples are performed under standard conditions and washed under stringent conditions, i.e., 0.2×SSC at 65° C. A DNA probe corresponding to all or a portion of the 32670 cDNA (SEQ ID NO:5 or SEQ ID NO:7) can be used. The DNA is radioactively labeled with 32P-dCTP using the Prime-It Kit (Stratagene, La Jolla, Calif.) according to the instructions of the supplier. Filters containing mRNA from mouse hematopoictic and endocrine tissues, and cancer cell lines (Clontech, Palo Alto, Calif.) are probed in ExpressHyb hybridization solution (Clontech) and washed at high stringency according to manufacturer's recommendations.

Example 3

Recombinant Expression of 32670 in Bacterial Cells

In this example, 32670 is expressed as a recombinant glutathione-S-transferase (GST) fusion polypeptide in *E. coli* and the fusion polypeptide is isolated and characterized. Specifically, 32670 is fused to GST and this fusion polypeptide is expressed in *E. coli*, e.g., strain PEB199. Expression of the GST-32670 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 32670 Protein in COS Cells

To express the 32670 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32670 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 32670 DNA sequence is amplified by PCR using two primers. The 5' primer contains the restriction site of interest followed by approximately twenty nucleotides of the 32670 coding sequence starting from the initiation codon; the 3' end sequence contains complementary sequences to the other restriction site of interest, a translation stop codon, the HA tag or FLAG tag and the last 20 nucleotides of the 32670 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 32670 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32670-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 32670 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32670 coding sequence is cloned directly into the polylinker of the pcDNA/Amp vector using the appropriate restriction sites. The resulting plasmid is transfected into COS cells in the manner described above, and the expression of the 32670 polypeptide is detected by radiolabelling and immunoprecipitation using a 32670 specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many

CHAPTER 3

5698, a DNA Fragmentation Factor-Like Molecule and Uses Thereof

BACKGROUND OF THE INVENTION

Apoptosis is fundamentally important in a variety of physiological and pathological processes. Apoptotic cells undergo an orchestrated cascade of events characterized by distinct morphological changes including membrane blebbing, cytoplasmic and nuclear degradation, chromatin aggregation, and formation of apoptotic bodies. A key molecular event in the process of apoptosis is the activation of the caspase cascade. Caspases are a family of serine proteases identified in mammalian cells. Caspase activation leads to cleavage of target protein and execution of the apoptotic program. Apoptotic signals, including growth factor and interleukin deprivation, activation of Fas, ionizing radiation, and a series of chemicals acting as upstream signals, can convert the precursors of caspases into the protease active enzymes.

One of the downstream substrates of caspase is a subunit of the DNA Fragmentation Factor (DFF) complex. DFF is a heterodimeric protein complex composed of DFF45 and DFF40 subunits. DFF45 has been found to be the substrate of caspase-3 and DFF40 has also been cloned and found to be a DNA fragmentation nuclease. Studies have shown that DFF45 can mediate the correct folding of DFF40 and remains associated with DFF40 to prevent DFF40 from being activated until a specific signal (the activation of caspase-3) is received. DFF45 therefore acts as a specific molecular chaperon and appears to provide a double safety control to prevent unwanted activation of DFF40. Following cleavage, the DFF45 dissociates from DFF40. The active component of DFF then triggers both DNA fragmentation and chromatin condensation during apoptosis (Gu et al. (1999) *The Journal of Biological Chemistry* 274:20759–20762).

DFF homologs have also been identified in the mouse. The mouse DFF is composed of three molecules: one caspase-activated DNAse (CAD) and two forms of CAD inhibitors (ICAD-L and ICAD-S). Mouse CAD and ICAD-L are apparently the counterpart of huma DFF40 (CPAN) and DFF45, respectively, whereas the human counterpart of mouse ICAD-S has not been identified.

In addition, cell death-inducing DFF45-like effector A and B (CIDE-A and CIDE-B) encode highly related proteins with homology to the N-terminal region of DFF45. CIDE-A and CIDE-B activate apoptosis and appear to function as positive effectors of the apoptotic pathway. Inohara et al. have demonstrated that CIDE-A and CIDE-B induce DNA fragmentation as well as other morphological features of apoptosis including nuclear condensation and membrane blebbing (Inohara et al. (1998) *EMBO J.* 17:2526–2533).

The proteins of the DFF complex influence DNA fragmentation and ultimately apoptosis and therefore play a role in various biological and pathological processes. For example, during normal CNS development, a significant proportion of neurons die by apoptosis to permit the matching of cells with their targets (Oppenheim et al. (1991) *Annu. Rev. Neuroscience* 14: 453–501). Apoptotic events also play an important role in specific pathological conditions including Alzheimer's and Huntington's disease (Portera-Calliau et al. (1995) *J. Neurosci* 15:3775–3787 and Samle et al. (1995) *Exp. Neruo.* 133:225–230), cerebral ischemia (MacManus et al. (1995) *J. Cereb. Blood Flow Metab.* 15:728–737), and HIV encephalitis (Petito et al. (1995) *Am. J. Pathol.* 146:1121–1130).

Furthermore, recent studies have demonstrated that apoptotic cell death occurs after traumatic spinal cord injury and following traumatic brain injury (Li et al. (1996) *J. Neruopathol. Exp. Neruol* 55:280–289). The apoptotic event is characterized by the activation of caspase-3 in the injured rat cortex and hippocampus. Regional and temporal changes in DFF-like proteins are observed following these trauma events. Zhang et al. observed that DFF45-like proteins labeled with the anti-human DFF45 antibody significantly decrease in the cortex after brain trauma. These changes in the DFF45-like proteins are suggestive of an early signal of DNA fragmentation and that the DFF proteins are playing a role during apoptosis following a traumatic brain injury (Zhang et al. (1999) *Journal of Neurochemistry* 73:1650–1659).

Evidence indicates DFF complex plays an important role in cellular apoptosis. Accordingly, it is valuable to the field of pharmaceutical development to identify and characterize previously unknown DFF-like polypeptides. The present invention advances the state of the art by providing previously unidentified DNA fragmentation factor-like nucleic acid and polypeptides.

SUMMARY OF THE INVENTION

Isolated nucleic acid molecules corresponding to DFF-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:11. Further provided are DFF-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The DFF-like molecules of the present invention are useful for modulating apoptotic events, including DNA fragmentation. The molecules are useful for the diagnosis and treatment of disorders associated with dysregulated apoptosis. Such disorders include cancers, autoimmune disorders, neurodegenerative diseases, ischemic injuries, and virus induced lymphocyte depletion. Additionally, the molecules of the invention are useful as modulating agents in a variety of cellular processes including DNA fragmentation, intracellular signaling, membrane blebbing, cytoplasmic and nuclear degradation, chromatin aggregation, and formation of apoptotic bodies. Accordingly, in one aspect, this invention provides isolated nucleic acid molecules encoding DFF-like proteins or biologically active portions thereof, as well as nucleic acid fragments suitable as primers or hybridization probes for the detection of DFF-like-encoding nucleic acids.

Another aspect of this invention features isolated or recombinant DFF-like proteins and polypeptides. Preferred DFF-like proteins and polypeptides possess at least one biological activity possessed by naturally occurring DFF-like proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the DFF-like polypeptides and fragments are provided. Such antibodies are useful in detecting the DFF-like polypeptides as well as in regulating apoptotic processes.

In another aspect, the present invention provides a method for detecting the presence of DFF-like activity or expression in a biological sample by contacting the biological sample with an agent capable of detecting an indicator of DFF-like activity such that the presence of DFF-like activity is detected in the biological sample.

In yet another aspect, the invention provides a method for modulating DFF-like activity comprising contacting a cell with an agent that modulates (inhibits or stimulates) DFF-like activity or expression such that DFF-like activity or expression in the cell is modulated. In one embodiment, the agent is an antibody that specifically binds to DFF-like protein. In another embodiment, the agent modulates expression of DFF-like protein by modulating transcription of a DFF-like gene, splicing of a DFF-like mRNA, or translation of a DFF-like mRNA. In yet another embodiment, the agent is a nucleic acid molecule having a nucleotide sequence that is antisense to the coding strand of the DFF-like mRNA or the DFF-like gene.

In one embodiment, the methods of the present invention are used to treat a subject having a disorder characterized by aberrant DFF-like protein activity or nucleic acid expression by administering an agent that is a DFF-like modulator to the subject. In one embodiment, the DFF-like modulator is a DFF-like protein. In another embodiment, the DFF-like modulator is a DFF-like nucleic acid molecule. In other embodiments, the DFF-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a DFF-like protein; (2) misregulation of a gene encoding a DFF-like protein; and (3) aberrant post-translational modification of a DFF-like protein, wherein a wild-type form of the gene encodes a protein with a DFF-like activity.

In another aspect, the invention provides a method for identifying a compound that binds to or modulates the activity of a DFF-like protein. In general, such methods entail measuring a biological activity of a DFF-like protein in the presence and absence of a test compound and identifying those compounds that alter the activity of the DFF-like protein.

The invention also features methods for identifying a compound that modulates the expression of DFF-like genes by measuring the expression of the DFF-like sequences in the presence and absence of the compound.

Other features and advantages of the invention will be apparent from the following detailed description and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides DFF-like molecules. By "DFF-like molecules" is intended a novel human sequence referred to as 5698, and variants and fragments thereof. These full-length gene sequences or fragments thereof are referred to as "DFF-like" sequences, indicating they share sequence similarity with DFF genes. Isolated nucleic acid molecules comprising nucleotide sequences encoding the 5698 polypeptide whose amino acid sequence is given in SEQ ID NO:11, or a variant or fragment thereof, are provided. A nucleotide sequence encoding the 5698 polypeptide is set forth in SEQ ID NO:10 or 12. The sequences are members of the DNA Fragmentation Factor family.

The disclosed invention relates to methods and compositions for the modulation, diagnosis, and treatment of disorders associated with dysregulated apoptosis. By "disregulted apoptosis" is intended an alteration in the apoptotic process that results in either an inappropriately low or high rate of apoptosis. Disorders associated with an inappropriately low rate of apoptosis may prolong survival of abnormal cells. These accumulated cells can give rise to cancers, especially those carcinomas with p53 mutations, or homo-dependent tumors, such as breast, prostate, or ovarian cancers. Autoimmune disorders also can arise if, for example, autoreactive lymphocytes are not removed following an immune response. The molecules are also useful for the diagnosis and treatment of disorders associated with increased apoptosis and excessive cell death. These disorders are characterized by a marked loss of normal or protective cells and include: neurodegenerative diseases, manifested by loss of specific sets of neurons, such as in the spinal muscular atrophies; ischemic injuries such as in myocardial infarction and stroke; and, virus induced lymphocyte depletion, such as in acquired immune deficiency syndrome.

Figure 20A:
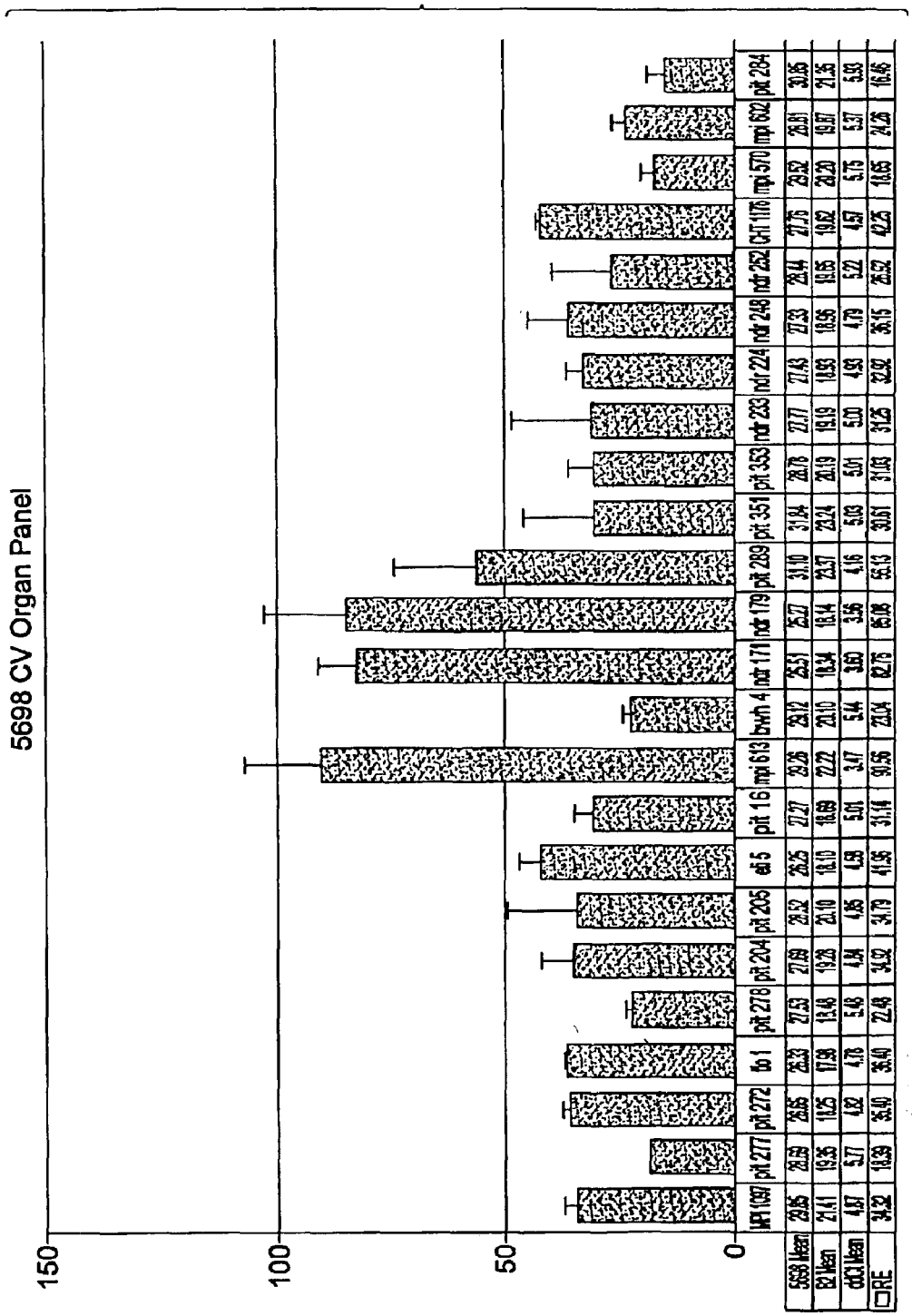
FIGS. 20A–B show the expression level of the 5698 mRNA transcript in various normal and diseased human tissues.
Figure 20B:
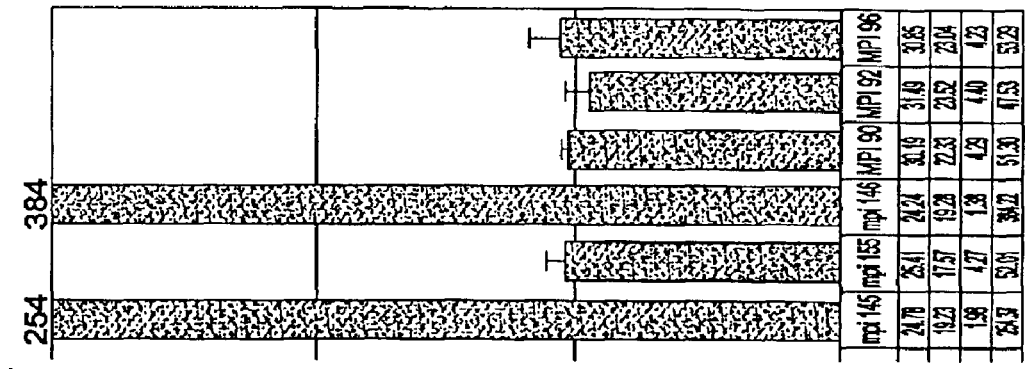
Figure 23:
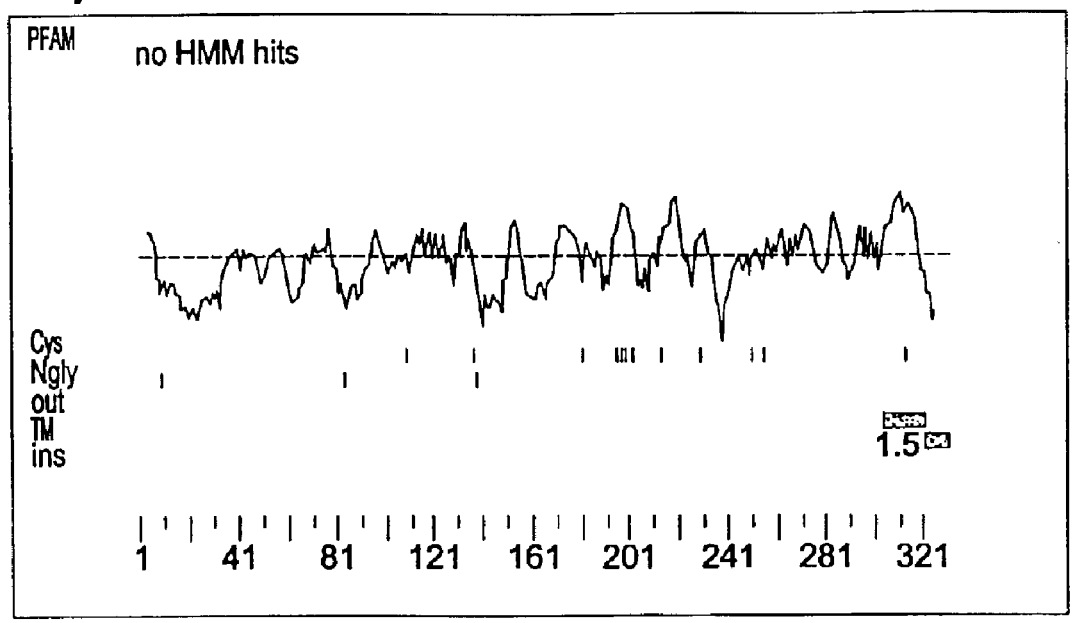
FIG. 23 depicts a hydropathy plot of human 32621. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:17) of human 32621 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 24A:
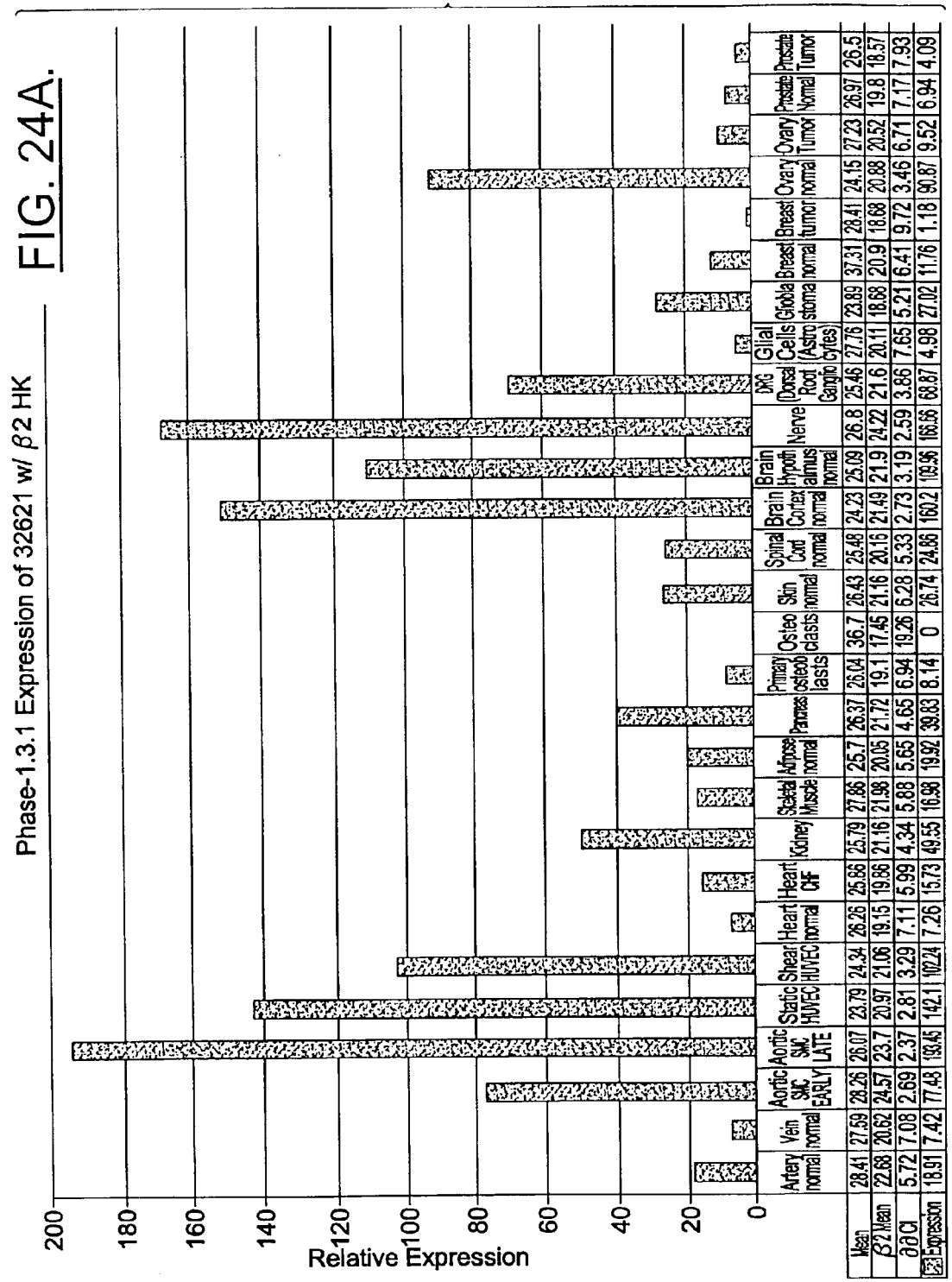
FIGS. 24A–B depict relative expression levels of 32621 in various human tissues and cells: artery (column 1); vein (column 2); aortic SMC, smooth muscle cells, early (column 3); aortic SMC late (column 4); static HUVEC, human umbilical vein endothelial cells (column 5); shear HUVEC (column 6); heart (column 7); heart CHF, congestive heart failure heart tissue (column 8); kidney (column 9); skeletal muscle (column 10); adipose (column 11); pancreas (column 12); primary osteoblasts (column 13); osteoclasts (column 14); skin (column 15); spinal cord (column 16); brain cortex (column 17); brain hypothalamus (column 18); nerve (column 19); DRG, dorsal root ganglion (column 20); glial cells (column 21); glioblastoma (column 22); breast (column 23); breast tumor (column 24); ovary (column 25); ovarian tumor (column 26); prostate (column 27); prostate tumor (column 28); prostate epithelial cells (column 29); colon (column 30); colon tumor (column 31); lung (column 32); lung tumor (column 33); lung COPD, chronic obstructive pulmonary diseased lung (column 34); colon IBD, inflammatory bowel diseased colon (column 35); liver (column 36); liver fibrosis (column 37); dermal cells (column 38); spleen (column 39); tonsil (column 40); lymph node (column 41); thymus (column 42); skin-decubitis (column 43); synovium (column 44); bone marrow mononuclear cells (column 45); and activated peripheral blood mononuclear cells (column 46). Expression levels were determined by quantitative RT-PCR (Taqman® brand quantitative PCR kit, Applied Biosystems). The quantitative RT-PCR reactions were performed according to the kit manufacturer's instructions.
Figure 24B:
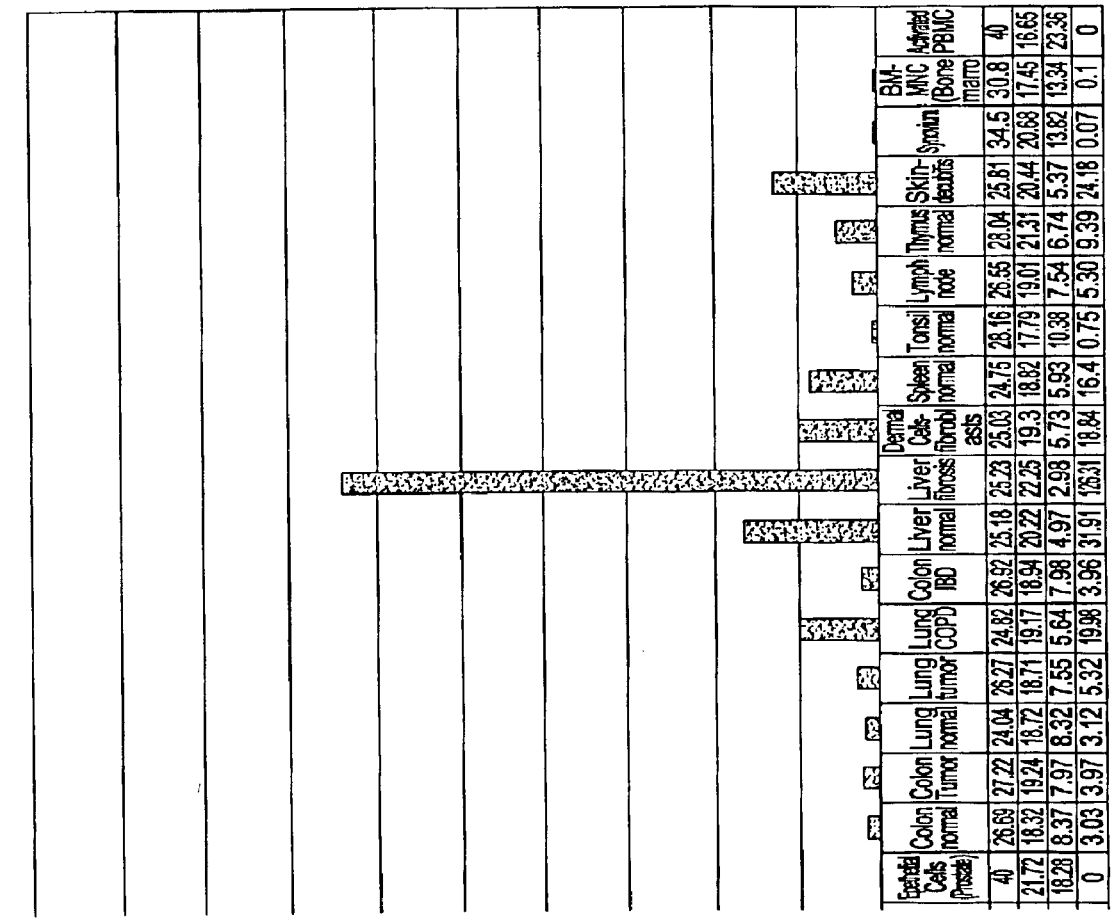
Figure 25B:
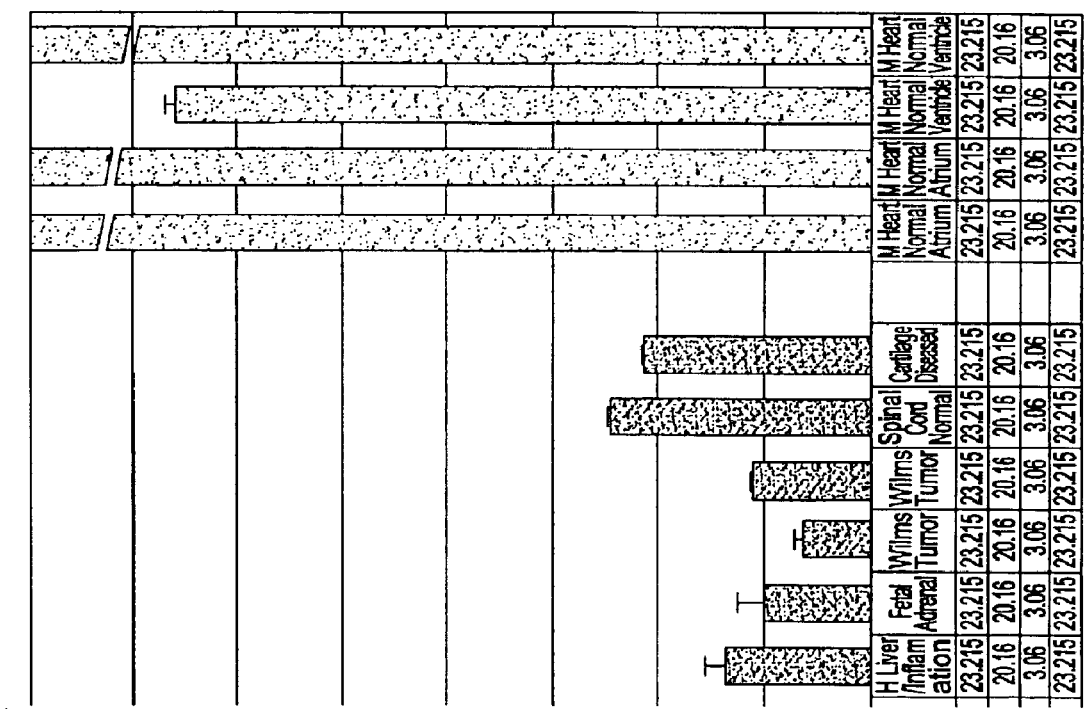
Figure 26:
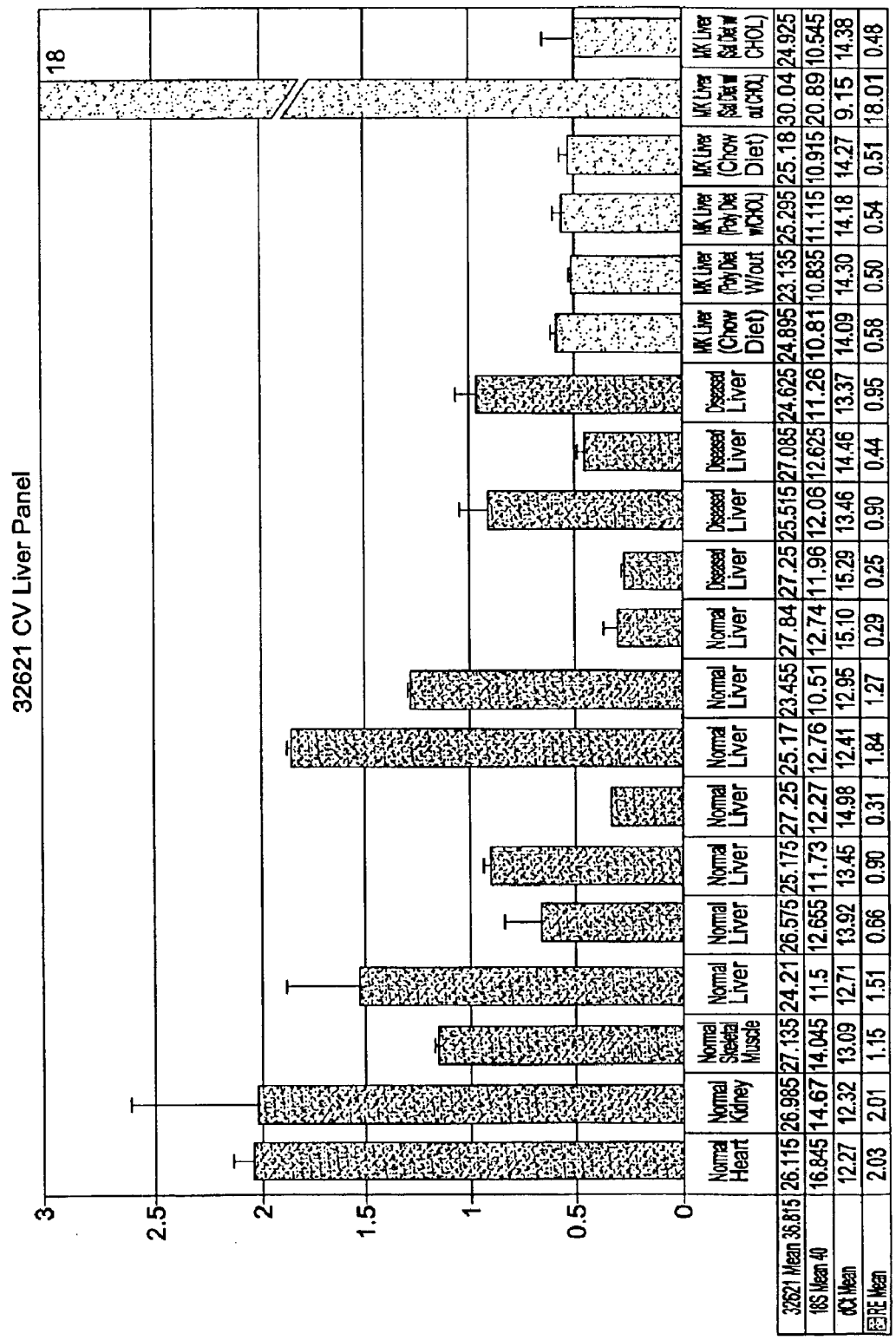
FIG. 26 depicts relative expression levels of 32621 in various organ and liver samples including liver samples from animals fed modified diets: normal human heart (column 1); normal human kidney (column 2); normal human skeletal muscle (column 3); normal human liver (column 4); normal human liver (column 5); normal human liver (column 6); normal human liver (column 7); normal human liver (column 8); normal human liver (column 9); normal human liver (column 10); diseased human liver (column 11); diseased human liver (column 12); diseased human liver (column 13); diseased human liver (column 14); MK liver (chow diet) (column 15); MK liver (poly diet without chol., cholesterol) (column 16); MK liver (poly diet with chol.) (column 17); MK liver (chow diet) (column 18); MK liver (Sat. Diet without chol.) (column 19); and MK liver (Sat diet with chol.) (column 20). Relative expression levels were determined as described in FIGS. 24A–B.
Figure 27:
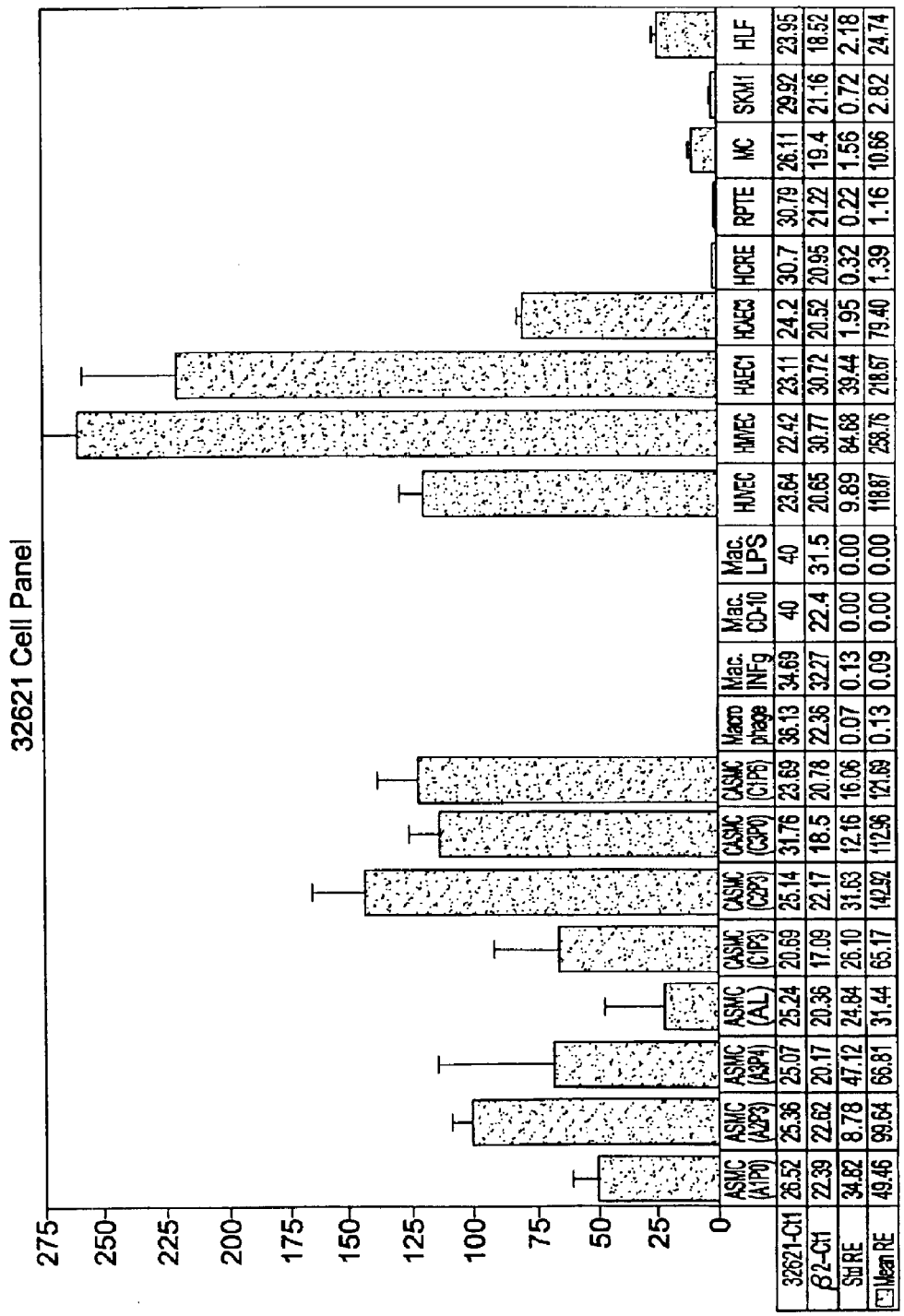
FIG. 27 depicts 32621 expression in various cell types: aortic smooth muscle cells(ASMC)-A1PO, (column 1); ASMC-A2P3 (column 2); ASMC-A3P4 (column 3); ASMC-AL (column 4); coronary artery smooth muscle cells (CASMC)-C1P3 (column 5); CASMC-C2P3 (column 6); CASMC-C5PO (column 7); CASMC-C1P6 (column 8); macrophage cells (column 9); macrophage cells treated with interferon y (column 10); CD40+ macrophage cells (column 11); macrophage cells treated with lipopolysaccharide (column 12); HUVEC, human umbilical vein endothelial cells (column 13); HMVEC, human microvascular endothelial cells (column 14); HAEC1, human aortic endothelial cells (column 15); HCAEC3, human coronary arterial endothelial cells (column 16); HCRE (column 17); RPTE, renal proximal tubule epithelial cells (column 18); MC (column 19); SKM1, myelogenous leukemia cells (column 20); and HLF, hepatocellular carcinoma cell line (column 21). Relative expression levels were determined as described in FIGS. 24A–B.
Figure 29:
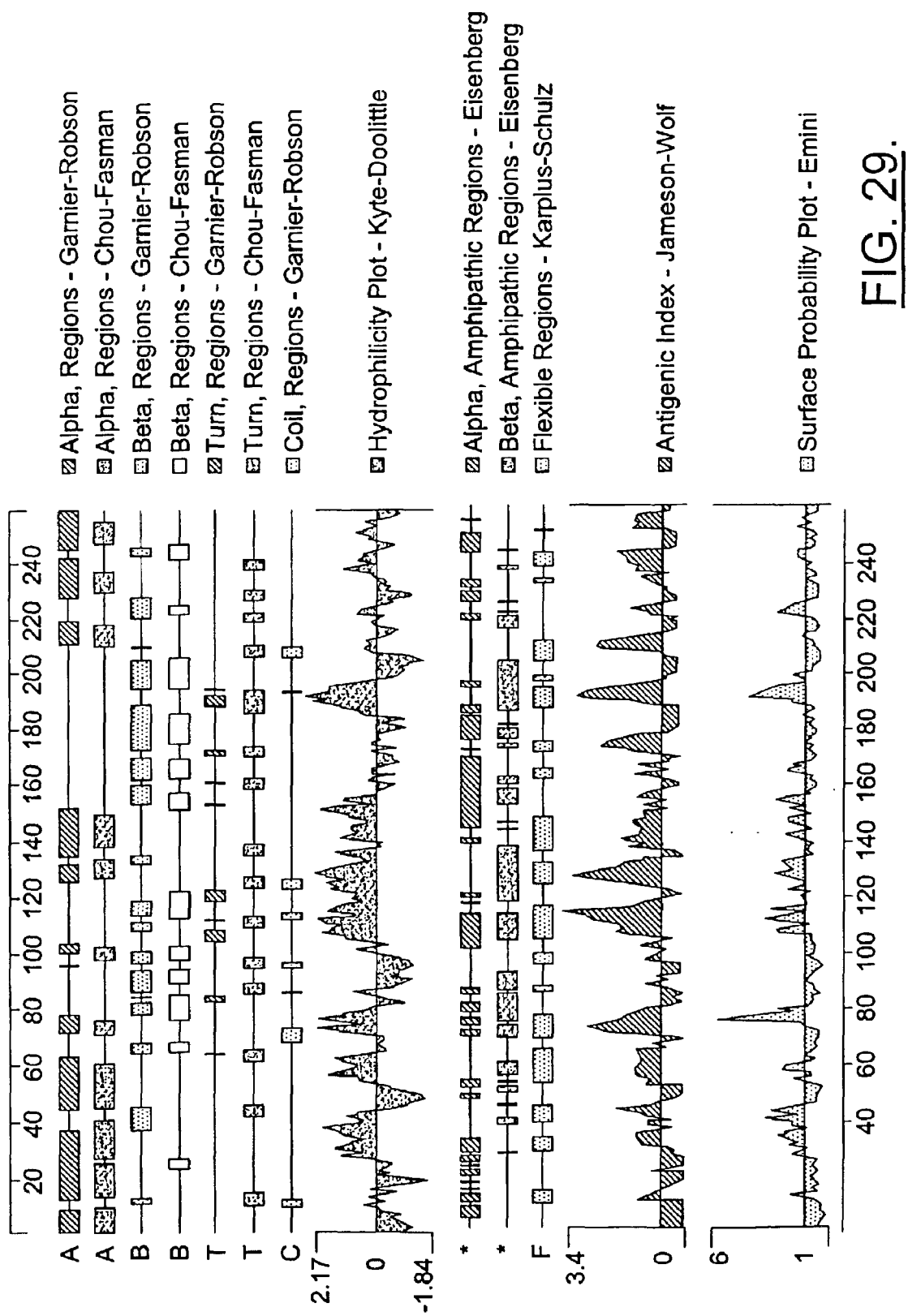
FIG. 29 shows an analysis of the 27802 amino acid sequence: αβ turn and coil regions; hydrophilicity; amphipathic regions; flexible regions; antigenic index; and surface probability plot.

The molecules are also useful for the diagnosis and treatment of disorders in tissues in which the transcript is expressed (see Example 1 and FIGS. 20A–B). Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the skeletal muscle include tumors such as rhabdomyosarcoma.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

The DFF-like sequences of the present invention find use in modulating a apoptosis. By "modulating" is intended the upregulating or downregulating of a response. That is, the compositions of the invention affect the targeted activity in either a positive or negative fashion. The activation of apoptosis is manifested by changes including membrane blebbing, DNA fragmentation, cytoplasmic and nuclear degredation, chromatin aggregation, formation of apoptotic bodies, and cell death.

Proteins and/or antibodies of the invention are also useful in modulating the apoptotic process.

The DFF-like gene, clone 5698 was identified in a human primary osteoblast cDNA library. Clone 5698 encodes an mRNA transcript having the corresponding cDNA set forth in SEQ ID NO:10. This transcript has a nucleotide open reading frame (nucleotides 169–828 of SEQ ID NO:10), which encodes a 219 amino acid protein (SEQ ID NO:11). Prosite program analysis was used to predict various sites within the 5698 protein. An N-glycosylation site was predicted at aa 18–21. Protein kinase C phosphorylation sites were predicted at aa 46–48 and 199–201. Casein kinase II phosphorylation sites were predicted at aa 55–58 and 82–85. N-myristoylation sites were predicted at aa 50–55 and 195–200. An amidation site was predicted at aa 23–26. A leucine zipper pattern was predicted at aa 179–200. The DFF-like protein possesses a CAD domain, from aa 36–108 as predicted by HMMer, Version 2. For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

As used herein, the term "CAD domain" includes an amino acid sequence of about 50–72 amino acid residues in length and having a bit score for the alignment of the sequence to the CAD domain (HMM) of at least 8. Preferably, an CAD domain includes at least about 1–72 amino acids, about 20–72 amino acid residues, or about 40–72 amino acids and has a bit score for the alignment of the sequence to the CAD domain (HMM) of at least 16 or greater (http://smart.embl-heidelberg.de/smart/selective.cgi?domains=cad&taxon_select=ALL&taxon_text=). An alignment of the CAD domain (amino acids 36 to 108 of SEQ ID NO:11) of the human DFF-like sequence of the invention with a consensus amino acid sequence derived from a hidden Markov model is depicted in FIG. 17.

In a preferred embodiment a DFF-like polypeptide or protein has a "CAD domain" or a region which includes at least about 100–250 more preferably about 130–200 or 160–200 amino acid residues and has at least about 60%, 70%, 80%, 90%, 95%, 99%, or 100% sequence identity with an "CAD domain," e.g., the CAD domain of a human DFF-like (e.g., amino acid residues 36–108 of SEQ ID NO:11).

To identify the presence of an "CAD" domain in a DFF-like protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

The 5698 protein displays similarity to the *Mus musculus* cell death activator CIDE-B (SP Accession Number 3114594; Genbank Accession Number AAC34986; SEQ ID NO:14) and with the *Homo sapiens* cell death activator CIDE-A (SP Accession Number 3114596; Genbank Accession Number AAC34987; SEQ ID NO:15). The sequence alignment was generated using the Clustal method. The 5698 protein shares approximately 83% identity with the murine CIDE-B and approximately 40% identity with the human CIDE-A amino acid sequence as determined by pairwise alignment.

The 5698 protein displays 37% identity from aa 36–209 to a ProDom consensus sequence found in murine FSP27 (Genbank Accession No. P56198) and human CIDE-A (Genbank Accession No. 060543). FSP27 is an adipocyte specific protein that belongs to the DFF-45/ICAD family. FSP27 is associated with terminal differentiation of fat cells and its expression is regulated by the tumor necrosis pathway. See, for example, Danesch et al. (1992) *J. Biol. Chem* 267:7185–7193 and Williams et al. (1992) *Mol Endocrinol* 6:1135–1141. CIDE-A has homology to the 45 kDa subunit of the DNA fragmentation factor. See, for example, Inohara et al. (1998) *Embo J.* 17:2526–2533. The 5698 protein also displays 46% identity to a ProDom consensus sequence found in the hypothetical protein F-121 of human adenovirus type 2.

The DFF-like sequences of the invention are members of a family of molecules (the "DNA fragmentation factor-like") having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred DFF-like polypeptides of the present invention have an amino acid sequence sufficiently identical to the amino acid sequence of SEQ ID NO:11. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to DFF-like nucleic acid molecules of the invention. BLAST protein searches can be performed with the XBLAST program, score=50, wordlength=3, to obtain amino acid sequences homologous to DFF-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated DFF-like proteins and polypeptides having a DFF-like protein activity. As used interchangeably herein, a "DFF-like protein activity", "biological activity of a DFF-like protein", or "functional activity of a DFF-like protein" refers to an activity exerted by a DFF-like protein, polypeptide, or nucleic acid molecule on a DFF-like responsive cell as determined in vivo, or in vitro, according to standard assay techniques. A DFF-like activity can be a direct activity, such as an association with or an enzymatic activity on a second protein, or an indirect activity, such as a cellular signaling activity mediated by interaction of the DFF-like protein with a second protein. In a preferred embodiment, a DFF-like activity includes at least one or more of the following activities: (1) modulating (stimulating and/or enhancing or inhibiting) apoptotic events, including DNA fragmentation, membrane blebbing, cytoplasmic and nuclear degredation, chromatin aggregation, and formtion of apoptotic bodies (2) modulating the programmed destruction of cells during embryogenesis including implantation, organogenesis, developmental involution and metamorphosis (3) modulating hormone-dependent involution in the adult, such as endometrial cell breakdown during the menstrual cycle, ovarian follicular atresia in the menopause, the regression of the lactating breast after weaning, and prostate atrophy after castration (4) modulating cell deletion in proliferating cell populations, such as intestinal crypt epithelia (5) modulating cell death in tumors (6) modulating the death of neutrophils during an acute inflammatory response (7) modulating the death of immune cells, both B and T lymphocytes after cytokine depletion (8) modulating the cell death induced by cytotoxic T-cells such as in cellular immune rejection and graft-verses-host diseases and (9) modulating atrophy in parenchymal organs after duct obstruction, such as occurs in the pancreas, parotid gland, and kidney.

An "isolated" or "purified" DFF-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated DFF-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A DFF-like protein that is substantially free of cellular material includes preparations of DFF-like protein having less than about 30%, 20%, 10%, or 5% (by dry weight) of non-DFF-like protein (also referred to herein as a "contaminating protein"). When the DFF-like protein or biologically active portion thereof is recombinantly produced, preferably, culture medium represents less than about 30%, 20%, 10%, or 5% of the volume of the protein preparation. When DFF-like protein is produced by chemical synthesis, preferably the protein preparations have less than about 30%, 20%, 10%, or 5% (by dry weight) of chemical precursors or non-DFF-like chemicals.

Various aspects of the invention are described in further detail in the following subsections.

I. Isolated Nucleic Acid Molecules

One aspect of the invention pertains to isolated nucleic acid molecules comprising nucleotide sequences encoding DFF-like proteins and polypeptides or biologically active portions thereof, as well as nucleic acid molecules sufficient for use as hybridization probes to identify DFF-like-encoding nucleic acids (e.g., DFF-like mRNA) and fragments for use as PCR primers for the amplification or mutation of DFF-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the DFF-like proteins of the present invention include sequences set forth in SEQ ID NO:10, 12 and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the DFF-like protein encoded by these nucleotide sequences is set forth in SEQ ID NO:11. The invention also encompasses nucleic acid molecules comprising nucleotide sequences encoding partial-length DFF-like proteins, including the sequence set forth in SEQ ID NO:10 or 12, and complements thereof.

Nucleic acid molecules that are fragments of these DFF-like nucleotide sequences are also encompassed by the present invention. By "fragment" is intended a portion of the nucleotide sequence encoding a DFF-like protein. A fragment of a DFF-like nucleotide sequence may encode a biologically active portion of a DFF-like protein, or it may be a fragment that can be used as a hybridization probe or PCR primer using methods disclosed below. A biologically active portion of a DFF-like protein can be prepared by isolating a portion of one of the DFF-like nucleotide sequences of the invention, expressing the encoded portion of the DFF-like protein (e.g., by recombinant expression in vitro), and assessing the activity of the encoded portion of the DFF-like protein. Nucleic acid molecules that are fragments of a DFF-like nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 nucleotides, or up to the number of nucleotides present in a full-length DFF-like nucleotide sequence disclosed herein (for example, 1284 nucleotides for SEQ ID NO:10) depending upon the intended use. Alternatively, a nucleic acid molecules that is a fragment of a DFF-like nucleotide sequence of the present invention comprises a nucleotide sequence consisting of nucleotides 1–100, 100–200, 200–300, 300–400, 400–500, 500–600, 600–700, 700–800, 800–900, 1000–1100, 1100–1200, 1200–1284 of SEQ ID NO:10 or 12.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a DFF-like nucleotide sequence that encodes a biologically active portion of a DFF-like protein of the invention will encode at least 15, 25, 30, 50, 75, 100, 125, 150, 175, or 200 contiguous amino acids, or up to the total number of amino acids present in a full-length DFF-like protein of the invention (for example, 219 amino acids for SEQ ID NO:11. Fragments of a DFF-like nucleotide sequence that are useful as hybridization probes for PCR primers generally need not encode a biologically active portion of a DFF-like protein.

Nucleic acid molecules that are variants of the DFF-like nucleotide sequences disclosed herein are also encompassed by the present invention. "Variants" of the DFF-like nucleotide sequences include those sequences that encode the DFF-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the DFF-like proteins disclosed in the present invention as discussed below. Generally, nucleotide sequence variants of the invention will have at least 45%, 55%, 65%, 75%, 85%, 95%, or 98% identity to a particular nucleotide sequence disclosed herein. A variant DFF-like nucleotide sequence will encode a DFF-like protein that has an amino acid sequence having at least 45%, 55%, 65%, 75%, 85%, 95%, or 98% identity to the amino acid sequence of a DFF-like protein disclosed herein.

In addition to the DFF-like nucleotide sequences shown in SEQ ID NOS:1 and 3, it will be appreciated by those skilled in the art that DNA sequence polymorphisms that lead to changes in the amino acid sequences of DFF-like proteins may exist within a population (e.g., the human population). Such genetic polymorphism in a DFF-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a DFF-like protein, preferably a mammalian DFF-like protein. As used herein, the phrase "allelic variant" refers to a nucleotide sequence that occurs at a DFF-like locus or to a polypeptide encoded by the nucleotide sequence. Such natural allelic variations can typically result in 1–5% variance in the nucleotide sequence of the DFF-like gene. Any and all such nucleotide variations and resulting amino acid polymorphisms or variations in a DFF-like sequence that are the result of natural allelic variation and that do not alter the functional activity of DFF-like proteins are intended to be within the scope of the invention.

Moreover, nucleic acid molecules encoding DFF-like proteins from other species (DFF-like homologues), which have a nucleotide sequence differing from that of the DFF-like sequences disclosed herein, are intended to be within the scope of the invention. For example, nucleic acid molecules corresponding to natural allelic variants and homologues of. the human DFF-like cDNA of the invention can be isolated based on their identity to the human DFF-like nucleic acid disclosed herein using the human cDNA, or a portion thereof, as a hybridization probe according to standard hybridization techniques under stringent hybridization conditions as disclosed below.

In addition to naturally-occurring allelic variants of the DFF-like sequences that may exist in the population, the skilled artisan will further appreciate that changes can be introduced by mutation into the nucleotide sequences of the invention thereby leading to changes in the amino acid sequence of the encoded DFF-like proteins, without altering the biological activity of the DFF-like proteins. Thus, an isolated nucleic acid molecule encoding a DFF-like protein having a sequence that differs from that of SEQ ID NO:11 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a DFF-like protein (e.g., the sequence of SEQ ID NO:11) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the growth factor and cytokine receptor signature 2 sequence and the U-PAR/Ly-6 domain sequence of SEQ ID NO:11, where such residues are essential for protein activity.

Alternatively, variant DFF-like nucleotide sequences can be made by introducing mutations randomly along all or part of a DFF-like coding sequence, such as by saturation mutagenesis, and the resultant mutants can be screened for DFF-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The DFF-like nucleotide sequences of the invention, and fragments and variants thereof, can be used as probes and/or primers to identify and/or clone DFF-like homologues in other cell types, e.g., from other tissues, as well as DFF-like homologues from other mammals. Such probes can be used to detect transcripts or genomic sequences encoding the same or identical proteins. These probes can be used as part of a diagnostic test kit for identifying cells or tissues that misexpress a DFF-like protein, such as by measuring levels of a DFF-like-encoding nucleic acid in a sample of cells from a subject, e.g., detecting DFF-like mRNA levels or determining whether a genomic DFF-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). DFF-like nucleotide sequences isolated based on their sequence identity to the DFF-like nucleotide sequences set forth herein or to fragments and variants thereof are encompassed by the present invention.

In a hybridization method, all or part of a known DFF-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known DFF-like nucleotide sequence disclosed herein. Degenerate primers designed on the basis of conserved nucleotides or amino acid residues in a known DFF-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a DFF-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified DFF-like nucleic acid molecule hybridizes under stringent conditions to a probe that is a nucleic acid molecule comprising one of the DFF-like nucleotide sequences of the invention or a fragment thereof. In another embodiment, the previously unknown DFF-like nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the DFF-like nucleotide sequences disclosed herein or a fragment thereof.

Accordingly, in another embodiment, an isolated previously unknown DFF-like nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:10, 12, or a complement, fragment, or variant thereof.

As used herein, the term "hybridizes under stringent conditions" is intended to describe conditions for hybridization and washing under which nucleotide sequences typically remain hybridized to each other. Such stringent conditions are known to those skilled in the art and can be found in *Current Protocols in Molecular Biology* (John Wiley & Sons, New York (1989)), 6.3.1–6.3.6. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule that hybridizes under stringent conditions to a DFF-like sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the DFF-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the DFF-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire DFF-like coding strand, or to only a portion thereof, e.g., all or part of the protein coding region (or open reading frame). An antisense nucleic acid molecule can be antisense to a noncoding region of the coding strand of a nucleotide sequence encoding a DFF-like protein. The noncoding regions are the 5' and 3' sequences that flank the coding region and are not translated into amino acids.

Given the coding-strand sequence encoding a DFF-like protein disclosed herein (e.g., SEQ ID NO:10 or 12), antisense nucleic acids of the invention can be designed according to the rules of Watson and Crick base pairing. The antisense nucleic acid molecule can be complementary to the entire coding region of DFF-like mRNA, but more preferably is an oligonucleotide that is antisense to only a portion of the coding or noncoding region of DFF-like mRNA. For example, the antisense oligonucleotide can be complementary to the region surrounding the translation start site of DFF-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DFF-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave DFF-like mRNA transcripts to thereby inhibit translation of DFF-like mRNA. A ribozyme having specificity for a DFF-like-encoding nucleic acid can be designed based upon the nucleotide sequence of a DFF-like cDNA disclosed herein (e.g., SEQ ID NO:10 or 12). See, e.g., Cech et al., U.S. Pat. No. 4,987,071; and Cech et al., U.S. Pat. No. 5,116,742. Alternatively, DFF-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, DFF-like gene expression can be inhibited by targeting nucleotide sequences complementary to the regulatory region of the DFF-like protein (e.g., the DFF-like promoter and/or enhancers) to form triple helical structures that prevent transcription of the DFF-like gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a DFF-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of a DFF-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated DFF-Like Proteins and Anti-DFF Antibodies

DFF-like proteins are also encompassed within the present invention. By "DFF-like protein" is intended a protein having the amino acid sequence set forth in SEQ ID NO:11, as well as fragments, biologically active portions, and variants thereof.

"Fragments" or "biologically active portions" include polypeptide fragments suitable for use as immunogens to raise anti-DFF-like antibodies. Fragments include peptides comprising amino acid sequences sufficiently identical to or derived from the amino acid sequence of a DFF-like protein, or partial-length protein, of the invention and exhibiting at least one activity of a DFF-like protein, but which include fewer amino acids than the full-length (SEQ ID NO:11) DFF-like protein disclosed herein. Typically, biologically active portions comprise a domain or motif with at least one activity of the DFF-like protein. A biologically active portion of a DFF-like protein can be a polypeptide which is, for example, 10, 25, 50, 100 or more amino acids in length. Alternatively, a fragment of a polypeptide of the present invention comprises an amino acid sequence consisting of amino acid residues 1–20, 20–40, 40–60, 60–80, 80–100, 100–120, 120–140, 140–160, 160–180, 180–200, 200–219 of SEQ ID NO:11. Such biologically active portions can be prepared by recombinant techniques and evaluated for one or more of the functional activities of a native DFF-like protein. As used here, a fragment comprises at least 5 contiguous amino acids of SEQ ID NO:11. The invention encompasses other fragments, however, such as any fragment in the protein greater than 6, 7, 8, or 9 amino acids.

By "variants" is intended proteins or polypeptides having an amino acid sequence that is at least about 45%, 55%, 65%, preferably about 75%, 85%, 95%, or 98% identical to the amino acid sequence of SEQ ID NO:11. Variants also include polypeptides encoded by a nucleic acid molecule that hybridizes to the nucleic acid molecule of SEQ ID NOS:1 or 3, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:11. If alignment is needed for this comparison the sequences should be aligned for maximum identity. "Looped" out sequences from deletions or insertions, or mismatches, are considered differences. Such variants generally retain the functional activity of the DFF-like proteins of the invention. Variants include polypeptides that differ in amino acid sequence due to natural allelic variation or mutagenesis.

The invention also provides DFF-like chimeric or fusion proteins. As used herein, a DFF-like "chimeric protein" or "fusion protein" comprises a DFF-like polypeptide operably linked to a non-DFF-like polypeptide. A "DFF-like polypeptide" refers to a polypeptide having an amino acid sequence corresponding to a DFF protein, whereas a "non-DFF-like polypeptide" refers to a polypeptide having an amino acid sequence corresponding to a protein that is not substantially identical to the DFF-like protein, e.g., a protein that is different from the DFF-like protein and which is derived from the same or a different organism. Within a DFF-like fusion protein, the DFF-like polypeptide can correspond to all or a portion of a DFF-like protein, preferably at least one biologically active portion of a DFF-like protein. Within the fusion protein, the term "operably linked" is intended to indicate that the DFF-like polypeptide and the non-DFF-like polypeptide are fused in-frame to each other. The non-DFF-like polypeptide can be fused to the N-terminus or C-terminus of the DFF-like polypeptide.

One useful fusion protein is a GST-DFF-like fusion protein in which the DFF-like sequences are fused to the C-terminus of the GST sequences. Such fusion proteins can facilitate the purification of recombinant DFF-like proteins.

In yet another embodiment, the fusion protein is a DFF-like-immunoglobulin fusion protein in which all or part of a DFF-like protein is fused to sequences derived from a member of the immunoglobulin protein family. The DFF-like-immunoglobulin fusion proteins of the invention can be incorporated into pharmaceutical compositions and administered to a subject to inhibit an interaction between a DFF-like ligand and a DFF-like protein on the surface of a cell, thereby suppressing DFF-like-mediated signal transduction in vivo. The DFF-like-immunoglobulin fusion proteins can be used to affect the bioavailability of a DFF-like cognate ligand. Inhibition of the DFF-like ligand/DFF-like interaction may be useful therapeutically, both for treating proliferative and differentiative disorders and for modulating (e.g., promoting or inhibiting) cell survival. Moreover, the DFF-like-immunoglobulin fusion proteins of the invention can be used as immunogens to produce anti-DFF-like antibodies in a subject, to purify DFF-like ligands, and in screening assays to identify molecules that inhibit the interaction of a DFF-like protein with a DFF-like ligand.

Preferably, a DFF-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a DFF-like-encoding nucleic acid can be cloned into a commercially available expression vector such that it is linked in-frame to an existing fusion moiety.

Variants of the DFF-like proteins can function as either DFF-like agonists (mimetics) or as DFF-like antagonists. Variants of the DFF-like protein can be generated by mutagenesis, e.g., discrete point mutation or truncation of the DFF-like protein. An agonist of the DFF-like protein can retain substantially the same, or a subset, of the biological activities of the naturally occurring form of the DFF-like protein. An antagonist of the DFF-like protein can inhibit one or more of the activities of the naturally occurring form of the DFF-like protein by, for example, competitively binding to a downstream or upstream member of a cellular signaling cascade that includes the DFF-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the DFF-like proteins.

Variants of a DFF-like protein that function as either DFF-like agonists or as DFF-like antagonists can be identified by screening combinatorial libraries of mutants, e.g., truncation mutants, of a DFF-like protein for DFF-like protein agonist or antagonist activity. In one embodiment, a variegated library of DFF-like variants is generated by combinatorial mutagenesis at the nucleic acid level and is encoded by a variegated gene library. A variegated library of DFF-like variants can be produced by, for example, enzymatically ligating a mixture of synthetic oligonucleotides into gene sequences such that a degenerate set of potential DFF-like sequences is expressible as individual polypeptides, or alternatively, as a set of larger fusion proteins (e.g., for phage display) containing the set of DFF-like sequences therein. There are a variety of methods that can be used to produce libraries of potential DFF-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DFF-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a DFF-like protein coding sequence can be used to generate a variegated population of DFF-like fragments for screening and subsequent selection of variants of a DFF-like protein. In one embodiment, a library of coding sequence fragments can be generated by treating a double-stranded PCR fragment of a DFF-like coding sequence with a nuclease under conditions wherein nicking occurs only about once per molecule, denaturing the double-stranded DNA, renaturing the DNA to form double-stranded DNA which can include sense/ antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the DFF-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of DFF-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify DFF-like variants (Arkin and Yourvan (1992) *Proc. Natl. Acad. Sci. USA* 89:7811–7815; Delgrave et al. (1993) *Protein Engineering* 6(3):327–331).

An isolated DFF-like polypeptide of the invention can be used as an immunogen to generate antibodies that bind DFF-like proteins using standard techniques for polyclonal and monoclonal antibody preparation. The full-length DFF-like protein can be used or, alternatively, the invention provides antigenic peptide fragments of DFF-like proteins for use as immunogens. The antigenic peptide of a DFF-like protein comprises at least 8, preferably 10, 15, 20, or 30 amino acid residues of the amino acid sequence shown in SEQ ID NO:11 and encompasses an epitope of a DFF-like protein such that an antibody raised against the peptide forms a specific immune complex with the DFF-like protein. Preferred epitopes encompassed by the antigenic peptide are regions of a DFF-like protein that are located on the surface of the protein, e.g., hydrophilic regions.

Accordingly, another aspect of the invention pertains to anti-DFF-like polyclonal and monoclonal antibodies that bind a DFF-like protein. Polyclonal anti-DFF-like antibodies can be prepared by immunizing a suitable subject (e.g., rabbit, goat, mouse, or other mammal) with a DFF-like immunogen. The anti-DFF-like antibody titer in the immunized subject can be monitored over time by standard techniques, such as with an enzyme linked immunosorbent assay (ELISA) using immobilized DFF-like protein. At an appropriate time after immunization, e.g., when the anti-DFF-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550–52; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-DFF-like antibody can be identified and isolated by screening a recombinant combinatorial immunoglobulin library (e.g., an antibody phage display library) with a DFF-like protein to thereby isolate immunoglobulin library members that bind the DFF-like protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-DFF-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; Shaw et al. (1988) J. Natl. Cancer Inst. 80:1553–1559); Morrison (1985) Science 229:1202–1207; Oi et al. (1986) Bio/Techniques 4:214; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12:899–903).

An anti-DFF-like antibody (e.g., monoclonal antibody) can be used to isolate DFF-like proteins by standard techniques, such as affinity chromatography or immunoprecipitation. An anti-DFF-like antibody can facilitate the purification of natural DFF -like protein from cells and of recombinantly produced DFF-like protein expressed in host cells. Moreover, an anti-DFF-like antibody can be used to detect DFF-like protein (e.g., in a cellular lysate or cell supernatant) in order to evaluate the abundance and pattern of expression of the DFF-like protein. Anti-DFF-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a DFF-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., DFF-like proteins, mutant forms of DFF-like proteins, fusion proteins, etc.).

It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of DFF-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264,166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to DFF-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a DFF-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) DFF-like protein. Accordingly, the invention further provides methods for producing DFF-like protein using the host cells of the invention. In one embodiment, the method comprises culturing the host cell of the invention, into which a recombinant expression vector encoding a DFF-like protein has been introduced, in a suitable medium such that DFF-like protein is produced. In another embodiment, the method further comprises isolating DFF-like protein from the medium or the host cell.

The host cells of the invention can also be used to produce nonhuman transgenic animals. For example, in one embodiment, a host cell of the invention is a fertilized oocyte or an embryonic stem cell into which DFF-like—coding sequences have been introduced. Such host cells can then be used to create nonhuman transgenic animals in which exogenous DFF-like sequences have been introduced into their genome or homologous recombinant animals in which endogenous DFF-like sequences have been altered. Such animals are useful for studying the function and/or activity of DFF-like genes and proteins and for identifying and/or evaluating modulators of DFF-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous DFF-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing DFF-like-encoding nucleic acid into the male pronuclei of a fertilized oocyte, e.g., by microinjection, retroviral infection, and allowing the oocyte to develop in a pseudopregnant female foster animal. The DFF-like cDNA sequence can be introduced as a transgene into the genome of a nonhuman animal. Alternatively, a homologue of the mouse DFF-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the DFF-like transgene to direct expression of DFF-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the DFF-like transgene in its genome and/or expression of DFF-like mRNA in tissues or cells of the animals. A transgenic founder animal can then be used to breed additional animals carrying the transgene. Moreover, transgenic animals carrying a transgene encoding DFF-like gene can further be bred to other transgenic animals carrying other transgenes.

To create a homologous recombinant animal, one prepares a vector containing at least a portion of a DFF-like gene or a homolog of the gene into which a deletion, addition, or substitution has been introduced to thereby alter, e.g., functionally disrupt, the DFF-like gene. In a preferred embodiment, the vector is designed such that, upon homologous recombination, the endogenous DFF-like gene is functionally disrupted (i.e., no longer encodes a functional protein; also referred to as a "knock out" vector). Alternatively, the vector can be designed such that, upon homologous recombination, the endogenous DFF-like gene is mutated or otherwise altered but still encodes functional protein (e.g., the upstream regulatory region can be altered to thereby alter the expression of the endogenous DFF-like protein). In the homologous recombination vector, the altered portion of the DFF-like gene is flanked at its 5' and 3' ends by additional nucleic acid of the DFF-like gene to allow for homologous recombination to occur between the exogenous DFF-like gene carried by the vector and an endogenous DFF-like gene in an embryonic stem cell. The additional flanking DFF-like nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced DFF-like gene has homologously recombined with the endogenous DFF-like gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The DFF-like nucleic acid molecules, DFF-like proteins, and anti-DFF-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary dose include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a DFF-like protein or anti-DFF-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express DFF-like protein (e.g., via a recombinant expression vector in a host cell in gene therapy applications), to detect DFF-like mRNA (e.g., in a biological sample) or a genetic lesion in a DFF-like gene, and to modulate DFF-like activity. In addition, the DFF-like proteins can be used to screen drugs or compounds that modulate apoptotic events as well as to treat disorders characterized by insufficient or excessive production of DFF-like protein or production of DFF-like protein forms that have decreased or aberrant activity compared to DFF-like wild type protein. In addition, the anti-DFF-like antibodies of the invention can be used to detect and isolate DFF-like proteins and modulate DFF-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to DFF-like proteins or have a stimulatory or inhibitory effect on, for example, DFF-like expression or DFF-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), orphage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the DFF-like protein can be accomplished, for example, by coupling the test compound with a radioisotope or enzymatic label such that binding of the test compound to the DFF-like protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the DFF-like protein to bind to or interact with a DFF-like target molecule. By "target molecule" is intended a molecule with which a DFF-like protein binds or interacts in nature. In a preferred embodiment, the ability of the DFF-like protein to bind to or interact with a DFF-like target molecule can be determined by monitoring the activity of the target molecule. For example, the activity of the target molecule can be monitored by detecting a morphological change induced by apoptosis (e.g., DNA fragmentation, membrane blebbing, cytoplasmic and nuclear degradation, etc.), detecting catalytic/enzymatic activity of the target on an appropriate substrate, or detecting the induction of a reporter gene (e.g., DFF-like—responsive regulatory element operably linked to a nucleic acid encoding a detectable marker, e.g. luciferase).

In yet another embodiment, an assay of the present invention is a cell-free assay comprising contacting a DFF-like protein or biologically active portion thereof with a test compound and determining the ability of the test compound to bind to the DFF-like protein or biologically active portion thereof. Binding of the test compound to the DFF-like protein can be determined either directly or indirectly as described above. In a preferred embodiment, the assay includes contacting the DFF-like protein or biologically active portion thereof with a known compound that binds DFF-like protein to form an assay mixture, contacting the assay mixture with a test compound, and determining the ability of the test compound to preferentially bind to DFF-like protein or biologically active portion thereof as compared to the known compound.

In another embodiment, an assay is a cell-free assay comprising contacting DFF-like protein or biologically active portion thereof with a test compound and determining the ability of the test compound to modulate (e.g., stimulate or inhibit) the activity of the DFF-like protein or biologically active portion thereof. Determining the ability of the test compound to modulate the activity of a DFF-like protein can be accomplished, for example, by determining the ability of the DFF-like protein to bind to a DFF-like target molecule as described above for determining direct binding. In an alternative embodiment, determining the ability of the test compound to modulate the activity of a DFF-like protein can be accomplished by determining the ability of the DFF-like protein to further modulate a DFF-like target molecule. For example, the catalytic/enzymatic activity of the target molecule on an appropriate substrate can be determined as previously described.

In yet another embodiment, the cell-free assay comprises contacting the DFF-like protein or biologically active portion thereof with a known compound that binds a DFF-like protein to form an assay mixture, contacting the assay mixture with a test compound, and determining the ability of the test compound to preferentially bind to or modulate the activity of a DFF-like target molecule.

In the above-mentioned assays, it may be desirable to immobilize either a DFF-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/DFF-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or DFF-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of DFF-like binding or activity determined using standard techniques.

Other techniques for immobilizing proteins on matrices can also be used in the screening assays of the invention. For example, either DFF-like protein or its target molecule can be immobilized utilizing conjugation of biotin and streptavidin. Biotinylated DFF-like molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a DFF-like protein or target molecules but which do not interfere with binding of the DFF-like protein to its target molecule can be derivatized to the wells of the plate, and unbound target or DFF-like protein trapped in the wells by antibody conjugation. Methods for detecting such complexes, in addition to those described above for the GST-immobilized complexes, include immunodetection of complexes using antibodies reactive with the DFF-like protein or target molecule, as well as enzyme-linked assays that rely on detecting an enzymatic activity associated with the DFF-like protein or target molecule.

In another embodiment, modulators of DFF-like expression are identified in a method in which a cell is contacted with a candidate compound and the expression of DFF-like mRNA or protein in the cell is determined relative to expression of DFF-like mRNA or protein in a cell in the absence of the candidate compound. When expression is greater (statistically significantly greater) in the presence of the candidate compound than in its absence, the candidate compound is identified as a stimulator of DFF-like mRNA or protein expression. Alternatively, when expression is less (statistically significantly less) in the presence of the candidate compound than in its absence, the candidate compound is identified as an inhibitor of DFF-like mRNA or protein expression. The level of DFF-like mRNA or protein expression in the cells can be determined by methods described herein for detecting DFF-like mRNA or protein.

In yet another aspect of the invention, the DFF-like proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with DFF-like protein ("DFF-like-binding proteins" or "DFF-like-bp") and modulate DFF-like activity. Such DFF-like-binding proteins are also likely to be involved in the propagation of signals by the DFF-like proteins as, for example, upstream or downstream elements of the DFF-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial DFF-like gene sequences of the invention can be used to map their respective DFF-like genes on a chromosome, thereby facilitating the location of gene regions associated with genetic disease. Computer analysis of DFF-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the DFF-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map a DFF-like sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of DFF-like genes uses DFF-like polypeptides and fragments and sequences of the present invention and antibodies specific thereto. This mapping can be carried out by specifically detecting the presence of a DFF-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a DFF-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the DFF-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DFF-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the DFF-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The DFF-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:10 can comfortably provide positive individual identification with a panel of perhaps 10 to 1,000 primers that each yield a noncoding amplified sequence of 100 bases. If a predicted coding sequence, such as that in SEQ ID NO:11, is used, a more appropriate number of primers for positive individual identification would be 500 to 2,000.

3. Use of Partial DFF-Like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:10 are particularly appropriate for this use as greater numbers of polymorphisms occur in the noncoding regions, making it easier to differentiate individuals using this technique. Examples of polynucleotide reagents include the DFF-like sequences or portions thereof, e.g., fragments derived from the noncoding regions of SEQ ID NO:10 having a length of at least 20 or 30 bases.

The DFF-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such DFF-like probes, can be used to identify tissue by species and/or by organ type. In a similar fashion, these reagents, e.g., DFF-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting DFF-like protein and/or nucleic acid expression as well as DFF-like activity, in the context of a biological sample. An exemplary method for detecting the presence or absence of DFF-like proteins in a biological sample involves obtaining a biological sample from a test subject and contacting the biological sample with a compound or an agent capable of detecting DFF-like protein or nucleic acid (e.g., mRNA, genomic DNA) that encodes DFF-like protein such that the presence of DFF-like protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting DFF-like mRNA or genomic DNA is a labeled nucleic acid probe capable of hybridizing to DFF-like mRNA or genomic DNA. The nucleic acid probe can be, for example, a full-length DFF-like nucleic acid, such as the nucleic acid of SEQ ID NO:10, or a portion thereof, such as a nucleic acid molecule of at least 15, 30, 50, 100, 250, or 500 nucleotides in length and sufficient to specifically hybridize under stringent conditions to DFF-like mRNA or genomic DNA. Other suitable probes for use in the diagnostic assays of the invention are described herein.

A preferred agent for detecting DFF-like protein is an antibody capable of binding to DFF-like protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect DFF-like mRNA, protein, or genomic DNA in a biological sample in vitro as well as in vivo. For example, in vitro techniques for detection of DFF-like mRNA include Northern hybridizations and in situ hybridizations. In vitro techniques for detection of DFF-like protein include enzyme linked immunosorbent assays (ELISAs), Western blots, immunoprecipitations, and immunofluorescence. In vitro techniques for detection of DFF-like genomic DNA include Southern hybridizations. Furthermore, in vivo techniques for detection of DFF-like protein include introducing into a subject a labeled anti-DFF-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

The invention also encompasses kits for detecting the presence of DFF-like proteins in a biological sample (a test sample). Such kits can be used to determine if a subject is suffering from or is at increased risk of developing a disorder associated with aberrant expression of DFF-like protein (e.g., a disorder resulting in dysregulated apoptosis). For example, the kit can comprise a labeled compound or agent capable of detecting DFF-like protein or mRNA in a biological sample and means for determining the amount of a DFF-like protein in the sample (e.g., an anti-DFF-like antibody or an oligonucleotide probe that binds to DNA encoding a DFF-like protein, e.g., SEQ ID NO:10 or 11). Kits can also include instructions for observing that the tested subject is suffering from or is at risk of developing a disorder associated with aberrant expression of DFF-like sequences if the amount of DFF-like protein or mRNA is above or below a normal level.

For antibody-based kits, the kit can comprise, for example: (1) a first antibody (e.g., attached to a solid support) that binds to DFF-like protein; and, optionally, (2) a second, different antibody that binds to DFF-like protein or the first antibody and is conjugated to a detectable agent. For oligonucleotide-based kits, the kit can comprise, for example: (1) an oligonucleotide, e.g., a detectably labeled oligonucleotide, that hybridizes to a DFF-like nucleic acid sequence or (2) a pair of primers useful for amplifying a DFF-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of DFF-like proteins.

2. Other Diagnostic Assays

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a DFF-like, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the DFF-like nucleic acid, polypeptide, or antibody.

The capture probes can be a set of nucleic acids from a selected sample, e.g., a sample of nucleic acids derived from a control or non-stimulated tissue or cell.

The method can include contacting the DFF-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of DFF-like. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express DFF-like or from a cell or subject in which a DFF-like mediated response has been elicited, e.g., by contact of the cell with DFF-like nucleic acid or protein, or administration to the cell or subject DFF-like nucleic acid or protein; contacting the array with one or more inquiry probe, wherein an inquiry probe can be a nucleic acid, polypeptide, or antibody (which is preferably other than DFF-like nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express DFF-like (or does not express as highly as in the case of the DFF-like positive plurality of capture probes) or from a cell or subject which in which a DFF-like mediated response has not been elicited (or has been elicited to a lesser extent than in the first sample); contacting the array with one or more inquiry probes (which is preferably other than a DFF-like nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing DFF-like, e.g., analyzing structure, function, or relatedness to other nucleic acid or amino acid sequences. The method includes: providing a DFF-like nucleic acid or amino acid sequence, comparing the DFF-like sequence with one or more preferably a plurality of sequences from a collection of sequences, e.g., a nucleic acid or protein sequence database; to thereby analyze DFF-like.

The method can include evaluating the sequence identity between a DFF-like sequence and a database sequence. The method can be performed by accessing the database at a second site, e.g., over the internet.

In another aspect, the invention features, a set of oligonucleotides, useful, e.g., for identifying SNP's, or identifying specific alleles of DFF-like. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with DFF-like protein, DFF-like nucleic acid expression, or DFF-like activity. Prognostic assays can be used for prognostic or predictive purposes to thereby prophylactically treat an individual prior to the onset of a disorder characterized by or associated with DFF-like protein, DFF-like nucleic acid expression, or DFF-like activity.

Thus, the present invention provides a method in which a test sample is obtained from a subject, and DFF-like protein or nucleic acid (e.g., mRNA, genomic DNA) is detected, wherein the presence of DFF-like protein or nucleic acid is diagnostic for a subject having or at risk of developing a disease or disorder associated with aberrant DFF-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease DFF-like activity) to effectively treat a disease or disorder associated with aberrant DFF-like expression or activity. In this manner, a test sample is obtained and DFF-like protein or nucleic acid is detected. The presence of DFF-like protein or nucleic acid is diagnostic for a subject that can be administered the agent to treat a disorder associated with aberrant DFF-like expression or activity.

The methods of the invention can also be used to detect genetic lesions or mutations in a DFF-like gene, thereby determining if a subject with the lesioned gene is at risk for a disorder characterized by dysregulated apoptosis. In preferred embodiments, the methods include detecting, in a sample of cells from the subject, the presence or absence of a genetic lesion or mutation characterized by at least one of an alteration affecting the integrity of a gene encoding a DFF-like-protein, or the misexpression of the DFF-like gene. For example, such genetic lesions or mutations can be detected by ascertaining the existence of at least one of: (1) a deletion of one or more nucleotides from a DFF-like gene; (2) an addition of one or more nucleotides to a DFF-like gene; (3) a substitution of one or more nucleotides of a DFF-like gene; (4) a chromosomal rearrangement of a DFF-like gene; (5) an alteration in the level of a messenger RNA transcript of a DFF-like gene; (6) an aberrant modification of a DFF-like gene, such as of the methylation pattern of the genomic DNA; (7) the presence of a non-wild-type splicing pattern of a messenger RNA transcript of a DFF-like gene; (8) a non-wild-type level of a DFF-like-protein; (9) an allelic loss of a DFF-like gene; and (10) an inappropriate post-translational modification of a DFF-like-protein. As described herein, there are a large number of assay techniques known in the art that can be used for detecting lesions in a DFF-like gene. Any cell type or tissue in which DFF-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the DFF-like-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DFF-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a DFF-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the DFF-like gene and detect mutations by comparing the sequence of the sample DF-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the DFF-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in DFF-like cDNAs obtained from samples of cells. See, e.g., Hsu et al. (1994) *Carcinogenesis* 15:1657–1662. According to an exemplary embodiment, a probe based on a DFF-like sequence, e.g., a wild-type DFF-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in DFF-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a DFF-like gene.

4. Pharmacogenomics

Agents, or modulators that have a stimulatory or inhibitory effect on DFF-like activity (e.g., DFF-like gene expression) as identified by a screening assay described herein, can be administered to individuals to treat (prophylactically or therapeutically) disorders associated with aberrant DFF-like activity as well as to modulate the phenotype of dysregulated apoptosis. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of DFF-like protein, expression of DFF-like nucleic acid, or mutation content of DFF-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a DFF-like molecule or DFF-like modulator as well as tailoring the dosage and/or therapeutic regimen of treatment with a DFF-like molecule or DFF-like modulator.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a DFF-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a DFF-like molecule or DFF-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a DFF-like molecule or DFF-like modulator, such as a modulator identified by one of the exemplary screening assays described herein.

The present invention further provides methods for identifying new agents, or combinations, that are based on identifying agents that modulate the activity of one or more of the gene products encoded by one or more of the DFF-like genes of the present invention, wherein these products may be associated with resistance of the cells to a therapeutic agent. Specifically, the activity of the proteins encoded by the DFF-like genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a DFF-like protein can be applied in clinical trials. For example, the effectiveness of an agent determined by a screening assay as described herein to increase DFF-like gene expression, protein levels, or upregulate DFF-like activity, can be monitored in clinical trials of subjects exhibiting decreased DFF-like gene expression, protein levels, or downregulated DFF-like activity. Alternatively, the effectiveness of an agent determined by a screening assay to decrease DFF-like gene expression, protein levels, or downregulate DFF-like activity, can be monitored in clinical trials of subjects exhibiting increased DFF-like gene expression, protein levels, or upregulated DFF-like activity. In such clinical trials, the expression or activity of a DFF-like gene, and preferably, other genes that have been implicated in, for example, a DFF-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of DFF-like protein, expression of DFF-like nucleic acid, or mutation content of DFF-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a DFF-like modulator, such as a modulator identified by one of the exemplary screening assays described herein.

5. Monitoring of Effects During Clinical Trials

Monitoring the influence of agents (e.g., drugs, compounds) on the expression or activity of DFF-like genes (e.g., the ability to modulate apoptotic events) can be applied not only in basic drug screening but also in clinical trials. For example, the effectiveness of an agent, as determined by a screening assay as described herein, to increase or decrease DFF-like gene expression, protein levels, or protein activity, can be monitored in clinical trials of subjects exhibiting decreased or increased DFF-like gene expression, protein levels, or protein activity. In such clinical trials, DFF-like expression or activity and preferably that of other genes that have been implicated in for example, a disorder resulting in dysregulated apoptosis, can be used as a marker of an apoptotic events of a particular cell.

For example, and not by way of limitation, genes that are modulated in cells by treatment with an agent (e.g., compound, drug, or small molecule) that modulates DFF-like activity (e.g., as identified in a screening assay described herein) can be identified. Thus, to study the effect of agents on cellular disorders resulting from dysregulated apoptosis, for example, in a clinical trial, cells can be isolated and RNA prepared and analyzed for the levels of expression of DFF-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of DFF-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a DFF-like protein, mRNA, or genomic DNA in the preadministration sample; (3) obtaining one or more postadministration samples from the subject; (4) detecting the level of expression or activity of the DFF-like protein, mRNA, or genomic DNA in the postadministration samples; (5) comparing the level of expression or activity of the DFF-like protein, mRNA, or genomic DNA in the preadministration sample with the DFF-like protein, mRNA, or genomic DNA in the postadministration sample or samples; and (vi) altering the administration of the agent to the subject accordingly to bring about the desired effect, i.e., for example, an increase or a decrease in the expression or activity of a DFF-like protein.

C. Methods of Treatment

The present invention provides for both prophylactic and therapeutic methods of treating a subject at risk of (or susceptible to) a disorder or having a disorder associated with aberrant DFF-like expression or activity. "Subject", as used herein, can refer to a mammal, e.g., a human, or to an experimental or animal or disease model. The subject can also be a non-human animal, e.g., a horse, cow, goat, or other domestic animal. Additionally, the compositions of the invention find use in the treatment of disorders described herein. Thus, therapies for disorders associated with a DFF-like molecule are encompassed herein. "Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

1. Prophylactic Methods

In one aspect, the invention provides a method for preventing in a subject a disease or condition associated with an aberrant DFF-like expression or activity by administering to the subject an agent that modulates DFF-like expression or at least one DFF-like gene activity. Subjects at risk for a disease that is caused, or contributed to, by aberrant DFF-like expression or activity can be identified by, for example, any or a combination of diagnostic or prognostic assays as described herein. Administration of a prophylactic agent can occur prior to the manifestation of symptoms characteristic of the DFF-like aberrancy, such that a disease or disorder is prevented or, alternatively, delayed in its progression. Depending on the type of DFF-like aberrancy, for example, a DFF-like agonist or DFF-like antagonist agent can be used for treating the subject. The appropriate agent can be determined based on screening assays described herein.

2. Therapeutic Methods

Another aspect of the invention pertains to methods of modulating DFF-like expression or activity for therapeutic purposes. The modulatory method of the invention involves contacting a cell with an agent that modulates one or more of the activities of DFF-like protein activity associated with the cell. An agent that modulates DFF-like protein activity can be an agent as described herein, such as a nucleic acid or a protein, a naturally-occurring cognate ligand of a DFF-like protein, a peptide, a DFF-like peptidomimetic, or other small molecule. In one embodiment, the agent stimulates one or more of the biological activities of DFF-like protein. Examples of such stimulatory agents include active DFF-like protein and a nucleic acid molecule encoding a DFF-like protein that has been introduced into the cell. In another embodiment, the agent inhibits one or more of the biological activities of DFF-like protein. Examples of such inhibitory agents include antisense DFF-like nucleic acid molecules and anti-DFF-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a DFF-like protein or nucleic acid molecule. In one embodiment, the method involves administering an agent (e.g., an agent identified by a screening assay described herein), or a combination of agents, that modulates (e.g., upregulates or downregulates) DFF-like expression or activity. In another embodiment, the method involves administering a DFF-like protein or nucleic acid molecule as therapy to compensate for reduced or aberrant DFF-like expression or activity.

Stimulation of DFF-like activity is desirable in situations in which a DFF-like protein is abnormally downregulated and/or in which increased DFF-like activity is likely to have a beneficial effect. Conversely, inhibition of DFF-like activity is desirable in situations in which DFF-like activity is abnormally upregulated and/or in which decreased DFF-like activity is likely to have a beneficial effect.

This invention is further illustrated by the following examples, which should not be construed as limiting.

EXAMPLE 1

Identification and Characterization of Human DFF-Like cDNAs

The human DFF-like sequence (SEQ ID NO:10), which is approximately 1284 nucleotides long including untranslated regions, contains a predicted methionine-initiated coding sequence of about 169 nucleotides (nucleotides 169–828 of SEQ ID NO:10). The coding sequence encodes a 219 amino acid protein (SEQ ID NO:11).

A search of the nucleotide and protein databases revealed that 5698 encodes a precursor polypeptide that shares similarity with several CIDE proteins. An alignment of the protein sequences having highest similarity to the 5698 precursor polypeptide is shown in FIG. 19. The alignment was generated using the Clustal method with PAM250 residue weight table and sequence identities were determined by FASTA (Pearson and Lipman (1988) *Proc. Natl. Acad. Sci. USA* 85:2444–2448).

EXAMPLE 2

Tissue Distribution of a DFF-Like mRNA

Northern blot hybridizations with various RNA samples can be performed under standard conditions and washed under stringent conditions, i.e., 0.2×SSC at 65° C. A DNA probe corresponding to all or a portion of the DFF-like cDNA (SEQ ID NO:10 or 3) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

TaqMan analysis of 5698 revealed expression in a number of tissues. See, for example, FIGS. 20A–B. A high level of expression was seen in liver, diseased and normal heart ventricle, normal kidney, kidney HT, atrium of normal heart, diseased heart ventricle, fetal heart, and skeletal muscle. The source number associated with each of these tissue types is provided below in Table 1.

TABLE 1

| Source # | CV Organ |
| --- | --- |
| MPI 1097 | H Heart Normal Atrium |
| pit 277 | H Heart Normal Atrium |
| pit 272 | H Heart Normal Ventricle |
| tlo 1 | H Heart Normal Ventricle |
| pit 278 | H Heart Normal Ventricle |
| pit 204 | H Heart Normal Ventricle |
| pit 205 | H Heart Normal Ventricle |
| eli 5 | H Heart Diseased Ventricle |
| pit 16 | H Heart Diseased Ventricle |
| mpi 613 | H Heart Diseased Ventricle |
| bwh 4 | H Fetal Heart |
| ndr 171 | H Kidney normal |
| ndr 179 | H Kidney normal |
| pit 289 | H Kidney normal |
| pit 351 | H Kidney normal |
| pit 353 | H Kidney normal |
| ndr 233 | H Kidney HT |
| ndr 224 | H Kidney HT |
| ndr 248 | H Kidney HT |
| ndr 252 | H Kidney HT |
| CHT 1176 | H Kidney HT |
| mpi 570 | H Skeletal Muscle |
| mpi 602 | H Skeletal Muscle |
| pit 284 | H Skeletal Muscle |
| mpi 145 | H Liver |
| mpi 155 | H Liver |
| mpi 146 | H Liver |
| MPI 90 | M Heart Normal Atrium |
| MPI 92 | M Heart Normal Atrium |
| MPI 96 | M Heart Normal Ventricle |
| MPI 538 | M Heart Normal Ventricle |

EXAMPLE 3

Recombinant Expression of DFF-Like Sequences in Bacterial Cells

In this example, the DFF-like sequence is expressed as a recombinant glutathione-S-transferase (GST) fusion polypeptide in *E. coli* and the fusion polypeptide is isolated and characterized. Specifically, the DFF-like sequence is fused to GST and this fusion polypeptide is expressed in *E. coli*, e.g., strain PEB199. Expression of the GST-DFF-like fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

EXAMPLE 4

Expression of Recombinant DFF-Like Protein in COS Cells

To express the DFF-like gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire DFF-like protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the DFF-like DNA sequence is amplified by PCR using two primers. The 5' primer contains the restriction site of interest followed by approximately twenty nucleotides of the DFF-like coding sequence starting from the initiation codon; the 3' end sequence contains complementary sequences to the other restriction site of interest, a translation stop codon, the HA tag or FLAG tag and the last 20 nucleotides of the DFF-like coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the DFF-like gene is inserted in the correct orientation. The ligation mixture is transformed into *E. coli* cells (strains HB11, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the DFF-like-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the DFF-like polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the DFF-like coding sequence is cloned directly into the polylinker of the pcDNA/Amp vector using the appropriate restriction sites. The resulting plasmid is transfected into COS cells in the manner described above, and the expression of the DFF-like polypeptide is detected by radiolabelling and immunoprecipitation using a DFF-like specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many

CHAPTER 4

32621, Novel Human Phospholipid Scramblase-Like Molecules and Uses Thereof

BACKGROUND OF THE INVENTION

Phospholipid asymmetry is a well-known characteristic of mammalian plasma membranes. The outer leaflet of the lipid bilayer is rich in choline-phospholipids, whereas aminophospholipids are preferentially in the inner leaflet (Bevers, E. M. et al., (1998) *Lupus Suppl.* 2: S126–S131). The plasma membrane phospholipids of erythrocytes (RBC), platelets, and vascular endothelium are normally asymmetrically distributed. Phosphatidylserine (PS) and phosphatidylethanolamine (PE) reside almost exclusively in the inner leaflet, and the phosphatidylcholine (PC) and sphyingomyelin are enriched in the outer leaflet. This asymmetric distribution of PL is maintained by an aminophospholipid translocase (APLT) which is a $Mg^{+2}$-dependent ATPase that transports PS and PE, but not PC, from the outer to the inner plasma membrane leaflet (Stout, J. G., et al. (1997) *J. Clin. Invest.* 99(9): 2232–2238).

The APLT activity has now been identified in numerous cell types, including platelets, lymphocytes, fibroblasts, and synaptosomes, suggesting that the asymmetry might be a general property of all cells (Woon, L. A., et al., (1999) *Cell Calcium* 25(4):313–320).

When PS and PE become exposed on the outer membrane leaflet by various mechanisms of cell activation, the $Mg^{+2}$-ATPase activity of APLT restores phospholipid asymmetry by transporting these lipids to the inner bilayer leaflet. A number of physiological and pathophysiological conditions may result in the disruption of the normal phospholipid asymmetry of the plasma membrane leading to the exposure of PS on the surface of cells. Exposure of PS creates a procoagulant surface on platelets, erythrocytes, and vascular endothelial cells. Also, there is evidence which indicates that clotting, cellular adhesion, fusion and phagocytosis of senescent or apoptotic cells are dependent on PS exposure (Woon et al. (1999) *Cell Calcium* 25(4):313–320).

A second mechanism which causes phospholipid redistribution in the plasma membrane has been linked to a phospholipid (PL) scramblase. The scramblase is an integral membrane protein that can mimic the action of $Ca^{+2}$ at the endothelial surface of the erythrocyte membrane (Zhao et al. (1998) *J. Biol. Chem.* 273(12):6603–6606). Zhao et al. demonstrated that the propensity for PS to become exposed at the cell surface can be manipulated by altering the level of expression of PL scramblase through plasmid transfection. Zhao et al. posit that the transfection of cells with PL scramblase cDNA promotes movement of PS to the cell surface and suggests that this protein is involved in the normal redistribution of plasma membrane phospholipids in activated, injured, and apoptotic cells.

Phospholipid (PL) scramblase is a plasma membrane protein that mediates accelerated transbilayer migration of PLs, upon binding of $Ca^{+2}$, facilitating rapid mobilization of phosphatidylserine to the cell surface upon elevation of internal calcium. (Stout, J. G. et al., (1998) *Biochemistry* 37:14860–14866). An increase in intracellular calcium due to cell activation, injury, or apoptosis causes rapid bidirectional movement of plasma membrane PL between leaflets. PL scramblase is responsible for this two-way movement of PL between the membrane leaflets, resulting in exposure of PS and PE at the cell surface (Kasukabe, T. et al., (1998) *Biochem. and Biophys. Res. Commun.* 249: 449–455). The PL scramblase can be assayed using methods as described by Zhou (Zhou, Q. et al., (1998) *Biochemistry* 37: 2356–2360).

One important clinical disorder which may be linked to defective PL scramblase is Scott syndrome. Scott syndrome is a congenital bleeding disorder related to defective expression of membrane coagulant activity. Circulating blood cells show decreased cell surface exposure of phosphatidylserine (PS) at elevated cystolic $Ca^{+2}$ indicating a defect or deficiency in PL scramblase (Stout, J. G. et al., (1997) *J. Clin. Invest.* 99(9):2232–2238). Scott syndrome is an extremely rare bleeding disorder associated with a defect of the outward transmembrane migration of pro-coagulant phospholipids at the surface of stimulated platelets or derived-microparticles. Scott syndrome is transmitted as an autosomal recessive trait as demonstrated in a familial study (Toti, F. et al., (1996) *Blood* 87:1409–1415).

Recently, the molecular cloning of murine and human PL scramblases has been reported. Zhou et al. reported the cDNA cloning of a 37-kDa human plasma membrane phospholipid scramblase from human erythrocytes (Zhou, Q. et al., (1997) *J. Biol. Chem.* 272(29):18240–18244). Antibody to the scramblase indicated an approximately 10-fold higher abundance of the PL scramblase in platelets as compared to erythrocytes. The work of Zhou et al. indicated that PL scramblase mRNA is found in a variety of hematalogic and nonhematologic cells and tissues. The resulting exposure of PS at the cell surface is thought to play a key role in the reticuloendothelial system, in addition to activation of both the plasma complement and coagulation systems.

More recently, the cDNA cloning of a human plasma membrane PL scramblase (MmTRA1b) from human monocytic U937 cells and the chromosome mapping of the gene was reported (Kaskube, T. et al., (1998) *Biochem. and Biophys. Res. Comm.* 249: 449–455). The MmTRA1b gene is the human homologue of the previously cloned mouse leukemogenesis-associated gene (MmTRA1a). The mouse MmTRA1a is the truncated form of mouse MmTRA1b. The human MmTRA1b cDNA predicted a 318 amino acid protein with a molecular weight of 35,047 Da.

The human MmTRA1b protein sequence shared a 78% amino acid identity with the mouse counterpart (328 amino acids). The human MmTRA1b gene was mapped to chromosome 3q23. Expression of the human homologue was increased during differentiation of U937 cells by most typical differentiation inducers. Also, the predicted amino acid sequence analysis of the human MmTRA1b cDNA revealed perfect identity with human plasma membrane phospholipid scramblase that is required for transbilayer movement of membrane phospholipids (Kaskukabe, T. et al., (1998) *Biochem. and Biophys. Res. Comm.* 249: 449–455).

According to homology searches against EMBL/Genbank/DDBJ data bases there are at least three homologous *C. elegans* genes which are more closely related with the mouse and human MmTRA1b than previously reported, as detailed by Kasukabe et al. Therefore, there appear to be at least two mouse genes (MmTRA1b and PL scramblase as reported by Zhou et al. and five *C. elegans* genes which constitute a whole new family of PL flip/flop genes.

The human phospholipid scramblase gene herein described may play an important role in erythrocyte, platelet, lymphocyte and endothelium physiology and function. It may play a particularly important role in the treatment and diagnosis of bleeding disorders such as Scott syndrome and other hematologic disease conditions, including but not limited to lymphocytic disorders, plasma cell dyscrasias, hemolytic anemias, autoimmune neutropenias, immune thrombocytopenias, lymphocytic leukemias, leukopenia, lymphomas, red cell disorders, platelet disorders, and coagulation disorders.

SUMMARY OF THE INVENTION

Isolated nucleic acid molecules corresponding to human phospholipid scramblase-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:17. Further provided are human phospholipid scramblase-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The human phospholipid scramblase-like molecules of the present invention are useful for modulating the immune, hematopoietic, and blood clotting systems. The molecules are useful for the diagnosis and treatment of disorders relevant but not limited to erythrocytes, platelets, endothelial and other cells and tissues known to expose plasma membrane phospholipid in response to elevated cystolic $Ca^{+2}$. Additionally, the molecules of the invention are useful as modulating agents in a variety of cellular processes where the transbilayer movement of phospholipids in the plasma membrane is important for proper cellular function and homeostasis.

Accordingly, in one aspect, this invention provides isolated nucleic acid molecules encoding human phospholipid scramblase-like proteins or biologically active portions thereof, as well as nucleic acid fragments suitable as primers or hybridization probes for the detection of human phospholipid scramblase-like encoding nucleic acids.

Another aspect of this invention features isolated or recombinant human phospholipid scramblase-like proteins and polypeptides. Preferred human phospholipid scramblase-like proteins and polypeptides possess at least one biological activity possessed by naturally occurring human phospholipid scramblase-like proteins.

Variant nucleic acid molecules and polypeptides substantially homologous to the nucleotide and amino acid sequences set forth in the sequence listings are encompassed by the present invention.

Antibodies and antibody fragments that selectively bind the human phospholipid scramblase-like polypeptides and fragments are provided. Such antibodies are useful in detecting the human phospholipid scramblase-like polypeptides.

In another aspect, the present invention provides a method for detecting the presence of human phospholipid scramblase-like activity or expression in a biological sample by contacting the biological sample with an agent capable of detecting an indicator of human phospholipid scramblase-like activity such that the presence of human phospholipid scramblase-like activity is detected in the biological sample.

In yet another aspect, the invention provides a method for modulating human phospholipid scramblase-like activity comprising contacting a cell with an agent that modulates (inhibits or stimulates) human phospholipid scramblase-like activity or expression such that human phospholipid scramblase-like activity or expression in the cell is modulated. In one embodiment, the agent is an antibody that specifically binds to human phospholipid scramblase-like protein. In another embodiment, the agent modulates expression of human phospholipid scramblase-like protein by modulating transcription of a human phospholipid scramblase-like gene, splicing of a human phospholipid scramblase-like mRNA, or translation of a human pho spho lipid scramblase-like mRNA. In yet another embodiment, the agent is a nucleic acid molecule having a nucleotide sequence that is antisense to the coding strand of the human phospholipid scramblase-like mRNA or the human phospholipid scramblase-like gene.

In one embodiment, the methods of the present invention are used to treat a subject having a disorder characterized by aberrant human phospholipid scramblase-like protein activity or nucleic acid expression by administering an agent that is a human phospholipid scramblase-like modulator to the subject. In one embodiment, the human phospholipid scramblase-like modulator is a human phospholipid scramblase-like protein. In another embodiment, the human phospholipid scramblase-like modulator is a human phospholipid scramblase-like nucleic acid molecule. In other embodiments, the human phospholipid scramblase-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a human phospholipid scramblase-like protein; (2) misregulation of a gene encoding a human phospholipid scramblase-like protein; and (3) aberrant post-translational modification of a human phospholipid scramblase-like protein, wherein a wild-type form of the gene encodes a protein with a human phospholipid scramblase-like activity.

In another aspect, the invention provides a method for identifying a compound that binds to or modulates the activity of a human phospholipid scramblase-like protein. In general, such methods entail measuring a biological activity of a human phospholipid scramblase-like protein in the presence and absence of a test compound and identifying those compounds that alter the activity of the human phospholipid scramblase-like protein.

The invention also features methods for identifying a compound that modulates the expression of human phospholipid scramblase-like genes by measuring the expression of the human phospholipid scramblase-like sequences in the presence and absence of the compound.

Other features and advantages of the invention will be apparent from the following detailed description and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides phospholipid scramblase-like molecules. By "phospholipid scramblase-like" is intended a novel human sequence referred to as 32621, and variants and fragments thereof. These full-length gene sequences or fragments thereof are referred to as "phospholipid scramblase-like" sequences, indicating they share sequence similarity with phospholipid scramblase genes. Isolated nucleic acid molecules comprising nucleotide sequences encoding the 32621 polypeptide whose amino acid sequence is given in SEQ ID NO:17, or a variant or fragment thereof, are provided. A nucleotide sequence encoding the 32621 polypeptide is set forth in SEQ ID NO:16 and SEQ ID NO:18.

The disclosed invention relates to methods and compositions for the modulation, diagnosis, and treatment of immune, hematopoietic, platelet, and blood coagulation disorders. Such immune disorders include, but not limited to, lymphocytic disorders, plasma cell dyscrasias, hemolytic anemias, autoimmune neutropenias, immune thrombocytopenias, lymphocytic leukemias, leukopenia, and lymphomas. The hematopoietic disorders include, but are not limited to, all bone marrow and red blood cell disorders. The blood coagulation disorders include, but are not limited to, hemophilia and Von Willebrand's disease. Platelet disorders include, but are not limited to, thrombocytopenia and Scott syndrome.

Disorders involving T cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and A/DS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sezary syndrome, and Hodgkin disease.

In normal bone marrow, the myelocytic series (polymorphonuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIG. 2-8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute mycloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, cosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadenoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arterioyenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin $B_{12}$ deficiency: pernicious anemia, and anemia of folate deficiency, iron deficiency anemia, anemia of chronic disease, aplastic anemia, pure red cell aplasia, and other forms of marrow failure.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-bome (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the skeletal muscle include tumors such as rhabdomyosarcoma.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the prostate include, but are not limited to, inflammations, benign enlargement, for example, nodular hyperplasia (benign prostatic hypertrophy or hyperplasia), and tumors such as carcinoma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

A novel human phospholipid scramblase-like gene sequence, referred to as 32621, is provided. This gene sequence and variants and fragments thereof are encompassed by the term "phospholipid scramblase-like" molecules or sequences as used herein. The phospholipid scramblase-like sequences find use in modulating a phospholipid scramblase function. By "modulating" is intended the upregulating or downregulating of a response. That is, the compositions of the invention affect the target activity in either a positive or negative fashion. The sequences of the invention find use in modulating the immune, hematopoiesis, blood coagulation, and plasma clotting systems.

The human phospholipid scramblase-like gene, clone 32621 was identified in a human primary osteoblast cDNA library. Clone 32621 encodes an mRNA transcript having the corresponding cDNA set forth in SEQ ID NO:16. This transcript has a 990 nucleotide open reading frame (nucleotides 156–1142 of SEQ ID NO:16; SEQ ID NO:18), which encodes a 329 amino acid protein (SEQ ID NO:17). A transmembrane segment from amino acids (aa) 304–320 was predicted by MEMSAT. Prosite program analysis was used to predict various sites within the h32621 protein. N-glycosylation sites were predicted at aa 18–21, 92–95, and 147–150. Protein kinase C phosphorylation sites were predicted at aa 170–172 and 204–206. Casein kinase II phosphorylation sites were predicted at aa 7–10, 135–138, and 259–262. A tyrosine kinase phosphorylation site was predicted at aa 146–154. N-myristoylation sites were predicted at aa 3–8, 55–60, 216–221, and 281–286.

The 32621 protein shares approximately 45% identity to the *Mus musculus* phospholipid scramblase-like and approximately 41% identity to the *Homo sapiens* hMmTRA1b protein as determined by pairwise alignment (FIG. 21).

The 32621 protein displays approximately 47% identity from aa 206–321 to a ProDom consensus sequence found in murine phospholipid scramblase-like 1; approximately 38% identity from aa 131–190 to a ProDom consensus sequence found in human phospholipid scramblase-like (MmTRA1b); approximately 59% identity from aa 108–129 to a ProDom consensus sequence found in murine phospholipid scramblase-like 1, human MmTRA1b, and murine transplantability associated protein 1 (TRA1); and, approximately 38% identity from aa 59–111 to a ProDom consensus sequence found in murine SRG3 and human BAF155. Phospholipid scramblase-like 1 is a plasma membrane protein that mediates accelerated transbilayer migration of phospholipids upon binding calcium ions. See for example, Zhou et al. (1998) *Biochemistry* 37:2356–2360. The plasma membrane protein, human phospholipid scramblase-like, also mediates transbilayer migration of phospholipids upon $Ca^{2+}$ binding. The human scramblase may play a central role in the initiation of fibrin clot formation and in the recognition of apoptotic and injured cells by the reticuloendothelial system. Defects or deficiency of this scramblase causes Scott syndrome and possibly other bleeding disorders. See, for example, Zho et al. (1997) *J. Biol. Chem.* 272:18240–18244, Kasukabe et al. (1998) *Biochem. Biophys. Res. Commun.* 249:449–455, Basse et al. (1996) *J. Biol. Chem.* 271:17205–17210, and Zhou et al. (1998) *Biochemistry* 37:2356–2360. Murine SRG3 belongs to a family of SWI/SNF related, matrix associated, actin dependent regulator of chromatin assembly. Human BAF155 is the 155 kDa subunit of the SWI/SNF complex (Wang et al. (1996) *Genes and Dev.* 10:2117–2130). The sequences were identified by the ProDom program, which is available from , GREG (107/94), MESR (ACC-SV13), the CNRS "Genome Initiative" and the European Union. The ProDom Program (http://www.toulouse.inra.fr/prodom.html) allows analysis of domain arrangements in proteins and protein families. A detailed description of ProDom analysis can be found in Corpet et al. (1999) *Nuc. Acids Res.* 27:263–267.

The human phospholipid scramblase-like sequences of the invention are members of a family of molecules (PL flip/flop genes). The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred human phospholipid scramblase-like polypeptides of the present invention have an amino acid sequence sufficiently identical to the amino acid sequence of SEQ ID NO:17. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 60%, 65%, 70%, 75% 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to 32621-like nucleic acid molecules of the invention. BLAST protein searches can be performed with the XBLAST program, score=50, wordlength=3, to obtain amino acid sequences homologous to 32621-like protein molecules of the invention. To obtain gapped aligrnents for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated human phospholipid scramblase-like proteins and polypeptides having a human phospholipid scramblase-like protein activity. As used interchangeably herein, a "human phospholipid scramblase-like protein activity", "biological activity of a human phospholipid scramblase-like protein", or "functional activity of a human phospholipid scramblase-like protein" refers to an activity exerted by a human phospholipid scramblase-like protein, polypeptide, or nucleic acid molecule on a human phospholipid scramblase-like responsive cell as determined in vivo, or in vitro, according to standard assay techniques. A human phospholipid scramblase-like activity can be a direct activity, such as an association with or an enzymatic activity on a second protein, or an indirect activity, such as a cellular signaling activity mediated by interaction of the human phospholipid scramblase-like protein with a second protein. In a preferred embodiment, a human phospholipid scramblase-like activity includes at least one or more of the following activities: modulating (stimulating and/or enhancing or inhibiting) phospholipid redistribution in the plasma membrane.

An "isolated" or "purified" human phospholipid scramblase-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated human phospholipid scramblase-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A human phospholipid scramblase-like protein that is substantially free of cellular material includes preparations of human phospholipid scramblase-like protein having less than about 30%, 20%, 10%, or 5% (by dry weight) of non-human phospholipid scramblase-like protein (also referred to herein as a "contaminating protein"). When the human phospholipid scramblase-like protein or biologically active portion thereof is recombinantly produced, preferably, culture medium represents less than about 30%, 20%, 10%, or 5% of the volume of the protein preparation. When human phospholipid scramblase-like protein is produced by chemical synthesis, preferably the protein preparations have less than about 30%, 20%, 10%, or 5% (by dry weight) of chemical precursors or non-human phospholipid scramblase-like chemicals.

Various aspects of the invention are described in further detail in the following subsections.

I. Isolated Nucleic Acid Molecules

One aspect of the invention pertains to isolated nucleic acid molecules comprising nucleotide sequences encoding human phospholipid scramblase-like proteins and polypeptides or biologically active portions thereof, as well as nucleic acid molecules sufficient for use as hybridization probes to identify human phospholipid scramblase-like-encoding nucleic acids (e.g., human phospholipid scramblase-like mRNA) and fragments for use as PCR primers for the amplification or mutation of human phospholipid scramblase-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the human phospholipid scramblase-like proteins of the present invention include sequences set forth in SEQ ID NO:17 and complements thereof By "complement" is intended a nucleotide sequence that is sufficiently complementary to a given nucleotide sequence such that it can hybridize to the given nucleotide sequence to thereby form a stable duplex. The corresponding amino acid sequence for the human phospholipid scramblase-like protein encoded by these nucleotide sequences is set forth in SEQ ID NO:16. The invention also encompasses nucleic acid molecules comprising nucleotide sequences encoding partial-length human phospholipid scramblase-like proteins, including the sequence set forth in SEQ ID NO:17, and complements thereof.

Nucleic acid molecules that are fragments of these human phospholipid scramblase-like nucleotide sequences are also encompassed by the present invention. By "fragment" is intended a portion of the nucleotide sequence encoding a human phospholipid scramblase-like protein. A fragment of a human phospholipid scramblase-like nucleotide sequence may encode a biologically active portion of a human phospholipid scramblase-like protein, or it may be a fragment that can be used as a hybridization probe or PCR primer using methods disclosed below. A biologically active portion of a human phospholipid scramblase-like protein can be prepared by isolating a portion of one of the human phospholipid scramblase-like nucleotide sequences of the invention, expressing the encoded portion of the human phospholipid scramblase-like protein (e.g., by recombinant expression in vitro), and assessing the activity of the encoded portion of the human phospholipid scramblase-like protein. Nucleic acid molecules that are fragments of a human phospholipid scramblase-like nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1500 nucleotides, or up to the number of nucleotides present in a full-length human phospholipid scramblase-like nucleotide sequence disclosed herein (for example, 1542 nucleotides for SEQ ID NO:16) depending upon the intended use. Alternatively, a nucleic acid molecules that is a fragment of an 32621-like nucleotide sequence of the present invention comprises a nucleotide sequence consisting of nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1542 of SEQ ID NO:16 or 18.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a human phospholipid scramblase-like nucleotide sequence that encodes a biologically active portion of a human phospholipid scramblase-like protein of the invention will encode at least 15, 25, 30, 50, 75, 100, 125, 150, 175, 200, 250, or 300 contiguous amino acids, or up to the total number of amino acids present in a full-length human phospholipid scramblase-like protein of the invention (for example, 329 amino acids for SEQ ID NO:17). Alternatively, a fragment of a polypeptide of the present invention comprises an amino acid sequence consisting of amino acid residues 1–20, 20–40, 40–60, 60–80, 80–100, 100–120, 120–140, 140–160, 160–180, 180–200, 200–220, 220–240, 240–260, 260–280, 280–300, 300–320, 320–329 of SEQ ID NO:17. Fragments of a human phospholipid scramblase-like nucleotide sequence that are useful as hybridization probes for PCR primers generally need not encode a biologically active portion of a human phospholipid scramblase-like protein.

Nucleic acid molecules that are variants of the human phospholipid scramblase-like nucleotide sequences disclosed herein are also encompassed by the present invention. "Variants" of the human phospholipid scramblase-like nucleotide sequences include those sequences that encode the human phospholipid scramblase-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the human phospholipid scramblase-like proteins disclosed in the present invention as discussed below. Generally, nucleotide sequence variants of the invention will have at least 45%, 55%, 65%, 75%, 85%, 95%, or 98% identity to a particular nucleotide sequence disclosed herein. A variant human phospholipid scramblase-like nucleotide sequence will encode a human phospholipid scramblase-like protein that has an amino acid sequence having at least 45%, 55%, 65%, 75%, 85%, 95%, or 98% identity to the amino acid sequence of a human phospholipid scramblase-like protein disclosed herein.

In addition to the human phospholipid scramblase-like nucleotide sequences shown in SEQ ID NO:16 it will be appreciated by those skilled in the art that DNA sequence polymorphisms that lead to changes in the amino acid sequences of human phospholipid scramblase-like proteins may exist within a population (e.g., the human population). Such genetic polymorphism in a human phospholipid scramblase-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a human phospholipid scramblase-like protein, preferably a mammalian human phospholipid scramblase-like protein. As used herein, the phrase "allelic variant" refers to a nucleotide sequence that occurs at a human phospholipid scramblase-like locus or to a polypeptide encoded by the nucleotide sequence. Such natural allelic variations can typically result in 1–5% variance in the nucleotide sequence of the human phospholipid scramblase-like gene. Any and all such nucleotide variations and resulting amino acid polymorphisms or variations in a human phospholipid scramblase-like sequence that are the result of natural allelic variation and that do not alter the functional activity of human phospholipid scramblase-like proteins are intended to be within the scope of the invention.

Moreover, nucleic acid molecules encoding human phospholipid scramblase-like proteins from other species (human phospholipid scramblase-like homologues), which have a nucleotide sequence differing from that of the human phospholipid scramblase-like sequences disclosed herein, are intended to be within the scope of the invention. For example, nucleic acid molecules corresponding to natural allelic variants and homologues of the human phospholipid scramblase-like cDNA of the invention can be isolated based on their identity to the human phospholipid scramblase-like nucleic acid disclosed herein using the human cDNA, or a portion thereof, as a hybridization probe according to standard hybridization techniques under stringent hybridization conditions as disclosed below.

In addition to naturally-occurring allelic variants of the human phospholipid scramblase-like sequences that may exist in the population, the skilled artisan will further appreciate that changes can be introduced by mutation into the nucleotide sequences of the invention thereby leading to changes in the amino acid sequence of the encoded human phospholipid scramblase-like proteins, without altering the biological activity of the human phospholipid scramblase-like proteins. Thus, an isolated nucleic acid molecule encoding a human phospholipid scramblase-like protein having a sequence that differs from that of SEQ ID NO:16 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a human phospholipid scramblase-like protein (e.g., the sequence of SEQ ID NO:17) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the growth factor and cytokine receptor signature 2 sequence and the U-PAR/Ly-6 domain sequence of SEQ ID NO:17, where such residues are essential for protein activity.

Alternatively, variant human phospholipid scramblase-like nucleotide sequences can be made by introducing mutations randomly along all or part of a human phospholipid scramblase-like coding sequence, such as by saturation mutagenesis, and the resultant mutants can be screened for human phospholipid scramblase-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The human phospholipid scramblase-like nucleotide sequences of the invention, and fragments and variants thereof, can be used as probes and/or primers to identify and/or clone human phospholipid scramblase-like homologues in other cell types, e.g., from other tissues, as well as human phospholipid scramblase-like homologues from other mammals. Such probes can be used to detect transcripts or genomic sequences encoding the same or identical proteins. These probes can be used as part of a diagnostic test kit for identifying cells or tissues that misexpress a human phospholipid scramblase-like protein, such as by measuring levels of a human phospholipid scramblase-like—encoding nucleic acid in a sample of cells from a subject, e.g., detecting human phospholipid scramblase-like mRNA levels or determining whether a genomic human phospholipid scramblase-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Human phospholipid scramblase-like nucleotide sequences isolated based on their sequence identity to the human phospholipid scramblase-like nucleotide sequences set forth herein or to fragments and variants thereof are encompassed by the present invention.

In a hybridization method, all or part of a known human phospholipid scramblase-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known human phospholipid scramblase-like nucleotide sequence disclosed herein. Degenerate primers designed on the basis of conserved nucleotides or amino acid residues in a known human phospholipid scramblase-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a human phospholipid scramblase-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified human phospholipid scramblase-like nucleic acid molecule hybridizes under stringent conditions to a probe that is a nucleic acid molecule comprising one of the human phospholipid scramblase-like nucleotide sequences of the invention or a fragment thereof. In another embodiment, the previously unknown human phospholipid scramblase-like nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the human phospholipid scramblase-like nucleotide sequences disclosed herein or a fragment thereof.

Accordingly, in another embodiment, an isolated previously unknown human phospholipid scramblase-like nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:17 or a complement, fragment, or variant thereof.

As used herein, the term "hybridizes under stringent conditions" is intended to describe conditions for hybridization and washing under which nucleotide sequences typically remain hybridized to each other. Such stringent conditions are known to those skilled in the art and can be found in Current Protocols in Molecular Biology (John Wiley & Sons, New York (1989)), 6.3.1–6.3.6. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule that hybridizes under stringent conditions to a 32621-like sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the human phospholipid scramblase-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the human phospholipid scramblase-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire human phospholipid scramblase-like coding strand, or to only a portion thereof, e.g., all or part of the protein coding region (or open reading frame). An antisense nucleic acid molecule can be antisense to a noncoding region of the coding strand of a nucleotide sequence encoding a human phospholipid scramblase-like protein. The noncoding regions are the 5' and 3' sequences that flank the coding region and are not translated into amino acids.

Given the coding-strand sequence encoding a human phospholipid scramblase-like protein disclosed herein (e.g., SEQ ID NO:17), antisense nucleic acids of the invention can be designed according to the rules of Watson and Crick base pairing. The antisense nucleic acid molecule can be complementary to the entire coding region of human phospholipid scramblase-like mRNA, but more preferably is an oligonucleotide that is antisense to only a portion of the coding or noncoding region of human phospholipid scramblase-like mRNA. For example, the antisense oligonucleotide can be complementary to the region surrounding the translation start site of human phospholipid scramblase-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a human phospholipid scramblase-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave human phospholipid scramblase-like mRNA transcripts to thereby inhibit translation of human phospholipid scramblase-like mRNA. A ribozyme having specificity for a human phospholipid scramblase-like—encoding nucleic acid can be designed based upon the nucleotide sequence of a human phospholipid scramblase-like cDNA disclosed herein (e.g., SEQ ID NO:17). See, e.g., Cech et al., U.S. Pat. No. 4,987,071; and Cech et al., U.S. Pat. No. 5,116,742. Alternatively, human phospholipid scramblase-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, human phospholipid scramblase-like gene expression can be inhibited by targeting nucleotide sequences complementary to the regulatory region of the human phospholipid scramblase-like protein (e.g., the human phospholipid scramblase-like promoter and/or enhancers) to form triple helical structures that prevent transcription of the human phospholipid scramblase-like gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a human phospholipid scramblase-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of a human phospholipid scramblase-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated Human Phospholipid Scramblase-Like Proteins and Anti-Human Phospholipid Scramblase-Like Antibodies Human phospholipid scramblase-like proteins are also encompassed within the present invention. By "human phospholipid scramblase-like protein" is intended a protein having the amino acid sequence set forth in SEQ ID NO:17, as well as fragments, biologically active portions, and variants thereof.

"Fragments" or "biologically active portions" include polypeptide fragments suitable for use as immunogens to raise anti-human phospholipid scramblase-like antibodies. Fragments include peptides comprising amino acid sequences sufficiently identical to or derived from the amino acid sequence of a human phospholipid scramblase-like protein, or partial-length protein, of the invention and exhibiting at least one activity of a human phospholipid scramblase-like protein, but which include fewer amino acids than the full-length (SEQ ID NO:17) human phospholipid scramblase-like protein disclosed herein. Typically, biologically active portions comprise a domain or motif with at least one activity of the human phospholipid scramblase-like protein. A biologically active portion of a human phospholipid scramblase-like protein can be a polypeptide which is, for example, 10, 25, 50, 100 or more amino acids in length. Such biologically active portions can be prepared by recombinant techniques and evaluated for one or more of the functional activities of a native human phospholipid scramblase-like protein. As used here, a fragment comprises at least 5 contiguous amino acids of SEQ ID NO:17. The invention encompasses other fragments, however, such as any fragment in the protein greater than 6, 7, 8, or 9 amino acids.

By "variants" is intended proteins or polypeptides having an amino acid sequence that is at least about 60%, 65%, or 70%, preferably about 75%, 85%, 90%, 91%, 92%, 93%, 94%, 95%, 96%, 97%, 98% or 99% identical to the amino acid sequence of SEQ ID NO:17. Variants also include polypeptides encoded by a nucleic acid molecule that hybridizes to the nucleic acid molecules of SEQ ID NO:16, SEQ ID NO:18, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:17. If alignment is needed for this comparison the sequences should be aligned for maximum identity. "Looped" out sequences from deletions or insertions, or mismatches, are considered differences. Such variants generally retain the functional activity of the 32621-like proteins of the invention. Variants include polypeptides that differ in amino acid sequence due to natural allelic variation or mutagenesis.

In one embodiment, a 32621-like protein includes at least one transmembrane domain. As used herein, the term "transmembrane domain" includes an amino acid sequence of about 15 amino acid residues in length that spans a phospholipid membrane. More preferably, a transmembrane domain includes about at least 16, 18, or 20 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, http://pfam.wustl.edu/cgi-bin/getdesc?name=7tm-1, and Zagotta W. N. et al. (1996) *Annual Rev. Neuronsci.* 19:235–63, the contents of which are incorporated herein by reference.

In a preferred embodiment, a 32621-like polypeptide or protein has at least one transmembrane domain or a region which includes at least 15, 16, 18, or 20 amino acid residues and has at least about 60%, 70% 80% 90% 95%, 99%, or 100% sequence identity with a "transmembrane domain," e.g., at least one transmembrane domain of human 32621-like (e.g., amino acid residues 304–320 of SEQ ID NO:17).

In another embodiment, a 32621-like protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring 32621-like, or 32621 like protein.

In a preferred embodiment, a 32621-like polypeptide or protein has a "non-transmembrane domain" or a region which includes at least about 1–312, preferably about 200–312, more preferably about 230–300, and even more preferably about 240–280 amino acid residues, and has at least about 60%, 70% 80% 90% 95%, 99% or 100% sequence identity with a "non-transmembrane domain", e.g., a non-transmembrane domain of human 32621-like (e.g., residues 1–303 or 321–329 of SEQ ID NO:17). Preferably, a non-transmembrane domain is capable of catalytic activity (e.g., phospholipid scramblase activity).

A non-transmembrane domain located at the N-terminus of a 32621-like protein or polypeptide is referred to herein as an "N-terminal non-transmembrane domain." As used herein, an "N-terminal non-transmembrane domain" includes an amino acid sequence having about 1–303, preferably about 30–303, more preferably about 50–303, or even more preferably about 80–290 amino acid residues in length and is located outside the boundaries of a membrane. For example, an N-terminal non-transmembrane domain is located at about amino acid residues 1–303 of SEQ ID NO:17.

Similarly, a non-transmembrane domain located at the C-terminus of a 32621-like protein or polypeptide is referred to herein as a "C-terminal non-transmembrane domain." As used herein, an "C-terminal non-transmembrane domain" includes an amino acid sequence having about 1–300, preferably about 15–290, preferably about 20–270, more preferably about 25–255 amino acid residues in length and is located outside the boundaries of a membrane. For example, an C-terminal non-transmembrane domain is located at about amino acid residues 321–329 of SEQ ID NO:17.

The invention also provides human phospholipid scramblase-like chimeric or fusion proteins. As used herein, a human phospholipid scramblase-like "chimeric protein" or "fusion protein" comprises a human phospholipid scramblase-like polypeptide operably linked to a non-human phospholipid scramblase-like polypeptide. A "human phospholipid scramblase-like polypeptide" refers to a polypeptide having an amino acid sequence corresponding to a human phospholipid scramblase-like protein, whereas a "non-human phospholipid scramblase-like polypeptide" refers to a polypeptide having an amino acid sequence corresponding to a protein that is not substantially identical to the human phospholipid scramblase-like protein, e.g., a protein that is different from the human phospholipid scramblase-like protein and which is derived from the same or a different organism. Within a human phospholipid scramblase-like fusion protein, the human phospholipid scramblase-like polypeptide can correspond to all or a portion of a human phospholipid scramblase-like protein, preferably at least one biologically active portion of a human phospholipid scramblase-like protein. Within the fusion protein, the term "operably linked" is intended to indicate that the human phospholipid scramblase-like polypeptide and the non-human phospholipid scramblase-like polypeptide are fused in-frame to each other. The non-human phospholipid scramblase-like polypeptide can be fused to the N-terminus or C-terminus of the human phospholipid scramblase-like polypeptide.

One useful fusion protein is a GST-human phospholipid scramblase-like fusion protein in which the human phospholipid scramblase-like sequences are fused to the C-terminus of the GST sequences. Such fusion proteins can facilitate the purification of recombinant human phospholipid scramblase-like proteins.

In yet another embodiment, the fusion protein is a human phospholipid scramblase-like—immunoglobulin fusion protein in which all or part of a human phospholipid scramblase-like protein is fused to sequences derived from a member of the immunoglobulin protein family. The human phospholipid scramblase-like—immunoglobulin fusion proteins of the invention can be incorporated into pharmaceutical compositions and administered to a subject to inhibit an interaction between a human phospholipid scramblase-like ligand and a human phospholipid scramblase-like protein on the surface of a cell, thereby suppressing human phospholipid scramblase-like—mediated signal transduction in vivo. The human phospholipid scramblase-like—immunoglobulin fusion proteins can be used to affect the bioavailability of a human phospholipid scramblase-like cognate ligand. Inhibition of the human phospholipid scramblase-like ligand/human phospholipid scramblase-like interaction may be useful therapeutically. Moreover, the human phospholipid scramblase-like—immunoglobulin fusion proteins of the invention can be used as immunogens to produce anti-human phospholipid scramblase-like antibodies in a subject, to purify human phospholipid scramblase-like ligands, and in screening assays to identify molecules that inhibit the interaction of a human phospholipid scramblase-like protein with a human phospholipid scramblase-like ligand.

Preferably, a human phospholipid scramblase-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a human phospholipid scramblase-like—encoding nucleic acid can be cloned into a commercially available expression vector such that it is linked in-frame to an existing fusion moiety.

Variants of the human phospholipid scramblase-like proteins can function as either human phospholipid scramblase-like agonists (mimetics) or as human phospholipid scramblase-like antagonists. Variants of the human phospholipid scramblase-like protein can be generated by mutagenesis, e.g., discrete point mutation or truncation of the human phospholipid scramblase-like protein. An agonist of the human phospholipid scramblase-like protein can retain substantially the same, or a subset, of the biological activities of the naturally occurring form of the human phospholipid scramblase-like protein. An antagonist of the human phospholipid scramblase-like protein can inhibit one or more of the activities of the naturally occurring form of the human phospholipid scramblase-like protein by, for example, competitively binding to a downstream or upstream member of a cellular signaling cascade that includes the human phospholipid scramblase-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the human phospholipid scramblase-like proteins.

Variants of a human phospholipid scramblase-like protein that function as either human phospholipid scramblase-like agonists or as human phospholipid scramblase-like antagonists can be identified by screening combinatorial libraries of mutants, e.g., truncation mutants, of a human phospholipid scramblase-like protein for human phospholipid scramblase-like protein agonist or antagonist activity. In one embodiment, a variegated library of human phospholipid scramblase-like variants is generated by combinatorial mutagenesis at the nucleic acid level and is encoded by a variegated gene library. A variegated library of human phospholipid scramblase-like variants can be produced by, for example, enzymatically ligating a mixture of synthetic oligonucleotides into gene sequences such that a degenerate set of potential human phospholipid scramblase-like sequences is expressible as individual polypeptides, or alternatively, as a set of larger fusion proteins (e.g., for phage display) containing the set of human phospholipid scramblase-like sequences therein. There are a variety of methods that can be used to produce libraries of potential human phospholipid scramblase-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential human phospholipid scramblase-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a human phospholipid scramblase-like protein coding sequence can be used to generate a variegated population of human phospholipid scramblase-like fragments for screening and subsequent selection of variants of a human phospholipid scramblase-like protein. In one embodiment, a library of coding sequence fragments can be generated by treating a double-stranded PCR fragment of a human phospholipid scramblase-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the human phospholipid scramblase-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of human phospholipid scramblase-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify human phospholipid scramblase-like variants (Arkin and Yourvan (1992) *Proc. Natl. Acad. Sci. USA* 89:7811–7815; Delgrave et al. (1993) *Protein Engineering* 6(3):327–331).

An isolated human phospholipid scramblase-like polypeptide of the invention can be used as an immunogen to generate antibodies that bind human phospholipid scramblase-like proteins using standard techniques for polyclonal and monoclonal antibody preparation. The full-length human phospholipid scramblase-like protein can be used or, alternatively, the invention provides antigenic peptide fragments of human phospholipid scramblase-like proteins for use as immunogens. The antigenic peptide of a human phospholipid scramblase-like protein comprises at least 8, preferably 10, 15, 20, or 30 amino acid residues of the amino acid sequence shown in SEQ ID NO:17 and encompasses an epitope of a human phospholipid scramblase-like protein such that an antibody raised against the peptide forms a specific immune complex with the human phospholipid scramblase-like protein. Preferred epitopes encompassed by the antigenic peptide are regions of a human phospholipid scramblase-like protein that are located on the surface of the protein, e.g., hydrophilic regions.

Accordingly, another aspect of the invention pertains to anti-human phospholipid scramblase-like polyclonal and monoclonal antibodies that bind a human phospholipid scramblase-like protein. Polyclonal anti-human phospholipid scramblase-like antibodies can be prepared by immunizing a suitable subject (e.g., rabbit, goat, mouse, or other mammal) with a human phospholipid scramblase-like immunogen. The anti-human phospholipid scramblase-like antibody titer in the immunized subject can be monitored over time by standard techniques, such as with an enzyme linked immunosorbent assay (ELISA) using immobilized human phospholipid scramblase-like protein. At an appropriate time after immunization, e.g., when the anti-human phospholipid scramblase-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550–52; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-human phospholipid scramblase-like antibody can be identified and isolated by screening a recombinant combinatorial immunoglobulin library (e.g., an antibody phage display library) with a human phospholipid scramblase-like protein to thereby isolate immunoglobulin library members that bind the human phospholipid scramblase-like protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-human phospholipid scramblase-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/01533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice. that are incapable of expressing endogenous immunoglobulin heavy and light chains genes, but which can express human heavy and light chain genes. See for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-human phospholipid scramblase-like antibody (e.g., monoclonal antibody) can be used to isolate human phospholipid scramblase-like proteins by standard techniques, such as affinity chromatography or immunoprecipitation. An anti-human phospholipid scramblase-like antibody can facilitate the purification of natural human phospholipid scramblase-like protein from cells and of recombinantly produced human phospholipid scramblase-like protein expressed in host cells. Moreover, an anti-human phospholipid scramblase-like antibody can be used to detect human phospholipid scramblase-like protein (e.g., in a cellular lysate or cell supernatant) in order to evaluate the abundance and pattern of expression of the human phospholipid scramblase-like protein. Anti-human phospholipid scramblase-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents hi Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a human phospholipid scramblase-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., human phospholipid scramblase-like proteins, mutant forms of human phospholipid scramblase-like proteins, fusion proteins, etc.). It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of human phospholipid scramblase-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cerevisiae* include pYepSecl (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms' "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to human phospholipid scramblase-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1 (1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin, and methotrexate. Nucleic acid encoding a selectable marker can be introduced into a host cell on the same vector as that encoding a human phospholipid scramblase-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) human phospholipid scramblase-like protein. Accordingly, the invention further provides methods for producing human phospholipid scramblase-like protein using the host cells of the invention. In one embodiment, the method comprises culturing the host cell of the invention, into which a recombinant expression vector encoding a human phospholipid scramblase-like protein has been introduced, in a suitable medium such that human phospholipid scramblase-like protein is produced. In another embodiment, the method further comprises isolating human phospholipid scramblase-like protein from the medium or the host cell.

The host cells of the invention can also be used to produce nonhuman transgenic animals. For example, in one embodiment, a host cell of the invention is a fertilized oocyte or an embryonic stem cell into which human phospholipid scramblase-like—coding sequences have been introduced. Such host cells can then be used to create nonhuman transgenic animals in which exogenous human phospholipid scramblase-like sequences have been introduced into their genome or homologous recombinant animals in which endogenous human phospholipid scramblase-like sequences have been altered. Such animals are useful for studying the function and/or activity of human phospholipid scramblase-like genes and proteins and for identifying and/or evaluating modulators of human phospholipid scramblase-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal.

As used herein, a "homologous recombinant animal" is a nonhuman animal, preferably a mammal, more preferably a mouse, in which an endogenous human phospholipid scramblase-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing human phospholipid scramblase-like— encoding nucleic acid into the male pronuclei of a fertilized oocyte, e.g., by microinjection, retroviral infection, and allowing the oocyte to develop in a pseudopregnant female foster animal. The human phospholipid scramblase-like cDNA sequence can be introduced as a transgene into the genome of a nonhuman animal. Alternatively, a homologue of the mouse human phospholipid scramblase-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the human phospholipid scramblase-like transgene to direct expression of human phospholipid scramblase-like protein to particular cells. Methods for generating transgenic animals via embryo manipulation and microinjection, particularly animals such as mice, have become conventional in the art and are described, for example, in U.S. Pat. Nos. 4,736,866, 4,870, 009, and 4,873,191 and in Hogan (1986) Manipulating the Mouse Embryo (Cold Spring Harbor Laboratory Press, Cold Spring Harbor, N.Y., 1986). Similar methods are used for production of other transgenic animals. A transgenic founder animal can be identified based upon the presence of the human phospholipid scramblase-like transgene in its genome and/or expression of human phospholipid scramblase-like mRNA in tissues or cells of the animals. A transgenic founder animal can then be used to breed additional animals carrying the transgene. Moreover, transgenic animals carrying a transgene encoding human phospholipid scramblase-like gene can further be bred to other transgenic animals carrying other transgenes.

To create a homologous recombinant animal, one prepares a vector containing at least a portion of a human phospholipid scramblase-like gene or a homolog of the gene into which a deletion, addition, or substitution has been introduced to thereby alter, e.g., functionally disrupt, the human phospholipid scramblase-like gene. In a preferred embodiment, the vector is designed such that, upon homologous recombination, the endogenous human phospholipid scramblase-like gene is functionally disrupted (i.e., no longer encodes a functional protein; also referred to as a "knock out" vector). Alternatively, the vector can be designed such that, upon homologous recombination, the endogenous human phospholipid scramblase-like gene is mutated or otherwise altered but still encodes functional protein (e.g., the upstream regulatory region can be altered to thereby alter the expression of the endogenous human phospholipid scramblase-like protein). In the homologous recombination vector, the altered portion of the human phospholipid scramblase-like gene is flanked at its 5' and 3' ends by additional nucleic acid of the human phospholipid scramblase-like gene to allow for homologous recombination to occur between the exogenous human phospholipid scramblase-like gene carried by the vector and an endogenous human phospholipid scramblase-like gene in an embryonic stem cell. The additional flanking human phospholipid scramblase-like nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation), and cells in which the introduced human phospholipid scramblase-like gene has homologously recombined with the endogenous human phospholipid scramblase-like gene are selected (see, e.g., Li et al. (1992) Cell 69:915). The selected cells are then injected into a blastocyst of an animal (e.g., a mouse) to form aggregation chimeras (see, e.g., Bradley (1987) in Teratocarcinomas and Embryonic Stem Cells: A Practical Approach, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) Nature 385:810–813 and PCT Publication Nos. WO 97/07668 and WO 97/07669.

IV. Pharmaceutical Compositions

The human phospholipid scramblase-like nucleic acid molecules, human phospholipid scramblase-like proteins, and anti-human phospholipid scramblase-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the skill of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a human phospholipid scramblase-like protein or anti-human phospholipid scramblase-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express human phospholipid scramblase-like protein (e.g., via a recombinant expression vector in a host cell in gene therapy applications), to detect human phospholipid scramblase-like mRNA (e.g., in a biological sample) or a genetic lesion in a human phospholipid scramblase-like gene, and to modulate human phospholipid scramblase-like activity. In addition, the human phospholipid scramblase-like proteins can be used to screen drugs or compounds that modulate the immune, hemopoetic, and blood clotting responses as well as to treat disorders characterized by insufficient or excessive production of human phospholipid scramblase-like protein or production of human phospholipid scramblase-like protein forms that have decreased or aberrant activity compared to human phospholipid scramblase-like wild type protein. In addition, the anti-human phospholipid scramblase-like antibodies of the invention can be used to detect and isolate human phospholipid scramblase-like proteins and modulate human phospholipid scramblase-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to human phospholipid scramblase-like proteins or have a stimulatory or inhibitory effect on, for example, human phospholipid scramblase-like expression or human phospholipid scramblase-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the human phospholipid scramblase-like protein can be accomplished, for example, by coupling the test compound with a radioisotope or enzymatic label such that binding of the test compound to the human phospholipid scramblase-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the human phospholipid scramblase-like protein to bind to or interact with a human phospholipid scramblase-like target molecule. By "target molecule" is intended a molecule with which a human phospholipid scramblase-like protein binds or interacts in nature. In a preferred embodiment, the ability of the human phospholipid scramblase-like protein to bind to or interact with a human phospholipid scramblase-like target molecule(s) can be determined by monitoring the activity of the target molecule. For example, the activity of the PS scramblase can be monitored by detecting the translocation of phospholipids in the plasma membrane in response to elevated $Ca^{+2}$ (Zhao, J. et al. (1998) *J. Biol. Chem.* 273(12): 6603–6606:

In yet another embodiment, an assay of the present invention is a cell-free assay comprising contacting a human phospholipid scramblase-like protein or biologically active portion thereof with a test compound and determining the ability of the test compound to bind to the human phospholipid scramblase-like protein or biologically active portion thereof. Binding of the test compound to the human phospholipid scramblase-like protein can be determined either directly or indirectly as described above. In a preferred embodiment, the assay includes contacting the human phospholipid scramblase-like protein or biologically active portion thereof with a known compound that binds human phospholipid scramblase-like protein to form an assay mixture, contacting the assay mixture with a test compound, and determining the ability of the test compound to preferentially bind to human phospholipid scramblase-like protein or biologically active portion thereof as compared to the known compound.

In another embodiment, an assay is a cell-free assay comprising contacting human phospholipid scramblase-like protein or biologically active portion thereof with a test compound and determining the ability of the test compound to modulate (e.g., stimulate or inhibit) the activity of the human phospholipid scramblase-like protein or biologically active portion thereof. Determining the ability of the test compound to modulate the activity of a human phospholipid scramblase-like protein can be accomplished, for example, by determining the ability of the human phospholipid scramblase-like protein to bind to a human phospholipid scramblase-like target molecule as described above for determining direct binding. In an alternative embodiment, determining the ability of the test compound to modulate the activity of a human phospholipid scramblase-like protein can be accomplished by determining the ability of the human phospholipid scramblase-like protein to further modulate a human phospholipid scramblase-like target molecule. For example, the catalytic/enzymatic activity of the target molecule on an appropriate substrate can be determined as previously described.

In yet another embodiment, the cell-free assay comprises contacting the human phospholipid scramblase-like protein or biologically active portion thereof with a known compound that binds a human phospholipid scramblase-like protein to form an assay mixture, contacting the assay mixture with a test compound, and determining the ability of the test compound to preferentially bind to or modulate the activity of a human phospholipid scramblase-like target molecule.

In the above-mentioned assays, it may be desirable to immobilize either a human phospholipid scramblase-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/human phospholipid scramblase-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or human phospholipid scramblase-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of human phospholipid scramblase-like binding or activity determined using standard techniques.

Other techniques for immobilizing proteins on matrices can also be used in the screening assays of the invention. For example, either human phospholipid scramblase-like protein or its target molecule can be immobilized utilizing conjugation of biotin and streptavidin. Biotinylated human phospholipid scramblase-like molecules or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a human phospholipid scramblase-like protein or target molecules but which do not interfere with binding of the human phospholipid scramblase-like protein to its target molecule can be derivatized to the wells of the plate, and unbound target or human phospholipid scramblase-like protein trapped in the wells by antibody conjugation. Methods for detecting such complexes, in addition to those described above for the GST-immobilized complexes, include immunodetection of complexes using antibodies reactive with the human phospholipid scramblase-like protein or target molecule, as well as enzyme-linked assays that rely on detecting an enzymatic activity associated with the human phospholipid scramblase-like protein or target molecule.

In another embodiment, modulators of human phospholipid scramblase-like expression are identified in a method in which a cell is contacted with a candidate compound and the expression of human phospholipid scramblase-like mRNA or protein in the cell is determined relative to expression of human phospholipid scramblase-like mRNA or protein in a cell in the absence of the candidate compound. When expression is greater (statistically significantly greater) in the presence of the candidate compound than in its absence, the candidate compound is identified as a stimulator of human phospholipid scramblase-like mRNA or protein expression. Alternatively, when expression is less (statistically significantly less) in the presence of the candidate compound than in its absence, the candidate compound is identified as an inhibitor of human phospholipid scramblase-like mRNA or protein expression. The level of human phospholipid scramblase-like mRNA or protein expression in the cells can be determined by methods described herein for detecting human phospholipid scramblase-like mRNA or protein.

In yet another aspect of the invention, the human phospholipid scramblase-like proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with human phospholipid scramblase-like protein ("human phospholipid scramblase-like—binding proteins" or "human phospholipid scramblase-like—bp") and modulate human phospholipid scramblase-like activity. Such human phospholipid scramblase-like—binding proteins are also likely to be involved in the propagation of signals by the human phospholipid scramblase-like proteins as, for example, upstream or downstream elements of the human phospholipid scramblase-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial human phospholipid scramblase-like gene sequences of the invention can be used to map their respective human phospholipid scramblase-like genes on a chromosome, thereby facilitating the location of gene regions associated with genetic disease. Computer analysis of human phospholipid scramblase-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the human phospholipid scramblase-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) Science 220:919–924). Somatic cell hybrids containing only fragments of human chromosomes can also be produced by using human chromosomes with translocations and deletions.

Other mapping strategies that can similarly be used to map a human phospholipid scramblase-like sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) Human Chromosomes: A Manual of Basic Techniques (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of human phospholipid scramblase-like genes uses human phospholipid scramblase-like polypeptides and fragments and sequences of the present invention and antibodies specific thereto. This mapping can be carried out by specifically detecting the presence of a human phospholipid scramblase-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) Cytogenet. Cell. Genet. 47:37–41 and Van Keuren et al. (1986) Hum. Genet. 74:34–40. Alternatively, the presence of a human phospholipid scramblase-like polypeptide in the somatic cell hybrids can be determined by assaying an activity or property of the polypeptide, for example, enzymatic activity, as described in Bordelon-Riser et al. (1979) Somatic Cell Genetics 5:597–613 and Owerbach et al. (1978) Proc. Natl. Acad. Sci. USA 75:5640–5644.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature 325:783–787.

Moreover, differences in the DNA sequences between individuals affected and unaffected with a disease associated with the human phospholipid scramblase-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The human phospholipid scramblase-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the human phospholipid scramblase-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The human phospholipid scramblase-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:16 can comfortably provide positive individual identification with a panel of perhaps 10 to 1,000 primers that each yield a noncoding amplified sequence of 100 bases. If a predicted coding sequence, such as that in SEQ ID NO:16 or SEQ ID NO:18, is used, a more appropriate number of primers for positive individual identification would be 500 to 2,000.

3. Use of Partial Human Phospholipid Scramblase-Like Sequences in Forensic Biology DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:16 are particularly appropriate for this use as greater numbers of polymorphisms occur in the noncoding regions, making it easier to differentiate individuals using this technique. Examples of polynucleotide reagents include the human phospholipid scramblase-like sequences or portions thereof, e.g., fragments derived from the noncoding regions of SEQ ID NO:16 having a length of at least 20 or 30 bases.

The human phospholipid scramblase-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such human phospholipid scramblase-like probes, can be used to identify tissue by species and/or by organ type.

In a similar fashion, these reagents, e.g., human phospholipid scramblase-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting human phospholipid scramblase-like protein and/or nucleic acid expression as well as human phospholipid scramblase-like activity, in the context of a biological sample. An exemplary method for detecting the presence or absence of human phospholipid scramblase-like proteins in a biological sample involves obtaining a biological sample from a test subject and contacting the biological sample with a compound or an agent capable of detecting human phospholipid scramblase-like protein or nucleic acid (e.g., mRNA, genomic DNA) that encodes human phospholipid scramblase-like protein such that the presence of human phospholipid scramblase-like protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting human phospholipid scramblase-like mRNA or genomic DNA is a labeled nucleic acid probe capable of hybridizing to human phospholipid scramblase-like mRNA or genomic DNA. The nucleic acid probe can be, for example, a full-length human phospholipid scramblase-like nucleic acid, such as the nucleic acid of SEQ ID NO:16, or a portion thereof, such as a nucleic acid molecule of at least 15, 30, 50, 100, 250, or 500 nucleotides in length and sufficient to specifically hybridize under stringent conditions to human phospholipid scramblase-like mRNA or genomic DNA. Other suitable probes for use in the diagnostic assays of the invention are described herein.

A preferred agent for detecting human phospholipid scramblase-like protein is an antibody capable of binding to human phospholipid scramblase-like protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect human phospholipid scramblase-like mRNA, protein, or genomic DNA in a biological sample in vitro as well as in vivo. For example, in vitro techniques for detection of human phospholipid scramblase-like mRNA include Northern hybridizations and in situ hybridizations. In vitro techniques for detection of human phospholipid scramblase-like protein include enzyme linked immunosorbent assays (ELISAs), Western blots, immunoprecipitations, and immunofluorescence. In vitro techniques for detection of human phospholipid scramblase-like genomic DNA include Southern hybridizations. Furthermore, in vivo techniques for detection of human phospholipid scramblase-like protein include introducing into a subject a labeled anti-human phospholipid scramblase-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

The invention also encompasses kits for detecting the presence of human phospholipid scramblase-like proteins in a biological sample (a test sample). Such kits can be used to determine if a subject is suffering from or is at increased risk of developing a disorder associated with aberrant expression of human phospholipid scramblase-like protein such as for Scott syndrome, a disorder in platelet clotting, or liver fibrosis. For example, the kit can comprise a labeled compound or agent capable of detecting human phospholipid scramblase-like protein or mRNA in a biological sample and means for determining the amount of a human phospholipid scramblase-like protein in the sample (e.g., an anti-human phospholipid scramblase-like antibody or an oligonucleotide probe that binds to DNA encoding a human phospholipid scramblase-like protein, e.g., SEQ ID NO:17). Kits can also include instructions for observing that the tested subject is suffering from or is at risk of developing a disorder associated with aberrant expression of human phospholipid scramblase-like sequences if the amount of human phospholipid scramblase-like protein or mRNA is above or below a normal level.

For antibody-based kits, the kit can comprise, for example: (1) a first antibody (e.g., attached to a solid support) that binds to human phospholipid scramblase-like protein; and, optionally, (2) a second, different antibody that binds to human phospholipid scramblase-like protein or the first antibody and is conjugated to a detectable agent. For oligonucleotide-based kits, the kit can comprise, for example: (1) an oligonucleotide, e.g., a detectably labeled oligonucleotide, that hybridizes to a human phospholipid scramblase-like nucleic acid sequence or (2) a pair of primers useful for amplifying a human phospholipid scramblase-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of human phospholipid scramblase-like proteins.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a phospholipid scramblase-like nucleic acid, preferably purified, polypeptide, preferably purified, or antibody, and thereby evaluating the plurality of capture probes. Binding, e.g., in the case of a nucleic acid, hybridization, with a capture probe at an address of the plurality, is detected, e.g., by signal generated from a label attached to the phospholipid scramblase-like nucleic acid, polypeptide, or antibody. The capture probes can be a set of nucleic acids from a selected sample, e.g., a sample of nucleic acids derived from a control or non-stimulated tissue or cell.

The method can include contacting the phospholipid scramblase-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a phospholipid scramblase-like sequence of the invention. Such methods can be used to diagnose a subject, e.g., to evaluate risk for a disease or disorder, to evaluate suitability of a selected treatment for a subject, to evaluate whether a subject has a disease or disorder. Thus, for example, the 32621 sequence set forth in SEQ ID NO:16 encodes a phospholipid scramblase-like polypeptide that is associated with blood coagulation, thus it is useful for evaluating bleeding disorders.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a phospholipid scramblase-like polypeptide of the invention or from a cell or subject in which a phospholipid scramblase-like mediated response has been elicited, e.g., by contact of the cell with a phospholipid scramblase-like nucleic acid or protein of the invention, or administration to the cell or subject a phospholipid scramblase-like nucleic acid or protein of the invention; contacting the array with one or more inquiry probes, wherein an inquiry probe can be a nucleic acid, polypeptide, or antibody (which is preferably other than a phospholipid scramblase-like nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a phospholipid scramblase-like sequence of the invention (or does not express as highly as in the case of the phospholipid scramblase-like positive plurality of capture probes) or from a cell or subject in which a phospholipid scramblase-like-mediated response has not been elicited (or has been elicited to a lesser extent than in the first sample); contacting the array with one or more inquiry probes (which is preferably other than a phospholipid scramblase-like nucleic acid, polypeptide, or antibody of the invention), and thereby evaluating the plurality of capture probes. Binding, e.g., in the case of a nucleic acid, hybridization, with a capture probe at an address of the plurality, is detected, e.g., by signal generated from a label attached to the nucleic acid, polypeptide, or antibody.

In another aspect, the invention features a method of analyzing a phospholipid scramblase-like sequence of the invention, e.g., analyzing structure, function, or relatedness to other nucleic acid or amino acid sequences. The method includes: providing a phospholipid scramblase-like nucleic acid or amino acid sequence, e.g., the 32621 sequence set forth in SEQ ID NO:17 or a portion thereof; comparing the phospholipid scramblase-like sequence with one or more preferably a plurality of sequences from a collection of sequences, e.g., a nucleic acid or protein sequence database; to thereby analyze the phospholipid scramblase-like sequence of the invention.

The method can include evaluating the sequence identity between a phospholipid scramblase-like sequence of the invention, e.g., the 32621 sequence, and a database sequence. The method can be performed by accessing the database at a second site, e.g., over the internet.

In another aspect, the invention features, a set of oligonucleotides, useful, e.g., for identifying SNP's, or identifying specific alleles of a phospholipid scramblase-like sequence of the invention, e.g., the 32621 sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with human phospholipid scramblase-like protein, human phospholipid scramblase-like nucleic acid expression, or human phospholipid scramblase-like activity. Prognostic assays can be used for prognostic or predictive purposes to thereby prophylactically treat an individual prior to the onset of a disorder characterized by or associated with human phospholipid scramblase-like protein, human phospholipid scramblase-like nucleic acid expression, or human phospholipid scramblase-like activity.

Thus, the present invention provides a method in which a test sample is obtained from a subject, and human phospholipid scramblase-like protein or nucleic acid (e.g., mRNA, genomic DNA) is detected, wherein the presence of human phospholipid scramblase-like protein or nucleic acid is diagnostic for a subject having or at risk of developing a disease or disorder associated with aberrant human phospholipid scramblase-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease human phospholipid scramblase-like activity) to effectively treat a disease or disorder associated with aberrant human phospholipid scramblase-like expression or activity. In this manner, a test sample is obtained and human phospholipid scramblase-like protein or nucleic acid is detected. The presence of human phospholipid scramblase-like protein or nucleic acid is diagnostic for a subject that can be administered the agent to treat a disorder associated with aberrant human phospholipid scramblase-like expression or activity.

The methods of the invention can also be used to detect genetic lesions or mutations in a human phospholipid scramblase-like gene, thereby determining if a subject with the lesioned gene is at risk for a disorder characterized by abnormal platelet disfunction or clotting or some other immune or hemopoetic disorder. In preferred embodiments, the methods include detecting, in a sample of cells from the subject, the presence or absence of a genetic lesion or mutation characterized by at least one of an alteration affecting the integrity of a gene encoding a human phospholipid scramblase-like—protein, or the misexpression of the human phospholipid scramblase-like gene. For example, such genetic lesions or mutations can be detected by ascertaining the existence of at least one of: (1) a deletion of one or more nucleotides from a human phospholipid scramblase-like gene; (2) an addition of one or more nucleotides to a human phospholipid scramblase-like gene; (3) a substitution of one or more nucleotides of a human phospholipid scramblase-like gene; (4) a chromosomal rearrangement of a human phospholipid scramblase-like gene; (5) an alteration in the level of a messenger RNA transcript of a human phospholipid scramblase-like gene; (6) an aberrant modification of a human phospholipid scramblase-like gene, such as of the methylation pattern of the genomic DNA; (7) the presence of a non-wild-type splicing pattern of a messenger RNA transcript of a human phospholipid scramblase-like gene; (8) a non-wild-type level of a human phospholipid scramblase-like—protein; (9) an allelic loss of a human phospholipid scramblase-like gene; and (10) an inappropriate post-translational modification of a human phospholipid scramblase-like—protein. As described herein, there are a large number of assay techniques known in the art that can be used for detecting lesions in a human phospholipid scramblase-like gene. Any cell type or tissue, preferably peripheral blood cells, in which human phospholipid scramblase-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the human phospholipid scramblase-like—gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a human phospholipid scramblase-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a human phospholipid scramblase-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the human phospholipid scramblase-like gene and detect mutations by comparing the sequence of the sample human phospholipid scramblase-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the human phospholipid scramblase-like gene include methods in which protection from cleavage agents is used to detect mismatched bases in RNA/RNA or RNA/DNA heteroduplexes (Myers et al. (1985) *Science* 230:1242). See also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in human phospholipid scramblase-like cDNAs obtained from samples of cells. See, e.g., Hsu et al. (1994) *Carcinogenesis* 15:1657–1662. According to an exemplary embodiment, a probe based on a human phospholipid scramblase-like sequence, e.g., a wild-type human phospholipid scramblase-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in human phospholipid scramblase-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a human phospholipid scramblase-like gene.

4. Pharmacogenomics

Agents, or modulators that have a stimulatory or inhibitory effect on human phospholipid scramblase-like activity (e.g., human phospholipid scramblase-like gene expression) as identified by a screening assay described herein, can be administered to individuals to treat (prophylactically or therapeutically) disorders associated with aberrant human phospholipid scramblase-like activity as well as to modulate the phenotype of an immune, hemopeotic, or blood clotting response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of human phospholipid scramblase-like protein, expression of human phospholipid scramblase-like nucleic acid, or mutation content of human phospholipid scramblase-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a phospholipid scramblase-like molecule or phospholipid scramblase-like modulator of the invention as well as tailoring the dosage and/or therapeutic regimen of treatment with a phospholipid scramblase-like molecule or phospholipid scramblase-like modulator of the invention.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a phospholipid scramblase-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a phospholipid scramblase-like molecule or phospholipid scramblase-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a phospholipid scramblase-like molecule or phospholipid scramblase-like modulator of the invention, such as a modulator identified by one of the exemplary screening assays described herein.

The present invention further provides methods for identifying new agents, or combinations, that are based on identifying agents that modulate the activity of one or more of the gene products encoded by one or more of the phospholipid scramblase-like genes of the present invention, wherein these products may be associated with resistance of the cells to a therapeutic agent. Specifically, the activity of the proteins encoded by the phospholipid scramblase-like genes of the present invention can be used as a basis for identifying agents for overcoming agent resistance. By blocking the activity of one or more of the resistance proteins, target cells, e.g., hepatic stellate cells, will become sensitive to treatment with an agent that the unmodified target cells were resistant to.

Monitoring the influence of agents (e.g., drugs) on the expression or activity of a phospholipid scramblase-like protein can be applied in clinical trials. For example, the effectiveness of an agent determined by a screening assay as described herein to increase phospholipid scramblase-like gene expression, protein levels, or upregulate Phospholipid scramblase-like activity, can be monitored in clinical trials of subjects exhibiting decreased phospholipid scramblase-like gene expression, protein levels, or downregulated phospholipid scramblase-like activity. Alternatively, the effectiveness of an agent determined by a screening assay to decrease phospholipid scramblase-like gene expression, protein levels, or downregulate phospholipid scramblase-like activity, can be monitored in clinical trials of subjects exhibiting increased phospholipid scramblase-like gene expression, protein levels, or upregulated phospholipid scramblase-like activity. In such clinical trials, the expression or activity of a phospholipid scramblase-like gene, and preferably, other genes that have been implicated in, for example, a phospholipid scramblase-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of human phospholipid scramblase-like protein, expression of human phospholipid scramblase-like nucleic acid, or mutation content of human phospholipid scramblase-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a human phospholipid scramblase-like modulator, such as a modulator identified by one of the exemplary screening assays described herein.

5. Monitoring of Effects During Clinical Trials

Monitoring the influence of agents (e.g., drugs, compounds) on the expression or activity of human phospholipid scramblase-like genes can be applied not only in basic drug screening but also in clinical trials. For example, the effectiveness of an agent, as determined by a screening assay as described herein, to increase or decrease human phospholipid scramblase-like gene expression, protein levels, or protein activity, can be monitored in clinical trials of subjects exhibiting decreased or increased human phospholipid scramblase-like gene expression, protein levels, or protein activity. In such clinical trials, human phospholipid scramblase-like expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates human phospholipid scramblase-like activity (e.g., as identified in a screening assay described herein) can be identified. Thus, to study the effect of agents disorders, for example, in a clinical trial, cells can be isolated and RNA prepared and analyzed for the levels of expression of human phospholipid scramblase-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of human phospholipid scramblase-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a human phospholipid scramblase-like protein, mRNA, or genomic DNA in the preadministration sample; (3) obtaining one or more postadministration samples from the subject; (4) detecting the level of expression or activity of the human phospholipid scramblase-like protein, mRNA, or genomic DNA in the postadministration samples; (5) comparing the level of expression or activity of the human phospholipid scramblase-like protein, mRNA, or genomic DNA in the preadministration sample with the human phospholipid scramblase-like protein, mRNA, or genomic DNA in the postadministration sample or samples; and (vi) altering the administration of the agent to the subject accordingly to bring about the desired effect, i.e., for example, an increase or a decrease in the expression or activity of a human phospholipid scramblase-like protein.

The present invention provides for both prophylactic and therapeutic methods of treating a subject at risk of (or susceptible to) a disorder or having a disorder associated with aberrant human phospholipid scramblase-like expression or activity. "Subject", as used herein, can refer to a mammal, e.g., a human, or to an experimental or animal or disease model. The subject can also be a non-human animal, e.g., a horse, cow, goat, or other domestic animal. Additionally, the compositions of the invention find use in the treatment of disorders described herein. Thus, therapies for disorders associated with aberrant human phospholipid scramblase activity are encompassed herein. "Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

1. Prophylactic Methods

In one aspect, the invention provides a method for preventing in a subject a disease or condition associated with an aberrant human phospholipid scramblase-like expression or activity by administering to the subject an agent that modulates human phospholipid scramblase-like expression or at least one human phospholipid scramblase-like gene activity. Subjects at risk for a disease that is caused, or contributed to, by aberrant human phospholipid scramblase-like expression or activity can be identified by, for example, any or a combination of diagnostic or prognostic assays as described herein. Administration of a prophylactic agent can occur prior to the manifestation of symptoms characteristic of the human phospholipid scramblase-like aberrancy, such that a disease or disorder is prevented or, alternatively, delayed in its progression. Depending on the type of human phospholipid scramblase-like aberrancy, for example, a human phospholipid scramblase-like agonist or human phospholipid scramblase-like antagonist agent can be used for treating the subject. The appropriate agent can be determined based on screening assays described herein.

2. Therapeutic Methods

Another aspect of the invention pertains to methods of modulating human phospholipid scramblase-like expression or activity for therapeutic purposes. The modulatory method of the invention involves contacting a cell with an agent that modulates one or more of the activities of human phospholipid scramblase-like protein activity associated with the cell. An agent that modulates human phospholipid scramblase-like protein activity can be an agent as described herein, such as a nucleic acid or a protein, a naturally-occurring cognate ligand of a human phospholipid scramblase-like protein, a peptide, a human phospholipid scramblase-like peptidomimetic, or other small molecule. In one embodiment, the agent stimulates one or more of the biological activities of human phospholipid scramblase-like protein. Examples of such stimulatory agents include active human phospholipid scramblase-like protein and a nucleic acid molecule encoding a human phospholipid scramblase-like protein that has been introduced into the cell. In another embodiment, the agent inhibits one or more of the biological activities of human phospholipid scramblase-like protein. Examples of such inhibitory agents include antisense human phospholipid scramblase-like nucleic acid molecules and anti-human phospholipid scramblase-like antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a human phospholipid scramblase-like protein or nucleic acid molecule. In one embodiment, the method involves administering an agent (e.g., an agent identified by a screening assay described herein), or a combination of agents, that modulates (e.g., upregulates or downregulates) human phospholipid scramblase-like expression or activity. In another embodiment, the method involves administering a human phospholipid scramblase-like protein or nucleic acid molecule as therapy to compensate for reduced or aberrant human phospholipid scramblase-like expression or activity.

Stimulation of human phospholipid scramblase-like activity is desirable in situations in which a human phospholipid scramblase-like protein is abnormally downregulated and/or in which increased human phospholipid scramblase-like activity is likely to have a beneficial effect. Conversely, inhibition of human phospholipid scramblase-like activity is desirable in situations in which human phospholipid scramblase-like activity is abnormally upregulated and/or in which decreased human phospholipid scramblase-like activity is likely to have a beneficial effect.

This invention is further illustrated by the following examples, which should not be construed as limiting.

EXPERIMENTAL

Example 1

Identification and Characterization of 32621 Human Scramblase

The human 32621-like sequence (SEQ ID NO:16), which is approximately 1542 nucleotides long including untranslated regions, contains a predicted methionine-initiated coding sequence of about 990 nucleotides (nucleotides 156–1145 of SEQ ID NO:16; SEQ ID NO:18). The coding sequence encodes a 329 amino acid protein (SEQ ID NO:17).

A search of the nucleotide and protein databases revealed that 32621 encodes a precursor polypeptide that shares similarity with several phospholipid scramblase proteins. An alignment of the protein sequences having highest similarity to the 32621 precursor polypeptide is shown in FIG. 21. The alignment was generated using the Clustal method with PAM250 residue weight table and sequence identities were determined by FASTA (Pearson and Lipman (1988) *Proc. Natl. Acad. Sci. USA* 85:2444–2448).

The 32621 protein displays similarity (approximately 45% identity over the full amino acid sequence) to the murine phospholipid scramblase-like polypeptide (SEQ ID NO:19; SP Accession Number 2935163; Zhou et al (1998) *Biochem.* 37:2356–2360 (see FIG. 21). It also displays similarity to the human Mm-1 cell derived transplantability-associated gene 1b (approximately 41% identity over the full amino acid sequence; SEQ ID NO:20; SP Accession Number 3510297; Kasukabe et al. (1998) *Biochem. Biophys. Res. Comm.* 249:449–455 (see FIG. 21).

Example 2

Tissue Distribution of 32621 mRNA

Expression levels of 32621 in various tissue and cell types were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions. The results of the Taqman® analysis are shown in FIGS. 24A–27.

Northern blot hybridizations with various RNA samples are performed under standard conditions and washed under stringent conditions, i.e., 0.2×SSC at 65° C. A DNA probe corresponding to all or a portion of the 32621 cDNA (SEQ ID NO:16) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

TaqMan analysis of 32621 revealed expression in a number of tissues, including the following: artery; vein; aortic SMC, smooth muscle cells, early); aortic SMC late; static HUVEC, human umbilical vein endothelial cells; shear HUVEC; heart; heart CHF, congestive heart failure heart tissue; kidney; skeletal muscle; adipose; pancreas; primary osteoblasts; osteoclasts; skin; spinal cord; brain cortex; brain hypothalamus; nerve; DRG, dorsal root ganglion; glial cells, astrocytes; glioblastoma; breast; breast tumor; ovary; ovarian tumor; prostate; prostate tumor; prostate epithelial cells; colon; colon tumor; lung; lung tumor; lung COPD, chronic obstructive pulmonary diseased lung; colon IBD, inflammatory bowel diseased colon; liver; liver fibrosis; dermal cells; spleen; tonsil; lymph node; thymus; skin-decubitis; synovium; bone marrow mononuclear cells; and activated peripheral blood mononuclear cells. High expression of 32621 occurred in aortic smooth muscle cells, HUVEC, brain cortex, brain hypothalamus, normal ovary, and fibrotic liver cells. See FIGS. 24A–B.

Expression of 32621 was further observed in various cell lines and tissues, including the following: conf HMVEC, microvascular endothelial cells; fetal heart; normal atrium; normal ventricle; heart diseased ventricle; normal kidney; kidney HT; skeletal muscle; skeletal muscle; liver; liver with inflammation; fetal adrenal; Wilms Tumor; spinal cord; and diseased cartilage. Relative expression levels of 32621 were also determined in various liver samples from animals fed modified diets. See FIGS. 25A–B and 26.

Expression of 32621 was observed in: aortic smooth muscle cells (ASMC)-A1P0; ASMC-A2P3; ASMC-A3P4; ASMC-AL; coronary artery smooth muscle cells (CASMC)-C1P3; CASMC-C2P3; CASMC-C5P0; CASMC-C1P6; macrophage cells; macrophage cells treated with interferon γ; CD40+ macrophage cells; macrophage cells treated with lipopolysaccharide; HUVEC, human umbilical vein endothelial cells; HMVEC, human microvascular endothelial cells; HAEC1, human aortic endothelial cells; HCAEC3, human coronary arterial endothelial cells; HCRE; RPTE, renal proximal tubule epithelial cells; MC; SKM1, myelogenous leukemia cells; and HLF, hepatocellular carcinoma cell line. Of these cell types, 32621 expression was high in microvascular endothelial cells, with microvascular endothelial cells exhibiting an expression level about 1990 times higher than in macrophage cells. See FIG. 27.

Example 3

Recombinant Expression of 32621 in Bacterial Cells

In this example, the 32621-like sequence is expressed as a recombinant glutathione-S-transferase (GST) fusion polypeptide in *E. coli* and the fusion polypeptide is isolated and characterized. Specifically, the 32621-like sequence is fused to GST and this fusion polypeptide is expressed in *E. coli*, e.g., strain PEB199. Expression of the GST-32621-like fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 32621-Like Protein in COS Cells

To express the 32621-like gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 32621-like protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 32621-like DNA sequence is amplified by PCR using two primers. The 5' primer contains the restriction site of interest followed by approximately twenty nucleotides of the 32621-like coding sequence starting from the initiation codon; the 3' end sequence contains complementary sequences to the other restriction site of interest, a translation stop codon, the HA tag or FLAG tag and the last 20 nucleotides of the 32621-like coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 32621-like gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32621-like—pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the 32621-like polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32621-like coding sequence is cloned directly into the polylinker of the pcDNA/Amp vector using the appropriate restriction sites. The resulting plasmid is transfected into COS cells in the manner described above, and the expression of the 32621-like polypeptide is detected by radiolabelling and immunoprecipitation using a 32621-like specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

CHAPTER 5

27802, A Novel Adenylate Kinase

BACKGROUND OF THE INVENTION

Adenylate kinases play a key role in the regulation of energy balance within cells, particularly maintenance of the ratio of ATP with its diphosphate (ADP) and monophosphate forms (AMP). ATP serves as the primary source of energy for biochemical reactions in cells and is also a key precursor in DNA and RNA synthesis during cellular growth and replication. The energy associated with the terminal phosphate bonds of ATP may be transferred to other nucleotides using a nucleoside monophosphate kinase such as adenylate kinase. In this manner, the terminal energy-rich phosphate bonds of ATP may be transferred to the appropriate nucleotides for use in a variety of biosynthetic and energy-requiring processes, such as biosynthesis of macromolecules, active ion transport, muscle contraction, thermogenesis, etc. A number of these energy-requiring biosynthetic reactions hydrolyze ATP into AMP plus pyrophosphate. Reutilization of the resulting AMP requires conversion back into the triphosphate form following conversion to ADP. Various nucleotide monophosphate kinases carry out the first step of phosphorylating AMP to its diphosphate form at the expense of ATP. In the case of adenylate kinase, this reversible reaction is given as AMP+ATP⇌2 ADP.

Adenylate kinases also play a role in regulating the flow of carbon between net accumulation of glucose via the gluconeogenesis pathway and its subsequent catabolism via the glycolytic pathway by way of their control over the ratio of AMP to ATP. AMP is a positive allosteric effector of the enzyme 6-phophofructo-1-kinase, which shifts, and a negative allosteric effector for the enzyme fructose-1,6-bisphosphatase. When the first of these enzymes is activated, carbon flow is shifted in the direction of glycolysis; when the second of these enzymes is activated, carbon flow shifts in the direction of gluconeogenesis. Thus, increases in the ratio of AMP to ATP shift carbon flow toward glycolysis, while decreases in the ratio of AMP to ATP shift carbon flow toward glucose formation.

These enzymes have been studied in a number of mammals, including rat, porcine, chicken, bovine, rabbit, and humans. Evidence from biochemical studies suggests that human tissues have five adenylate kinase isozymes, AK1–AK5. Thus far the cDNAs of human AK1, AK2, AK4, and AK5 have been cloned. Adenylate kinase isoforms in humans are sequence related and also related to UMP/CMP kinases from several species. See Rompay et al. (1999) *Eur. J. Biochem.* 261:509–516, and the references cited therein.

The adenylate kinase isozymes AK1 (or myokinase), which is a cytosolic enzyme present in brain, skeletal muscle, and erythrocytes, and AK2, which is associated with the mitochondrial membrane in liver, spleen, heart, and kidney, both utilize ATP as their nucleoside triphosphate donor substrate. AK3 (or GTP:AMP phosphotransferase) is located in the mitochondrial matrix, primarily in heart and liver cells, and uses MgGTP instead of MgATP. AK4 and AK5 are both localized in brain tissue.

Several regions of AK family enzymes are well conserved, including the nucleoside triphosphate binding glycine-rich region, the nucleoside monophosphate binding site, and the lid domain that closes over the substrate upon binding (see Schulz (1987) *Cold Spring Harbor Symp. Quant. Biol.* 52:429–439).

These enzymes assist with maintenance of energy production and utilization within cells, particularly in cells having high rates of growth and metabolic activity such as in heart, skeletal muscle, and liver. In fact, adenylate kinase deficiency has been linked to hemolytic anemia and neurological disorders such as neurofibromatosis (Xu et al. (1992) *Genomics* 13:537–542. In addition, targeting regulation of ATP synthesis has been the basis of antiproliferative drugs for treatment of viral infections and cancer.

Adenylate kinases are also useful for activating nucleoside analogues used as pharmaceuticals, especially for cancer and viral infection. Most of these analogues must be phosphorylated to the triphosphate form in order to be pharmaceutically active. The first phosphorylation step in the activation of nucleoside analogs is catalyzed by deoxyribonucleoside kinases. Phosphorylation to the di- and triphosphates are then required.

Accordingly, adenylate kinases are a major target for drug action and development. Thus, it is valuable to the field of pharmaceutical development to identify and characterize previously unknown adenylate kinases. The present invention advances the state of the art by providing a previously unidentified human adenylate kinase.

SUMMARY OF THE INVENTION

Isolated nucleic acid molecules corresponding to adenylate kinase nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:22. Further provided are adenylate kinase polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The adenylate kinase molecules of the present invention are useful for modulating cellular growth and/or cellular metabolic pathways particularly for regulating one or more proteins involved in growth and metabolism. Accordingly, in one aspect, this invention provides isolated nucleic acid molecules encoding adenylate kinase proteins or biologically active portions thereof, as well as nucleic acid fragments suitable as primers or hybridization probes for the detection of adenylate kinase-encoding nucleic acids.

Another aspect of this invention features isolated or recombinant adenylate kinase proteins and pQlypeptides. Preferred adenylate kinase proteins and polypeptides possess at least one biological activity possessed by naturally occurring adenylate kinase proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the adenylate kinase polypeptides and fragments are provided. Such antibodies are useful in detecting the adenylate kinase polypeptides as well as in regulating the T-cell immune response and cellular activity, particularly growth and proliferation.

In another aspect, the present invention provides a method for detecting the presence of adenylate kinase activity or expression in a biological sample by contacting the biological sample with an agent capable of detecting an indicator of adenylate kinase activity such that the presence of adenylate kinase activity is detected in the biological sample.

In yet another aspect, the invention provides a method for modulating adenylate kinase activity comprising contacting a cell with an agent that modulates (inhibits or stimulates) adenylate kinase activity or expression such that adenylate kinase activity or expression in the cell is modulated. In one embodiment, the agent is an antibody that specifically binds to adenylate kinase protein. In another embodiment, the agent modulates expression of adenylate kinase protein by modulating transcription of an adenylate kinase gene, splicing of an adenylate kinase mRNA, or translation of an adenylate kinase mRNA. In yet another embodiment, the agent is a nucleic acid molecule having a nucleotide sequence that is antisense to the coding strand of the adenylate kinase mRNA or the adenylate kinase gene.

In one embodiment, the methods of the present invention are used to treat a subject having a disorder characterized by aberrant adenylate kinase protein activity or nucleic acid expression by administering an agent that is an adenylate kinase modulator to the subject. In one embodiment, the adenylate kinase modulator is an adenylate kinase protein. In another embodiment, the adenylate kinase modulator is an adenylate kinase nucleic acid molecule. In other embodiments, the adenylate kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding an adenylate kinase protein; (2) misregulation of a gene encoding an adenylate kinase protein; and (3) aberrant post-translational modification of an adenylate kinase protein, wherein a wild-type form of the gene encodes a protein with an adenylate kinase activity.

In another aspect, the invention provides a method for identifying a compound that binds to or modulates the activity of an adenylate kinase protein. In general, such methods entail measuring a biological activity of an adenylate kinase protein in the presence and absence of a test compound and identifying those compounds that alter the activity of the adenylate kinase protein.

The invention also features methods for identifying a compound that modulates the expression of adenylate kinase genes by measuring the expression of the adenylate kinase sequences in the presence and absence of the compound.

Other features and advantages of the invention will be apparent from the following detailed description and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is based, at least in part, on the identification of novel molecules, referred to herein as adenylate kinase nucleic acid and polypeptide molecules, which play a role in, or function in, numerous biochemical pathways associated with cellular growth and/or cellular metabolic activity. These growth and metabolic pathways are described in Lodish et al. (1995) *Molecular Cell Biology* (Scientific American Books Inc., New York, N.Y.) and Devlin (1997) *Textbook of Biochemistry with Clinical Correlations* (Wiley-Liss, Inc., New York, N.Y.), the contents of which are incorporated herein by reference.

Specifically, the present invention provides isolated nucleic acid molecules comprising nucleotide sequences encoding the adenylate kinase polypeptide whose amino acid sequence is given in SEQ ID NO:22, or a variant or fragment of the polypeptides. A nucleotide sequence encoding an adenylate kinase polypeptide of the invention, more particularly the polypeptide of SEQ ID NO:22, is set forth in SEQ ID NO:21.

A novel human gene, termed clone h27802 is provided. This sequence, and complements thereof, are referred to as "adenylate kinase" indicating that the gene sequences share sequence similarity to adenylate kinase genes.

The novel h27802 adenylate kinase gene encodes an approximately 1.45 Kb mRNA transcript having the corresponding cDNA set forth in SEQ ID NO:21. This transcript encodes a 258 amino acid protein (SEQ ID NO:22). An analysis of the full-length h27802 polypeptide predicts that the N-terminal 56 amino acids may represent a region comprising a signal peptide. Prosite program analysis was used to predict various sites within the h27802 protein. See FIG. 31.

The h27802 adenylate kinase protein possesses adenylate kinase domain sequences, as shown in FIG. 34. There are three functional subdomains common to nucleoside monophosphate kinases: the nucleoside triphosphate binding glycine-rich region, the nucleoside monophosphate binding site, and the lid domain that closes over the substrate upon binding (see Schulz (1987) *Cold Spring Harbor Symp. Quant. Biol.* 52:429–439).

Human 27802 was aligned with two consensus amino acid sequences for adenylate kinase domains derived from hidden Markov models. For general information regarding PFAM identifiers, PS prefix and PF prefix domain identification numbers, refer to Sonnhammer et al. (1997) *Protein* 28:405–420 and the information available at URL www.psc.edu/general/software/packages/pfam/pfam.html. The first adenylate kinase domain (SEQ ID NO:24) aligns with amino acids 41–120 of SEQ ID NO:22 and the second adenylate kinase domain (SEQ ID NO:25) aligns with amino acids 201–251 of SEQ ID NO:22 (see FIG. 34).

As used herein, the term "adenylate kinase domain" includes an amino acid sequence of about 30–200 amino acid residues in length and having a bit score for the alignment of the sequence to the adenylate kinase domain (HMM) of at least 8. Preferably, an adenylate kinase domain includes at least about 40–150 amino acids, more preferably about 50–100 amino acid residues, or about 50–80 amino acids and has a bit score for the alignment of the sequence to the adenylate kinase domain (HMM) of at least 16 or greater. The adenylate kinase domain (HMM) has been assigned the PFAM Accession PF00406; see also the information available at URL pfam.wustl.edu/).

In a preferred embodiment a 27802-like polypeptide or protein has "adenylate kinase domains" or regions which include at least about 30–200, more preferably about 40–100, or 50–80 amino acid residues and has at least about 60%, 70%, 80%, 85%, 90%, 95%, 99%, or 100% sequence identity with an "adenylate kinase domain," e.g., the adenylate kinase domain of human 27802-like (e.g., amino acid residues 41–120 and 201–251 of SEQ ID NO:22).

To identify the presence of an adenylate kinase domain in a 27802-like protein sequence, and make the determination that a polypeptide or protein of interest has a particular profile, the amino acid sequence of the protein can be searched against a database of HMMs (e.g., the Pfam database, release 2.1) using the default parameters described at the URL www.sanger.ac.uk/Software/Pfam/HMM_search. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

A BLASTN search using the 27802 cDNA clone of the invention as the subject was performed. The 27802 clone shares 97% to 100% identity to the top five search hits. These hits are 1) a partial cDNA clone isolated from a brain glioblastoma (Accession No: AI359456) with homology to maize adenylate kinase; 2) a partial 3' cDNA clone isolated from Jia bone marrow stroma (Accession No: AW069362); 3) a partial cDNA clone isolated from a brain glioblastoma (Accession No: AI362274) with homology to maize adenylate kinase; 4) a partial cDNA clone isolated from a brain anaplastic oligodendroglioma (Accession No: AI826091) with homology to maize adenylate kinase; and 5) a partial cDNA clone isolated from adult heart (Accession No: C03497).

Figure 35B:
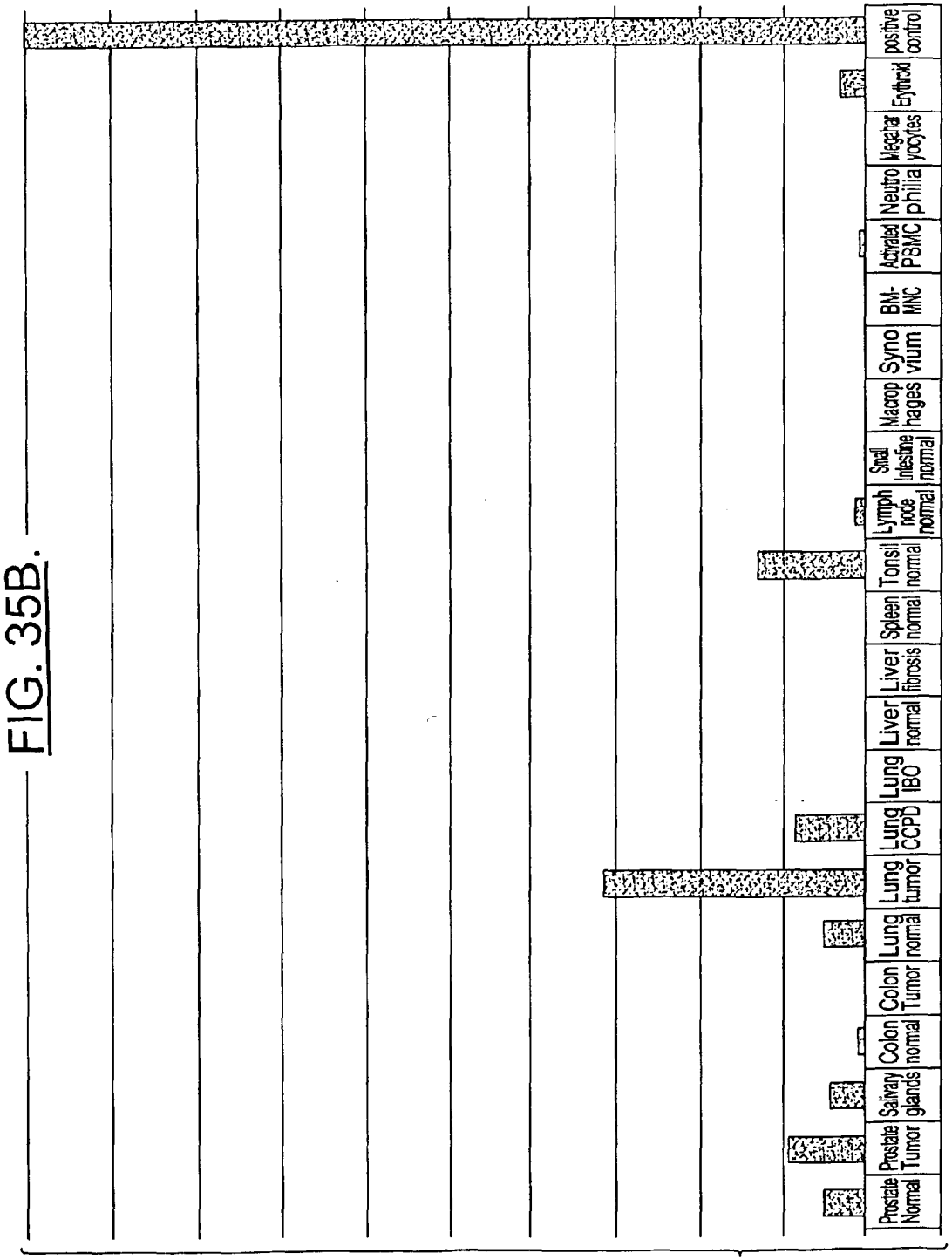

The expression levels of 27802 were determined in various tissues by quantitative PCR (FIG. 35). The highest levels of expression of 27802 were observed in artery, kidney, brain cortex and brain hypothalamus, ovary, lung (tumor), and tonsil. The expression of 27802 in a tissue indicates that modulation of the expression or activity of 27802 in that tissue may be used in the treatment of disorders involving such a tissue.

In one embodiment, the adenylate kinase molecules modulate the activity of one or more proteins involved in cellular growth or differentiation, e.g., cardiac, epithelial, or neuronal cell growth or differentiation. In another embodiment, the adenylate kinase molecules of the present invention are capable of modulating the phosphorylation state of a nucleoside mono-, di-, or triphosphate molecule or the phosphorylation state of one or more proteins involved in cellular growth or differentiation, e.g., cardiac, epithelial, or neuronal cell growth or differentiation, as described in, for example, Lodish et al. (1995) and Devlin (1997), supra.

In addition, the adenylate kinase of the present invention are targets of drugs described in Goodman and Gilman (1996), *The Pharmacological Basis of Therapeutics* (9$^{th}$ ed.) Hartman & Limbard Editors, the contents of which are incorporated herein by reference. Particularly, the adenylate kinases of the invention may modulate phosphorylation activity in tissues and cells including, but not limited to, human brain. In addition, expression of the gene is also observed in lymphoma. In one embodiment, the adenylate kinase sequences of the invention are used to manipulate the nucleoside mono-, di-, and triphosphate pool to alter cellular metabolic pathways, such as glycolysis and gluconeogenesis.

Adenylate kinases play an important role in the regulation of energy balance within cells and in energy-requiring biochemical processes associated with cellular growth and development. Inhibition or over-stimulation of the activity of adenylate kinases affects the cellular equilibrium between nucleoside mono-, di-, and triphosphates, particularly AMP, ADP, and ATP, all of which are integrally involved in energy-requiring biochemical processes associated with cellular growth and development. Disruption or modulation of this equilibrium can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy.

Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., lymphoma, melanoma, prostate cancer, cervical cancer, breast cancer, colon cancer, or sarcoma.

Furthermore, adenylate kinase activity increases in cerebrospinal fluid at the acute onset of ischemic brain damage and is correlated with the severity of the lesion (Buttner et al. (1986) *J. Neurol.* 233:297–303). Adenyl kinase activity also increases in cerebrospinal fluid in some brain tumors (Ronquist et al. (1977) *Lancet i:* 1284–1286). Further, adenylate kinase may be expressed in damaged tissue and therefore is a useful target to measure tissue damage. Finally, deletions at 1p31 locus in many tumors is associated with hemolytic anemia (Matsuura et al. (1989) *J. Biol. Chem.* 264:10148–10155 and Mitelman et al. (1997) *Nature Genet.* 15:417–474). Accordingly, the compositions are also useful for treatment and diagnosis related to these disorders.

The disclosed invention relates to methods and compositions for the modulation, diagnosis, and treatment of cellular proliferative and/or differentiative, neurological, immune, inflammatory, lymphatic, cardiovascular, respiratory, and hematological disorders.

Immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Disorders involving blood vessels include, but are not limited to, responses of vascular cell walls to injury, such as endothelial dysfunction and endothelial activation and intimal thickening; vascular diseases including, but not limited to, congenital anomalies, such as arterioyenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Hematologic disorders include but are not limited to anemias including sickle cell and hemolytic anemia, hemophilias including types A and B, leukemias, thalassemias, spherocytosis, Von Willebrand disease, chronic granulomatous disease, glucose-6-phosphate dehydrogenase deficiency, thrombosis, clotting factor abnormalities and deficiencies including factor VIII and IX deficiencies, hemarthrosis, hematemesis, hematomas, hematuria, hemochromatosis, hemoglobinuria, hemolytic-uremic syndrome, thrombocytopenias including HIV-associated thrombocytopenia, hemorrhagic telangiectasia, idiopathic thrombocytopenic purpura, thrombotic microangiopathy, hemosiderosis.

Respiratory disorders include, but are not limited to, apnea, asthma, particularly bronchial asthma, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Preferred disorders include, but are not limited to disorders of brain and lymph node, especially lymphoma.

The disclosed invention also relates to methods and compositions for the modulation, diagnosis, and treatment of disorders involving the brain and lymph nodes.

Disorders involving the brain include, but are limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and lowflow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyclination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telangiectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sezary syndrome, and Hodgkin disease.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. Accordingly, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; (leukemias are encompassed with and without differentiation); chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyclocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphom$^{4a}$), intestinal T-cell lymphoma, adult T-cell leukemia/lymphoma, and anaplastic large cell lymphoma.

The adenylate kinase sequences of the invention are members of a family of molecules having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred adenylate kinase polypeptides of the present invention have an amino acid sequence sufficiently identical to the amino acid sequence of SEQ ID NO:22. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 60%, 65%, 70%, 75%, 80%, 85%, 90%, 95%, 96%, 97%, 98% or 99% identity are defined herein as sufficiently identical.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at the URL www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 27802 nucleic acid molecules of the invention. BLAST protein searches can be performed with the XBLAST program, score=50, wordlength=3 to obtain amino acid sequences homologous to 27802 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See information at the URL www.ncbi.nlm.nih.gov.

Accordingly, another embodiment of the invention features isolated adenylate kinase proteins and polypeptides having an adenylate kinase protein activity. As used interchangeably herein, an "adenylate kinase protein activity", "biological activity of an adenylate kinase protein", or "functional activity of an adenylate kinase protein" refers to an activity exerted by an adenylate kinase protein, polypeptide, or nucleic acid molecule on an adenylate kinase responsive cell as determined in vivo, or in vitro, according to standard assay techniques. An adenylate kinase activity can be a direct activity, such as an association with or an enzymatic activity on a second protein, or an indirect activity, such as a cellular activity mediated by interaction of the adenylate kinase protein with a second protein. In a preferred embodiment, an adenylate kinase activity includes at least one or more of the following activities: (1) modulating (stimulating and/or enhancing or inhibiting) cellular proliferation, differentiation, and/or function, particularly in cells in which the sequences are expressed, for example, cells of the lymph node, including Th1, Th2, T cells, natural killer T cells, lymphocytes, leukocytes, etc., and brain, such as glial cells and neurons; (2) modulating a target cell's energy balance, particularly the ratio between AMP and ATP; (3) modulating the glycolytic pathway; (4) modulating the gluconeogenesis pathway; (4) modulating cell growth; (5) modulating the entry of cells into mitosis; (6) modulating cellular differentiation; (7) modulating cell death; and (8) modulating an immune response.

An "isolated" or "purified" adenylate kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated adenylate kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An adenylate kinase protein that is substantially free of cellular material includes preparations of adenylate kinase protein having less than about 30%, 20%, 10%, or 5% (by dry weight) of non-adenylate kinase protein (also referred to herein as a "contaminating protein"). When the adenylate kinase protein or biologically active portion thereof is recombinantly produced, preferably, culture medium represents less than about 30%, 20%, 10%, or 5% of the volume of the protein preparation. When adenylate kinase protein is produced by chemical synthesis, preferably the protein preparations have less than about 30%, 20%, 10%, or 5% (by dry weight) of chemical precursors or non-adenylate kinase chemicals.

Various aspects of the invention are described in further detail in the following subsections.

I. Isolated Nucleic Acid Molecules

One aspect of the invention pertains to isolated nucleic acid molecules comprising nucleotide sequences encoding adenylate kinase proteins and polypeptides or biologically active portions thereof, as well as nucleic acid molecules sufficient for use as hybridization probes to identify adenylate kinase-encoding nucleic acids (e.g., adenylate kinase mRNA) and fragments for use as PCR primers for the amplification or mutation of adenylate kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the adenylate kinase proteins of the present invention include sequences set forth in SEQ ID NO:21 and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the adenylate kinase protein encoded by these nucleotide sequences is set forth in SEQ ID NO:22.

Nucleic acid molecules that are fragments of these adenylate kinase nucleotide sequences are also encompassed by the present invention. By "fragment" is intended a portion of the nucleotide sequence encoding an adenylate kinase protein. A fragment of an adenylate kinase nucleotide sequence may encode a biologically active portion of an adenylate kinase protein, or it may be a fragment that can be used as a hybridization probe or PCR primer using methods disclosed below. A biologically active portion of an adenylate kinase protein can be prepared by isolating a portion of one of the adenylate kinase nucleotide sequences of the invention, expressing the encoded portion of the adenylate kinase protein (e.g., by recombinant expression in vitro), and assessing the activity of the encoded portion of the adenylate kinase protein. Nucleic acid molecules that are fragments of an adenylate kinase nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 nucleotides, or up to the number of nucleotides present in a full-length adenylate kinase nucleotide sequence disclosed herein (for example, 1452 nucleotides for SEQ ID NO:21) depending upon the intended use.

Alternatively, a nucleic acid molecule that is a fragment of an 27802-like nucleotide sequence of the present invention comprises a nucleotide sequence consisting of at least 5, 10, 15, 20, 25, 30, 35, or 40 contiguous nucleotides of nucleotides 215–370, or nucleotides 843–941 of SEQ ID NO:21. A fragment of a nucleotide sequence of the present invention comprises a nucleotide sequence consisting of nucleotides 215–300, 300–370, 843–900, 900–941 of SEQ ID NO:21.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 5–10, 10–15, 15–20, 20–25, 25–30, 30–35, 35–40, 40–45, 45–5 50–75, 75–100 or more contiguous nucleotides. Other regions of the nucleotide sequence may comprise fragments of various sizes, depending upon potential homology with previously disclosed sequences.

A fragment of an adenylate kinase nucleotide sequence that encodes a biologically active portion of an adenylate kinase protein of the invention will encode at least 15, 25, 30, 50, 75, 100, 125, 150, 175, 200, or 225 contiguous amino acids, or up to the total number of amino acids present in a full-length adenylate kinase protein of the invention (for example, 258 amino acids for SEQ ID NO:22). A nucleic acid molecule that is a fragment of an 27802-like nucleotide sequence of the present invention comprises a nucleotide sequence encoding at least 15, 20, 25, 30, 35, or 40 contiguous amino acids of amino acids 1–51, or 209–241 of SEQ ID NO:22. A fragment of a nucleotide sequence of the present invention comprises a nucleotide sequence encoding amino acids 1–25, 25–51, 209–241 of SEQ ID NO:22.

Fragments of an adenylate kinase nucleotide sequence that are useful as hybridization probes for PCR primers generally need not encode a biologically active portion of an adenylate kinase protein.

Nucleic acid molecules that are variants of the adenylate kinase nucleotide sequences disclosed herein are also encompassed by the present invention. "Variants" of the adenylate kinase nucleotide sequences include those sequences that encode the adenylate kinase proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the adenylate kinase proteins disclosed in the present invention as discussed below. Generally, nucleotide sequence variants of the invention with have at least 60%, 65%, 70%, 75%, 80%, 85%, 90%, 91%, 92%, 93%, 94%, 95%, 96%, 97%, 98%, or 99% identity to the nucleotide sequence disclosed herein. A variant adenylate kinase nucleotide sequence will encode an adenylate kinase protein that has an amino acid sequence having at least 45%, 55%, 60%, 65%, 70%, 75%, 80%, 85%, 90%, 91%, 92%, 93%, 94%, 95%, 96%, 97%, 98%, or 99% identity to the amino acid sequence of an adenylate kinase protein disclosed herein. Such variants retain the functional activity (e.g., the adenylate kinase activity) of the polypeptide set forth in SEQ ID NO:22.

In addition to the adenylate kinase nucleotide sequence shown in SEQ ID NO:21, it will be appreciated by those skilled in the art that DNA sequence polymorphisms that lead to changes in the amino acid sequences of adenylate kinase proteins may exist within a population (e.g., the human population). Such genetic polymorphism in an adenylate kinase gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an adenylate kinase protein, preferably a mammalian adenylate kinase protein. As used herein, the phrase "allelic variant" refers to a nucleotide sequence that occurs at an adenylate kinase locus or to a polypeptide encoded by the nucleotide sequence. Such natural allelic variations can typically result in 1–5% variance in the nucleotide sequence of the adenylate kinase gene. Any and all such nucleotide variations and resulting amino acid polymorphisms or variations in an adenylate kinase sequence that are the result of natural allelic variation and that do not alter the functional activity of adenylate kinase proteins are intended to be within the scope of the invention.

Moreover, nucleic acid molecules encoding adenylate kinase proteins from other species (adenylate kinase homologs), which have a nucleotide sequence differing from that of the adenylate kinase sequence disclosed herein, are intended to be within the scope of the invention. For example, nucleic acid molecules corresponding to natural allelic variants and homologs of the human adenylate kinase cDNA of the invention can be isolated based on their identity to the human adenylate kinase nucleic acid disclosed herein using the human cDNA, or a portion thereof, as a hybridization probe according to standard hybridization techniques under stringent hybridization conditions as disclosed below.

In addition to naturally-occurring allelic variants of the adenylate kinase sequences that may exist in the population, the skilled artisan will further appreciate that changes can be introduced by mutation into the nucleotide sequences of the invention thereby leading to changes in the amino acid sequence of the encoded adenylate kinase proteins, without altering the biological activity of the adenylate kinase proteins. Thus, an isolated nucleic acid molecule encoding an adenylate kinase protein having a sequence that differs from that of SEQ ID NO:22 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

Figure 30:
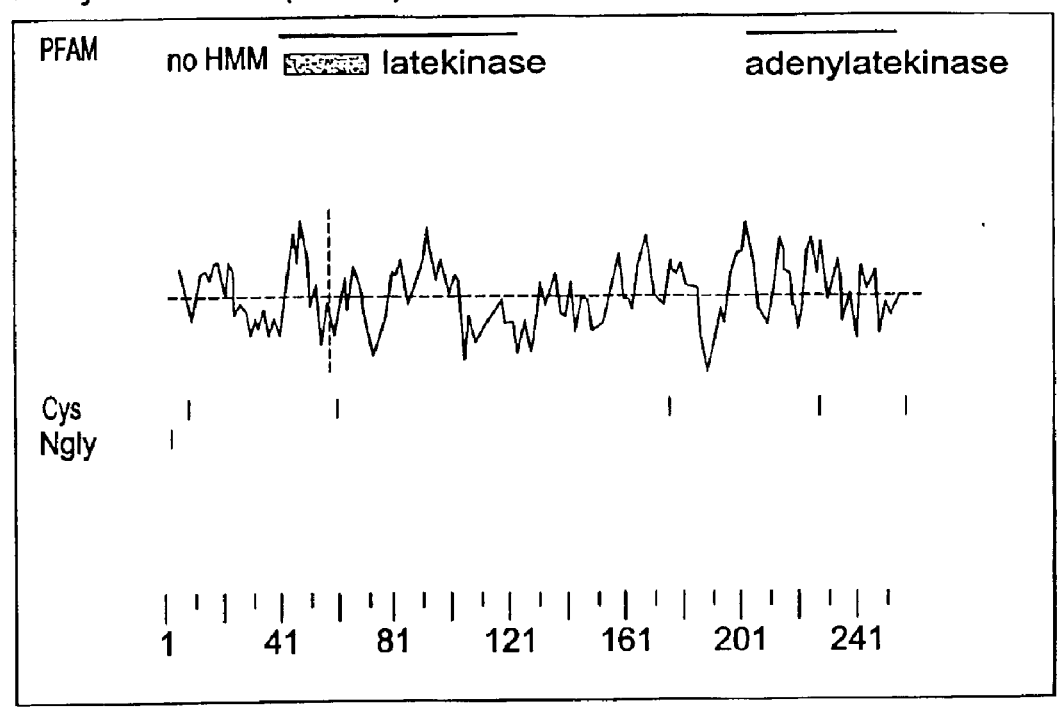
FIG. 30 shows a 27802 receptor hydrophobicity plot. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:22) of human 27802 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.

For example, preferably, conservative amino acid substitutions may be made at one or more predicted, preferably nonessential amino acid residues. A "nonessential" amino acid residue is a residue that can be altered from the wild-type sequence of an adenylate kinase protein (e.g., the sequence of SEQ ID NO:22) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the adenylate kinase domain sequence of SEQ ID NO:22 (see FIG. 30), where such residues are essential for protein activity.

Alternatively, variant adenylate kinase nucleotide sequences can be made by introducing mutations randomly along all or part of an adenylate kinase coding sequence, such as by saturation mutagenesis, and the resultant mutants can be screened for adenylate kinase biological activity to identify mutants that retain activity. Following mutagenesis, the encoded protein can be expressed recombinantly, and the activity of the protein can be determined using standard assay techniques.

Thus the nucleotide sequence of the invention includes the sequence disclosed herein as well as fragments and variants thereof. The adenylate kinase nucleotide sequence of the invention, and fragments and variants thereof, can be used as probes and/or primers to identify and/or clone adenylate kinase homologs in other cell types, e.g., from other tissues, as well as adenylate kinase homologs from other mammals. Such probes can be used to detect transcripts or genomic sequences encoding the same or identical proteins. These probes can be used as part of a diagnostic test kit for identifying cells or tissues that misexpress an adenylate kinase protein, such as by measuring levels of an adenylate kinase-encoding nucleic acid in a sample of cells from a subject, e.g., detecting adenylate kinase mRNA levels or determining whether a genomic adenylate kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Adenylate kinase nucleotide sequences isolated based on their sequence identity to the adenylate kinase nucleotide sequence set forth herein or to fragments and variants thereof are encompassed by the present invention.

In a hybridization method, all or part of a known adenylate kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known adenylate kinase nucleotide sequence disclosed herein. Degenerate primers designed on the basis of conserved nucleotides or amino acid residues in a known adenylate kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an adenylate kinase nucleotide sequence of the invention or a fragment or variant thereof. Preparation of probes for hybridization is generally known in the art and is disclosed in Sambrook et al (1989) *Molecular Cloning: A Laboratory Manual* (2d ed., Cold Spring Harbor Laboratory Press, Plainview, N.Y.), herein incorporated by reference.

For example, in one embodiment, a previously unidentified adenylate kinase nucleic acid molecule hybridizes under stringent conditions to a probe that is a nucleic acid molecule comprising the adenylate kinase nucleotide sequence of the invention or a fragment thereof. In another embodiment, the previously unknown adenylate kinase nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising the adenylate kinase nucleotide sequence disclosed herein or a fragment thereof.

Accordingly, in another embodiment, an isolated previously unknown adenylate kinase nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising the nucleotide sequence of the invention, preferably the coding sequence set forth in SEQ ID NO:21 or a complement, fragment, or variant thereof.

As used herein, the term "hybridizes under stringent conditions" describes conditions for hybridization and washing. Stringent conditions are known to those skilled in the art and can be found in *Current Protocols in Molecular Biology* John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:21, or SEQ ID NO:23, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

Thus, in addition to the adenylate kinase nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the adenylate kinase nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire adenylate kinase coding strand, or to only a portion thereof, e.g., all or part of the protein coding region (or open reading frame). An antisense nucleic acid molecule can be antisense to a noncoding region of the coding strand of a nucleotide sequence encoding an adenylate kinase protein. The noncoding regions are the 5' and 3' sequences that flank the coding region and are not translated into amino acids.

Given the coding-strand sequence encoding an adenylate kinase protein disclosed herein (SEQ ID NO:21), antisense nucleic acids of the invention can be designed according to the rules of Watson and Crick base pairing. The antisense nucleic acid molecule can be complementary to the entire coding region of adenylate kinase mRNA, but more preferably is an oligonucleotide that is antisense to only a portion of the coding or noncoding region of adenylate kinase mRNA. For example, the antisense oligonucleotide can be complementary to the region surrounding the translation start site of adenylate kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an adenylate kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) Nature 334:585–591)) can be used to catalytically cleave adenylate kinase mRNA transcripts to thereby inhibit translation of adenylate kinase mRNA. A ribozyme having specificity for an adenylate kinase-encoding nucleic acid can be designed based upon the nucleotide sequence of an adenylate kinase cDNA disclosed herein (e.g., SEQ ID NO:21). See, e.g., Cech et al., U.S. Pat. No. 4,987,071; and Cech et al., U.S. Pat. No. 5,116,742. Alternatively, adenylate kinase mRNA can be used to select a catalytic RNA having a specific ribonuclease activity from a pool of RNA molecules. See, e.g., Bartel and Szostak (1993) Science 261:1411–1418.

The invention also encompasses nucleic acid molecules that form triple helical structures. For example, adenylate kinase gene expression can be inhibited by targeting nucleotide sequences complementary to the regulatory region of the adenylate kinase protein (e.g., the adenylate kinase promoter and/or enhancers) to form triple helical structures that prevent transcription of the adenylate kinase gene in target cells. See generally Helene (1991) Anticancer Drug Des. 6(6):569; Helene (1992) Ann. N.Y. Acad. Sci. 660:27; and Maher (1992) Bioassays 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) Proc. Natl. Acad. Sci. USA 93:14670.

PNAs of an adenylate kinase molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR claiping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of an adenylate kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) Nucleic Acids Res. 24(17):3357–63; Mag et al. (1989) Nucleic Acids Res. 17:5973; and Peterson et al. (1975) Bioorganic Med. Chem. Lett. 5:1119.

II. Isolated Adenylate Kinase Proteins and Anti-Adenylate Kinase Antibodies

Adenylate kinase proteins are also encompassed within the present invention. By "adenylate kinase protein" is intended a protein having the amino acid sequence set forth in SEQ ID NO:22, as well as fragments, biologically active portions, and variants thereof.

"Fragments" or "biologically active portions" include polypeptide fragments suitable for use as immunogens to raise anti-adenylate kinase antibodies. Fragments include peptides comprising amino acid sequences sufficiently identical to or derived from the amino acid sequence of an adenylate kinase protein of the invention and exhibiting at least one activity of an adenylate kinase protein, but which include fewer amino acids than the full-length (SEQ ID NO:22) adenylate kinase protein disclosed herein. Typically, biologically active portions comprise a domain or motif with at least one activity of the adenylate kinase protein. A biologically active portion of an adenylate kinase protein can be a polypeptide that is, for example, 10–15, 15–20, 20–25, 25–30, 30–35, 35–40, 40–45, 45–50, 50–55, 55–60, 70, 80, 90, 100 or more amino acids in length. Such biologically active portions can be prepared by recombinant techniques and evaluated for one or more of the functional activities of a native adenylate kinase protein. As used here, a fragment comprises at least 5 contiguous amino acids of SEQ ID NO:22. The invention encompasses other fragments, however, such as any fragment in the protein greater than 5 amino acids, depending upon the intended use.

By "variants" is intended proteins or polypeptides having an amino acid sequence that is at least about 45%, 55%, 65%, preferably about 70%, 75%, 80%, 85%, 90%, 91%, 92%, 93%, 94%, 95%, 96%, 97%, 98%, or 99% identical to the amino acid sequence of SEQ ID NO:22. Variants also include polypeptides encoded by a nucleic acid molecule that hybridizes to the nucleic acid molecule of SEQ ID NO:21, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:22. If alignment is needed for this comparison the sequences should be aligned for maximum identity. "Looped" out sequences from deletions or insertions, or mismatches, are considered differences. Such variants generally retain the functional activity of the 27802-like proteins of the invention. Variants include polypeptides that differ in amino acid sequence due to natural allelic variation or mutagenesis.

The invention also provides adenylate kinase chimeric or fusion proteins. In the case where an expression cassette contains two protein coding regions joined in a contiguous manner in the same reading frame, the encoded polypeptide is herein defined as a "heterologous polypeptide" or a "chimeric polypeptide" or a "fusion polypeptide". As used herein, an adenylate kinase "heterologous protein" or "chimeric protein" or "fusion protein" comprises an adenylate kinase polypeptide operably linked to a non-adenylate kinase polypeptide. An "adenylate kinase polypeptide" refers to a polypeptide having an amino acid sequence corresponding to an adenylate kinase protein, whereas a "non-adenylate kinase polypeptide" refers to a polypeptide having an amino acid sequence corresponding to a protein that is not substantially identical to the adenylate kinase protein, e.g., a protein that is different from the adenylate kinase protein and which is derived from the same or a different organism. Within an adenylate kinase fusion protein, the adenylate kinase polypeptide can correspond to all or a portion of an adenylate kinase protein, preferably at least one biologically active portion of an adenylate kinase protein. Within the fusion protein, the term "operably linked" is intended to indicate that the adenylate kinase polypeptide and the non-adenylate kinase polypeptide are fused in-frame to each other. The non-adenylate kinase polypeptide can be fused to the N-terminus or C-terminus of the adenylate kinase polypeptide.

One useful fusion protein is a GST-adenylate kinase fusion protein in which the adenylate kinase sequences are fused to the C-terminus of the GST sequences. Such fusion proteins can facilitate the purification of recombinant adenylate kinase proteins.

In yet another embodiment, the fusion protein is an adenylate kinase-immunoglobulin fusion protein in which all or part of an adenylate kinase protein is fused to sequences derived from a member of the immunoglobulin protein family. The adenylate kinase-immunoglobulin fusion proteins of the invention can be incorporated into pharmaceutical compositions and administered to a subject to inhibit an interaction between an adenylate kinase ligand and an adenylate kinase protein on the surface of a cell, thereby suppressing adenylate kinase-mediated signal transduction in vivo. The adenylate kinase-immunoglobulin fusion proteins can be used to affect the bioavailability of an adenylate kinase cognate ligand. Inhibition of the adenylate kinase ligand/adenylate kinase interaction may be useful therapeutically, both for treating proliferative and differentiative disorders and for modulating (e.g., promoting or inhibiting) cell survival. Moreover, the adenylate kinase-immunoglobulin fusion proteins of the invention can be used as immunogens to produce anti-adenylate kinase antibodies in a subject, to purify adenylate kinase ligands, and in screening assays to identify molecules that inhibit the interaction of an adenylate kinase protein with an adenylate kinase ligand.

Preferably, an adenylate kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, an adenylate kinase-encoding nucleic acid can be cloned into a commercially available expression vector such that it is linked in-frame to an existing fusion moiety.

Variants of the adenylate kinase proteins can function as either adenylate kinase agonists (mimetics) or as adenylate kinase antagonists. Variants of the adenylate kinase protein can be generated by mutagenesis, e.g., discrete point mutation or truncation of the adenylate kinase protein. An agonist of the adenylate kinase protein can retain substantially the same, or a subset, of the biological activities of the naturally occurring form of the adenylate kinase protein. An antagonist of the adenylate kinase protein can inhibit one or more of the activities of the naturally occurring form of the adenylate kinase protein by, for example, competitively binding to a downstream or upstream member of a cellular signaling cascade that includes the adenylate kinase protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the adenylate kinase proteins.

Variants of the adenylate kinase proteins can function as either adenylate kinase agonists (mimetics) or as adenylate kinase antagonists. Variants of the adenylate kinase protein can be generated by mutagenesis, e.g. discrete point mutation or truncation of the adenylate kinase protein. An agonist of the adenylate kinase protein can retain substantially the same, or a subset, of the biological activities of the naturally occurring form of the adenylate kinase protein. An antagonist of the adenylate kinase protein can inhibit one or more of the activities of the naturally occurring form of the adenylate kinase protein by, for example, competitively binding to a downstream or upstream member of a cellular signaling cascade that includes the adenylate kinase protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the adenylate kinase proteins.

Variants of an adenylate kinase protein that function as either adenylate kinase agonists or as adenylate kinase antagonists can be identified by screening combinatorial libraries of mutants, e.g., truncation mutants, of an adenylate kinase protein for adenylate kinase protein agonist or antagonist activity. In one embodiment, a variegated library of adenylate kinase variants is generated by combinatorial mutagenesis at the nucleic acid level and is encoded by a variegated gene library. A variegated library of adenylate kinase variants can be produced by, for example, enzymatically ligating a mixture of synthetic oligonucleotides into gene sequences such that a degenerate set of potential adenylate kinase sequences is expressible as individual polypeptides, or alternatively, as a set of larger fusion proteins (e.g., for phage display) containing the set of adenylate kinase sequences therein. There are a variety of methods that can be used to produce libraries of potential adenylate kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential adenylate kinase sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of an adenylate kinase protein coding sequence can be used to generate a variegated population of adenylate kinase fragments for screening and subsequent selection of variants of an adenylate kinase protein. In one embodiment, a library of coding sequence fragments can be generated by treating a double-stranded PCR fragment of an adenylate kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the adenylate kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of adenylate kinase proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify adenylate kinase variants (Arkin and Yourvan (1992) *Proc. Natl. Acad. Sci. USA* 89:7811–7815; Delgrave et al. (1993) *Protein Engineering* 6(3):327–331).

An isolated adenylate kinase polypeptide of the invention can be used as an immunogen to generate antibodies that bind adenylate kinase proteins using standard techniques for polyclonal and monoclonal antibody preparation. The full-length adenylate kinase protein can be used or, alternatively, the invention provides antigenic peptide fragments of adenylate kinase proteins for use as immunogens. The antigenic peptide of an adenylate kinase protein comprises at least 8, preferably 10–15, 15–20, 20–25, or 30 or more amino acid residues of the amino acid sequence shown in SEQ ID NO:22 and encompasses an epitope of an adenylate kinase protein such that an antibody raised against the peptide forms a specific immune complex with the adenylate kinase protein. Preferred epitopes encompassed by the antigenic peptide are regions of a adenylate kinase protein that are located on the surface of the protein, e.g., hydrophilic regions.

Accordingly, another aspect of the invention pertains to anti-adenylate kinase polyclonal and monoclonal antibodies that bind an adenylate kinase protein. Polyclonal anti-adenylate kinase antibodies can be prepared by immunizing a suitable subject (e.g., rabbit, goat, mouse, or other mammal) with an adenylate kinase immunogen. The anti-adenylate kinase antibody titer in the immunized subject can be monitored over time by standard techniques, such as with an enzyme linked immunosorbent assay (ELISA) using immobilized adenylate kinase protein. At an appropriate time after immunization, e.g., when the anti-adenylate kinase antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-adenylate kinase antibody can be identified and isolated by screening a recombinant combinatorial immunoglobulin library (e.g., an antibody phage display library) with an adenylate kinase protein to thereby isolate immunoglobulin library members that bind the adenylate kinase protein. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-adenylate kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-adenylate kinase antibody (e.g., monoclonal antibody) can be used to isolate adenylate kinase proteins by standard techniques, such as affinity chromatography or immunoprecipitation. An anti-adenylate kinase antibody can facilitate the purification of natural adenylate kinase protein from cells and of recombinantly produced adenylate kinase protein expressed in host cells. Moreover, an anti-adenylate kinase antibody can be used to detect adenylate kinase protein (e.g., in a cellular lysate or cell supernatant) in order to evaluate the abundance and pattern of expression of the adenylate kinase protein. Anti-adenylate kinase antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al.(1985) "Monoclonal Antibodies for Immunotargeting of Drugs in Cancer Therapy," in *Monoclonal Antibodies And Cancer Therapy*, ed. Reisfeld et al. (Alan R. Liss, Inc.), pp. 243–56); Hellstrom et al. (1987) "Antibodies for Drug Delivery," in Controlled Drug Delivery, ed. Robinson et al. (2d ed., Marcel Dekker, Inc.), pp. 623–53; Thorpe (1985) "Antibody Carriers of Cytotoxic Agents in Cancer Therapy: A Review", in *Monoclonal Antibodies '84:Biological And Clinical Applications*, ed. Pinchera et al., pp. 475–506; "Analysis, Results, and Future Prospective of the Therapeutic Use of Radiolabeled Antibody in Cancer Therapy," in *Monoclonal Antibodies For Cancer Detection And Therapy*, ed. Baldwin et al. (Academic Press, NY), pp. 303–316; and Thorpe et al. (1982) *Immunol. Rev.* 62:119–58. Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding an adenylate kinase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., adenylate kinase proteins, mutant forms of adenylate kinase proteins, fusion proteins, etc.).

It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of adenylate kinase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSecl (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) Cell 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to adenylate kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an adenylate kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) adenylate kinase protein. Accordingly, the invention further provides methods for producing adenylate kinase protein using the host cells of the invention. In one embodiment, the method comprises culturing the host cell of the invention, into which a recombinant expression vector encoding an adenylate kinase protein has been introduced, in a suitable medium such that adenylate kinase protein is produced. In another embodiment, the method further comprises isolating adenylate kinase protein from the medium or the host cell.

The host cells of the invention can also be used to produce nonhuman transgenic animals. In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

For example, in one embodiment, a host cell of the invention is a fertilized oocyte or an embryonic stem cell into which adenylate kinase-coding sequences have been introduced. Such host cells can then be used to create nonhuman transgenic animals in which exogenous adenylate kinase sequences have been introduced into their genome or homologous recombinant animals in which endogenous adenylate kinase sequences have been altered. Such animals are useful for studying the function and/or activity of adenylate kinase genes and proteins and for identifying and/or evaluating modulators of adenylate kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous adenylate kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing adenylate kinase-encoding nucleic acid into the male pronuclei of a fertilized oocyte, e.g., by microinjection, retroviral infection, and allowing the oocyte to develop in a pseudopregnant female foster animal. The adenylate kinase cDNA sequence can be introduced as a transgene into the genome of a nonhuman animal. Alternatively, a homolog of the mouse adenylate kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the adenylate kinase transgene to direct expression of adenylate kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the adenylate kinase transgene in its genome and/or expression of adenylate kinase mRNA in tissues or cells of the animals. A transgenic founder animal can then be used to breed additional animals carrying the transgene. Moreover, transgenic animals carrying a transgene encoding adenylate kinase gene can further be bred to other transgenic animals carrying other transgenes.

To create a homologous recombinant animal, one prepares a vector containing at least a portion of an adenylate kinase gene or a homolog of the gene into which a deletion, addition, or substitution has been introduced to thereby alter, e.g., functionally disrupt, the adenylate kinase gene. In a preferred embodiment, the vector is designed such that, upon homologous recombination, the endogenous adenylate kinase gene is functionally disrupted (i.e., no longer encodes a functional protein; also referred to as a "knock out" vector). Alternatively, the vector can be designed such that, upon homologous recombination, the endogenous adenylate kinase gene is mutated or otherwise altered but still encodes functional protein (e.g., the upstream regulatory region can be altered to thereby alter the expression of the endogenous adenylate kinase protein). In the homologous recombination vector, the altered portion of the adenylate kinase gene is flanked at its 5' and 3' ends by additional nucleic acid of the adenylate kinase gene to allow for homologous recombination to occur between the exogenous adenylate kinase gene carried by the vector and an endogenous adenylate kinase gene in an embryonic stem cell. The additional flanking adenylate kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced adenylate kinase gene has homologously recombined with the endogenous adenylate kinase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The adenylate kinase nucleic acid molecules, adenylate kinase proteins, and anti-adenylate kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents that modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an adenylate kinase protein or anti-adenylate kinase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

V. Uses and Methods of the Invention

The nucleic acid molecules, proteins, protein homologs, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The uses and methods of the invention are particularly relevant in tissues and cells in which the adenylate kinase is expressed and especially where expression differs from that in a normal tissue or cell. The uses and methods are also particularly relevant in disorders involving such tissues and cells. Accordingly, the uses and methods are particularly relevant for disorders involving expression of the adenylate kinase of the invention. The isolated nucleic acid molecules of the invention can be used to express adenylate kinase protein (e.g., via a recombinant expression vector in a host cell in gene therapy applications), to detect adenylate kinase mRNA (e.g., in a biological sample) or a genetic lesion in an adenylate kinase gene, and to modulate adenylate kinase activity. In addition, the adenylate kinase proteins can be used to screen drugs or compounds that modulate the immune response as well as to treat disorders characterized by insufficient or excessive production of adenylate kinase protein or production of adenylate kinase protein forms that have decreased or aberrant activity compared to adenylate kinase wild, type protein. In addition, the anti-adenylate kinase antibodies of the invention can be used to detect and isolate adenylate kinase proteins and modulate adenylate kinase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to adenylate kinase proteins or have a stimulatory or inhibitory effect on, for example, adenylate kinase expression or adenylate kinase activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *BioTechniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the adenylate kinase protein can be accomplished, for example, by coupling the test compound with a radioisotope or enzymatic label such that binding of the test compound to the adenylate kinase protein or biologically active portion thereof can be determined by detecting the labeled compound in a complex. For example, test compounds can be labeled with $^{125}I$, $^{35}S$, $^{14}C$, or $^3H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the adenylate kinase protein to bind to or interact with an adenylate kinase target molecule. By "target molecule" is intended a molecule with which an adenylate kinase protein binds or interacts in nature. In a preferred embodiment, the ability of the adenylate kinase protein to bind to or interact with an adenylate kinase target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., an adenylate kinase-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting an adenylate kinase protein or biologically active portion thereof with a test compound and determining the ability of the test compound to bind to the adenylate kinase protein or biologically active portion thereof. Binding of the test compound to the adenylate kinase protein can be determined either directly or indirectly as described above. In a preferred embodiment, the assay includes contacting the adenylate kinase protein or biologically active portion thereof with a known compound that binds adenylate kinase protein to form an assay mixture, contacting the assay mixture with a test compound, and determining the ability of the test compound to preferentially bind to adenylate kinase protein or biologically active portion thereof as compared to the known compound.

In another embodiment, an assay is a cell-free assay comprising contacting adenylate kinase protein or biologically active portion thereof with a test compound and determining the ability of the test compound to modulate (e.g., stimulate or inhibit) the activity of the adenylate kinase protein or biologically active portion thereof. Determining the ability of the test compound to modulate the activity of an adenylate kinase protein can be accomplished, for example, by determining the ability of the adenylate kinase protein to bind to an adenylate kinase target molecule as described above for determining direct binding. In an alternative embodiment, determining the ability of the test compound to modulate the activity of an adenylate kinase protein can be accomplished by determining the ability of the adenylate kinase protein to further modulate an adenylate kinase target molecule. For example, the catalytic/enzymatic activity of the target molecule on an appropriate substrate can be determined as previously described.

In yet another embodiment, the cell-free assay comprises contacting the adenylate kinase protein or biologically active portion thereof with a known compound that binds an adenylate kinase protein to form an assay mixture, contacting the assay mixture with a test compound, and determining the ability of the test compound to preferentially bind to or modulate the activity of an adenylate kinase target molecule.

In the above-mentioned assays, it may be desirable to immobilize either an adenylate kinase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/adenylate kinase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or adenylate kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of adenylate kinase binding or activity determined using standard techniques.

Other techniques for immobilizing proteins on matrices can also be used in the screening assays of the invention. For example, either adenylate kinase protein or its target molecule can be immobilized utilizing conjugation of biotin and streptavidin. Biotinylated adenylate kinase molecules or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with an adenylate kinase protein or target molecules but which do not interfere with binding of the adenylate kinase protein to its target molecule can be derivatized to the wells of the plate, and unbound target or adenylate kinase protein trapped in the wells by antibody conjugation. Methods for detecting such complexes, in addition to those described above for the GST-immobilized complexes, include immunodetection of complexes using antibodies reactive with the adenylate kinase protein or target molecule, as well as enzyme-linked assays that rely on detecting an enzymatic activity associated with the adenylate kinase protein or target molecule.

In another embodiment, modulators of adenylate kinase expression are identified in a method in which a cell is contacted with a candidate compound and the expression of adenylate kinase mRNA or protein in the cell is determined relative to expression of adenylate kinase mRNA or protein in a cell in the absence of the candidate compound. When expression is greater (statistically significantly greater) in the presence of the candidate compound than in its absence, the candidate compound is identified as a stimulator of adenylate kinase mRNA or protein expression. Alternatively, when expression is less (statistically significantly less) in the presence of the candidate compound than in its absence, the candidate compound is identified as an inhibitor of adenylate kinase mRNA or protein expression. The level of adenylate kinase mRNA or protein expression in the cells can be determined by methods described herein for detecting adenylate kinase mRNA or protein.

In yet another aspect of the invention, the adenylate kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *BioTechniques* 14:920–924; Iwabuchi et al. (1993) *Oncogene* 8:1693–1696; and PCT Publication No. WO 94/10300), to identify other proteins, which bind to or interact with adenylate kinase protein ("adenylate kinase-binding proteins" or "adenylate kinase-bp") and modulate adenylate kinase activity. Such adenylate kinase-binding proteins are also likely to be involved in the propagation of signals by the adenylate kinase proteins as, for example, upstream or downstream elements of the adenylate kinase pathway.

This invention further pertains to novel agents identified by the above-described screening assays and uses thereof for treatments as described herein. Accordingly the invention is directed to agents that modulate the level or activity of the polypeptide or nucleic acid of the invention, the agents being identified by screening cells, tissues, cell extracts, or tissue extracts with the agents. Agents that alter the level or activity can then be tested further for clinical diagnostic or therapeutic use. Any method of screening that allows expression to be measured, such as those disclosed herein, are relevant to produce the identification of these agents. Thus, the invention is directed to agents identified by the screening processes involving measuring or detecting expression (level or activity) of the polypeptides or nucleic acids of the invention. It is understood that agents affecting the ability of the protein or nucleic acid to interact with a cellular component, as in competition binding, would be construed as affecting expression. Accordingly, screening processes also include assays for agents that themselves bind to the protein or nucleic acid of the invention, such as those disclosed herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial adenylate kinase gene sequences of the invention can be used to map their respective adenylate kinase genes on a chromosome, thereby facilitating the location of gene regions associated with genetic disease. Computer analysis of adenylate kinase sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the adenylate kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map an adenylate kinase sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma eta a. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the adenylate kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The adenylate kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the adenylate kinase sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The adenylate kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:21 can comfortably provide positive individual identification with a panel of perhaps 10 to 1,000 primers that each yield a noncoding amplified sequence of 100 bases. If a predicted coding sequence, such as that in SEQ ID NO:21, is used, a more appropriate number of primers for positive individual identification would be 500 to 2,000.

3. Use of Partial Adenylate Kinase Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:21 are particularly appropriate for this use as greater numbers of polymorphisms occur in the noncoding regions, making it easier to differentiate individuals using this technique. Examples of polynucleotide reagents include the adenylate kinase sequences or portions thereof, e.g., fragments derived from the noncoding regions of SEQ ID NO:21 having a length of at least 20 or 30 bases.

The adenylate kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such adenylate kinase probes, can be used to identify tissue by species and/or by organ type.

In a similar fashion, these reagents, e.g., adenylate kinase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting adenylate kinase protein and/or nucleic acid expression as well as adenylate kinase activity, in the context of a biological sample. An exemplary method for detecting the presence or absence of adenylate kinase proteins in a biological sample involves obtaining a biological sample from a test subject and contacting the biological sample with a compound or an agent capable of detecting adenylate kinase protein or nucleic acid (e.g., mRNA, genomic DNA) that encodes adenylate kinase protein such that the presence of adenylate kinase protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels; i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting adenylate kinase mRNA or genomic DNA is a labeled nucleic acid probe capable of hybridizing to adenylate kinase mRNA or genomic DNA. The nucleic acid probe can be, for example, a full-length adenylate kinase nucleic acid, such as the nucleic acid of SEQ ID NO:21, or a portion thereof, such as a nucleic acid molecule of at least about 15, 30, 50, 100, 250, or 500 nucleotides in length and sufficient to specifically hybridize under stringent conditions to adenylate kinase mRNA or genomic DNA. Other suitable probes for use in the diagnostic assays of the invention are described herein.

A preferred agent for detecting adenylate kinase protein is an antibody capable of binding to adenylate kinase protein, preferably an antibody with a detectable label. Antibodies can be polyclonal, or more preferably, monoclonal. An intact antibody, or a fragment thereof (e.g., Fab or $F(abN)_2$)can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect adenylate kinase mRNA, protein, or genomic DNA in a biological sample in vitro as well as in vivo. For example, in vitro techniques for detection of adenylate kinase mRNA include Northern hybridizations and in situ hybridizations. In vitro techniques for detection of adenylate kinase protein include enzyme linked immunosorbent assays (ELISAs), Western blots, immunoprecipitations, and immunofluorescence. In vitro techniques for detection of adenylate kinase genomic DNA include Southern hybridizations. Furthermore, in vivo techniques for detection of adenylate kinase protein include introducing into a subject a labeled anti-adenylate kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

The invention also encompasses kits for detecting the presence of adenylate kinase proteins in a biological sample (a test sample). Such kits can be used to determine if a subject is suffering from or is at increased risk of developing a disorder associated with aberrant expression of adenylate kinase protein (e.g., an immunological disorder). For example, the kit can comprise a labeled compound or agent capable of detecting adenylate kinase protein or mRNA in a biological sample and means for determining the amount of an adenylate kinase protein in the sample (e.g., an anti-adenylate kinase antibody or an oligonucleotide probe that binds to DNA encoding an adenylate kinase protein, e.g., SEQ ID NO:21). Kits can also include instructions for observing that the tested subject is suffering from or is at risk of developing a disorder associated with aberrant expression of adenylate kinase sequences if the amount of adenylate kinase protein or mRNA is above or below a normal level.

For antibody-based kits, the kit can comprise, for example: (1) a first antibody (e.g., attached to a solid support) that binds to adenylate kinase protein; and, optionally, (2) a second, different antibody that binds to adenylate kinase protein or the first antibody and is conjugated to a detectable agent. For oligonucleotide-based kits, the kit can comprise, for example: (1) an oligonucleotide, e.g., a detectably labeled oligonucleotide, that hybridizes to an adenylate kinase nucleic acid sequence or (2) a pair of primers useful for amplifying an adenylate kinase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of adenylate kinase proteins.

2. Prognostic Assays

The methods described herein can furthermore be utilized as diagnostic or prognostic assays to identify subjects having or at risk of developing a disease or disorder associated with adenylate kinase protein, adenylate kinase nucleic acid expression, or adenylate kinase activity. Prognostic assays can be used for prognostic or predictive purposes to thereby prophylactically treat an individual prior to the onset of a disorder characterized by or associated with adenylate kinase protein, adenylate kinase nucleic acid expression, or adenylate kinase activity.

Thus, the present invention provides a method in which a test sample is obtained from a subject, and adenylate kinase protein or nucleic acid (e.g., mRNA, genomic DNA) is detected, wherein the presence of adenylate kinase protein or nucleic acid is diagnostic for a subject having or at risk of developing a disease or disorder associated with aberrant adenylate kinase expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease adenylate kinase activity) to effectively treat a disease or disorder associated with aberrant adenylate kinase expression or activity. In this manner, a test sample is obtained and adenylate kinase protein or nucleic acid is detected. The presence of adenylate kinase protein or nucleic acid is diagnostic for a subject that can be administered the agent to treat a disorder associated with aberrant adenylate kinase expression or activity.

The methods of the invention can also be used to detect genetic lesions or mutations in an adenylate kinase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding an adenylate kinase-protein, or the misexpression of the adenylate kinase gene. For example, such genetic lesions or mutations can be detected by ascertaining the existence of at least one of: (1) a deletion of one or more nucleotides from an adenylate kinase gene; (2) an addition of one or more nucleotides to an adenylate kinase gene; (3) a substitution of one or more nucleotides of an adenylate kinase gene; (4) a chromosomal rearrangement of an adenylate kinase gene; (5) an alteration in the level of a messenger RNA transcript of an adenylate kinase gene; (6) an aberrant modification of an adenylate kinase gene, such as of the methylation pattern of the genomic DNA; (7) the presence of a non-wild-type splicing pattern of a messenger RNA transcript of an adenylate kinase gene; (8) a non-wild-type level of an adenylate kinase-protein; (9) an allelic loss of an adenylate kinase gene; and (10) an inappropriate post-translational modification of an adenylate kinase-protein. As described herein, there are a large number of assay techniques known in the art that can be used for detecting lesions in an adenylate kinase gene. Any cell type or tissue, preferably peripheral blood leukocytes, in which adenylate kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the adenylate kinase gene (see, e.g., Abravaya et al. (1995) Nucleic Acids Res. 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) Proc. Natl. Acad. Sci. USA 87:1874–1878), transcriptional amplification system (Kwoh et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an adenylate kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in an adenylate kinase molecule can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). In yet another embodiment, any of a variety of sequencing reactions known in the art can be used to directly sequence the adenylate kinase gene and detect mutations by comparing the sequence of the sample adenylate kinase gene with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the adenylate kinase gene include methods in which protection from cleavage agents is used to detect mismatched bases in RNA/RNA or RNA/DNA heteroduplexes (Myers et al. (1985) Science 230:1242). See, also Cotton et al. (1988) Proc. Natl. Acad. Sci. USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in adenylate kinase cDNAs obtained from samples of cells. See, e.g., Hsu et al. (1994) *Carcinogenesis* 15:1657–1662. According to an exemplary embodiment, a probe based on an adenylate kinase sequence, e.g., a wild-type adenylate kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in adenylate kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving an adenylate kinase gene.

3. Pharmacogenomics

Agents or modulators that have a stimulatory or inhibitory effect on adenylate kinase activity (e.g., adenylate kinase gene expression) as identified by a screening assay described herein, can be administered to individuals to treat (prophylactically or therapeutically) disorders associated with aberrant adenylate kinase activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of adenylate kinase protein, expression of adenylate kinase nucleic acid, or mutation content of adenylate kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a)drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of adenylate kinase protein, expression of adenylate kinase nucleic acid, or mutation content of adenylate kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an adenylate kinase modulator, such as a modulator identified by one of the exemplary screening assays described herein.

4. Monitoring of Effects During Clinical Trials

Monitoring the influence of agents (e.g., drugs, compounds) on the expression or activity of adenylate kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease adenylate kinase gene expression, protein levels, or protein activity, can be monitored in clinical trials of subjects exhibiting decreased or increased adenylate kinase gene expression, protein levels, or protein activity. In such clinical trials, adenylate kinase expression or activity and preferably that of other genes that have been implicated in for example, a cellular proliferation disorder, can be used as a marker of the responsiveness of a particular cell.

For example, and not by way of limitation, genes that are modulated in cells by treatment with an agent (e.g., compound, drug, or small molecule) that modulates adenylate kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of adenylate kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of adenylate kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of an adenylate kinase protein, mRNA, or genomic DNA in the preadministration sample; (3) obtaining one or more postadministration samples from the subject; (4) detecting the level of expression or activity of the adenylate kinase protein, mRNA, or genomic DNA in the postadministration samples; (5) comparing the level of expression or activity of the adenylate kinase protein, mRNA, or genomic DNA in the preadministration sample with the adenylate kinase protein, mRNA, or genomic DNA in the postadministration sample or samples; and (vi) altering the administration of the agent to the subject accordingly to bring about the desired effect, i.e., for example, an increase or a decrease in the expression or activity of an adenylate kinase protein.

C. Methods of Treatment

The present invention provides for both prophylactic and therapeutic methods of treating a subject at risk of (or susceptible to) a disorder or having a disorder associated with aberrant adenylate kinase expression or activity. Additionally, the compositions of the invention find use in the treatment of disorders described herein. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject", as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides. Thus, therapies for disorders associated with adenylate kinase expression are encompassed herein.

1. Prophylactic Methods

In one aspect, the invention provides a method for preventing in a subject a disease or condition associated with an aberrant adenylate kinase expression or activity by administering to the subject an agent that modulates adenylate kinase expression or at least one adenylate kinase gene activity. Subjects at risk for a disease that is caused, or contributed to, by aberrant adenylate kinase expression or activity can be identified by, for example, any or a combination of diagnostic or prognostic assays as described herein. Administration of a prophylactic agent can occur prior to the manifestation of symptoms characteristic of the adenylate kinase aberrancy, such that a disease or disorder is prevented or, alternatively, delayed in its progression. Depending on the type of adenylate kinase aberrancy, for example, an adenylate kinase agonist or adenylate kinase antagonist agent can be used for treating the subject. The appropriate agent can be determined based on screening assays described herein.

2. Therapeutic Methods

Another aspect of the invention pertains to methods of modulating adenylate kinase expression or activity for therapeutic purposes. The modulatory method of the invention involves contacting a cell with an agent that modulates one or more of the activities of adenylate kinase protein activity associated with the cell. An agent that modulates adenylate kinase protein activity can be an agent as described herein, such as a nucleic acid or a protein, a naturally-occurring cognate ligand of an adenylate kinase protein, a peptide, an adenylate kinase peptidomimetic, or other small molecule. In one embodiment, the agent stimulates one or more of the biological activities of adenylate kinase protein. Examples of such stimulatory agents include active adenylate kinase protein and a nucleic acid molecule encoding an adenylate kinase protein that has been introduced into the cell. In another embodiment, the agent inhibits one or more of the biological activities of adenylate kinase protein. Examples of such inhibitory agents include antisense adenylate kinase nucleic acid molecules and anti-adenylate kinase antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of an adenylate kinase protein or nucleic acid molecule. In one embodiment, the method involves administering an agent (e.g., an agent identified by a screening assay described herein), or a combination of agents, that modulates (e.g., upregulates or downregulates) adenylate kinase expression or activity. In another embodiment, the method involves administering an adenylate kinase protein or nucleic acid molecule as therapy to compensate for reduced or aberrant adenylate kinase expression or activity.

Stimulation of adenylate kinase activity is desirable in situations in which an adenylate kinase protein is abnormally downregulated and/or in which increased adenylate kinase activity is likely to have a beneficial effect. Conversely, inhibition of adenylate kinase activity is desirable in situations in which adenylate kinase activity is abnormally upregulated and/or in which decreased adenylate kinase activity is likely to have a beneficial effect.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 27802, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 27802 nucleic acid, polypeptide, or antibody.

The capture probes can be a set of nucleic acids from a selected sample, e.g., a sample of nucleic acids derived from a control or non-stimulated tissue or cell.

The method can include contacting the 27802 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 27802. Such methods can be used to diagnose a subject, e.g., to evaluate risk for a disease or disorder, to evaluate suitability of a selected treatment for a subject, to evaluate whether a subject has a disease or disorder. 27802 is associated with adenylate kinase activity, thus it is useful for disorders associated with abnormal cellular growth and/or metabolism.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 27802 or from a cell or subject in which a 27802 mediated response has been elicited, e.g., by contact of the cell with 27802 nucleic acid or protein, or administration to the cell or subject 27802 nucleic acid or protein; contacting the array with one or more inquiry probe, wherein an inquiry probe can be a nucleic acid, polypeptide, or antibody (which is preferably other than 27802 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 27802 (or does not express as highly as in the case of the 27802 positive plurality of capture probes) or from a cell or subject which in which a 27802 mediated response has not been elicited (or has been elicited to a lesser extent than in the first sample); contacting the array with one or more inquiry probes (which is preferably other than a 27802 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 27802, e.g., analyzing structure, function, or relatedness to other nucleic acid or amino acid sequences. The method includes: providing a 27802 nucleic acid or amino acid sequence; comparing the 27802 sequence with one or more preferably a plurality of sequences from a collection of sequences, e.g., a nucleic acid or protein sequence database; to thereby analyze 27802.

Preferred databases include GenBank™. The method can include evaluating the sequence identity between a 27802 sequence and a database sequence. The method can be performed by accessing the database at a second site, e.g., over the internet.

In another aspect, the invention features, a set of oligonucleotides, useful, e.g., for identifying SNP's, or identifying specific alleles of 27802. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide which hybridizes to a second allele.

This invention is further illustrated by the following examples which should not be construed as limiting. The contents of all references, patents and published patent applications cited throughout this application are incorporated herein by reference.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1

Identification and Characterization of Human 27802 cDNAs

The human 27802 sequence (FIG. 28; SEQ ID NO:21), which is approximately 1452 nucleotides long including untranslated regions, contains a predicted methionine-initiated coding sequence of about 774 nucleotides (nucleotides 219–992 of SEQ ID NO:21; SEQ ID NO:23). The coding sequence encodes a 258 amino acid protein (SEQ ID NO:22).

Example 2

Tissue Distribution of 27802 mRNA

Northern blot hybridizations with various RNA samples are performed under standard conditions and washed under stringent conditions, i.e., 0.2×SSC at 65° C. A DNA probe corresponding to all or a portion of the 27802 cDNA (SEQ ID NO:21) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

Expression levels were determined by quantitative PCR (Taqman® brand quantitative PCR kit, Applied Biosystems). The quantitative PCR reactions were performed according to the kit manufacturer's instructions. The highest levels of expression of 27802 were observed in artery, kidney, brain cortex and brain hypothalamus, ovary, lung (tumor), and tonsil (see FIG. 35).

Example 3

Recombinant Expression of 27802 in Bacterial Cells

In this example, 27802 polypeptide is expressed as a recombinant glutathione-S-transferase (GST) fusion polypeptide in E. coli and the fusion polypeptide is isolated and characterized. Specifically, 27802 is fused to GST and this fusion polypeptide is expressed in E. coli, e.g., strain PEB199. Expression of the GST-27802 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 27802 Protein in COS Cells

To express the 27802 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 27802 protein and an, HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 27802 DNA sequence is amplified by PCR using two primers. The 5' primer contains the restriction site of interest followed by approximately twenty nucleotides of the 27802 coding sequence starting from the initiation codon; the 3' end sequence contains complementary sequences to the other restriction site of interest, a translation stop codon, the HA tag or FLAG tag and the last 20 nucleotides of the 27802 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 27802 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 27802-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 27802 polypeptide is detected by radiolabelling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 27802 coding sequence is cloned directly into the polylinker of the pcDNA/Amp vector using the appropriate restriction sites. The resulting plasmid is transfected into COS cells in the manner described above, and the expression of the 27802 polypeptide is detected by radiolabelling and immunoprecipitation using a 27802 specific monoclonal antibody.

That which is claimed:

1. An isolated polypeptide comprising the amino acid sequence of SEQ ID NO:2.

2. A method for identifying a compound which binds to the polypeptide of claim 1 comprising the steps of:
   a) contacting said polypeptide, or a cell expressing a polypeptide of claim 1 with a test compound; and
   b) determining whether the polypeptide binds to the test compound.

3. The method of claim 2, wherein the binding of the test compound to the polypeptide is detected by a method selected from the group consisting of:
   a) detection of binding by direct detecting of test compound/polypeptide binding; and,
   b) detection of binding using a competition binding assay.

4. A method for modulating the activity of the polypeptide of claim 1 comprising contacting said polypeptide or a cell expressing a polypeptide of claim 1 with a compound which binds to the polypeptide in a sufficient concentration to modulate the activity of the polypeptide.

5. A method for identifying a compound which modulates the activity of the polypeptide of claim 1, comprising:
   a) contacting the polypeptide of claim 1 with a test compound; and
   b) determining the effect of the test compound on the activity of the polypeptide to thereby identify a compound which modulates the activity of the polypeptide.

* * * * *